US010920223B2

(12) United States Patent
Sehgal et al.

(10) Patent No.: US 10,920,223 B2
(45) Date of Patent: Feb. 16, 2021

(54) SERPINA1 IRNA COMPOSITIONS AND METHODS OF USE THEREOF

(71) Applicant: Alnylam Pharmaceuticals, Inc., Cambridge, MA (US)

(72) Inventors: Alfica Sehgal, Medford, MA (US); Klaus Charisse, Acton, MA (US); Brian Bettencourt, Groton, MA (US); Martin A. Maier, Belmont, MA (US); Kallanthottathil G. Rajeev, Wayland, MA (US); Gregory Hinkle, Plymouth, MA (US); Muthiah Manoharan, Weston, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 16/008,461

(22) Filed: Jun. 14, 2018

(65) Prior Publication Data
US 2018/0346910 A1 Dec. 6, 2018

Related U.S. Application Data

(63) Continuation of application No. 15/399,820, filed on Jan. 6, 2017, now Pat. No. 10,030,244, which is a continuation of application No. 14/284,745, filed on May 22, 2014, now Pat. No. 9,574,192.

(60) Provisional application No. 61/989,028, filed on May 6, 2014, provisional application No. 61/979,727, filed on Apr. 15, 2014, provisional application No. 61/898,695, filed on Nov. 1, 2013, provisional application No. 61/826,125, filed on May 22, 2013.

(51) Int. Cl.
  *C07H 21/02* (2006.01)
  *A61K 48/00* (2006.01)
  *C12N 15/113* (2010.01)
  *A61K 31/712* (2006.01)
  *A61K 31/713* (2006.01)

(52) U.S. Cl.
  CPC .......... *C12N 15/113* (2013.01); *A61K 31/712* (2013.01); *A61K 31/713* (2013.01); *C12N 2310/11* (2013.01); *C12N 2310/14* (2013.01); *C12N 2310/315* (2013.01); *C12N 2310/32* (2013.01); *C12N 2310/321* (2013.01); *C12N 2310/331* (2013.01); *C12N 2310/332* (2013.01); *C12N 2310/343* (2013.01); *C12N 2310/344* (2013.01); *C12N 2310/346* (2013.01); *C12N 2310/351* (2013.01); *C12N 2320/32* (2013.01); *C12N 2320/34* (2013.01); *C12N 2320/51* (2013.01); *C12N 2330/30* (2013.01)

(58) Field of Classification Search
  CPC .............. C12N 15/113; C12N 2310/11; C12N 2310/14
  See application file for complete search history.

(56) References Cited

U.S. PATENT DOCUMENTS

| 7,691,997 | B2 | 4/2010 | Khvorova et al. |
| 9,574,192 | B2 | 2/2017 | Sehgal et al. |
| 9,839,649 | B2 * | 12/2017 | Khvorova ........ C12Y 502/0100 |
| 9,879,261 | B2 | 1/2018 | Sehgal et al. |
| 10,370,655 | B2 | 8/2019 | Brown et al. |
| 2002/0115595 | A1 * | 8/2002 | Grissom ............ A61K 41/0028 514/20.9 |
| 2005/0137153 | A1 | 6/2005 | McSwiggen et al. |
| 2005/0245475 | A1 | 11/2005 | Khvorova et al. |
| 2006/0234247 | A1 | 10/2006 | Puttaraju et al. |
| 2015/0087691 | A1 | 3/2015 | Monia et al. |
| 2018/0195069 | A1 | 7/2018 | Li et al. |

FOREIGN PATENT DOCUMENTS

| EP | 1752536 A1 | 2/2007 |
| WO | WO-2004/045543 A2 | 6/2004 |
| WO | WO-2006/006948 A2 | 1/2006 |
| WO | WO-2009/073809 A2 | 6/2009 |
| WO | WO-2009/120878 A2 | 10/2009 |
| WO | WO-2009/134487 A2 | 11/2009 |
| WO | WO-2010/148013 A2 | 12/2010 |
| WO | WO-2012/178033 A2 | 12/2012 |
| WO | WO-2014/190137 A1 | 11/2014 |
| WO | WO-2016/028649 A1 | 2/2016 |

OTHER PUBLICATIONS

Wu et al. (Frontiers in Bioscience 1, d717-725, Mar. 2002).*
Allerson et al. (J. Med. Chem., 2005, 48, 4, 901-904).*
Elbashir et al. (The EMBO Journal, vol. 20, No. 23, pp. 6877-6888, 2001).*
International Search Report and Written Opinion from PCT/US2014/039109 dated Oct. 21, 2014.
Sehgal, Alfica, et al. "Developing and RNAi Therapeutic for Liver Disease Associated with Alpha-I-Antitrypsin Deficiency", Hepatology, vol. 58, No. SI, Oct. 15, 2013, p. 412A.
GenBank Acession AC_235087; Jun. 24, 2009 [online] downloaded from: http://www.ncbi.nlm.nih.gov/nuccore/226938113/ on Jan. 18, 2017.
GenBank Acession M_26123; Oct. 30, 1994 [online] downloaded from: http://www.ncbi.nlm.nih.gov/nuccore/177815/ on Jan. 18, 2017.
GenBank Acession BC_011991; Jul. 15, 2006 [online] downloaded from: http://www.ncbi.nlm.nih.gov/nuccore/15080498/ on Jan. 18, 2017.
GenBank Acession DQ_682455; Jul. 22, 2006 [online] downloaded from: http://www.ncbi.nlm.nih.gov/nuccore/110350938/ on Jan. 18, 2017.

(Continued)

*Primary Examiner* — Amy H Bowman
(74) *Attorney, Agent, or Firm* — McCarter & English, LLP; Maria Laccotripe Zacharakis; Deborah L. Nagle

(57) ABSTRACT

The invention relates to RNAi agents, e.g., double-stranded RNAi agents, targeting the Serpina1 gene, and methods of using such RNAi agents to inhibit expression of Serpina1 and methods of treating subjects having a Serpina1 associated disease, such as a liver disorder.

45 Claims, 42 Drawing Sheets
Specification includes a Sequence Listing.

(56) References Cited

OTHER PUBLICATIONS

GenBank Acession CU_680153; Feb. 19, 2008 [online] downloaded from: http://www.ncbi.nlm.nih.gov/nuccore/Cu680153/ on Jan. 18, 2017.
GenBank Acession GZ_281832; Jun. 4, 2012 [online] downloaded from: http://www.ncbi.nlm.nih.gov/nuccore/389820151/ on Jan. 18, 2017.
GenBank Acession HV_439167; Sep. 27, 2011 [online] downloaded from: http://www.ncbi.nlm.nih.gov/nuccore/hv439167/ on Jan. 18, 2017.
GenBank Acession HC_680729; May 13, 2010 [online] downloaded from: http://www.ncbi.nlm.nih.gov/nuccore/HC680729 on Jan. 18, 2017.
GenBank Acession DM_075322; Apr. 21, 2009 [online] downloaded from: http://www.ncbi.nlm.nih.gov/nuccore/DM075322 on Jan. 18, 2017.
GenBank Acession GC_604704; Dec. 10, 2008 online] downloaded from: http://www.ncbi.nlm.nih.gov/nuccore/217168445/ on Jan. 18, 2017.
GenBank Acession EA_307422; Dec. 14, 2007 [online] downloaded from: http://www.ncbi.nlm.nih.gov/nuccore/162460313/ on Jan. 18, 2017.
GenBank Acession DL_143111; Sep. 26, 2008 [online] downloaded from: http://www.ncbi.nlm.nih.gov/nuccore/DL143111 on Jan. 18, 2017.
GenBank Acession BD_472318; Nov. 4, 2005 [online] downloaded from: http://www.ncbi.nlm.nih.gov/nuccore/BD472318 on Jan. 18, 2017.
GenBank Acession CS_273919; Jul. 17, 2006 [online] downloaded from: http://www.ncbi.nlm.nih.gov/nuccore/CS273919 on Jan. 18, 2017.
GenBank Acession AR_791176; Apr. 5, 2006 [online] downloaded from: http://www.ncbi.nlm.nih.gov/nuccore/91138047/ on Jan. 18, 2017.
GenBank Acession AR_583727; Dec. 15, 2004 [online] downloaded from: http://www.ncbi.nlm.nih.gov/nuccore/56621150 on Jan. 18, 2017.
GenBank Acession CQ_896528; Nov. 5, 2004 [online] downloaded from: http://www.ncbi.nlm.nih.gov/nuccore/CQ896528 on Jan. 18, 2017.
GenBank Acession CQ_541805; Jan. 30, 2004 [online] downloaded from: http://www.ncbi.nlm.nih.gov/nuccore/CQ541805 on Jan. 18, 2017.
GenBank Acession CQ_663228; Feb. 3, 2004 [online] downloaded from: http://www.ncbi.nlm.nih.gov/nuccore/CQ663228 on Jan. 18, 2017.
GenBank Acession AX_616365; Feb. 20, 2003 [online] downloaded from: http://www.ncbi.nlm.nih.gov/nuccore/AX616365 on Jan. 18, 2017.
GenBank Acession AR_044165; Sep. 29, 1999 [online] downloaded from: http://www.ncbi.nlm.nih.gov/nuccore/5965630 on Jan. 18, 2017.
GenBank Acession GU_727620; Jan. 11, 2011 [online] downloaded from: http://www.ncbi.nlm.nih.gov/nuccore/317040113/ on Jan. 18, 2017.
Cruz et al., "In vivo post-transcriptional gene silencing of a-1 antitrypsin by adeno-associated virus vectors expressing siRNA", Laboratory Investigation (2007) 87, 893-902.
U.S. Appl. No. 14/284,745 U.S. Pat. No. 9,574,192, filed May 22, 2014 Feb. 21, 2017, US 20140350071, Granted.
U.S. Appl. No. 15/399,820 U.S. Pat. No. 10,030,244, filed Jan. 6, 2017 Jul. 24, 2018, US 20170114342, Granted.
PCT/US2017/062701, Nov. 21, 2017, WO 2018/098117, Published.
Reynolds et al., "Rational siRNA design for RNA interference," Nature Biotechnology, vol. 22, pp. 326-330, 2004.
Fairbanks et al., "Liver Disease in Alpha 1-Antitrypsin Deficiency: A Review", Am J Gastroenterol 2008;103:2136-2141.

* cited by examiner

```
>gi|189163524|ref|NM_000295.4| Homo sapiens serpin peptidase inhibitor,
clade A (alpha-1 antiproteinase, antitrypsin), member 1 (SERPINA1),
transcript variant 1, mRNA
ACAATGACTCCTTTCGGTAAGTGCAGTGGAAGCTGTACACTGCCCAGGCAAAGCGTCCGGGCAGCGTAGG
CGGGCGACTCAGATCCCAGCCAGTGGACTTAGCCCCTGTTTGCTCCTCCGATAACTGGGGTGACCTTGGT
TAATATTCACCAGCAGCCTCCCCCGTTGCCCCTCTGGATCCACTGCTTAAATACGGACGAGGACAGGGCC
CTGTCTCCTCAGCTTCAGGCACCACCACTGACCTGGGACAGTGAATCGACAATGCCGTCTTCTGTCTCGT
GGGGCATCCTCCTGCTGGCAGGCCTGTGCTGCCTGGTCCCTGTCTCCCTGGCTGAGGATCCCCAGGGAGA
TGCTGCCCAGAAGACAGATACATCCCACCATGATCAGGATCACCCAACCTTCAACAAGATCACCCCCAAC
CTGGCTGAGTTCGCCTTCAGCCTATACCGCCAGCTGGCACACCAGTCCAACAGCACCAATATCTTCTTCT
CCCCAGTGAGCATCGCTACAGCCTTTGCAATGCTCTCCCTGGGGACCAAGGCTGACACTCACGATGAAAT
CCTGGAGGGCCTGAATTTCAACCTCACGGAGATTCCGGAGGCTCAGATCCATGAAGGCTTCCAGGAACTC
CTCCGTACCCTCAACCAGCCAGACAGCCAGCTCCAGCTGACCACCGGCAATGGCCTGTTCCTCAGCGAGG
GCCTGAAGCTAGTGGATAAGTTTTTGGAGGATGTTAAAAAGTTGTACCACTCAGAAGCCTTCACTGTCAA
CTTCGGGGACACCGAAGAGGCCAAGAAACAGATCAACGATTACGTGGAGAAGGGTACTCAAGGGAAAATT
GTGGATTTGGTCAAGGAGCTTGACAGAGACACAGTTTTTGCTCTGGTGAATTACATCTTCTTTAAAGGCA
AATGGGAGAGACCCTTTGAAGTCAAGGACACCGAGGAAGAGGACTTCCACGTGGACCAGGTGACCACCGT
GAAGGTGCCTATGATGAAGCGTTTAGGCATGTTTAACATCCAGCACTGTAAGAAGCTGTCCAGCTGGGTG
CTGCTGATGAAATACCTGGGCAATGCCACCGCCATCTTCTTCCTGCCTGATGAGGGGAAACTACAGCACC
TGGAAAATGAACTCACCCACGATATCATCACCAAGTTCCTGGAAAATGAAGACAGAAGGTCTGCCAGCTT
ACATTTACCCAAACTGTCCATTACTGGAACCTATGATCTGAAGAGCGTCCTGGGTCAACTGGGCATCACT
AAGGTCTTCAGCAATGGGGCTGACCTCTCCGGGGTCACAGAGGAGGCACCCCTGAAGCTCTCCAAGGCCG
TGCATAAGGCTGTGCTGACCATCGACGAGAAAGGGACTGAAGCTGCTGGGGCCATGTTTTTAGAGGCCAT
ACCCATGTCTATCCCCCCGAGGTCAAGTTCAACAAACCCTTTGTCTTCTTAATGATTGAACAAAATACC
AAGTCTCCCCTCTTCATGGGAAAAGTGGTGAATCCCACCCAAAAATAACTGCCTCTCGCTCCTCAACCCC
TCCCCTCCATCCCTGGCCCCCTCCCTGGATGACATTAAAGAAGGGTTGAGCTGGTCCCTGCCTGCATGTG
ACTGTAAATCCCTCCCATGTTTTCTCTGAGTCTCCCTTTGCCTGCTGAGGCTGTATGTGGGCTCCAGGTA
ACAGTGCTGTCTTCGGGCCCCCTGAACTGTGTTCATGGAGCATCTGGCTGGGTAGGCACATGCTGGGCTT
GAATCCAGGGGGGACTGAATCCTCAGCTTACGGACCTGGGCCCATCTGTTTCTGGAGGGCTCCAGTCTTC
CTTGTCCTGTCTTGGAGTCCCCAAGAAGGAATCACAGGGGAGGAACCAGATACCAGCCATGACCCCAGGC
TCCACCAAGCATCTTCATGTCCCCCTGCTCATCCCCACTCCCCCCACCCAGAGTTGCTCATCCTGCCA
GGGCTGGCTGTGCCCACCCCAAGGCTGCCCTCCTGGGGCCCCAGAACTGCCTGATCGTGCCGTGGCCCA
GTTTTGTGGCATCTGCAGCAACACAAGAGAGAGGACAATGTCCTCCTCTTGACCCGCTGTCACCTAACCA
GACTCGGGCCCTGCACCTCTCAGGCACTTCTGGAAAATGACTGAGGCAGATTCTTCCTGAAGCCCATTCT
CCATGGGGCAACAAGGACACCTATTCTGTCCTTGTCCTTCCATCGCTGCCCCAGAAAGCCTCACATATCT
CCGTTTAGAATCAGGTCCCTTTCTCCCAGATGAAGAGGAGGGTCTCTGCTTTGTTTTCTCTATCTCCTCC
TCAGACTTGACCAGGCCCAGCAGGCCCCAGAAGACCATTACCCTATATCCCTTCTCCTCCCTAGTCACAT
GGCCATAGGCCTGCTGATGGCTCAGGAAGGCCATTGCAAGGACTCCTCAGCTATGGGAGACGAAGCACAT
CACCCATTGACCCCCGCAACCCCTCCCTTTCCTCCTCTGAGTCCCGACTGGGGCCACATGCAGCCTGACT
TCTTTGTGCCTGTTGCTGTCCCTGCAGTCTTCAGAGGGCCACGGCAGCTCCAGTGCCACGGCAGGAGGCT
GTTCCTGAATAGCCCTGTGGTAAGGGCCAGGAGAGTCCTTCCATCCTCCAAGGCCCTGCTAAAGGACAC
AGCAGCCAGGAAGTCCCTGGGCCCCTAGCTGAAGGACAGCCTGCTCCCTCCGTCTCTACCAGGAATGGC
CTTGTCCTATGGAAGGCACTGCCCCATCCCAAACTAATCTAGGAATCACTGTCTAACCACTCACTGTCAT
GAATGTGTACTTAAAGGATGAGGTTGAGTCATACCAAATAGTGATTTCGATAGTTCAAAATGGTGAAATT
AGCAATTCTACATGATTCAGTCTAATCAATGGATACCGACTGTTTCCCACACAAGTCTCCTGTTCTCTTA
AGCTTACTCACTGACAGCCTTTCACTCTCCACAAATACATTAAAGATATGGCCATCACCAAGCCCCCTAG
GATGACACCAGACCTGAGAGTCTGAAGACCTGGATCCAAGTTCTGACTTTTCCCCCTGACAGCTGTGTGA
CCTTCGTGAAGTCGCCAAACCCTCTCTGAGCCCCAGTCATTGCTAGTAAGACCTGCCTTTGAGTTGGTATG
ATGTTCAAGTTAGATAACAAAATGTTTATACCCATTAGAACAGAGAATAAATAGAACTACATTTCTTGCA
```

Figure 8A

SEQ ID NO:2
>gi|189163525|ref|NM_001002235.2| Homo sapiens serpin peptidase inhibitor,
clade A (alpha-1 antiproteinase, antitrypsin), member 1 (SERPINA1),
transcript variant 3, mRNA
TGGGCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCGAGGAAGCCCTAGCCGCTGCTGCTGCCAGGAATTCCAGG
TTGGAGGGGCGGCAACCTCCTGCCAGCCTTCAGGCCACTCTCCTGTGCCTGCCAGAAGAGACAGAGCTTG
AGGAGAGCTTGAGGAGAGCAGGAAAGGACAATGCCGTCTTCTGTCTCGTGGGCATCCTCCTGCTGGCAG
GCCTGTGCTGCCTGGTCCCTGTCTCCCTGGCTGAGGATCCCCAGGGAGATGCTGCCCAGAAGACACATAC
ATCCCACCATGATCAGGATCACCCAACCTTCAACAAGATCACCCCCAACCTGGCTGAGTTCGCCTTCAGC
CTATACCGCCAGCTGGCACACCAGTCCAACAGCACCAATATCTTCTTCTCCCCAGTGAGCATCGCTACAG
CCTTTGCAATGCTCTCCCTGGGGACCAAGGCTGACACTCACGATGAAATCCTGGAGGGCCTGAATTTCAA
CCTCACGGAGATTCCGGAGGCTCAGATCCATGAAGGCTTCCAGGAACTCCTCCGTACCCTCAACCAGCCA
GACAGCCAGCTCCAGCTGACCACCGGCAATGGCCTGTTCCTCAGCGAGGGCCTGAAGCTAGTGGATAAGT
TTTTGGAGGATGTTAAAAAGTTGTACCACTCAGAAGCCTTCACTGTCAACTTCGGGGACACCGAAGAGGC
CAAGAAACAGATCAACGATTACGTGGAGAAGGGTACTCAAGGGAAAATTGTGGATTTGGTCAAGGAGCTT
GACAGAGACACAGTTTTTGCTCTGGTGAATTACATCTTCTTTAAAGGCAAATGGGAGAGACCCTTTGAAG
TCAAGGACACCGAGGAAGAGGACTTCCACGTGGACCAGGTGACCACCGTGAAGGTGCCTATGATGAAGCG
TTTAGGCATGTTTAACATCCAGCACTGTAAGAAGCTGTCCAGCTGGGTGCTGCTGATGAAATACCTGGGC
AATGCCACCGCCATCTTCTTCCTGCCTGATGAGGGGAAACTACAGCACCTGGAAAATGAACTCACCCACG
ATATCATCACCAAGTTCCTGGAAAATGAAGACAGAAGGTCTGCCAGCTTACATTTACCCAAACTGTCCAT
TACTGGAACCTATGATCTGAAGAGCGTCCTGGGTCAACTGGGCATCACTAAGGTCTTCAGCAATGGGGCT
GACCTCTCCGGGGTCACAGAGGAGGCACCCCTGAAGCTCTCCAAGGCCGTGCATAAGGCTGTGCTGACCA
TCGACGAGAAAGGGACTGAAGCTGCTGGGGCCATGTTTTTAGAGGCCATACCCATGTCTATCCCCCCCGA
GGTCAAGTTCAACAAACCCTTTGTCTTCTTAATGATTGAACAAAATACCAAGTCTCCCCTCTTCATGGGA
AAAGTGGTGAATCCCACCCAAAAATAACTGCCTCTCGCTCCTCAACCCCTCCCCTCCATCCCTGGCCCCC
TCCCTGGATGACATTAAAGAAGGGTTGAGCTGGTCCCTGCCTGCATGTGACTGTAAATCCCTCCCATGTT
TTCTCTGAGTCTCCCTTTGCCTGCTGAGGCTGTATGTGGGCTCCAGGTAACAGTGCTGTCTTCGGGCCCC
CTGAACTGTGTTCATGGAGCATCTGGCTGGGTAGGCACATGCTGGGCTTGAATCCAGGGGGGACTGAATC
CTCAGCTTACGGACCTGGGCCCATCTGTTTCTGGAGGGCTCCAGTCTTCCTTGTCCTGTCTTGGAGTCCC
CAAGAAGGAATCACAGGGGAGGAACCAGATACCAGCCATGACCCCAGGCTCCACCAAGCATCTTCATGTC
CCCCTGCTCATCCCCCACTCCCCCCCACCCAGAGTTGCTCATCCTGCCAGGGCTGGCTGTGCCCACCCCA
AGGCTGCCCTCCTGGGGGCCCAGAACTGCCTGATCGTGCCGTGGCCCAGTTTTGTGGCATCTGCAGCAA
CACAAGAGAGAGGACAATGTCCTCCTCTTGACCCGCTGTCACCTAACCAGACTCGGGCCCTGCACCTCTC
AGGCACTTCTGGAAAATGACTGAGGCAGATTCTTCCTGAAGCCCATTCTCCATGGGCAACAAGGACACC
TATTCTGTCCTTGTCCTTCCATCGCTGCCCCAGAAAGCCTCACATATCTCCGTTTAGAATCAGGTCCCTT
CTCCCCAGATGAAGAGGAGGGTCTCTGCTTTGTTTTCTCATCTCCTCCTCAGACTTGACCAGGCCCAGC
AGGCCCCAGAAGACCATTACCCTATATCCCTTCTCCTCCCTAGTCACATGGCCATAGGCCTGCTGATGGC
TCAGCAAGGCCATTGCAAGGACTCCTCAGCTATGGGAGAGGAAGCACATCACCCATTGACCCCGCAACC
CCTCCCTTTCCTCCTCTGAGTCCCGACTGGGCCACATGCAGCCTGACTTCTTTGTGCCTGTTGCTGTCC
CTGCAGTCTTCAGAGGGCCACCGCAGCTCCAGTGCCACGGCAGGAGGCTGTTCCTGAATAGCCCTGTGG
TAAGGGCCAGGAGAGTCCTTCCATCCTCCAAGGCCCTGCTAAAGGACACAGCAGCCAGGAAGTCCCCTGG
GCCCCTAGCTGAAGGACAGCCTGCTCCCTCCGTCTCTACCAGGAATGGCCTTGTCCTATGGAAGGCACTG
CCCCATCCCAAACTAATCTAGGAATCACTGTCTAACCACTCACTGTCATGAATGTGTACTTAAAGGATGA
GGTTGAGTCATACCAAATAGTGATTTCGATAGTTCAAAATGGTGAAATTAGCAATTCTACATGATTCAGT
CTAATCAATGGATACCGACTGTTTCCCACACAAGTCTCCTGTTCTCTTAAGCTTACTCACTGACAGCCTT
TCACTCTCCACAAATACATTAAAGATATGGCCATCACCAAGCCCCTAGGATGACACCAGACCTGAGAGT
CTCAAGACCTGGATCCAAGTTCTGACTTTTCCCCCTGACAGCTGTGTGACCTTCGTGAAGTCGCCAAACC
TCTCTGAGCCCCAGTCATTGCTAGTAAGACCTGCCTTTGAGTTGGTATGATGTTCAAGTTAGATAACAAA
ATGTTTATACCCATTAGAACAGAGAATAAATAGAACTACATTTCTTGCA

Figure 8B

SEQ ID NO:3
>gi|189163526|ref|NM_001002236.2| Homo sapiens serpin peptidase inhibitor,
clade A (alpha-1 antiproteinase, antitrypsin), member 1 (SERPINA1),
transcript variant 2, mRNA

```
TGGGCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCGAGGAAGGCCTAGCCGCTGCTGCTGCCAGGAATTCCAGG
TTGGAGGGGCGGCAACCTCCTGCCAGCCTTCAGGCCACTCTCCTGTGCCTGCCAGAAGAGACAGAGCTTG
AGGAGAGCTTGAGGAGAGCAGGAAAGGGCGGCAGTAAGTCTTCAGCATCAGGCATTTTGGGGTGACTCAG
TAAATGGTAGATCTTGCTACCAGTGGAACAGCCACTAAGGATTCTGCAGTGAGAGCAGAGGGCCAGCTAA
GTGGTACTCTCCAGAGACTGTCTGACTCACGCCACCCCTCCACCTTGGACACAGGACGCTGTGGTTTC
TGAGCCAGGTACAATGACTCCTTTCGCAGCCTCCCCCGTTGCCCCTCTGGATCCACTGCTTAAATACGGA
CGAGGACAGGGCCCTGTCTCCTCAGCTTCAGGCACCACCACTGACCTGGGACAGTGAATCGACAATGCCG
TCTTCTGTCTCGTGGGGCATCCTCCTGCTGGCAGGCCTGTCTGCCTGGTCCCTGTCTCCCTGGCTGAGG
ATCCCCAGGGAGATGCTGCCCAGAAGACAGATACATCCCACCATGATCAGGATCACCCAACCTTCAACAA
GATCACCCCCAACCTGGCTGAGTTCGCCTTCAGCCTATACCGCCAGCTGGCACACCAGTCCAACAGCACC
AATATCTTCTTCTCCCCAGTGAGCATCGCTACAGCCTTTGCAATGCTCTCCCTGGGGACCAAGGCTGACA
CTCACGATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAATGGCCTG
TTCCTCAGCGAGGGCCTGAAGCTAGTGGATAAGTTTTTGGAGGATGTTAAAAAGTTGTACCACTCAGAAG
CCTTCACTGTCAACTTCGGGGACACCGAAGAGGCCAAGAAACAGATCAACGATTACGTGGAGAAGGGTAC
TCAAGGGAAAATTGTGGATTTGGTCAAGGAGCTTGACAGAGACACAGTTTTTGCTCTGGTGAATTACATC
TTCTTTAAAGGCAAATGGGAGAGACCCTTTGAAGTCAAGGACACCGAGGAAGAGGACTTCCACGTGGACC
AGGTGACCACCGTGAAGGTGCCTATGATGAAGCGTTTAGGCATGTTTAACATCCAGCACTGTAAGAAGCT
GTCCAGCTGGGTGCTGCTGATGAAATACCTGGGCAATGCCACCGCCATCTTCTTCCTGCCTGATGAGGGG
AAACTACAGCACCTGGAAAATGAACTCACCCACGATATCATCACCAAGTTCCTGGAAAATGAAGACAGAA
GGTCTGCCAGCTTACATTTACCCAAACTGTCCATTACTGGAACCTATGATCTGAAGAGCGTCCTGGGTCA
ACTGGGCATCACTAAGGTCTTCAGCAATGGGGCTGACCTCTCCGGGGTCACAGAGGAGGCACCCCTGAAG
CTCTCCAAGGCCGTGCATAAGGCTGTGCTGACCATCGACGAGAAAGGGACTGAAGCTGCTGGGGCCATGT
TTTTAGAGGCCATACCCATGTCTATCCCCCCCGAGGTCAAGTTCAACAAACCCTTTGTCTTCTTAATGAT
TGAACAAAATACCAAGTCTCCCCTCTTCATGGGAAAAGTGGTGAATCCCACCCAAAAATAACTGCCTCTC
GCTCCTCAACCCCTCCCCTCCATCCCTGGCCCCCTCCCTGGATGACATTAAAGAAGGGTTGAGCTGGTCC
CTGCCTGCATGTGACTGTAAATCCCTCCCATGTTTTCTCTGAGTCTCCCTTTGCCTGCTGAGGCTGTATG
TGGGCTCCAGGTAACAGTGCTGTCTTCGGGCCCCCTGAACTGTGTTCATGGAGCATCTGGCTGGGTAGGC
ACATGCTGGGCTTGAATCCAGGGGGGACTGAATCCTCAGCTTACGGACCTGGGCCCATCTGTTTCTGGAG
GGCTCCAGTCTTCCTTGTCCTGTCTTGGAGTCCCCAAGAAGGAATCACAGGGGAGGAACCAGATACCAGC
CATGACCCCAGGCTCCACCAAGCATCTTCATGTCCCCCTGCTCATCCCCCACTCCCCCCCACCCAGAGTT
GCTCATCCTGCCAGGGCTGGCTGTGCCCACCCAAGGCTGCCCTCCTGGGGGCCCCAGAACTGCCTGATC
GTGCCGTGGCCCAGTTTTGTGGCATCTGCAGCAACACAAGAGAGAGGACAATGTCCTCCTCTTGACCCGC
TGTCACCTAACCAGACTCGGGCCCTGCACCTCTCAGGCACTTCTGGAAAATGACTGAGGCAGATTCTTCC
TGAAGCCCATTCTCCATGGGCAACAAGGACACCTATTCTGTCCTTGTCCTTCCATCGCTGCCCCAGAAA
GCCTCACATATCTCCGTTTAGAATCAGGTCCCTTCTCCCAGATGAAGAGGAGGGTCTCTGCTTTGTTTTT
CTCTATCTCCTCCTCAGACTTGACCAGGCCCAGCAGGCCCCAGAAGACCATTACCCTATATCCCTTCTCC
TCCCTAGTCACATGGCCATAGGCCTGCTGATGGCTCAGGAAGGCCATTGCAAGGACTCCTCAGCTATGGG
AGAGGAAGCACATCACCCATTGACCCCCGCAACCCCTCCCTTTCCTCCTCTGAGTCCGACTGGGGCCAC
ATGCAGCCTGACTTCTTTGTGCCTGTTGCTGTCCCTGCAGTCTTCAGAGGGCCACCGCAGCTCCAGTGCC
ACGGCAGGAGGCTGTTCCTGAATAGCCCTGTGGTAAGGGCCAGGAGAGTCCTTCCATCCTCCAAGGCCC
TGCTAAAGGACACAGCAGCCAGGAAGTCCCCTGGGCCCCTAGCTGAAGGACAGCCTGCTCCCTCCGTCTC
TACCAGGAATGGCCTTGTCCTATGGAAGGCACTGCCCCATCCCAAACTAATCTAGGAATCACTGTCTAAC
CACTCACTGTCATGAATGTGTACTTAAAGGATGAGGTTGAGTCATACCAAATAGTGATTTCGATAGTTCA
AAATGGTGAAATTAGCAATTCTACATGATTCAGTCTAATCAATGGATACCGACTGTTTCCCACACAAGTC
TCCTGTTCTCTTAAGCTTACTCACTGACAGCCTTTCACTCTCCACAAATACATTAAACATATGGCCATCA
CCAAGCCCCTAGGATGACACCAGACCTGAGAGTCTGAAGACCTGGATCCAAGTTCTGACTTTTCCCCCT
GACAGCTGTGTGACCTTCGTGAAGTCGCCAAACCTCTCTGAGCCCAGTCATTGCTAGTAAGACCTGCCT
TTGAGTTGGTATGATGTTCAACTTAGATAACAAAATGTTTATACCCATTAGAACAGAGAATAAATAGAAC
TACATTTCTTGCA
```

Figure 8C

SEQ ID NO:4
>gi|189163527|ref|NM_001127700.1| Homo sapiens serpin peptidase inhibitor,
clade A (alpha-1 antiproteinase, antitrypsin), member 1 (SERPINA1),
transcript variant 4, mRNA
TGGGCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCAGGAAGGCCTAGCCGCTGCTGCTGCCAGGAATTCCAGG
TTGGAGGGGCGGCAACCTCCTGCCAGCCTTCAGGCCACTCTCCTGTGCCTGCCAGAAGAGACAGAGCTTG
AGGAGAGCTTGAGGAGAGCAGGAAAGGTGGGACATTGCTGCTGCTGTCACTCAGTTCCACAGGACAATG
CCGTCTTCTGTCTCGTGGGGCATCCTCCTGCTGGCAGGCCTGTGCTGCCTGGTCCCTGTCTCCCTGGCTG
AGGATCCCCAGGGAGATGCTGCCCAGAAGACAGATACATCCCACCATGATCAGGATCACCCAACCTTCAA
CAAGATCACCCCCAACCTGGCTGAGTTCGCCTTCAGCCTATACCGCCAGCTGGCACACCAGTCCAACAGC
ACCAATATCTTCTTCTCCCCAGTGAGCATCGCTACAGCCTTTGCAATGCTCTCCCTGGGGACCAAGGCTG
ACACTCACGATGAAATCCTGGAGGGCCTGAATTTCAACCTCACGGAGATTCCGGAGGCTCAGATCCATGA
AGGCTTCCAGGAACTCCTCCGTACCCTCAACCAGCCAGACAGCCAGCTCCAGCTGACCACCGGCAATGGC
CTGTTCCTCAGCGAGGGCCTGAAGCTAGTGGATAAGTTTTTGGAGGATGTTAAAAAGTTGTACCACTCAG
AAGCCTTCACTGTCAACTTCGGGGACACCGAAGAGGCCAAGAAACAGATCAACGATTACGTGGAGAAGGG
TACTCAAGGGAAAATTGTGGATTTGGTCAAGGAGCTTGACAGAGACACAGTTTTTGCTCTGGTGAATTAC
ATCTTCTTTAAAGGCAAATGGGAGAGACCCTTTGAAGTCAAGGACACCGAGGAAGAGGACTTCCACGTGG
ACCAGGTGACCACCGTGAAGGTGCCTATGATGAAGCGTTTAGGCATGTTTAACATCCAGCACTGTAAGAA
GCTGTCCAGCTGGGTGCTGCTGATGAAATACCTGGGCAATGCCACCGCCATCTTCTTCCTGCCTGATGAG
GGGAAACTACAGCACCTGGAAAATGAACTCACCCACGATATCATCACCAAGTTCCTGGAAAATGAAGACA
GAAGGTCTGCCAGCTTACATTTACCCAAACTGTCCATTACTGGAACCTATGATCTGAAGAGCGTCCTGGG
TCAACTGGGCATCACTAAGGTCTTCAGCAATGGGGCTGACCTCTCCGGGGTCACAGAGGAGGCACCCCTG
AAGCTCTCCAAGGCCGTGCATAAGGCTGTGCTGACCATCGACGAGAAAGGGACTGAAGCTGCTGGGGCCA
TGTTTTTAGAGGCCATACCCATGTCTATCCCCCCGAGGTCAAGTTCAACAAACCCTTTGTCTTCTTAAT
GATTGAACAAAATACCAAGTCTCCCCTCTTCATGGGAAAAGTGGTGAATCCCACCCAAAAATAACTGCCT
CTCGCTCCTCAACCCCTCCCCTCCATCCCTGGCCCCCTCCCTGGATGACATTAAAGAAGGGTTGAGCTGG
TCCCTGCCTGCATGTGACTGTAAATCCCTCCCATGTTTTCTCTGAGTCTCCCTTTGCCTGCTGAGGCTGT
AGTGGGCTCCAGGTAACAGTGCTGTCTTCGGGCCCCCTGAACTGTGTTCATGGAGCATCTGGCTGGGTA
GGCACATGCTGGGCTTGAATCCAGGGGGACTGAATCCTCAGCTTACGGACCTGGGCCCATCTGTTTCTG
GAGGGCTCCAGTCTTCCTTGTCCTGTCTTGGAGTCCCCAAGAAGGAATCACAGGGGAGGAACCACAATACC
AGCCATGACCCCAGGCTCCACCAAGCATCTTCATGTCCCCCTGCTCATCCCCCACTCCCCCCCACCCAGA
GTTGCTCATCCTGCCAGGGCTGGCTGTGCCCACCCCAAGGCTGCCCTCCTGGGGGCCCCAGAACTGCCTG
ATCGTGCCGTGGCCCAGTTTTGTGGCATCTGCAGCAACACAAGAGAGAGGACAATGTCCTCCTCTTGACC
CGCTGTCACCTAACCAGACTCGGGGCCTGCACCTCTCAGGCACTTCTGGAAAATGACTGAGGCAGATTCT
TCCTGAAGCCCATTCTCCATGGGGCAACAAGGACACCTATTCTGTCCTTGTCCTTCCATCGCTGCCCCAG
AAAGCCTCACATATCTCCGTTTAGAATCAGGTCCCTTCTCCCAGATGAAGAGGAGGGTCTCGCTTTGT
TTTCTCTATCTCCTCCTCAGACTTGACCAGGCCCAGCAGGCCCAGAAGACCATTACCCTATATCCCTTC
TCCTCCCTAGTCACATGGCCATAGGCCTGCTGATGGCTCAGGAAGGCCATTGCAAGGACTCCTCAGCTAT
GGGAGAGGAAGCACATCACCCATTGACCCCCGCAACCCCTCCCTTTCCTCCTCTGAGTCCGACTGGGGC
CACATGCAGCCTGACTTCTTTGTGCCTGTTGCTGTCCCTGCAGTCTTCAGAGGGCCACCGCAGCTCCAGT
GCCACGGCAGGAGGCTGTTCCTGAATAGCCCCTGTGGTAAGGGCCAGGAGAGTCCTTCCATCCTCCAAGG
CCCTGCTAAAGGACACAGCAGCCAGGAAGTCCCCTGGGCCCTAGCTGAAGGACAGCCTGCTCCCTCCGT
CTCTACCAGGAATGGCCTTGTCCTATGGAAGGCACTGCCCCATCCCAAACTAATCTAGGAATCACTGTCT
AACCACTCACTGTCATGAATGTGTACTTAAAGGATGAGGTTGAGTCATACCAAATAGTGATTTCGATAGT
TCAAAATGGTGAAATTAGCAATTCTACATCATTCAGTCTAATCAATGGATACCGACTGTTTCCCACACAA
GTCTCCTGTTCTCTTAAGCTTACTCACTGACAGCCTTTCACTCTCCACAAATACATTAAAGATATGGCCA
TCACCAAGCCCCCTAGGATGACACCAGACCTGAGAGTCTGAAGACCTGGATCCAAGTTCTGACTTTTCCC
CCTGACAGCTGTGTGACCTTCGTCAAGTCGCCAAACCTCTCTGAGCCCCAGTCATTGCTAGTAAGACCTG
CCTTTCAGTTGGTATGATGTTCAAGTTAGATAACAAAATGTTTATACCCATTAGAACAGACAATAAATAG
AACTACATTTCTTGCA

Figure 8D

SEQ ID NO:5
>gi|189163529|ref|NM_001127701.1| Homo sapiens serpin peptidase inhibitor, clade A (alpha-1 antiproteinase, antitrypsin), member 1 (SERPINA1), transcript variant 5, mRNA
TGGGCAGGAACTGGGCACTGTGCCCAGGGCATGCACTGCCTCCACGCAGCAACCCTCAGAGTCCTGAGCT
GAACCAAGAAGGAGGAGCCGGTCGGGCCTCCGAGGAAGGCCTAGCCGCTGCTGCTGCCAGGAATTCCACG
TTGGAGGGGCGGCAACCTCCTGCCAGCCTTCAGGCCACTCTCCTGTGCCTGCCAGAAGAGACAGAGCTTG
AGCAGAGCTTGAGGAGAGCAGGAAAGGTGGGACATTGCTGCTGCTGCTCACTCAGTTCCACAGGGCGGCA
GTAAGTCTTCAGCATCAGGCATTTTGGGGTGACTCAGTAAATGGTAGATCTTGCTACCAGTGGAACAGCC
ACTAAGGATTCTGCAGTGAGAGCAGAGGGCCAGCTAAGTGGTACTCTCCCAGAGACTGTCTGACTCACGC
CACCCCCTCCACCTTGGACACAGGACGCTGTGGTTCTGAGCCAGCAGCCTCCCCCGTTGCCCCTCTGGA
TCCACTGCTTAAATACGGACGAGGACAGGGCCCTGTCTCCTCAGCTTCAGGCACCACCACTGACCTGGGA
CAGTGAATCGACAATGCCGTCTTCTGTCTCGTGGGCATCCTCCTGCTGGCAGGCCTGTGCTGCCTGGTC
CCTGTCTCCCTGGCTGAGGATCCCCAGGGAGATGCTGCCCAGAAGACAGATACATCCCACCATGATCAGG
ATCACCCAACCTTCAACAAGATCACCCCCAACCTGGCTGAGTTCGCCTTCAGCCTATACCGCCAGCTGGC
ACACCAGTCCAACAGCACCAATATCTTCTTCTCCCCAGTGAGCATCGCTACAGCCTTTGCAATGCTCTCC
CTGGGGACCAAGGCTGACACTCACGATGAAATCCTGGAGGGCCTGAATTTCAACCTCACGGAGATTCCGG
AGGCTCAGATCCATGAAGGCTTCCAGGAACTCCTCCGTACCCTCAACCAGCCAGACAGCCAGCTCCAGCT
GACCACCGGCAATGGCCTGTTCCTCAGCGAGGGCCTGAAGCTAGTGGATAAGTTTTTGGAGGATGTTAAA
AAGTTGTACCACTCAGAAGCCTTCACTGTCAACTTCGGGGACACCGAAGAGGCCAAGAAACAGATCAACG
ATTACGTGGAGAAGGGTACTCAAGGCAAAATTGTGGATTTGGTCAAGGAGCTTGACAGAGACACAGTTTT
TGCTCTGGTGAATTACATCTTCTTTAAAGGCAAATGGGAGAGACCCTTTGAAGTCAAGGACACCGAGGAA
GAGGACTTCCACGTGGACCAGGTGACCACCGTGAAGGTGCCTATGATGAAGCGTTTAGGCATGTTTAACA
TCCAGCACTGTAAGAAGCTGTCCAGCTGGGTGCTGCTGATGAAATACCTGGGCAATGCCACCGCCATCTT
CTTCCTGCCTGATGAGGGGAAACTACAGCACCTGGAAAATGAACTCACCCACGATATCATCACCAAGTTC
CTGGAAAATGAAGACAGAAGGTCTGCCAGCTTACATTTACCCAAACTGTCCATTACTGGAACCTATGATC
TGAAGAGCGTCCTGGGTCAACTGGGCATCACTAAGGTCTTCAGCAATGGGGCTGACCTCTCCGGGGTCAC
AGAGGAGGCACCCCTGAAGCTCTCCAAGGCCGTGCATAAGGCTGTGCTGACCATCGACGAGAAAGGGACT
GAAGCTGCTGGGGCCATGTTTTTAGAGGCCATACCCATGTCTATCCCCCCCGAGGTCAAGTTCAACAAAC
CCTTTGTCTTCTTAATGATTGAACAAAATACCAAGTCTCCCCTCTTCATGGGAAAAGTGGTGAATCCCAC
CCAAAAATAACTGCCTCTCGCTCCTCAAGCCCCTCCCCTCCATCCCTGGCCCCCTCCCTGGATGACATTAA
AGAAGGGTTGAGCTGGTCCCTGCCTGCATGTGACTGTAAATCCCTCCCATGTTTTCTCTGAGTCTCCCTT
TGCCTGCTGAGGCTGTATGTGGGCTCCAGCTAACAGTGCTGTCTTCGGGCCCCCTGAACTGTGTTCATGG
AGCATCTGGCTGGGTAGGCACATGCTGGGCTTGAATCCAGGGGGGACTGAATCCTCAGCTTACGGACCTG
GGCCCATCTGTCTCTGGAGGGCTCCAGTCTTCCTTGTCCTGTCTTGGAGTCCCCAAGAAGGAATCACAGG
GGAGGAACCAGATACCAGCCATGACCCCAGGCTCCACCAAGCATCTTCATGTCCCCCTGCTCATCCCCCA
CTCCCCCCACCCAGAGTTGCTCATCCTGCCAGGGCTGGCTGTGCCCACCCCAAGGCTGCCCTCCTGGGG
GCCCAGAACTGCCTGATCGTGCCGTGGCCCAGTTTTGTGGCATCTGCAGCAACACAAGAGAGGACAA
TGTCCTCCTCTTGACCCGCTGTCACCTAACCAGACTCGGGCCCTGCACCTCTCAGGCACTTCTGGAAAAT
GACTGAGGCAGATTCTTCCTGAAGCCCATTCTCCATGGGGCAACAAGGACACCTATTCTGTCCTTGTCCT
TCCATCGCTGCCCCAGAAAGCCTCACATATCTCCGTTTAGAATCAGGTCCCTTCTCCCCAGATGAAGAGG
AGGGTCTCTGCTTTGTTTCTCTATCTCCTCCTCAGACTTGACCAGGCCCAGCAGGCCCCAGAAGACCAT
TACCCTATATCCTTCTCCTCCCTAGTCACATGGCCATAGGCCTGCTGATGGCTCAGGAAGGCCATTGCA
AGGACTCCTCAGCTATGGGAGAGGAAGCACATCACCCATTGACCCCCGCAACCCCTCCCTTTCCTCCTCT
GAGTCCCGACTGGGCCACATGCAGCCTGACTTCTTTGTGCCTGTTGCTGTCCCTGCAGTCTTCAGAGGG
CCACCGCAGCTCCAGTGCCACGGCAGGAGGCTGTTCCTGAATAGCCCCTGTGGTAAGGGCCAGGAGAGTC
CTTCCATCCTCCAAGGCCCTGCTAAAGGACACAGCAGCCAGGAAGTCCCTGGGCCCCTAGCTGAAGGAC
AGCCTGCTCCCTCGTCTCTACCAGGAATGGCCTTGTCCTATGGAAGGCACTGCCCCATCCCAAACTAAT
CTAGGAATCACTGTCTAACCACTCACTGTCATGAATGTGTACTTAAAGGATGAGGTTGAGTCATACCAAA
TAGTGATTTCGATAGTTCAAAATGGTGAAATTAGCAATTCTACATGATTCAGTCTAATCAATGGATACCG
ACTGTTTCCCACACAAGTCTCCTGTTCTCTTAAGCTTACTCACTGACAGCCTTTCACTCTCCACAAATAC
ATTAAACATATGGCCATCACCAAGCCCCTAGGATGACACCAGACCTGAGAGTCTGAAGACCTGGATCCA
AGTTCTGACTTTTCCCCCTGACAGCTGTGTGACCTTCGTGAAGTCGCCAAACCTCTCTGAGCCCAGTCA
TTGCTAGTAAGACCTGCCTTTGAGTTGGTATGATGTTCAAGTTAGATAACAAAATGTTTATACCCATTAG
AACAGACAATAAATAGAACTACATTTCTTGCA

Figure 8E

SEQ ID NO:6
>gi|189163831|ref|NM_001127702.1| Homo sapiens serpin peptidase inhibitor,
clade A (alpha-1 antiproteinase, antitrypsin), member 1 (SERPINA1),
transcript variant 6, mRNA
TGGGCAGGAACTGGGCACTGTGCCCAGGGCATGCACTGCCTCCACGCAGCAACCTCAGAGTCCTGAGCT
GAACCAAGAAGCAGGAGGGGGTCGGGCCTCCGAGGAAGGCCTAGCCGCTGCTGCTGCCAGGAATTCCACG
TTGGAGGGGCGGCAACCTCCTGCCAGCCTTCAGGCCACTCTCCTGTGCCTGCCAGAAGAGACAGACCTTG
AGCAGAGCTTGAGGAGAGCAGGAAAGGTGGACATTGCTGCTGCTCACTCAGTTCCACAGCAGCCTC
CCCCGTTGCCCCTCTGGATCCACTGCTTAAATACGGACGAGGACAGGGCCTGCTCCTCAGCTTCAGGC
ACCACCACTGACCTGGGACAGTGAATCGACAATGCCGTCTTCTGTCTCGTGGGCATCCTCCTGCTGGCA
GGCCTGTGCTGCCTGGTCCCTGTCTCCCTGGCTGAGGATCCCCAGGGAGATGCTGCCCAGAAGACAGATA
CATCCCACCATGATCAGGATCACCCAACCTTCAACAAGATCACCCCCAACCTGCTGAGTTCGCCTTCAG
CCTATACCGCCAGCTGGCACACCAGTCCAACAGCACCAATATCTTCTTCTCCCAGTGAGCATCGCTACA
GCCTTTGCAATGCTCTCCCTGGGGACCAAGGCTGACACTCACGATGAAATCCTGGAGGGCCTGAATTTCA
ACCTCACGGAGATTCCGGAGGCTCAGATCCATGAAGGCTTCCAGGAACTCCTCCGTACCCTCAACCAGCC
AGACAGCCAGCTCCAGCTGACCACCGGCAATGGCCTGTTCCTCAGCGAGGGCCTGAAGCTAGTGGATAAG
TTTTTGGAGGATGTTAAAAAGTTGTACCACTCAGAAGCCTTCACTGTCAACTTCGGGGACACCGAAGAGG
CCAAGAAACAGATCAACGATTACGTGGAGAAGGGTACTCAAGGGAAAATTGTGGATTTGGTCAAGGAGCT
TGACAGAGACACAGTTTTTGCCCTGGTGAATTACATCTTCTTTAAAGGCAAATGGGAGAGACCCTTTGAA
GTCAAGGACACCGAGGAAGAGGCACTTCCACGTGGACCAGGTGACCACCGTGAAGGTGCCTATGATGAAGC
GTTTAGGCATGTTTAACATCCAGCACTGTAAGAAGCTGTCCAGCTGGGTGCTGCTGATGAAATACCTGGG
CAATGCCACCGCCATCTTCTTCCTGCCTGATGAGGGGAAACTACAGCACCTGGAAAATGAACTCACCCAC
GATATCATCACCAAGTTCCTGGAAAATGAAGACAGAAGGTCTGCCAGCTTACATTTACCCAAACTGTCCA
TTACTGGAACCTATGATCTGAAGAGCGTCCTGGGTCAACTGGGCATCACTAAGGTCTTCAGCAATGGGGC
TGACCTCTCCGGGGTCACAGAGGAGGCACCCCTGAAGCTCTCCAAGGCCGTGCATAAGGCTGTGCTGACC
ATCGACGAGAAAGGGACTGAAGCTGCTGGGGCCATGTTTTTAGAGGCCATACCCATGTCTATCCCCCCCG
AGGTCAAGTTCAACAAACCCTTTGTCTTCTTAATGATTGAACAAAATACCAAGTCTCCCCTCTTCATGGG
AAAAGTGGTGAATCCCACCCAAAAATAACTGCCTCTCGCTCCTCAACCCCTCCCCTCCATCCCTGGCCCC
CTCCCTGGATGACATTAAAGAAGGGTTGAGCTGGTCCCTGCCTGCATGTGACTGTAAATCCCTCCCATGT
TTTCTCTGAGTCTCCCTTTGCCTGCTGAGGCTGTATGTGGGCTCCAGGTAACAGTGCTGTCTTCGGGCCC
CCTGAACTGTGTTCATGGAGCATCTGGCTGGGTAGGCACATGCTGGGCTTGAATCCAGGGGGGACTGAAT
CCTCAGCTTACGGACCTGGGCCCATCTGTTTCTGGAGGGCTCCAGTCTTCCTTGTCCTGTCTTGGAGTCC
CCAAGAAGGAATCACAGGGGAGGAACCACATACCAGCCATGACCCCAGGCTCCACCAAGCATCTTCATGT
CCCCCTGCTCATCCCCACTCCCCCCCACCCAGAGTTGCTCATCCTGCCAGGGCTGGCTGTGCCCACCCC
AAGGCTGCCCTCCTGGGGGCCCCAGAACTGCCTGATCGTGCCGTGGCCCAGTTTGTGGCATCTGCAGCA
ACACAAGAGAGGACAATGTCCTCCTCTTGACCCGCTGTCACCTAACCAGACTCGGGCCCTGCACCTCT
CAGGCACTTCTGGAAAATGACTGAGGCAGATTCTTCCTGAAGCCCATTCTCCATGGGGCAACAAGGACAC
CTATTCTGTCCTTGTCCTTCCATCGCTGCCCCAGAAAGCCTCACATATCTCCGTTAGAATCAGGTCCCT
TCTCCCCAGATGAAGAGGAGGGTCTCTGCTTTGTTTTCTCTATCTCCTCCTCAGACTTGACCAGGCCCAG
CAGGCCCCAGAAGACCATTACCCTATATCCCTTCTCCTCCCTAGTCACATGGCCATAGGCCTGCTGATGG
CTCAGGAAGGCCATTGCAAGGACTCCTCAGCTATGGGAGAGGAAGCACATCACCCATTGACCCCCGCAAC
CCCTCCCTTTCCTCCTCTGAGTCCCGACTGGGGCCACATGCAGCCTGACTTCTTTGTGCCTGTTGCTGTC
CCTGCAGTCTTCAGAGGGCCACCGCAGCTCCAGTGCCACGGCAGGAGGCTGTTCCTGAATAGCCCCTGTG
GTAAGGGCCAGGAGAGTCCTTCCATCCTCCAAGGCCCTGCTAAAGGACACAGCAGCCAGGAAGTCCCCTG
GCCCCTAGCTGAAGGACAGCCTGCTCCCTCCGTCTCTACCAGGAATGGCCTTGTCCTATGGAAGGCACT
GCCCCATCCCAAACTAATCTAGGAATCACTGTCTAACCACTCACTGTCATGAATGTGTACTTAAAGGATG
AGGTTGAGTCATACCAAATAGTGATTTCGATAGTTCAAAATGGTGAAATTAGCAATTCTACATGATTCAG
TCTAATCAATGGATACCGACTGTTTCCCACACAAGTCTCCTGTTCTCTTAAGCTTACTCACTGACAGCCT
TTCACTCTCCACAAATACATTAAAGATATGGCCATCACCAAGCCCCCTAGGATGACACCAGACCTGAGAG
TCTGAAGACCTGGATCCAAGTTCTGACTTTTCCCCCTGACAGCTGTGTGACCTTCGTGAAGTCGCCAAAC
CTCTCTGAGCCCCAGTCATTGCTAGTAAGACCTGCTTTGACTTGGTATGATCTTCAAGTTAGATAACAA
AATGTTTATACCCATTAGAACAGAGAATAAATAGAACTACATTTCTTGCA

Figure 8F

SEQ ID NO:7
>gi|189163533|ref|NM_001127703.1| Homo sapiens serpin peptidase inhibitor,
clade A (alpha-1 antiproteinase, antitrypsin), member 1 (SERPINA1),
transcript variant 7, mRNA
TGGCCAGGAACTGGGCACTGTGCCCAGGGCATGCACTGCCTCCACGCAGCAACCCTCAGAGTCCTGAGCT
GAACCAAGAAGGAGGAGGGGTCGGGCCTCCGAGGAAGGCCTAGCCGCTGCTGCTGCCAGGAATTCCAGG
TTGGAGGGGCGGCAACCTCCTGCCAGCCTTCAGCCCACTCTCCTGTGCCTGCCAGAAGAGACAGAGCTTG
AGGAGAGCTTGAGGAGAGCAGGAAAGGGCGGCAGTAAGTCTTCAGCATCAGGCATTTGGGGTGACTCAG
TAAATGGTAGATCTTGCTACCAGTGGAACAGCCACTAAGGATTCTGCAGTGAGAGCAGAGGGCCAGCTAA
GTGGTACTCTCCAGAGACTGTCTGACTCACGCCACCCCTCCACCTTGGACACAGGACGCTGTGGTTTC
TGAGCCAGCAGCCTCCCCCGTTGCCCCTCTGGATCCACTGCTTAAATACGGACGAGGACAGGGCCCTGTC
TCCTCAGCTTCAGGCACCACCACTGACCTGGGACAGTGAATCGACAATGCCGTCTTCTGTCTCGTGGGGC
ATCCTCCTGCTGGCAGGCCTGTGCTGCCTGGTCCCTGTCTCCTGGCTGAGGATCCCCAGGGAGATGCTG
CCCAGAAGACAGATACATCCCACCATGATCAGGATCACCCAACCTTCAACAAGATCACCCCCAACCTGGC
TGAGTTCGCCTTCAGCCTATACCGCCAGCTGGCACACCAGTCCAACAGCACCAATATCTTCTTCTCCCCA
GTGAGCATCGCTACAGCCTTTGCAATGCTCTCCCTGGGGACCAAGGCTGACACTCACGATGAAATCCTGG
AGGGCCTGAATTTCAACCTCACGGAGATTCCGGAGGCTCAGATCCATGAAGGCTTCCAGGAACTCCTCCG
TACCCTCAACCAGCCAGACAGCCAGCTCCAGCTGACCACCGGCAATGGCCTGTTCCTCAGCGAGGGCCTG
AAGCTAGTGGATAAGTTTTTGGAGGATGTTAAAAAGTTGTACCACTCAGAAGCCTTCACTGTCAACTTCG
GGGACACCGAAGAGGCCAAGAAACAGATCAACGATTACGTGGAGAAGGGTACTCAAGGGAAAATTGTGGA
TTTGGTCAAGGAGCTTGACAGAGACACAGTTTTTGCTCTGGTGAATTACATCTTCTTTAAAGGCAAATGG
GAGAGACCCTTTGAAGTCAAGGACACCGAGGAAGAGGACTTCCACGTGGACCAGGTGACCACCGTGAAGG
TGCCTATGATGAAGCGTTTAGGCATGTTTAACATCCAGCACTGTAAGAAGCTGTCCAGCTGGGTGCTGCT
GATGAAATACCTGGGCAATGCCACCGCCATCTTCTTCCTGCCTGATGAGGGGAAACTACAGCACCTGGAA
AATGAACTCACCCACGATATCATCACCAAGTTCCTGGAAAATGAAGACAGAAGGTCTGCCAGCTTACATT
TACCCAAACTGTCCATTACTGGAACCTATGATCTGAAGAGCGTCCTGGGTCAACTGGGCATCACTAAGGT
CTTCAGCAATGGGGCTGACCTCTCCGGGGTCACAGAGGAGGCACCCCTGAAGCTCTCCAAGGCCGTGCAT
AAGGCTGTGCTGACCATCGACGAGAAAGGGACTGAAGCTGCTGGGGCCATGTTTTTAGAGGCCATACCCA
TGTCTATCCCCCCCGAGGTCAAGTTCAACAAACCCTTTGTCTTCTTAATGATTGAACAAAATACCAAGTC
TCCCCTCTTCATGGGAAAAGTGGTGAATCCCACCCAAAAATAACTGCCTCTCGCTCCTCAACCCCTCCCC
TCCATCCCTGGCCCCCTCCCTGGATGACATTAAAGAAGGGTTGAGCTGGTCCCTGCCTGCATGTGACTGT
AAATCCCTCCCATGTTTTCTCTGAGTCTCCCTTTGCCTGCTGAGGCTGTATGTGGGCTCCAGGTAACAGT
GCTGTCTTCGGGCCCCCTGAACTGTGTTCATGGAGCATCTGGCTGGGTAGGCACATGCTGGGCTTGAATC
CAGGGGGGACTGAATCCTCAGCTTACGGACCTGGGCCCATCTGTTTCTGGAGGGCTCCAGTCTTCCTTGT
CCTGTCTTGGAGTCCCCAAGAAGGAATCACAGGGGAGGAACCAGATACCAGCCATGACCCCAGGCTCCAC
CAAGCATCTTCATGTCCCCCTGCTCATCCCCCACTCCCCCCACCCAGAGTTGCTCATCCTGCCAGGGCT
GGCTGTGCCCACCCCAAGGCTGCCCTCCTGGGGGCCCCAGAACTGCCTGATCGTGCCGTGGCCCAGTTTT
GTGGCATCTGCAGCAACACAAGACAGAGGACAATGTCCTCCTCTTGACCCGCTGTCACCTAACCAGACTC
GGGCCCTGCACCTCTCAGGCACTTCTGGAAAATGACTGAGGCAGATTCTTCCTGAAGCCCATTCTCCATG
GGGCAACAAGGACACCTATTCTGTCCTTGTCCTTCCATCGCTGCCCCAGAAAGCCTCACATATCTCCGTT
TAGAATCAGGTCCCTTCTCCCCAGATGAAGAGGAGGGTCTCTGCTTTGTTTCTCTATCTCCTCCTCAGA
CTTGACCAGGCCCAGCAGGCCCCAGAAGACCATTACCCTATATCCCTTCCTCCCCTAGTCACATGGCCA
TAGGCCTGCTGATGGCTCAGGAAGGCCATTGCAAGGACTCCTCAGCTATGGGAGAGGAAGCACATCACCC
ATTGACCCCCGCAACCCCTCCCTTTCCTCCTCTGAGTCCCGACTGGGGCCACATGCAGCCTGACTTCTTT
GTGCCTGTTGCTGTCCCTGCAGTCTTCAGAGGGCCACCGCAGCTCCAGTGCCACGGCAGGAGGCTGTTCC
TGAATAGCCCCTGTGGTAAGGGCCAGGAGAGTCCTTCCATCCTCCAAGGCCCTGCTAAAGGACACAGCAG
CCAGGAAGTCCCCTGGGCCCCTAGCTGAAGGACAGCCTGCTCCCTCCGTCTCTACCAGGAATGGCCTTGT
CCTATGGAAGGCACTGCCCCATCCCAAACTAATCTAGGAATCACTGTCTAACCACTCACTGTCATGAATG
TGTACTTAAAGGATGAGGTTGAGTCATACCAAATAGTGATTTCGATAGTTCAAAATGGTGAAATTAGCAA
TTCTACATGATTCAGTCTAATCAATGGATACCGACTGTTTCCCACACAAGTCTCCTGTTCTCTTAAGCTT
ACTCACTGACAGCCTTTCACTCTCCACAAATACATTAAAGATATGGCCATCACCAAGCCCCCTAGGATGA
CACCAGACCTGAGAGTCTGAAGACCTGGATCCAAGTTCTGACTTTTCCCCCTGACAGCTGTGTGACCTTC
GTGAAGTCGCCAAACCTCTCTGAGCCCCAGTCATTGCTAGTAAGACCTGCCTTTGAGTTGGTATGATGTT
CAAGTTAGATAACAAAATGTTTATACCCATTAGAACAGAGAATAAATAGAACTACATTTCTTGCA

Figure 8G

SEQ ID NO:8
>gi|189163535|ref|NM_001127704.1| Homo sapiens serpin peptidase inhibitor,
clade A (alpha-1 antiproteinase, antitrypsin), member 1 (SERPINA1),
transcript variant 8, mRNA
TGGGCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCGAGGAAGGCCTAGCCGCTGCTGCTGCCAGGAATTCCAGG
TTGGAGGGGCGGCAACCTCCTGCCAGCCTTCAGGCCACTCTCCTGTGCCTGCCAGAAGAGACAGAGCTTG
AGCAGAGCTTGAGGAGAGCAGGAAAGGGCGGCAGTAAGTCTTCAGCATCAGGCATTTTGGGGTGACTCAG
TAAATGGTAGATCTTGCTACCAGTGGAACAGCCACTAAGGATTCTGCAGTGAGAGCAGAGGGCCAGCTAA
GTGGTACTCTCCCAGAGACTGTCTGACTCACGCCACCCCCTCCACCTTGGACACAGGACGCTGTGGTTTC
TGAGCCAGCCTCCCCCGTTGCCCCTCTGGATCCACTGCTTAAATACGGACGAGGACAGGGCCCTGTCTCC
TCAGCTTCAGGCACCACCACTGACCTGGGACAGTGAATCGACAATGCCGTCTTCTGTCTCGTGGGGCATC
CTCCTGCTGGCAGGCCTGTGCTGCCTGGTCCCTGTCTCCCTGGCTGAGGATCCCAGGGAGATGCTGCCC
AGAAGACAGATACATCCCACCATGATCAGGATCACCCAACCTTCAACAAGATCACCCCCAACCTGGCTGA
GTTCGCCTTCAGCCTATACCGCCAGCTGGCACACCAGTCCAACAGCACCAATATCTTCTTCTCCCCAGTG
AGCATCGCTACAGCCTTTGCAATGCTCTCCCTGGGGACCAAGGCTGACACTCACGATGAAATCCTGGAGG
GCCTGAATTTCAACCTCACGGAGATTCCGGAGGCTCAGATCCATGAAGGCTTCCAGGAACTCCTCCGTAC
CCTCAACCAGCCAGACAGCCAGCTCCAGCTGACCACCGGCAATGGCCTGTTCCTCAGCGAGGGCCTGAAG
CTAGTGGATAAGTTTTTGGAGGATGTTAAAAAGTTGTACCACTCAGAAGCCTTCACTGTCAACTTCGGGG
ACACCGAAGAGGCCAAGAAACAGATCAACGATTACGTGGAGAAGGGTACTCAAGGCAAAATTGTGGATTT
GGTCAAGGAGCTTGACAGAGACACACTTTTTGCTCTGGTGAATTACATCTTCTTTAAAGGCAAATGGGAG
AGACCCTTTGAAGTCAAGGACACCGAGGAAGAGGACTTCCACGTGGACCAGGTGACCACCGTGAAGGTGC
CTATGATGAAGCGTTTAGGCATGTTTAACATCCAGCACTGTAAGAAGCTGTCCAGCTGGGTGCTGCTGAT
GAAATACCTGGGCAATGCCACCGCCATCTTCTTCCTGCCTGATGAGGGGAAACTACAGCACCTGGAAAAT
GAACTCACCCACGATATCATCACCAAGTTCCTGGAAAATGAAGACAGAAGGTCTGCCAGCTTACATTTAC
CCAAACTGTCCATTACTGGAACCTATGATCTGAAGAGCGTCCTGGGTCAACTGGGCATCACTAAGGTCTT
CAGCAATGGGGCTGACCTCTCCGGGGTCACAGAGGAGGCACCCCTGAAGCTCTCCAAGGCCGTGCATAAG
GCTGTGCTGACCATCGACGAGAAAGGGACTGAAGCTGCTGGGGCCATGTTTTTAGAGGCCATACCCATGT
CTATCCCCCCGAGGTCAAGTTCAACAAACCCTTTGTCTTCTTAATGATTGAACAAAATACCAAGTCTCC
CCTCTTCATGGGAAAAGTGGTGAATCCCACCCAAAAATAACTGCCTCTCGCTCCTCAACCCCTCCCCTCC
ATCCCTGGCCCCCTCCCTGGATGACATTAAAGAAGGGTTGAGCTGGTCCCTGCCTGCATGTGACTGTAAA
TCCCTCCCATGTTTTCTCTGAGTCTCCCTTTGCCTGCTGAGGCTGTATGTGGGCTCCAGGTAACAGTGCT
GTCTTCGGGCCCCCTGAACTGTGTTCATGGAGCATCTGGCTGGGTAGGCACATGCTGGGCTTGAATCCAG
GGGGACTGAATCCTCAGCTTACGGACCTGGGCCCATCTGTTTCTGGAGGGCTCCAGTCTTCCTTGTCCT
GTCTTGGAGTCCCCAAGAAGGAATCACAGGGGAGGAACCAGATACCAGCCATGACCCCAGGCTCCACCAA
GCATCTTCATGTCCCCCTGCTCATCCCCCACTCCCCCCCACCCAGAGTTGCTCATCCTGCCAGGGCTGGC
TGTGCCCACCCCAAGGCTGCCCTCCTGGGGGCCCCAGAACTGCCTGATCGTGCCGTGGCCCAGTTTTGTG
GCATCTGCAGCAACACAAGAGAGGACAATGTCCTCCTCTTGACCCGCTGTCACCTAACCAGACTCGGG
CCCTGCACCTCTCAGGCACTTCTGGAAAATGACTGAGGCAGATTCTTCCTGAAGCCCATTCTCCATGGGG
CAACAAGGACACCTATTCTGTCCTGTCCTCCATCGCTGCCCAGAAAGCCTCACATATCTCCGTTTAG
AATCAGGTCCCTTCTCCCACAGATGAAGAGGAGGGTCTCTGCTTTGTTTTCTCTATCTCCTCCTCAGACTT
GACCAGGCCCAGCAGGCCCCAGAAGACCATTACCCTATATCCCTTCTCCTCCCAGTCACATGGCCATAG
GCCTGCTGATGGCTCAGGAAGCCATTGCAAGGACTCCTCAGCTATGGGAGAGGAAGCACATCACCCATT
GACCCCCGCAACCCCTCCCTTTCCTCCTCTGAGTCCCGACTGGGGCCACATGCAGCCTGACTTCTTTGTG
CCTGTTGCTGTCCCTGCAGTCTTCAGAGGGCCACCGCAGCTCCAGTGCCACGGCAGGAGGCTGTTCCTGA
ATAGCCCCTGTGGTAAGGGCCAGGAGAGTCCTTCCATCCTCCAAGGCCCTGCTAAAGGACACAGCAGCCA
GGAAGTCCCCTGGGCCCCTAGCTGAAGGACAGCCTGCTCCCTCCGTCTCTACCAGGAATGGCCTTGTCCT
ATGGAAGGCACTGCCCCATCCCAAACTAATCTAGGAATCACTGTCTAACCACTCACTGTCATGAATCTGT
ACTTAAACGATGAGGTTGACTCATACCAAATAGTGATTTCGATAGTTCAAAATGGTGAAATTAGCAATTC
TACATGATTCAGTCTAATCAATGGATACCGACTGTTTCCCACACAAGTCTCCGTTCCTTAAGCTTACT
CACTGACAGCCTTTCACTCTCCACAAATACATTAAAGATATGGCCATCACCAAGCCCCTAGGATGACAC
CAGACCTGAGAGTCTGAAGACCTGGATCCAAGTTCTGACTTTTCCCCCTGACAGCTGTGTGACCTTCGTG
AAGTCGCCAAACCTCTCTGAGCCCCAGTCATTGCTAGTAAGACCTGCCTTTGAGTTGGTATGATGTTCAA
GTTAGATAACAAAATGTTTATACCCATTAGAACAGAGAATAAATAGAACTACATTCTTGCA

Figure 8H

```
SEQ ID NO:9
>gi|189163537|ref|NM_001127705.1| Homo sapiens serpin peptidase inhibitor,
clade A (alpha-1 antiproteinase, antitrypsin), member 1 (SERPINA1),
transcript variant 9, mRNA
TGGCCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCGAGGAAGGCCTAGCCGCTGCTGCTGCCAGGAATTCCAGG
TTGGAGGGGCGGCAACCTCCTCCAGCCTTCAGGCCACTCTCCTGTGCCTGCCAGAAGAGACAGAGCTTG
AGCAGAGCTTGAGGAGAGCAGGAAAGGGCGGCAGTAAGTCTTCAGCATCAGGCATTTTGGGGTGACTCAG
TAAATGGTAGATCTTGCTACCAGTGGAACAGCCACTAAGGATTCTGCAGTGAGAGCAGAGGGCCAGCTAA
GTGGTACTCTCCCAGAGACTGTCTGACTCACGCCACCCCCTCCACCTTGGACACAGGACGCTGTGGTTTC
TGAGCCAGGTACAATGACTCCTTTCGCCTCCCCGTTGCCCCTCTGGATCCACTGCTTAAATACGGACCA
GGACAGGGCCCTGTCTCCTCAGCTTCAGGCACCACCACTGACCTGGGACAGTGAATCGACAATGCCGTCT
TCTGTCTCGTGGGGCATCCTCCTGCTGGCAGGCCTGTGCTGCTGGTCCCTGTCTCCTGGCTGAGGATC
CCCAGGGAGATGCTGCCCAGAAGACAGAGACATCCCACCATGATCAGGATCACCCAACCTTCAACAAGAT
CACCCCCAACCTGGCTGAGTTCGCCTTCAGCCTATACCGCCAGCTGGCACACCAGTCCAACAGCACCAAT
ATCTTCTTCTCCCCAGTGAGCATCGCTACAGCCTTTGCAATGCTCTCCCTGGGGACCAAGGCTGACACTC
ACGATGAAATCCTGGAGGGCCTGAATTTCAACCTCACGGAGATTCCGGAGGCTCAGATCCATGAAGGCTT
CCAGGAACTCCTCCGTACCCTCAACCAGCCAGACAGCCAGCTCCAGCTGACCACCGGCAATGGCCTGTTC
CTCAGCGAGGGCCTGAAGCTAGTGGATAAGTTTTTGGAGGATGTTAAAAAGTTGTACCACTCAGAAGCCT
TCACTGTCAACTTCGGGGACACCGAAGAGGCCAAGAAACAGATCAACGATTACGTGGAGAAGGGTACTCA
AGGGAAAATTGTGGATTTGGTCAAGGAGCTTGACAGAGACACAGTTTTTGCTCTGGTGAATTACATCTTC
TTTAAAGGCAAATGGGAGAGACCCTTTGAAGTCAAGGACACCGAGGAAGAGGACTTCCACGTGGACCAGG
TGACCACCGTGAAGGTGCCTATGATGAAGCGTTTAGGCATGTTTAACATCCAGCACTGTAAGAAGCTGTC
CAGCTGGGTGCTGCTGATGAAATACCTGGGCAATGCCACCGCCATCTTCTTCCTGCCTGATGAGGGGAAA
CTACAGCACCTGGAAAATGAACTCACCCACGATATCATCACCAAGTTCCTGGAAAATGAAGACAGAAGGT
CTGCCAGCTTACATTTACCCAAACTGTCCATTACTGGAACCTATGATCTGAAGAGCGTCCTGGGTCAACT
GGGCATCACTAAGGTCTTCAGCAATGGGGCTGACCTCTCCGGGGTCACAGAGGAGGCACCCCTGAAGCTC
TCCAAGGCCGTGCATAAGGCTGTGCTGACCATCGACGAGAAAGGGACTGAAGCTGCTGGGGCCATGTTTT
TAGAGGCCATACCCATGTCTATCCCCCCCGAGGTCAAGTTCAACAAACCCTTTGTCTTCTTAATGATTGA
ACAAAATACCAAGTCTCCCCTCTTCATGGGAAAAGTGGTGAATCCCACCCAAAAATAACTGCCTCTCGCT
CCTCAACCCCTCCCCTCCATCCTGGCCCCCTCCCTGGATGACATTAAAGAAGGGTTGAGCTGGTCCCTG
CCTGCATGTGACTGTAAATCCCTCCCATGTTTTCTCTGAGTCTCCCTTTGCCTGCGAGGCTGTATGTGG
GCTCCAGGTAACAGTGCTGTCTTCGGGCCCCCTGAACTGTGTTCATGGAGCATCTGGCTGGGTAGGCACA
TGCTGGGCTTGAATCCAGGGGGGACTGAATCCTCAGCTTACGGACCTGGGCCCATCTGTTTCTGGAGGGC
TCCAGTCTTCCTTGTCCTGTCTTGGAGTCCCCAAGAAGGAATCACAGGGGAGGAACCAGATACCAGCCAT
GACCCCAGGCTCCACCAAGCATCTTCATGTCCCCCTGCTCATCCCCCACTCCCCCCCACCCAGAGTTGCT
CATCCTGCCAGGGCTGGCTGTGCCCACCCCAAGGCTGCCCTCCTGGGGGCCCCAGAACTGCCTGATCGTG
CCGTGGCCCAGTTTTGTGGCATCTGCAGCAACACAAGAGAGAGGACAATGTCCTCCTCTTCACCCGCTGT
CACCTAACCAGACTCGGGCCCTGCACCTCTCAGGCACTTCTGGAAAATGACTGAGGCAGATTCTTCCTGA
AGCCCATTCTCCATGGGGCAACAAGGACACCTATTCTGTCCTTGTCCTTCCATCGCTGCCCCACAAAGCC
TCACATATCTCCGTTTAGAATCAGGTCCCTTCTCCCCAGATGAAGAGGAGGGTCTCTGCTTTGTTTCTC
TATCTCCTCCTCAGACTTGACCAGGCCCAGCAGGCCCAGAAGACCATTACCCTATATCCCTTCTCCTCC
CTAGTCACATGGCCATAGGCCTGCTGATGGCTCAGGAAGGCATTGCAAGGACTCCTCAGCTATGGAGA
GGAAGCACATCACCCATTGACCCCCGCAACCCCTCCCTTCCTCCTCTGAGTCCCGACTGGGGCCACATG
CAGCCTGACTTCTTTGTGCCTGTTGCTGTCCCTGCAGTCTTCAGAGGGCACCGCAGCTCCAGTGCCACG
GCAGGAGGCTGTTCCTGAATAGCCCCTGTGGTAAGGGCCAGCAGAGTCCTTCCATCCTCCAAGGCCCTGC
TAAAGGACACAGCAGCCAGGAAGTCCCCTGGGCCCTAGCTGAAGGACAGCCTGCTCCCTCCGTCTCTAC
CAGGAATGGCCTTGTCCTATGGAAGGCACTGCCCCATCCCAAACTAATCTAGGAATCACTGTCTAACCAC
TCACTGTCATGAATGTGTACTTAAAGGATGAGGTTGAGTCATACCAAATAGTGATTTCGATAGTTCAAAA
TGGTGAAATTAGCAATTCTACATGATTCAGTCTAATCAATGGATACCGACTGTTTCCCACACAAGTCTCC
TGTTCTCTTAAGCTTACTCACTGACAGCCTTTCACTCTCCACAAATACATTAAAGATATGGCCATCACCA
AGCCCCCTAGGATGACACCAGACCTGAGAGTCTGAAGACCTGGATCCAAGTTCTGACTTTTCCCCCTGAC
AGCTGTGTCACCTTCGTGAAGTCGCCAAACCTCTCTGAGCCCCAGTCATTGCTAGTAAGACCTGCCTTTG
AGTTGGTATGATGTTCAAGTTAGATAACAAAATGTTTATACCCATTAGAACAGAGAATAAATAGAACTAC
ATTTCTTGCA
```

Figure 8I

SEQ ID NO:10
>gi|189163539|ref|NM_001127706.1| Homo sapiens serpin peptidase inhibitor,
clade A (alpha-1 antiproteinase, antitrypsin), member 1 (SERPINA1),
transcript variant 10, mRNA
TGGGCAGGAACTGGGCACTGTGCCCAGGGCATGCACTGCCTCCACGCAGCAACCCTCAGAGTCCTGAGCT
GAACCAAGAAGGAGGAGGGGGTCGGGCCTCCGAGGAAGGCCTAGCCGCTGCTGCTGCCAGGAATGCCAGG
TTGCAGGGGCGGCAACCTCCTGCCAGCCTTCAGGCCACTCTCCTGTGCCTGCCAGAAGACACAGAGCTTG
AGGAGAGCTTGAGGAGAGCAGGAAAGCAGCCTCCCCGTTGCCCCTCTGGATCCACTGCTTAAATACGGA
CGAGGACAGGGCCCTGTCTCCTCAGCTTCAGGCACCACCACTGACCTGGGACAGTGAATCGACAATGCCG
TCTTCTGTCTCGTGGGCATCCTCCTGCTGGCAGGCCTGTGCTGCCTGGTCCCTGTCTCCCTGGCTGAGG
ATCCCCAGGGAGATGCTGCCCAGAAGACAGATACATCCACCATGATCAGGATCACCCAACCTTCAACAA
GATCACCCCCAACCTGGCTGAGTTCGCCTTCAGCCTATACCGCCAGCTGGCACACCAGTCCAACAGCACC
AATATCTTCTTCTCCCCAGTGAGCATCGCTACAGCCTTTGCAATGCTCTCCCTGGGGACCAAGGCTGACA
CTCACGATGAAATCCTGGAGGGCCTGAATTTCAACCTCACGGAGATTCCGGAGGCTCAGATCCATGAAGG
CTTCCAGGAACTCCTCCGTACCCTCAACCAGCCAGACAGCCAGCTCCAGCTGACCACCGGCAATGGCCTG
TTCCTCAGCGAGGGCCTGAAGCTAGTGGATAAGTTTTTGGAGGATGTTAAAAAGTTGTACCACTCAGAAG
CCTTCACTGTCAACTTCGGGGACACCGAAGAGGCCAAGAAACAGATCAACGATTACGTGGAGAAGGGTAC
TCAAGGGAAAATTGTGGATTTGGTCAAGGAGCTTGACAGAGACACAGTTTTTGCTCTGGTGAATTACATC
TTCTTTAAAGGCAAATGGGACAGACCCTTTGAAGTCAAGGACACCGAGGAAGAGGACTTCCACGTGGACC
AGGTGACCACCGTGAAGGTGCCTATGATGAAGCGTTTAGGCATGTTTAACATCCAGCACTGTAAGAAGCT
GTCCAGCTGGGTGCTGCTGATGAAATACCTGGGCAATGCCACCGCCATCTTCTTCCTGCCTGATGAGGGG
AAACTACAGCACCTGGAAAATGAACTCACCCACGATATCATCACCAAGTTCCTGGAAAATGAAGACAGAA
GGTCTGCCAGCTTACATTTACCCAAACTGTCCATTACTGGAACCTATGATCTGAAGAGCGTCCTGGGTCA
ACTGGGCATCACTAAGGTCTTCAGCAATGGGGCTGACCTCTCCGGGGTCACAGAGGAGGCACCCCTGAAG
CTCTCCAAGGCCGTGCATAAGGCTGTGCTGACCATCGACGAGAAAGGGACTGAAGCTGCTGGGGCCATGT
TTTTAGAGGCCATACCCATGTCTATCCCCCCGAGGTCAAGTTCAACAAACCCTTTGTCTTCTTAATGAT
TGAACAAAATACCAAGTCTCCCCTCTTCATGGGAAAAGTGGTGAATCCCACCCAAAAATAACTGCCTCTC
GCTCCTCAACCCCTCCCCTCCATCCCTGGCCCCCTCCCTGGATGACATTAAAGAAGGGTTGAGCTGGTCC
CTGCCTGCATGTGACTGTAAATCCCTCCCATGTTTTCTCTGAGTCTCCCTTTGCCTGCTGAGGCTGTATG
TGGGCTCCAGGTAACAGTGCTGTCTTCGGGCCCCCTGAACTGTGTTCATGGAGCATCTGGCTGGGTAGGC
ACATGCTGGGCTTGAATCCAGGGGGGACTGAATCCTCAGCTTACGGACCTGGGCCCATCTGTTTCTGGAG
GGCTCCAGTCTTCCTTGTCCTGTCTTGGAGTCCCCAAGAAGGAATCACAGGGGCAGGAACCAGATACCAGC
CATGACCCCAGGCTCCACCAAGCATCTTCATGTCCCCCTGCTCATCCCCCACTCCCCCCACCCAGAGTT
GCTCATCCTGCCAGGGCTGGCTGTGCCCACCCCAAGGCTGCCCTCCTGGGGGGCCCAGAACTGCCTGATC
GTGCCGTGGCCCAGTTTTGTGGCATCTGCAGCAACACAAGAGAGAGGACAATGTCCTCCTCTTGACCCGC
TGTCACCTAACCAGACTCGGGCCCTGCACCTCTCAGGCACTTCTGGAAAATGACTGAGGCAGATTCTTCC
TGAAGCCCATTCTCCATGGGGCAACAAGGACACCTATTCTGTCCTTGTCCTTCCATCGCTGCCCCAGAAA
GCCTCACATATCTCCCGTTTAGAATCAGGTCCCTTCTCCCAGATGAAGAGGACGGGTCTGCTTTGTTTT
CTCTATCTCCTCCTCAGACTTGACCAGGCCCAGCAGGCCCAGAAGACCATTACCCTATATCCTTCTCC
TCCTAGTCACATGGCCATAGCCTGCTGATGGCTCAGGAAGGCCATTGCAAGGACTCCTCAGCTATGGG
AGAGGAAGCACATCACCCATTGACCCCCGCAACCCCTCCCTTTCCTCCTCTGAGTCCCGACTGGGCCAC
ATGCAGCCTGACTTCTTTGTGCCTGTTGCTGTCCCTGCAGTCTTCAGAGGGCCACCGCAGCTCCAGTGCC
ACGGCAGGAGGCTGTTCCTGAATAGCCCCTGTGGTAAGGGCCAGGAGAGTCCTTCCATCCTCCAAGGCCC
TGCTAAAGGACACAGCAGCCAGGAAGTCCCCTGGGCCCCTAGCTGAAGGACAGCCTGCTCCTCCGTCTC
TACCAGGAATGGCCTTGTCCTATGGAAGGCACTGCCCCATCCCAAACTAATCTAGGAATCACTGTCTAAC
CACTCACTGTCATGAATGTGTACTTAAAGGATGAGTTGAGTCATACCAAATAGTGATTTCGATAGTTCA
AAATGGTGAAATTAGCAATTCTACATGATTCAGTCTAATCAATGGATACCGACTGTTTCCCACACAAGTC
TCCTGTTCTCTAAAGCTTACTCACTGACAGCCTTTCACTCTCCACAAATACATTAAAGATATGGCCATCA
CCAAGCCCCCTAGGATGACACCACACCTGAGAGTCTGAAGACCTGGATCCAAGTTCTGACTTTTCCCCCT
GACAGCTGTGTGACCTTCGTGAAGTCGCCAAACCTCTCTGAGCCCAGTCATTGCTAGTAAGACCTGCCT
TTCAGTTGGTATGATGTTCAAGTTAGATAACAAAATGTTTATACCCATTAGAACAGAGAATAAATAGAAC
TACATTTCTTGCA

Figure 8J

SEQ ID NO:11
>gi|189163541|ref|NM_001127707.1| Homo sapiens serpin peptidase inhibitor,
clade A (alpha-1 antiproteinase, antitrypsin), member 1 (SERPINA1),
transcript variant 11, mRNA
TGGGCAGGAACTGGGCACTGTGCCCAGGGCATGCACTGCCTCCACGCAGCAACCCTCAGAGTCCTGAGCT
GAACCAAGAAGGAGGAGGGGTCGGGCCTCCGAGGAAGGCCTAGCCGCTGCTGCTGCCAGGAATTCCAGG
TTGGAGGGGCGGCAACCTCCTGCCAGCCTTCAGGCCACTCTCCTGTGCCTGCCAGAAGAGACACAGCTTG
AGGAGAGCTTGAGGAGAGCAGGAAAGCCTCCCCCGTTGCCCCTCTGGATCCACTGCTTAAATACGGACGA
GGACAGGGCCCTGTCTCCTCAGCTTCAGGCACCACCACTGACCTGGGACAGTGAATCGACAATGCCGTCT
TCTGTCTCGTGGGGCATCCTCCTGCTGGCAGGCCTGTGCTGCCTGGTCCCTGTCTCCCTGGCTGAGGATC
CCCAGGGAGATGCTGCCCAGAAGACAGATACATCCCACCATGATCAGGATCACCCAACCTTCAACAAGAT
CACCCCCAACCTGGCTGAGTTCGCCTTCAGCCTATACCGCCAGCTGGCACACCAGTCCAACAGCACCAAT
ATCTTCTTCTCCCCAGTGAGCATCGCTACAGCCTTTGCAATGCTCTCCCTGGGGACCAAGGCTGACACTC
ACGATGAAATCCTGGAGGGCCTGAATTTCAACCTCACGGAGATTCCGGAGGCTCAGATCCATGAAGGCTT
CCAGGAACTCCTCCGTACCCTCAACCAGCCAGACAGCCAGCTCCAGCTGACCACCGGCAATGGCCTGTTC
CTCAGCGAGGGCCTGAAGCTAGTGGATAAGTTTTTGGAGGATGTTAAAAAGTTGTACCACTCAGAACCCT
TCACTGTCAACTTCGGGGACACCGAAGAGGCCAAGAAACAGATCAACGATTACGTGGAGAAGGGTACTCA
AGGGAAAATTGTGGATTTGGTCAAGGAGCTTGACAGAGACACAGTTTTTGCTCTGGTGAATTACATCTTC
TTTAAAGGCAAATGGGAGAGACCCTTTGAAGTCAAGGACACCGAGGAAGAGGACTTCCACGTGGACCAGG
TGACCACCGTGAAGGTGCCTATGATGAAGCGTTTAGGCATGTTTAACATCCAGCACTGTAAGAAGCTGTC
CAGCTGGGTGCTGCTGATGAAATACCTGGGCAATGCCACCGCCATCTTCTTCCTGCCTGATGAGGGGAAA
CTACAGCACCTGGAAAATGAACTCACCCACGATATCATCACCAAGTTCCTGGAAAATGAAGACAGAAGGT
CTGCCAGCTTACATTTACCCAAACTGTCCATTACTGGAACCTATGATCTGAAGAGCGTCCTGGGTCAACT
GGGCATCACTAAGGTCTTCAGCAATGGGGCTGACCTCTCCGGGGTCACAGAGGAGGCACCCCTGAAGCTC
TCCAAGGCCGTGCATAAGGCTGTGCTGACCATCGACGAGAAAGGGACTGAAGCTGCTGGGGCCATGTTTT
TAGAGGCCATACCCATGTCTATCCCCCCCGAGGTCAAGTTCAACAAACCCTTTGTCTTCTTAATGATTGA
ACAAAATACCAAGTCTCCCCTCTTCATGGGAAAAGTGGTGAATCCCACCCAAAAATAACTGCCTCTCGCT
CCTCAACCCCTCCCCTCCATCCCTGGCCCCCTCCCTGGATGACATTAAAGAAGGGTTGAGCTGGTCCCTG
CCTGCATGTGACTGTAAATCCCTCCCATGTTTTCTCTGAGTCTCCCTTTGCCTGCTGAGGCTGTATGTGG
GCTCCAGGTAACAGTGCTGTCTTCGGGCCCCCTGAACTGTGTTCATGGAGCATCTGGCTGGGTAGGCACA
TGCTGGGCTTGAATCCAGGGGGACTGAATCCTCAGCTTACGGACCTGGGCCCATCTGTTTCTGGAGGGC
TCCAGTCTTCCTTGTCCTGTCTTGGAGTCCCCAAGAAGGAATCACAGGGGGAGGAACCAGATACCAGCCAT
GACCCCAGGCTCCACCAAGCATCTTCATGTCCCCTGCTCATCCCCCACTCCCCCCCACCCAGAGTTGCT
CATCCTGCCAGGGCTGGCTGTGCCCACCCCAAGGCTGCCCTCCTGGGGGCCCCAGAACTGCCTGATCGTC
CCGTGGCCCAGTTTTGTGGCATCTGCAGCAACACAAGAGAGAGGACAATGTCCTCCTCTTGACCCGCTGT
CACCTAACCAGACTCGGGCCCTGCACCTCTCAGGCACTTCTGGAAAATGACTGAGGCAGATTCTTCCTGA
AGCCCATTCTCCATGGGGCAACAAGGACACCTATTCTGTCCTTGTCCTTCCATCGCTGCCCCAGAAAGCC
TCACATATCTCCGTTTAGAATCAGGTCCCTTCTCCCCAGATGAAGAGGAGGGTCTCTGCTTTGTTTTCTC
TATCTCCTCCTCAGACTTCACCAGGCCCAGCAGGCCCCAGAAGACCATTACCCTATATCCCTTCTCCTCC
CTAGTCACATGGCCATAGGCCTGCTGATGGCTCAGGAAGGCCATTGCAAGGACTCCTCAGCTATGGGAGA
GGAAGCACATCACCCATTGACCCCGCAACCCCTCCCTTCCTCCTCTGAGTCCCGACTGGGGCCACATG
CAGCCTGACTTCTTTGTGCCTGTTGCTGTCCCTGCAGTCTTCAGAGGGCCACCGCAGCTCCAGTGCCACG
GCAGGAGGCTGTTCCTGAATAGCCCCTGTGGTAAGGGCCAGGAGAGTCCTTCCATCCTCCAAGGCCCTGC
TAAAGGACACAGCAGCCAGGAAGTCCCCTGGGCCCTAGCTGAAGGACAGCCTGCTCCCTCCGTCTCTAC
CAGGAATGGCCTTGTCCTATGGAAGGCACTGCCCCATCCCAAACTAATCTAGGAATCACTGTCTAACCAC
TCACTGTCATGAATGTGTACTTAAAGGATGAGGTTGAGTCATACCAAATAGTGATTTCGATAGTTCAAAA
TGGTGAAATTAGCAATTCTACATGATTCAGTCTAATCAATGGATACCGACTGTTTCCCACACAAGTCTCC
TGTTCTCTTAAGCTTACTCACTGACAGCCTTTCACTCTCCACAAATACATTAAAGATATGGCCATCACCA
AGCCCCCTAGGATGACACCAGACCTGAGACTCTGAAGACCTGGATCCAAGTTCTGACTTTTCCCCCTGAC
AGCTGTGTGACCTTCGTGAAGTCGCCAAACCTCTCTGAGCCCCAGTCATTGCTAGTAAGACCTGCCTTTG
AGTTGGTATGATGTTCAAGTTAGATAACAAAATGTTTATACCCATTAGAACAGAGAATAAATAGAACTAC
ATTTCTTGCA

Figure 8K

SEQ ID NO:12
>gi|402766667|ref|NM_001266017.2| Macaca mulatta serpin peptidase
inhibitor, clade A (alpha-1 antiproteinase, antitrypsin), member 1
(SERPINA1), mRNA
CAGGACAATGCCATCTTCTGTCTCATGGGCGTCCTCCTGCTGGCAGGCCTGTGCTGCCTGCTCCCCGGC
TCTCTGGCTGAGGATCCCCAGGGAGATGCTGCCCAGAAGACGGATACATCCCACCATGATCAGGACCACC
CAACCCTCAACAAGATCACCCCCAGCCTGGCTGAGTTCGGCTTCAGCCTATACCGCCAGCTGGCACACCA
GTCCAACAGCACCAATATCTTCTTCTCCCCAGTGAGCATCGCTACAGCCTTTGCAATGCTCTCCCTGGGG
ACCAAGGCTGACACTCACAGTGAAATCCTGGAGGGCCTGAATTTCAACCTCACGGAGACCCCCGAGGCTC
AGGTCCATGAAGGCTTCCAGGAACTCCTCCATACCCTCAACCAGCCAGACAGCCAGCTCCAGCTGACCAC
CGGCAACGGCCTGTTCCTCAACAAGAGCCTGAAGGTAGTGGATAAGTTTTTGGAGGATGTCAAAAAACTG
TACCACTCAGAAGCCTTCTCTGTCAACTTTGAGGACACCGAAGAGGCCAAGAAACAGATCAACAATTACG
TGGAGAAGGAAACTCAAGGGAAAATTGTGGATTTGGTCAAGGAGCTTGACAGAGACACAGTTTTTGCTCT
GGTGAATTACATCTTCTTTAAAGGCAAATGGGAGAGACCCTTTGAGGTTGAGGCCACCAAGGAAGAGGAC
TTCCACGTGGACCAGGCGACCACCGTGAAGGTGCCCATGATGAGGCGTTTAGGCATGTTTAACATCTACC
ACTGTGAGAAGCTGTCCAGCTGGGTGCTGCTGATGAAATACCTGGGCAATGCCACCGCCATCTTCTTCCT
GCCTGATGAGGGAAAACTGCAGCACCTGGAAAATGAACTCACCCATGATATCATCACCAAGTTCCTGGAA
AATGAAACAGCAGGTCTGCCAACTTACATTTACCAGACTGGCCAGTACTGGAACCTATGATCTGAAGA
CAGTCCTGGGCCACCTGGGTATCACTAAGGTCTTCAGCAATGGGGCTGACCTCTCCGGGATCACGCAGGA
GGCACCCTGAAGCTCTCCAAGGCCGTGCATAAGGCTGTGCTGACCATCGATGAGAAGGGACTGAAGCT
GCTGGGGCCATGTTTTTAGAGGCCATACCCATGTCTATTCCCCCGAGGTCAAGTTCAACAAACCCTTTG
TCTTCTTAATGATTGAACAAAATACCAAGTCTCCCCTCTTCATGGGAAAAGTGGTGAATCCCACCCAGAA
ATAACTGCCTGTCACTCCTCAGCCCCTCCCCTCCATCCCTGGCCCCCTCCCTGAATGACAT

Figure 8L

SEQ ID NO:13
>gi|297298519|ref|XM_001099255.2| PREDICTED: Macaca mulatta serpin
peptidase inhibitor, clade A (alpha-1 antiproteinase, antitrypsin), member
1, transcript variant 6 (SERPINA1), mRNA
GCCCAGTCTTGTGTCTGCCTGGCAATGGGCAAGGCCCCTTCCTGCCCAAGCTCCCCGCCCCTCCCAACC
TATTGCCTCCGCCACCCGCCACCCGAGGCCAACTTCCTGGGTGGGCAGGAACTGGGCCCTGTGCCCAGGG
CGTGCACTGCCTCCACGCAGCAACCCTCAGAGTACTGAGCTGAGCAAAGGAGGAGGAGGGGATCAGCACT
CTGAGGAAGGCCTAGCCACTGCTGCTGCCAGGAATTCCAGGGCGGCATCAGTCTTCAGCATCAGGCATTT
CGGGGTGAATTAGTAAATGGTAGATCTTGCTACCAGTGGAACAGCCGCTAAGGATTCTGCAGTGAGAGCA
GAGGGCCAGCAAAGTGGTACTCTCCCAGCGACTGGCTGACTCACGCCACCCCCTCCACCTTGGACGCAGG
ACACTGTGGTTTCTGAGCCAGGTACAATGACTCCTTTTGGTACGTGCAGTGGAGGCTGTATGCTGCTCAG
GCAGAGCGTCCCGACAGCGTGGCGGGCGACTCAGCGCCCAGCCTGTGAACTTAGTCCCTGTTTGCTCCT
CCGGTAACTGGGGTGATCTTGGTAATATTCACCAGCAGCCTCCCCCGTTGCCCCTCTGCACCCACTGCT
TAAATACGGACAAGGACAGGGCTCTGTCTCCTCAGCCTCAGGCACCACCACTGACCTGGGACGGTGAATC
GACAATGCCATCTTCTGTCTCATGGGGCGCCTCCTGCTGGCAGGCCTGTGCTGCCTGCTCCCCGGCTCT
CTGGCTGAGGATCCCCAGGGAGATGCTGCCCAGAAGACGGATACATCCCACCATGATCAGGACCACCAA
CCCTCAACAAGATCACCCCCAGCCTGGCTGAGTTCGGCTTCAGCCTATACCGCCAGCTGGCACACCAGTC
CAACAGCACCAATATCTTCTTCTCCCCAGTGAGCATCGCTACAGCCTTTGCAATGCTCTCCCTGGGGACC
AAGGCTGACACTCACAGTGAAATCCTGGAGGGCCTGAATTTCAACGTCACGGAGATTCCGGAGGCTCAGG
TCCATGAAGGCTTCCAGGAACTCCTCCATACCCTCAACAAGCCAGACAGCCAGCTCCAGCTGACCACCGG
CAACGGCCTGTTCCTCAACAAGAGCCTGAAGGTAGTGGATAAGTTTTTGGAGGATGTCAAAAAACTGTAC
CACTCAGAAGCCTTCTCTGTCAACTTTGAGGACACCGAAGAGGCCAAGAAACAGATCAACAATTACGTGG
AGAAGGAAACTCAAGGGAAAATTGTGGATTTGGTCAAGGAGCTTGACAGAGACACAGTTTTTGCTCTGGT
GAATTACATCTTCTTTAAAGGCAAATGGGAGAGACCCTTGACGTTGAGGCCACCAAGGAAGAGGACTTC
CACGTGGACCAGGCGACCACCGTGAAGGTGCCCATGATGAGGCGTTTAGGCATGTTTAACATCTACCACT
GTGAGAAGCTGTCCAGCTGGGTGCTGCTGATGAAATACCTGGGCAATGCCACCGCCATCTTCTTCCTGCC
TGATGAGGGGAAACTGCAGCACCTGGAAAATGAACTCACCCATGATATCATCACCAAGTTCCTGGAAAAT
GAAAACAGCAGGTCTGCCAACTTACATTTACCCAGACTGGCCATTACTGGAACCTATGATCTGAAGACAG
TCCTGGGCCACCTGGGTATCACTAAGGTCTTCAGCAATGGGGCTGACCTCTCGGGGATCACGGAGGAGGC
ACCCCTGAAGCTCTCCAAGGCCGTGCATAAGGCTGTGCTGACCATCGATGAGAAAGGGACTGAAGCTGCT
GGGGCCATGTTTTTAGAGGCCATACCCATGTCTATTCCCCCGAGGTCAAGTTCAACAAACCCTTTGTCT
TCTTAATGATTGAACAAAATACCAAGTCTCCCCTCTTCATGGGAAAAGTGGTGAATCCCACCCAGAAATA
ACTGCCTGTCACTCCTCAGCCCCTCCCTCCATCCCTGGCCCCCTCCCTGAATGACATTAAAGAAGGGTT
GAGCTGGTCCCTGCCTGCGTGTGTGACTGCAAAC
```

Figure 8M

SEQ ID NO:14
>gi|297298520|ref|XM_001099044.2| PREDICTED: Macaca mulatta serpin peptidase inhibitor, clade A (alpha-1 antiproteinase, antitrypsin), member 1, transcript variant 4 (SERPINA1), mRNA
TCTTGTGTCTGCCTGGCAATGGGCAAGGCCCCTTCCTGCCCAAGCTCCCCGCCCCTCCCCAACCTATTGC
CTCCGCCACCGCCACCCGAGGCCAACTTCCTGGGTGGGCAGGAACTGGGCCCTGTGCCCAGGGCGTGCA
CTGCCTCCACGCAGCAACCCTCAGAGTACTGAGCTGAGCAAAGGAGGAGGAGGGATCAGCACTCTGAGG
AAGGGCTAGCCACTGCTGCTGCCAGGAATTCCAGGACAATGCCATCTTCTGTCTCATGGGCGTCCTCCT
GCTGGCAGGCCTGTGCTGCCTGCTCCCCGGCTCTCTGGCTGAGGATCCCCAGGGAGATGCTGCCCAGAAG
ACGGATACATCCCACCATGATCAGGACCACCCAACCCTCAACAAGATCACCCCCAGCCTGGCTGAGTTCG
GCTTCAGCCTATACCGCCAGCTGGCACACCAGTCCAACAGCACCAATATCTTCTTCTCCCCAGTGAGCAT
CGCTACAGCCTTTGCAATGCTCTCCCTGGGGACCAAGGCTGACACTCACAGTGAAATCCTGGAGGGCCTG
AATTTCAACGTCACGGAGATTCCGGAGGCTCAGGTCCATGAAGGCTTCCAGGAACTCCTCCATACCCTCA
ACAAGCCAGACAGCCAGCTCCAGCTGACCACCGGCAACGGCCTGTTCCTCAACAAGAGCCTGAAGGTAGT
GGATAAGTTTTTGGAGGATGTCAAAAAACTGTACCACTCAGAAGCCTTCTCTGTCAACTTTGAGGACACC
GAAGAGGCCAAGAAACAGATCAACAATTACGTGGAGAAGGAAACTCAAGGGAAAATTGTGGATTTGGTCA
AGGAGCTTGACAGAGACACAGTTTTTGCTCTGGTGAATTACATCTTCTTTAAAGGCAAATGGGAGAGACC
CTTTGACGTTGAGGCCACCAAGGAAGAGGACTTCCACGTGGACCAGGCGACCACCGTGAAGGTGCCCATG
ATGAGGCGTTTAGGCATGTTTAACATCTACCACTGTGAGAAGCTGTCCAGCTGGGTGCTGCTGATGAAAT
ACCTGGGCAATGCCACCGCCATCTTCTTCCTGCCTGATGAGGGGAAACTGCAGCACCTGGAAAATGAACT
CACCCATGATATCATCACCAAGTTCCTGGAAAATGAAAACAGCAGGTCTGCCAACTTACATTTACCCAGA
CTGGCCATTACTGGAACCTATGATCTGAAGACAGTCCTGGGCCACCTGGGTATCACTAAGGTCTTCAGCA
ATGGGGCTGACCTCTCGGGGATCACGGAGGAGGCACCCCTGAAGCTCTCCAAGGCCGTGCATAAGGCTGT
GCTGACCATCGATGAGAAGGGACTGAAGCTGCTGGGGCCATGTTTTTAGAGGCCATACCCATGTCTATT
CCCCCCGAGGTCAAGTTCAACAAACCCTTTGTCTTCTTAATGATTGAACAAAATACCAAGTCTCCCCTCT
TCATGGGAAAAGTGGTGAATCCCACCCAGAAATAACTGCCTGTCACTCCTCAGCCCCTCCCCTCCATCCC
TGGCCCCCTCCCTGAATGACATTAAAGAAGGGTTGAGCTGGTCCCTGCCTGCGTGTGTGACTGCAAAC

Figure 8N

SEQ ID NO:15
Reverse Complement of SEQ ID NO:1
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGGAAAAGTCAGAACTTGGATCCAGGTCTTCAGACTCTCAGGTCTGGTGTCATCCTAGGGGGCTTG
GTGATGGCCATATCTTTAATGTATTTGTGGAGAGTGAAAGGCTGTCAGTGAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGGAGG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGACAAGGGATATAGGGTAATGGTCTTCTGGGGCC
TGCTGGGCCTGGTCAAGTCTGAGGAGGAGATAGAGAAAACAAAGCAGAGACCCTCCTCTTCATCTGGGCAGAAG
GGACCTGATTCTAAACGGAGATATGTGAGGCTTTCTGGGGCAGCGATGGAAGGACAAGGCACAGAATAGGTGTCC
TTGTTGCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTTCTGGGGCCCCAGGAGGGCAGCCTTGGGGTGGCACAGCCAGC
CCTGGCAGGATGAGCAACTCTGGGTGGGGGGAGTGGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGGGGTGAT
CTTGTTGAAGGTTGGGTGATCCTGATCATGGTGGCATGTATCTGTCTTCTGGGCAGCATCTCCCTGGGCATCCT
CAGCCAGGGAGACAGGGACCAGGCAGCACAGGCCTGCCAGCAGGAGGATGCCCCACGAGACAGAAGACGGCATT
GTCGATTCACTGTCCCAGGTCAGTGGTGGTGCCTGAAGCTGAGGAGACAGGGCCCTGTCCTCGTCCCTATTTAA
GCAGTGGATCCAGAGGGGCAACGGGGAGGCTGCTGGTGAATATTAACCAAGGTCACCCCAGTTATCGCAGGAG
CAAACAGGGGCTAAGTCCACTGCTGGGATCTGAGTCGCCGCCTACGCTGCCCGGACGCTTTGCCTGGGCAGT
GTACAGCTTCCACTGCACTTACCGAAAGGAGTCATTGT SEQ ID NO:16
Reverse Complement of SEQ ID NO:2
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGCTCAGAGAGGTTTGCCCACTTCACGAAGGTCACACAG
CTGTCAGGGGAAAAGTCAGAACTTGGATCCAGTGTCTTCACACTCTCAGGTCTGGTGTCATCCTAGGGGCTTG
GTGATGGCCATATCTTTAATGTATTTGTGGACAGTGAAAGGCTGTCAGTGAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGACG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGGCCTGGTCAAGTCTGAGGAGGAGATAGAGAAAACAAACCAGAGACCCTCCTCTTCATCTGGGGAGAAG
GGACCTGATTCTAAACGGAGATATGTGAGGCTTCTGGGGCAGCGATGGAAGGACAAGGACAGAATAGGTGTCC
TTGTTGCCCCATGGAGAATGGGCTTCAGGAACAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTTCTGGGGGCCCCAGGAGGGCAGCCTTGGGGTGGGCACAGCCAGC
CCTGGCAGGATGAGCAACTCTGGGTGGGGGGAGTGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGCATTTACAGTCACATGCAGGCAGGGACC
AGCTCAACCCTTCTTTAATGTCATCCAGGGAGGGGGCCAGGGATGGAGGGGAGGGGTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTGAACTTGACCTCGGGGGGATAGACATGGGTATCGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTCAGGAACAGGCCATTGCCGGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGGGGTGAT
CTTGTTGAAGGTTGGGTGATCCTGATCATGGTGGGATGTATCGTCTTCTGGGCAGCATCTCCCTGGGCATCCT
CAGCCAGGCAGACAGGGACCAGGCAGCACAGGCCTGCCAGCAGGAGGATGCCCACGAGACAGAAGACGGCATT
GTCCTTCCTGCTCTCCTCAAGCTCTCCTCAAGCTCTGTCTCTTCTGGCAGGCACAGGAGAGTGGCCTGAAGGC
TGGCAGGAGTTGCCGCCCCTCCAACCTGGAATTCCTGGCAGCAGCAGCGGCTAGGCCTTCCTCGGAGGCCCGA
CCCCCTCCTCCTTCTTGGTTCAGCTCAGGACTCTGAGGGTTGCTGCGTGGAGGCAGTGCATGCCCTGGGCACAG
TGCCCAGTTCCTGCCCA

Figure 8P

SEQ ID NO:17
Reverse Complement of SEQ ID NO:3
TGCAAGAAATGTAGTTCTATTTATTCTCTGTTCTAATGGGTATAAACATTTTCTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGGAAAAGTCAGAACTTGGATCCAGGTCTTCAGACTCTCAGGTCTGGTGTCATCCTAGGGGCTTG
GTCATGGCCATATCTTTAATGTATTTGTGGAGAGTGAAAGGCTGTCAGTGAGTAAGCTTAAGAGAACAGGAGAC
TTGTGTGGGAAACAGTCGGTATCCATTGATTAGACTGAATCATGTAGAATTGCTAATTTCACCATTTTGAACTA
TGAAATCACTATTTGGTATGACTCAACCTCATCCTTAACTACACATTCATGACAGTGAGTGGTTAGACAGTG
ATTCCTAGATTACTTTGGCATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATCGCCATGTGACTAGGGAGGAGAAGGGATATACGGTAATGGTCTTCTGGGGCC
TGCTGGGCCTGGTCAAGTCTGAGGAGGAGATAGAGAAAACAAAGCAGAGACCCTCCTCTTCATCTGGGGAGAAG
GGACCTGATTCTAAACGGAGATATGTGAGGCTTTCTGGGGCAGCGATGGCAAGGACAAGGACAGAATAGGTGTCC
TTGTTGCCCCATGGAGAATGGGCTTCAGGAAGAATCTGCCTCAGTCATTTTCCAGAAGTGCCTGACAGGTGCAG
GGCCCGAGTCTGGTTAGGTGACAGCGGGTCAAGAGGCAGGACATTGTCCTCTCTCTTGTGTTGCTGCAGATGCCA
CAAAACTGGGCCACGGCACGATCAGGCAGTTCTGGGGCCTCCAGGAGGGCAGCCTTGGGGTGGGCACAGCCAGC
CCTGGCAGGATGAGCAACTCTGGGTGGGGGGCAGTGGGGATGAGCAGGGGGACATGAAGATGCTTGTGTGGAGC
CTGGGGTCATGGCTGGTATCTGGTCCTCCCCTGTGATTCCTTCTTGGGGACTCCAAGACAGGACAAGGAAGAC
TGGAGCCCTCCAGAAACAGATGGGCCCAGGTCGGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTGAACTTGACCTCGGGGGGGATAGACATGGGTATGGCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTACTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGGGGTGAT
CTTGTTGAAGGTTGGGTGATCCTGATCATGGTGGCATGTATCTGTCTTCTGGGCAGCATCTCCCTGGGGATCCT
CAGCCAGGGAGACAGGGACCAGGCAGCACAGGCCTGCCAGCAGGAGGATGCCCCACGAGACAGAAGACGGCATT
GTCGATTCACTGTCCCAGGTCAGTGGTGGTGCCTGAAGCTGAGGAGACAGGGCCCTGTCCTCGTCCCGTATTTAA
GCAGTGGATCCAGAGGGGCAACGGGGAGGCTGCGAAAGGAGTCATTGTACCTGGCTCAGAAACCACAGCGTCC
TGTGTCCAAGGTGGAGGGGTGGCGTGAGTCAGACAGTCTCTGGGAGAGTACCACTTAGCTGGCCCTCTGCTCT
CACTGCAGAATCCTTAGTGGCTGTTCCACTGGTAGCAAGATCTACCATTTACTGAGTCACCCCAAAATGCCTGA
TGCTGAAGACTTACTGCCGCCCTTTCCTGCTCTCCTCAAGCTCTCCTCAAGCTCTGTCTCTTCTGGCAGGCACA
GGAGAGTGGCCTGAAGGCTGGCAGGAGGTTGCCGCCCTCCAACCTGGAATTCCTGGCAGCAGCAGCGGCTAGG
CCTTCCTCGGAGGCCCGACCCCCTCCTCCTTCTTGGTTCAGCTCAGGACTCTGAGGGTTGCTGCGTGGAGGCAG
TGCATGCCCTGGGCACAGTGCCCAGTCCTGCCCA SEQ ID NO:18
Reverse Complement of SEQ ID NO:4
TGCAACAAATCTAGTTCTATTTATTCTCTCTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGAAAAGTCAGAACTTGGATCCAGGTCTTCAGACTCTCAGGTCTGGTGTCATCCTAGGGGCTTG
GTGATGGCCATATCTTTAATGTATTTGTGGAGAGTGAAAGGCTGTCAGTGAGTAAGCTAACAGAACAGGAGAC
TTGTGTGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGCCCCTTACCACAGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAACGGGATATAGGGTAATGGTCTTCTGGGGCC
TGCTGGGCCTGGTCAAGTCTGAGGAGGACATAGAGAAAACAAAGCAGACACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTTCTGGGGCCCCAGGAGGGCAGCCTTGGGGTGGGCACAGCCAGC
CCTGGCAGGATGAGCAACTCTGGGTGGGGGGAGTGGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGACACTTGGTATTTGTTCAATCATTAAGAAGA
CAAAGGGTTTGTTGAACTTGACCTCGGGGGGGATAGACATGGGTATCGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCAGGTATTTCATCAGCAGCACCCAGCTGGACAGCTTCTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGACTGGTACAACTTTTTAACATCCTCCAAAAACTTATCCACTAGCTTC
AGGCCCTCGCTGAGGAACAGGCCATTGCCCGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGGGGTGAT
CTTGTTGAAGGTTGGGTCATCCTGATCATGGTGGGATGTATCTGTCTTCTGGGCAGCATCTCCCTGGGGATCCT
CAGCCAGGGAGACAGGGACCAGGCAGCACAGGCCTGCCAGCAGGAGGATGCCCCACGAGACAGAAGACGGCATT
GTCCTGTGGAACTGACTGAGCAGCAGCAGCAATGTCCCACCTTTCCTGCTCTCCTCAAGCTCTCCTCAAGCTCT
GTCTCTTCGGCAGGCACAGGAGAGTGGCCTGAAGGCTGGCAGGAGGTTGCCGCCCCTCCAACCTGGAATTCCT
GGCAGCAGCAGCGGCTAGGCCTTCCTCGGAGGCCCGACCCCTCCTCCTTCTTGGTTCAGCTCAGGACTCTGAG
GGTTGCTGCGTGGAGGCAGTGCATGCCCTGGGCACAGTGCCCAGTTCCTGCCCA

Figure 8R

SEQ ID NO:19
Reverse Complement of SEQ ID NO:5
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGAAAAGTCAGAACTTGGATCCAGGTCTTCAGACTCTCAGGTCTGGTGTCATCCTAGGGGGCTTG
GTGATGGCCATATCTTTAATGTATTTGTGGAGACTGAAAGGCTGTCAGTCAGTAAGCTTAAGAGAACAGGAGAC
TTGTCTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGGTTGCGGGGGTCAATGGGTGATGTGCTTCCTCTCCCATAGCTGAGCAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGCCCTGGTCAAGTCTGAGGAGGAGATAGAGAAAACAAAGCAGAGACCCTCCTCTTCATCTGGGGAGAAG
GGACCTGATTCTAAACGGAGATATGTGAGGCTTTCTGGGCAGCGATGGAAGGACAAGGACAGAATAGGTGTCC
TTGTTGCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACCATCAGGCAGTTCTGGGGCCCCAGGAGGGCAGCCTTGGGGTGGGCACAGCCAGC
CCTGGCAGGATGAGCAACTCTGGGTGGGGGGAGTGGGGATGAGCAGGGGACATGAAGATGCTTGGTGGAGC
CTGGGGTCATGGCTGGTATCTGGTTCCTCCCCTGTGATTCCTTCTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTGTTCAATCATTAAGAAGA
CAAAGGGTTTGTTGAACTTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGCTGAAGGCCAACTCAGCCAGGTTGGGGGTGAT
CTTGTTCAAGGTTGGGTGATCCTGATCATGGTGGATGTATCTGTCTTCTGGGCAGCATCTCCCTGGGCATCCT
CAGCCAGGGAGACAGGGACCAGGCAGCACAGGCCTGCCAGCAGGAGGATGCCCACGAGACAGAAGACGGCATT
GTCGATTCACTGTCCCAGGTCAGTGGTGGTGCCTGAAGCTGAGGAGACAGGGCCCTGTCCTCGTCCGTATTTAA
GCAGTGGATCCAGAGGGGCAACGGGGAGGCTGCTGGCTCAGAAACCACAGCGTCCTGTGTCCAAGGTGGAGGG
GGTGGCGTGAGTCAGACAGTCTCTGGCAGAGTACCACTTAGCTGGCCCTCTGCTCTCACTGCAGAATCCTTAGT
GGCTGTTCCACTGCTAGCAAGATCTACCATTTACTGAGTCACCCCAAAATGCCTGATGCTGAAGACTTACTGCC
GCCCTGTGGAACTGAGTGAGCAGCAGCAGCAATGTCCCACCTTTCCTGCTCTCCTCAAGCTCTCCTCAAGCTCT
GTCTCTTCTGGCAGGCACAGGAGAGTGGCCTGAAGGCTGGCAGGAGGTTGCCGCCCCTCCAACCTGGAATTCCT
GGCAGCAGCAGCGGCTAGGCCTTCCTCGGAGGCCCGACCCCTCCTCCTTCTTGGTTCAGCTCAGGACTCTGAG
GGTTGCTGCGTGGAGGCAGTGCATGCCCTGGGCACAGTGCCCAGTTCCTGCCCA

Figure 8S

```
SEQ ID NO:20
Reverse Complement of SEQ ID NO:6
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGAAAAGTCAGAACTTGGATCCAGGTCTTCAGACTCTCAGGTCTGGTGTCATCCTAGGGGCTTG
GTCATGGCCATATCTTTAATGTATTTGTGGAGAGTGAAAGGCTGTCAGTCAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGCATGGGGCAGTGCCTTCCATAGGACAAGGCTATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGCAGGGTTGCGGGGGTCAATGGGTGATGTGCTTCCTCTCCCATAGCTGAGGAGTCCTTGCAATGGCCTT
CCTCAGCCATCAGCAGGCCTATGGCCATGTGACTAGGGAGGAGAAGGGATATAGGGTAATGGTCTTCTGGGGCC
TGCTGGCCCTGGTCAAGTCTGAGGAGCAGATAGAGAAAACAAAGCAGAGACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCCATGGAGAATGGGCTTCAGGAAGAATCTGCCTCAGTCATTTTCCAGAAGTGCCTGAGAGGTGCAG
GGCCCGAGTCTGGTTAGGTGACACGGGGTCAAGAGGAGGACATTGTCCTCTCTCTTGTGTTGCTGCAGATGCCA
CAAAACTGGGCCACGGCACCATCAGGCAGTTCTGGGGCCCCAGGAGGGCAGCCTTGGGGTGGGCACAGCCAGC
CCTGGCAGGATCAGCAACTCTGGGTGGGGGGAGTGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGCAGCTGGCTGTCTGGCTGGTTGAGGGTACGGAG
GAGTTCCTGCAAGCCTTCATGGATCTGAGCCTCCGGAATCTCCGTGAGGTTGAAATTCAGGCCCTCCAGGATTT
CATCGTCAGTGTCAGCCTTGGTCCCCAGGGAGAGCATTGCAAAGGCTGTAGCCATGCTCACTGGGGAGAAGAAG
ATATTGGTCCTGTTGGACTGGTGTGCCAGCTGGCGGTATAGGCTGAAGGCGAACTCAGCCAGGTTGGGGGTGAT
CTTGTTGAAGGTTGGGTGATCCTGATCATGGTGGATGTATCTGTCTTCTGGGCAGCATCTCCCTGGGGATCCT
CAGCCAGGGAGACAGGGACCAGGCAGCACAGGCCTGCCAGCAGGAGGATGCCCACGAGACAGAAGACGGCATT
GTCGATTCACTGTCCCAGGTCAGTGGTGGTGCCTGAAGCTGAGGAGACAGGGCCCTGTCCTCGTCCGTATTTAA
GCAGTGGATCCAGAGGGGCAACGGGGAGGCTGCTGTGCAACTGAGTGAGCAGCAGCAGCAATGTCCCACCTTT
CCTGCTCTCCTCAAGCTCTCCTCAAGCTCTGTCTCTTCTGGCAGGCACAGGAGAGTGGCCTGAAGGCTGGCAGG
AGGTTGCCGCCCTCCAACCTGGAATTCCTGGCAGCAGCAGCGGCTAGGCCTTCCTCGGAGGCCCGACCCCTC
CTCCTTCTTGGTTCAGCTCAGGACTCTGAGGGTTGCTGCGTGGAGGCAGTGCATGCCCTGGGCACAGTGCCCAG
TTCCTGCCCA
```

Figure 8T

SEQ ID NO:21
Reverse Complement of SEQ ID NO:7
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGCAAAAGTCAGAACTTGGATCCAGGTCTTCAGACTCTCAGGTCTGGTGTCATCCTAGGGGCTTG
GTGATGGCCATATCTTTAATGTATTTGTGCAGAGTGAAAGGCTGTCAGTCAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGCAGG
AAAGGCAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGGCCTGGTCAAGTCTGAGGAGCAGATAGAGAAAACAAAGCAGAGACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCCATGGAGAATGGGCTTCAGGAAGAATCTGCCTCAGTCATTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTTCTGGGGCCCCCAGGAGGGCAGCCTTGGGGTGGGCACAGCCAGC
CCTGGCAGGATGAGCAACTCTGGGTGGGGGGAGTGGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAACATGGGAGGGATTTACAGTCACATGCAGGCAGGGACC
AGCTCAACCCTTCTTTAATGTCATCCAGGGAGGGGGCCAGGGATGGAGGGAGGGGTTGAGGAGCGAGAGGCAG
TTATTTTTGGGTGGGATTCACCACTTTTCCCATGAAGAGGGGAGACTTGGTATTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCCGTGGTCAGCTGGAGCTGGCTGTCTGGCTGGTTGAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTGGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGGGTGAT
CTTGTTGAAGGTTGGGTGATCCTGATCATGGTGGATGTATCTGTCTTCTGGGCAGCATCTCCCTGGGGATCCT
CAGCCAGGGACACAGGGACCAGGCAGCACAGGCCTGCCAGCAGGAGGATGCCCCACGAGACAGAAGACGGCATT
GTCGATCACTGTCCCAGGTCAGTGGTGGTGCCTGAAGCTGAGGAGACAGGGCCCTGCCTCGTCCGTATTTAA
GCAGTGGATCCAGAGGGGCAACGGGGAGGCTGCTGGCTCAGAAACCACAGCGTCCTGTGTCCAAGGTGGAGGG
GGTGGCGTCAGTCAGACAGTCTCTGGAGAGTACCACTTAGCTGGCCCTCTGCTCTCACTGCAGAATCCTTAGT
GGCTGTTCCACTGGTAGCAAGATCTACCATTTACTGAGTCACCCCAAAATGCCTGATGCTGAAGACTTACTGCC
GCCCTTCCTCCTCTCCTCAAGCTCTCCTCAAGCTCTGTCTCTTCTGGCAGGCACAGGAGAGTGGCCTGAAGGC
TGGCAGGAGGTTGCCGCCCCTCCAACCTGGAATTCCTGGCAGCAGCAGCGGCTAGGCCTTCCTCGGAGGCCCGA
CCCCCTCCTCCTTCTTGGTTCAGCTCAGGACTCTGAGGGTTGCTGCGTGGAGGCAGTGCATGCCCTGGGCACAG
TGCCCAGTTCCTGCCCA

Figure 8U

SEQ ID NO:22
Reverse Complement of SEQ ID NO:9
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGCAAAAGTCAGAACTTGGATCCAGGTCTTCAGACTCTCAGGTCTGGTGTCATCCTAGGGGCTTG
GTGATGGCCATATCTTTAATGTATTTGTGGAGAGTGAAAGGCTGTCAGTGAGTAAGCTAACAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTAGCAGGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATCGTCTTCTGGGCCC
TGCTGGGCCTGGTCAAGTCTGAGGAGGAGATAGAGAAAACAAAGCAGAGACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTTCTGGGGCCCCAGGAGGGCAGCCTTGGGGTGGGCACAGCCAGC
CCTGGCAGGATGAGCAACTCTCGGTGGGGGGCAGTGGGGATGAGCAGGGGACATGAAGATGCTTGGTGGAGC
CTGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGCCCGAAGACAGCACTGTTACCTGGAGCCCAC
ATACAGCCTCAGCAGGCAAAGGAGACTCAGAGAAAACATGGGAGGGATTTACAGTCACATGCAGGCAGGGACC
AGCTCAACCCTTCTTTAATGTCATCCAGGGAGGGGCCAGGGATGGAGGGAGGGGTTGAGGAGCGAGAGGCAG
TTATTTTTGGGTGGGATTCACCACTTTTCCCATGAAGAGGGGAGACTTGGTATTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTCGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTCACAGTGAAGGCTTCTGAGTGGTACAACTTTTAACATCCTCCAAAAACTTATCCACTAGCTTC
AGCCCTCGCTGAGGAACACGCCATTGCCGGTGGTCAGCTGGAGCTGGCTGTCTGGCTGGTTGACGGTACGCAG
GAGTTCCTGGAAGCCTTCATGGATCTGAGCCTCCGGAATCTCGTGAGGTTGAAATTCAGGCCCTCCAGGATTT
CATCGTGAGTGTCAGCCTTGGTCCCCAGGGAGAGCATTGCAAAGGCTGTAGCCATGCTCACTGGGAGAAGAAG
ATATTGGTGCTGTTGGACTGGTGTGCCAGCTGGCGGTATAGGCTGAAGGCGAACTCAGCCAGGTTGGGGTGAT
CTTGTTGAAGGTTGGGTGATCCTGATCATGGTGGGATGTATCTGTCTTCTGGGCAGCATCTCCCTGGGGATCCT
CAGCCAGGGAGACAGGGACCAGGCAGCACAGGCCTGCCAGCAGGAGGATGCCCCACGAGACAGAAGACGGCATT
GTCGATTCACTGTCCCAGGTCAGTGGTGGTGCCTGAAGCTGAGGAGACAGGGCCCTGTCCTCGTCCGTATTTAA
GCAGTGGATCCAGAGGGGCAACGGGGAGGCTGGCTCAGAAACCACAGCGTCCTGTGTCCAAGGTGGAGGGGT
GGCGTGAGTCAGACAGTCTCTGGGAGAGTACCACTTAGCTGGCCCTCTGCTCTCACTGCAGAATCCTTAGTGGC
TGTTCCACTGCTAGCAAGATCTACCATTTACTGAGTCACCCCAAAATGCCTGATGCTGAAGACTTACTGCCGCC
CTTTCCTGCTCTCCTCAAGCTCTCCTCAAGCTCTGTCTCTTCTGGCAGGCACAGGAGAGTGGCCTGAAGGCTGG
CAGGAGGTTGCCCGCCCCTCCAACCTGGAATTCCTGGCAGCAGCAGCGGCTAGGCCTTCCTCGGAGGCCCGACCC
CCTCCTCCTTCTTGGTTCAGCTCAGGACTCTGAGGGTTGCTGCCTGGAGGCACTGCATGCCCTGGGCACAGTGC
CCAGTTCCTGCCCA

Figure 8V

SEQ ID NO:23
Reverse Complement of SEQ ID NO.9
TCCAACAAATGTAGTTCTATTTATTCTCTGTTCTAATGGGTATAAACATTTTGTTATCTAACTTGAACATCATA
CCAACTCAAAGGCAGGTCTTACTAGCAATGACTGGGGCTCAGAGAGGTTTGGCGACTTCACGAAGGTCACACAG
CTGTCAGGGGAAAAGTCAGAACTTGGATCCAGGTCTTCAGACTCTCAGGTCTGGTGTCATCCTAGGGGCTTG
GTGATGGCCATATCTTTAATGTATTTGTGGAGACTGAAAGGCTGTCAGTCAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGGCCTGGTCAASTCTGAGGAGGAGATAGAGAAAACAAAGCAGAGACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTTGTGTTGCTGCAGATGCCA
CAAAACTGGGCCACGGCACGATCAGGCAGTTCTGGGGCCCCCAGGAGGGCAGCCTTGGGGTGGGCACAGCCAGC
CCTGGCAGGATGAGCAACTCTGGGTGCGGGGCAGTGGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTCAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTTGAGGGTACGCAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCCAACTCAGCCAGGTTGCGGGTGAT
CTTGTTCAAGTTGGGTGATCCTGATCATGGTGGGATGTATCTGTCTTCTGGGCAGCATCTCCCTGGGGATCCT
CAGCCAGGGAGACAGGGACCAGGCAGCACAGGCCTGCCAGCAGGAGGATGCCCCACGAGACAGAAGACGGCATT
GTCGATCACTGTCCCAGGTCAGTGGTGGTGCCTGAAGCTGAGGAGACAGGGCCCTGTCCTCGTCCCTATTTAA
GCAGTGGATCCAGAGGGGCAACGGGGGAGGCGAAAGGAGTCATTGTACCTGGCTCAGAAACCACAGCGTCCTGT
GTCCAAGGTGGAGGGGGTGGCGTGAGTCAGACAGTCTCTGGGAGAGTACCACTTAGCTGGCCCTCTGCTCTCAC
TGCAGAATCCTTAGTGGCTGTTCCACTGGTAGCAAGATCTACCATTACTGAGTCACCCCAAAATGCCTGATGC
TGAAGACTTACTGCCGCCCTTTCCTGCTCTCCTCAAGCTCTCCTCAAGCTCTGTCTCTTCTGGCAGGCACAGGA
GAGTGGCCTGAAGGCTGGCAGGAGGTTGCCGCCCCTCCAACCTGGAATTCCTGGCAGCAGCAGCGGCTAGGCCT
TCCTCGGAGGCCCGACCCCCTCCTCCTTCTTGGTTCAGCTCAGGACTCTGAGGGTTGCTGCGTGGAGGCAGTGC
ATGCCCTGGGCACAGTGCCCAGTTCCTGCCCA

Figure 8W

SEQ ID NO:24
Reverse Complement of SEQ ID NO:10
TGCAAGAAATGTAGTTCTATTTATTCTCTGTTCTAATGGGTATAAACATTTTGTTATCTAACTTGAACATCATA
CCAACTCAAAGGCAGGTCTTACTAGCAATGACTGGGCTCAGAGACGGTTTGGCGACTTCACGAAGGTCACACAG
CTGTCAGGGGCAAAAGTCAGAACTTGGATCCAGGTCTTCAGACTCTCAGGTCTGGTGTCATCCTAGGGGCTTG
GTGATGGCCATATCTTTAATGTATTTGTGGAGAGTGAAAGGCTGTCAGTGAGTAAGCTTAAGAGAACAGGAGAC
TTGTGTGGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGCATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGGCCTGGTCAAGTCTGAGGAGGAGATAGAGAAAACAAAGCAGAGACCCTCCTCTTCATCTGGGGACAAG
GGACCTGATTCTAAACGGAGATATGTGAGGCTTTCTGGGGCAGCGATGGAAGGACAAGGACAGAATAGGTGTCC
TTGTTGCCCCATGGAGAATGGGCTTCAGGAAGAATCTGCCTCAGTCATTTTCCAGAAGTGCCTGAGAGGTGCAG
GGCCCGAGTCTGGTTAGGTGACACGCGGGTCAAGAGGAGGACATTGTCCTCTCTCTTGTGTTGCTGCAGATGCCA
CAAAACTGGGCCACGGCACGATCAGGCAGTTCTGGGGCCCCCAGGAGGGCAGCCTGGGGTGGGCACAGCCAGC
CCTGGCAGGATCAGCAACTCTCGGTGGGGGGAGTGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGGAGCCCTCCAGAAACAGATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCCAGGCAAAGGGAGACTCAGAGAAAACATGGGAGGGATTTACAGTCACATGCAGGCAGGGACC
AGCTCAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTTCCAGTAATGGACAGTTTGGGTAAATGTAAGCTGGCAGACCTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTGAGGGTACGGAG
GACTTCCTGGAAGCCTTCATGGATCTGAGCCTCCGGAATCTCCGTGAGGTTGAAATTCAGGCCCTCCAGGATTT
CATCGTGAGTCTCAGCCTTGGTCCCCAGGGAGAGCATTGCAAAGGCTGTAGCGATGCTCACTGGGGAGAAGAAG
ATATTGGTGCTGTTGGACTGGTGTGCCAGCTGGCGGTATAGGCTGAAGGCGAACTCAGCCAGGTTGGCGGTGAT
CTTGTTGAAGGTTGGGTGATCCTGATCATGGTGGGATGTATCTGTCTTCTGGGCAGCATCTCCCTGCGGATCCT
CAGCCAGGGACACAGGGACCAGGCAGCACAGGCCTGCCAGCAGGAGGATGCCCCACGAGACAGAAGACGGCATT
GTCGATTCACTGTCCCAGGTCAGTGGTGGTGCCTGAAGCTGAGGAGACAGGGCCCTGTCCTCGTCCCTATTTAA
GCAGTGGATCCAGAGGGGCAACGGGGAGGCTGCTTTCCTGCTCTCCTCAAGCTCTCCTCAAGCTCTGTCTCTT
CTGGCAGGCACAGGAGAGTGGCCTGAAGGCTGGCAGGAGGTTGCCGCCCCTCCAACCTGGAATTCCTGGCAGCA
GCAGCGGCTAGGCCTTCCTCGGAGGCCCGACCCCCTCCTCCTTCTTGGTTCAGCTCAGGACTCTGAGGGTTGCT
GGCTGCAGGCAGTGCATGCCCTGGGCACAGTGCCCAGTTCCTGCCCA

Figure 8X

SEQ ID NO:25
Reverse Complement of SEQ ID NO:11
TGCAAGAAATGTAGTTCTATTTATTCTCTGTTCTAATGGGTATAAACATTTTGTTATCTAACTGAACATCATA
CCAACTCAAAGGCAGGTCTTACTAGCAATGACTGGGGCTCAGAGAGGTTTGGCGACTTCACGAAGGTCACACAG
CTGTCAGGGGAAAAGTCAGAACTTGGATCCAGGTCTTCAGACTCTCAGGTCTGGTGTCATCCTAGGGGGCTTG
GTGATGGCCATATCTTTAATGTATTTGTGGAGAGTGAAAGGCTGTCAGTGAGTAAGCTTAAGAGAACAGGAGAC
TTGTGTGGAAACAGTCGGTATCCATTGATTAGACTGAATCATGTAGAATTGCTAATTTCACCATTTTGAACTA
TCGAAATCACTATTTGGTATGACTCAACCTCATCCTTTAAGTACACATTCATGACAGTGAGTGGTTAGACAGTG
ATTCCTAGATTAGTTTGGGATGGGGCAGTGCCTTCCATAGGACAAGGCCATTCCTGGTAGAGACGGAGGGAGCA
GGCTGTCCTTCAGCTAGGGGCCCAGGGGACTTCCTGGCTGCTGTGTCCTTAGCAGGGCCTTGGAGGATGGAAG
GACTCTCCTGGCCCTTACCACAGGGGCTATTCAGGAACAGCCTCCTGCCGTGGCACTGGAGCTGCGGTGGCCCT
CTGAAGACTGCAGGGACAGCAACAGGCACAAAGAAGTCAGGCTGCATGTGGCCCCAGTCGGGACTCAGAGGAGG
AAAGGGAGGGTTGCGGGGGTCAATGGGTGATGTGCTTCCTCTCCCATAGCTGAGGAGTCCTTGCAATGGCCTT
CCTGAGCCATCAGCAGGCCTATGGCCATGTGACTAGGGAGGAGAAGGGATATAGGGTAATGGTCTTCTGGGGCC
TGCTGGGCCTGGTCAAGTCTGAGGAGGAGATAGAGAAAACAAAGCAGAGACCCTCCTCTTCATCTGGGGAGAAG
GGACCTGATTCTAAACGGAGATATGTGAGGCTTTCTGGGGCAGCGATGGAAGGACAAGGACAGAATAGGTGTCC
TTGTTGCCCATGGAGAATGGGCTTCAGGAAGAATCTGCCTCAGTCATTTTCCAGAAGTGCCTGAGAGGTGCAG
GGCCCGAGTCTGGTTAGGTGACAGCGGGTCAAGAGGAGGACATTGTCCTCTCTCTTGTGTTGCTGCAGATGCCA
CAAAACTGGGCCACGGCACGATCAGGCAGTGCTGGGGCCCCAGGAGGGCAGCCTTGGGGTGGGCACAGCCAGC
CCTGGCAGGATGAGCAACTCTGGGTGGGGGGAGTGGGGGATGAGCAGGGGACATGAAGATGCTTGGTGGAGC
CTGGGGTCATGGCTGGTATCTGGTTCCTCCCCTGTGATTCCTTCTTGGGGACTCCAAGACAGGACAAGGAAGAC
TGCAGCCCTCCAGAAACACATGGGCCCAGGTCCGTAAGCTGAGGATTCAGTCCCCCCTGGATTCAAGCCCAGCA
TGTGCCTACCCAGCCAGATGCTCCATGAACACAGTTCAGGGGGCCCGAAGACAGCACTGTTACCTGGAGCCCAC
ATACAGCCTCAGCAGGCAAAGGGAGACTCAGAGAAAACATGGGAGGGATTTACAGTCACATGCAGGCACGGACC
AGCTCAAACCCTTCTTTAATGTCATCCAGGGAGGGGGCCAGGGATGGAGGGGAGGGGTTGAGGAGCGAGAGGCAG
TTATTTTTGGGTGGGATTCACCACTTTTCCCATGAAGAGGGGAGACTTGGTATTTTGTTCAATCATTAAGAAGA
CAAAGGGTTTGTTGAACTTGACCTCGGGGGGGATAGACATGGGTATGGCCTCTAAAAACATGGCCCCAGCAGCT
TCAGTCCCTTTCTCGTCGATGGTCAGCACAGCCTTATGCACGGCCTTGGAGAGCTTCAGGGGTGCCTCCTCTGT
GACCCCGGAGAGGTCAGCCCCATTGCTGAAGACCTTAGTGATGCCCAGTTGACCCAGGACGCTCTTCAGATCAT
AGGTCCAGTAATGGACAGTTTGGGTAAATGTAAGCTGGCAGACTTCTGTCTTCATTTTCCAGGAACTTGGTG
ATGATATCGTGGGTGAGTTCATTTTCCAGGTGCTGTAGTTTCCCCTCATCAGGCAGGAAGAAGATGGCGGTGGC
ATTGCCCAGGTATTTCATCAGCAGCACCCAGCTGGACAGCTTCTTACAGTGCTGGATGTTAAACATGCCTAAAC
GCTTCATCATAGGCACCTTCACGGTGGTCACCTGGTCCACGTGGAAGTCCTCTTCCTCGGTGTCCTTGACTTCA
AAGGGTCTCTCCCATTTGCCTTTAAAGAAGATGTAATTCACCAGAGCAAAAACTGTGTCTCTGTCAAGCTCCTT
GACCAAATCCACAATTTTCCCTTGAGTACCCTTCTCCACGTAATCGTTGATCTGTTTCTTGGCCTCTCGGTGT
CCCCGAAGTTGACAGTGAAGGCTTCTGAGTGGTACAACTTTTTAACATCCTCCAAAAACTTATCCACTAGCTTC
AGGCCCTCGCTGAGGAACAGGCCATTGCCGGTGGTCAGCTGGAGCTGGCTGTCTGGCTGGTTCAGGGTACGGAG
GAGTTCCTGGAAGCCTTCATGGATCTGAGCCTCCGGAATCTCCGTGAGGTTGAAATTCAGGCCCTCCAGGATTT
CATCGTGAGTGTCAGCCTTGGTCCCCAGGGAGAGCATTGCAAACGGCTGTAGCGATGCTCACTGGGCAGAAGAAG
ATATTGGTGCTCTTGGACTGGTGTGCCAGCTGGCGGTATAGGCTGAAGGCGAACTCAGCCAGGTTGGGGGTGAT
CTTGTTGAAGGTTGGGTGATCCTGATCATGGTGGGATGTATCTGTCTTCTGGGCAGCATCTCCCTGGGGATCCT
CAGCCAGGGAGACAGGGACCAGGCAGCACAGGCCTGCCAGCAGGAGGATGCCCACGAGACACAAGACGGCATT
GTCGATTCACTGTCCCAGGTCAGTGGTGGTGCCTGAAGCTGAGGAGACAGGGCCCTGTCCTCGTCGGTATTTAA
GCAGTGGATCCAGAGGGGCAACGGGGAGGCTTTCCTGCTCTCCTCAAGCTCTCCTCAAGCTCTGTCTCTTCTG
GCAGGCACAGGAGAGTGGCCTGAAGGCTGGCAGGAGGTTGCCGCCCCTCCAACCTGGAATTCCTGGCAGCAGCA
GCGGCTAGGCCTTCCTCGGAGGCCCGACCCCCTCCTCCTTCTTGGTTCAGCTCAGGACTCTGAGGGTTGCTGCG
TGGAGGCAGTGCATGCCCTGGGCACAGTGCCCAGTTCCTGCCCA

Figure 8Y

SEQ ID NO:26
Reverse Complement of SEQ ID NO:12
ATGTCATTCAGGGAGGGGCCAGGGATGGAGGGGAGGGGCTGAGGAGTGACAGGCAGTTATTTCTGGGTGGGAT
TCACCACTTTTCCCATGAAGAGGGGAGACTTGGTATTTTGTTCAATCATTAAGAAGACAAAGGGTTTGTTGAAC
TTGACCTCGGGGGGAATAGACATGGGTATGGCCTCTAAAAACATGGCCCCAGCAGCTTCAGTCCCTTTCTCATC
GATGGTCAGCACAGCCTTATGCACGGCCTTGGAGAGCTTCAGGGGTGCCTCCTCCGTGATCCCCGAGAGGTCAG
CCCCATTGCTGAAGACCTTAGTGATACCCAGGTGGCCCAGGACTGTCTTCAGATCATAGGTTCCAGTAATGGCC
AGTCTGGGTAAAGTAAGTTGGCAGACCTGCTGTTTTCATTTCCAGGAACTTGGTGATGATATCATGGGTGAG
TTCATTTTCCAGGTGCTGCAGTTTCCCCTCATCAGGCAGGAAGAAGATGGCGGTGGCATTGCCCAGGTATTTCA
TCAGCAGCACCCAGCTGGACAGCTTCTCACAGTGGTAGATGTTAAACATGCCTAAACGCCTCATCATGGGCACC
TTCACGGTGGTGCCTGGTCCACGTGGAAGTCCTCTTCCTTGGTGGCCTCAACGTCAAAGGGTCTCTCCCATTT
GCCTTAAAGAAGATGTAATTCACCAGAGCAAAAACTGTGTCTCTGTCAAGCTCCTTGACCAAATCCACAATTT
TCCCTTGAGTTTCCTTCTCCACGTAATTGTTGATCTGTTCTTGGCCTCTTGGGTGTCCTCAAAGTTGACAGAG
AAGGCTTCTGAGTGGTACAGTTTTTTGACATCCTCCAAAAACTGATCCACTACCTTCAGGCTCTTGTTGAGGAA
CAGGCCGTTGCCGGTGGTCAGCTGGAGCTGGCTGTCTGGCTTGTTGAGGGTATGGAGGAGTTCCTGGAAGCCTT
CATGGACCTGAGCCTCGGAATCTCCGTGACGTTGAAATTCAGGCCCTCCAGGATTTCACTGTGAGTGTCAGCC
TTGTTCCCAGGGAGAGCATTGCAAAGGCTGTAGCGATGCTCACTGGGGAGAAGAAGATATTGGTGCTGTTGGA
CTGGTGTGCCAGCTGGCGGTATAGGCTGAAGCCGAACTCAGCCAGGCTGGGGGTGATCTTCTTGAGGGTTGGGT
GGTCCTGATCATGGTGGGATGTATCCGTCTTCTGGGCAGCATCTCCCTGGGGATCCTCAGCCAGAGAGCCGGGC
AGCAGGCAGCACAGGCCTGCCAGCAGGAGGACGCCCATGAGACAGAAGATGGCATTGTCCTG

Figure 8Z

SEQ ID NO:27
Reverse Complement of SEQ ID NO:13
GTTTCCAGTCACACACGCAGGCAGGGACCAGCTCAACCCTTCTTAATGTCATTCAGGGAGGGGGCCAGGGATG
GAGGGGAGGGGCTGAGGAGTGACAGGCAGTTATTTCTGGGTGGATTCACTACTTTTCCCATGAAGAGGGCAGA
CTTGGTATTTTGTTCAATCATTAAGAAGACAAAGGGTTTGTTGAACTTGACCTCGGGGGGAATAGACATGGGTA
TGGCCTCTAAAAACATGGCCCCAGCAGCTTCAGTCCCTTTCTCATCGATGGTCAGCACAGCCTTATGCACGGCC
TTGGAGAGCTTCAGGGGTGCCTCCTCCGTGATCCCCGAGAGGTCAGCCCCATTGCTGAAGACCTTAGTGATACC
CAGGTGGCCCAGGACTGTCTTCAGATCATAGGTTCCAGTAATGGCCAGTCTGGGTAAATGTAAGTTGGCAGACC
TGCTGTTTTCATTTTCCAGGAACTTGGTGATGATATCATGGGTGAGTTCATTTTCCAGGTGCTGCAGTTTCCCC
TCATCAGGCAGGAAGAAGATGGCGGTGGCATTGCCCAGGTATTTCATCAGCAGCACCCAGCTGGACAGCTTCTC
ACAGTGGTAGATGTTAAACATGCCTAAACGCCTCATCATGGGCACCTTCACGGTGGTCGCCTGGTCCACGTGGA
AGTCCTCTTCCTTGGTGGCCTCAACGTCAAAGGGTCTCTCCCATTTGCCTTTAAAGAAGATGTAATTCACCAGA
GCAAAACTGTGTCTCTGTCAAGCTCCTTGACCAAATCCACAATTTTCCCTTGAGTTTCCTTCTCCACGTAATT
GTTGATCTGTTCTTGGCCTCTTCGGTGTCCTCAAAGTTGACAGAGAAGGCTTCTGAGTGGTACAGTTTTTTGA
CATCCTCCAAAAACTTATCCACTACCTTCAGGCTCTTGTTGAGGAACAGGCCGTTGCCGGTGGTCAGCTGGAGC
TGGCTGTCTGGCTTGTGAGGGTATGGAGGAGTTCCTGGAAGCCTTCATGGACCTGAGCCTCCGGAATCTCCGT
GACGTTGAAATTCAGGCCCTCCAGGATTTCACTGTGAGTGTCAGCCTTGGTCCCCAGGGAGAGCATTGCAAAGG
CTGTAGCGATGCTCACTGGGGAGAAGAAGATATTGGTGCTGTTGGACTGGTGTGCCAGCTGGCGGTATAGGCTG
AAGCCGAACTCAGCCAGGCTGGGGGTGATCTTGTTGAGGCTTGGGTGGTCCTGATCATGGTGGGATGTATCCGT
CTTCTGGGCAGCATCTCCCTGGGGATCCTCAGCCAGAGAGCCGGGGAGCAGGCAGCACAGGCCTGCCAGCAGGA
GGACGCCCATGAGACAGAAGATGGCATTGTCGATTCACCGTCCCAGGTCAGTGGTGGTGCCTGAGGCTGAGGA
GACAGAGCCCTGTCCTTGTCCGTATTTAAGCAGTGGGTGCAGAGGGGCAACGGGGAGGCTGCTGGTGAATATT
AACCAAGATCACCCCAGTTACCGGAGGAGCAAACAGGGACTAAGTTCACAGGCTGGGCGCTGAGTCGCCCGCCC
ACGCTGTCCGGACGCTCTGCCTGAGCAGCATACAGCCTCCACTGCACGTACCAAAAGGAGTCATTGTACCTGGC
TCAGAAACCACAGTGTCCTGCGTCCAAGGTGGAGGGGGTGGCGTGAGTCAGCCAGTCGCTGGGAGAGTACCACT
TTGCTGGCCCTCTGCTCTCACTGCAGAATCCTTAGCGGCTGTTCCACTGGTAGCAAGATCTACCATTTACTAAT
TCACCCCGAAATGCCTGATGCTGAAGACTGATGCCGCCCTGGAATTCCTGGCAGCAGCAGTGGCTAGGCCTTCC
TCAGAGTGCTGATCCCCTCCTCCTCCTTTGCTCAGCTCAGTACTCTGAGGGTTGCTGCGTGGAGGCAGTGCACG
CCCTGGGCACAGGGCCCAGTTCCTGCCCACCCAGGAAGTTGGCCTCGGGTGGCGGGTGGCGGAGGCAATAGGTT
GGGGAGGGGCGGGGAGCTTGGGCAGGAAGGGGCCTTGCCCATTGCCAGGCAGACACAAGACTGGGC

Figure 8AA

```
SEQ ID NO:28
Reverse Complement of SEQ ID NO:14
GTTTGCAGTCACACACGCAGGCAGGGACCAGCTCACCCTTCTTTAATGTCATTCAGGGAGGCGGCCAGGGATG
CAGGGGAGGGCTGAGGAGTGACAGGCAGTTATTCTGGGTGGGATTCACCACTTTTCCCATGAAGAGGGGAGA
CTTGGTATTTGTTCAATCATTAAGAAGACAAAGGGTTTGTTGAACTTGACCTCGGGGGGAATAGACATGGGTA
TGGCCTCTAAAAACATGGCCCCAGCAGCTTCAGTCCCTTTCTCATCGATGGTCAGCACAGCCTTATCCATGGCC
TTGGAGAGCTTCAGGGGTGCCTCCTCCGTGATCCCCGAGAGCTCAGCCCCATTGCTGAAGACCTTAGTGATACC
CAGGTGGCCCAGGACTGTCTTCAGATCATAGGTTCCAGTAATGGCCAGTCTGGGTAAATGTAAGTTGGCAGACC
TGCTGTTTCATTTCCAGGAACTTGGTGATGATATCATGGGTGAGTTCATTTTCCAGGTGCTGCAGTTTCCCC
TCATCAGGCAGGAAGAAGATGGCGGTGGCATTGCCCAGGTATTTCATCAGCAGCACTCAGCTGGACAGCTTCTC
ACAGTGGTAGATGTAAACATGCCTAAACGCCTCATCATGGGCACCTTCACGGTGCTCGCCTGGTCCACGTGGA
AGTCCTCTCCCTTGGTGGGCCTCAACGTCAAAGGGTCTCTCCCATTGCCTTTAAAGAAGATGTAATTCACCAGA
GCAAAAACTGTGTCTCTGTCAAGCTCCTTGACCAAATCCACAATTTTCCCTTGAGTTTCCTTCTCCACGTAGTT
GTTGATCTGTTCTTGCCCTCTCGGTGTCCTCAAAGTTGACAGAGAAGGCTTCTGAGTGGTACAGTTTTTCA
CATCCTTCAAAAACTTATCCACTACCTCAGGCTCTTGTTGAGGAACAGGCCGTTGCCGGTGGTCAGCCTGGAGC
TGGCTGTCGGCTGGTTGAGGGTATGGAGGAGTTCCTGGAAGCCTTCATGGACCTGAGGCCTCCGGAATCTCCGT
CACGTTGAAATTCAGGCCCTCCAGGATTTCACTGTGAGTGTCAGCCCTTGGTCCCCAGGGAGAGCTATTGCAAAGG
CTGTAGCGATCCTCACTGGGCAGAAGAAGATATTGGTGCTGTTGGACTGGTGTGCCAGCTGGCCGTATAGGCTG
AAGCCGAACTCAGCCACGCTGCGGGTGATCTTGTTGAGGGTTGGGTGGTCCTGATCATGGTGGGATGTATCCGT
CTTCTGGGCAGCAGCTCCCTGGGGATCCTCAGCCAGAGAGCCGGGGAGCAGGCAGCACAGGCCTGCCAGCAGGA
GGACGCCTCATGAGACAGAAGATGGCATTGTCCTGGAATTCCTGGCAGCAGCAGTGGCTAGGCCTTCCTCAGAG
TGCTGATCCCCTCCTCCTCCTTTGCTCAGCTCAGTACTCTGAGGGTTGCTGGCTGGAGGCAGTGCACGTCCTGG
GCATAGGGCCCAGTTGCTGCCACCCAGGAAGTTGGCCTCGGGTGGCGGGTGGCGGAGGCAATAGGTTGGGGAG
GGGCGGGAGCTTGGGCAGGAAGGGGCCTTGCCCATTGTCAGGTAGACACAAGA
```

SERPINA1 IRNA COMPOSITIONS AND METHODS OF USE THEREOF

RELATED APPLICATIONS

This application is a continuation of U.S. patent application Ser. No. 15/399,820, filed on Jan. 6, 2017, which is a continuation of U.S. patent application Ser. No. 14/284,745, now U.S. Pat. No. 9,574,192, issued on Feb. 21, 2017, which claims the benefit of priority to U.S. Provisional Application No. 61/826,125, filed on May 22, 2013, U.S. Provisional Application No. 61/898,695, filed on Nov. 1, 2013, U.S. Provisional Application No. 61/979,727, filed on Apr. 15, 2014, and U.S. Provisional Application No. 61/989,028, filed on May 6, 2014. This application is related to U.S. Provisional Application No. 61/561,710, filed on Nov. 18, 2011, and PCT/US2012/065601, filed on Nov. 16, 2012. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. Said ASCII copy, created on May 30, 2018, is named 121301_00607_Seq_Listing.txt and is 199,280 bytes in size.

BACKGROUND OF THE INVENTION

Serpina1 encodes alpha-1-antitrypsin which predominantly complexes with and inhibits the activity of neutrophil elastase produced by hepatocytes, mononuclear monocytes, alveolar macrophages, enterocytes, and myeloid cells. Subjects having variations in one or both copies of the Serpina1 gene may suffer from alpha-1-antitrypsin deficiency and are at risk of developing pulmonary emphysema and/or chronic liver disease due to greater than normal elastase activity in the lungs and liver.

In affected subjects, the deficiency in alpha-1-antitrypsin is a deficiency of wild-type, functional alpha-1-antitrypsin. In some cases, a subject having a variation in one or both copies of the Serpina1 gene is carrying a null allele. In other cases, a subject having a variation in one or both copies of the Serpina1 gene is carrying a deficient allele.

For example, a subject having a deficient allele of Serpina1, such as the PIZ allele, may be producing misfolded proteins which cannot be properly transported from the site of synthesis to the site of action within the body. Such subjects are typically at risk of developing lung and/or liver disease. Subjects having a Serpina1 null allele, such as the PINULL (Granite Falls), are typically only at risk of developing lung disease.

Liver disease resulting from alpha-1 antitrypsin deficiency is the result of variant forms of alpha-1-antitrypsin produced in liver cells which misfold and are, thus, not readily transported out of the cells. This leads to a buildup of misfolded protein in the liver cells and can cause one or more diseases or disorders of the liver including, but not limited to, chronic liver disease, liver inflammation, cirrhosis, liver fibrosis, and/or hepatocellular carcinoma.

There are currently very limited options for the treatment of patients with liver disease arising from alpha-1-antitrypsin deficiency, including hepatitis vaccination, supportive care, and avoidance of injurious agents (e.g., alcohol and NSAIDs). Although replacement alpha-1-antitrypsin therapy is available, such treatment has no impact liver disease in these subjects and, although liver transplantation may be effective, it is a difficult, expensive and risky procedure and liver organs are not readily available.

Accordingly, there is a need in the art for effective treatments for Serpina1-associated diseases, such as a chronic liver disease, liver inflammation, cirrhosis, liver fibrosis, and/or hepatocellular carcinoma.

SUMMARY OF THE INVENTION

As described in more detail below, disclosed herein are compositions comprising agents, e.g., single-stranded and double-stranded polynucleotides, e.g., RNAi agents, e.g., double-stranded iRNA agents, targeting Serpina1. Also disclosed are methods using the compositions of the invention for inhibiting Serpina1 expression and for treating Serpina1 associated diseases, e.g., chronic liver disease, liver inflammation, cirrhosis, liver fibrosis, and/or hepatocellular carcinoma.

Accordingly, in one aspect, the present invention provides double stranded RNAi agents for inhibiting expression of Serpina1 in a cell. The double stranded RNAi agents comprise a sense strand and an antisense strand forming a double-stranded region, wherein the sense strand comprises at least 15 contiguous nucleotides differing by no more than 3 nucleotides from any one of the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the antisense strand comprises at least 15 contiguous nucleotides differing by no more than 3 nucleotides from any one of the nucleotide sequences of SEQ ID NO: 15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, wherein substantially all of the nucleotides of the sense strand and substantially all of the nucleotides of the antisense strand are modified nucleotides, and wherein the sense strand is conjugated to a ligand attached at the 3'-terminus.

In one embodiment, one of the 3 nucleotide differences in the nucleotide sequence of the antisense strand is a nucleotide mismatch in the seed region of the antisense strand. In one embodiment, the antisense strand comprises a universal base at the mismatched nucleotide.

In one embodiment, all of the nucleotides of the sense strand and all of the nucleotides of the antisense strand are modified nucleotides.

In one embodiment, the sense strand and the antisense strand comprise a region of complementarity which comprises at least 15 contiguous nucleotides differing by no more than 3 nucleotides from any one of the sequences listed in any one of Tables 1, 2, 5, 7, 8, and 9.

In one embodiment, at least one of the modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, and a terminal nucleotide linked to a cholesteryl derivative or a dodecanoic acid bisdecylamide group.

In one embodiment, at least one strand comprises a 3' overhang of at least 1 nucleotide.

In another embodiment, at least one strand comprises a 3' overhang of at least 2 nucleotides.

In another aspect, the present invention provides RNAi agents, e.g., double-stranded RNAi agents, capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

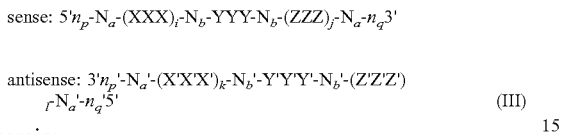

(III)

wherein:

i, j, k, and l are each independently 0 or 1;

p, p', q, and q' are each independently 0-6;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

each $n_p$, $n_p'$, $n_q$, and $n_q'$, each of which may or may not be present, independently represents an overhang nucleotide;

XXX, YYY, ZZZ, X'X'X', Y'Y'Y', and Z'Z'Z' each independently represent one motif of three identical modifications on three consecutive nucleotides;

modifications on $N_b$ differ from the modification on Y and modifications on $N_b'$ differ from the modification on Y'; and wherein the sense strand is conjugated to at least one ligand.

In one embodiment, Na' comprises 1-25 nucleotides, and wherein one of the 1-25 nucleotides at one of positions 2-9 from the 5' end is a nucleotide mismatch. In one embodiment, the mismatched base is a universal base.

In one embodiment, i is 0; j is 0; i is 1; j is 1; both i and j are 0; or both i and j are 1. In another embodiment, k is 0; l is 0; k is 1; l is 1; both k and l are 0; or both k and l are 1.

In one embodiment, XXX is complementary to X'X'X', YYY is complementary to Y'Y'Y', and ZZZ is complementary to Z'Z'Z'.

In one embodiment, YYY motif occurs at or near the cleavage site of the sense strand.

In one embodiment, Y'Y'Y' motif occurs at the 11, 12 and 13 positions of the antisense strand from the 5'-end.

In one embodiment, Y' is 2'-O-methyl.

In one embodiment, formula (III) is represented by formula (IIIa):

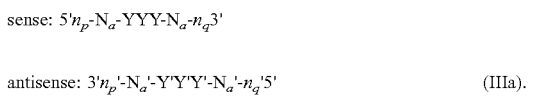

(IIIa).

In another embodiment, formula (III) is represented by formula (IIIb):

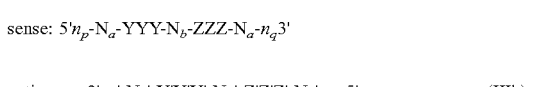

(IIIb)

wherein each $N_b$ and $N_b'$ independently represents an oligonucleotide sequence comprising 1-5 modified nucleotides.

In yet another embodiment, formula (III) is represented by formula (IIIc):

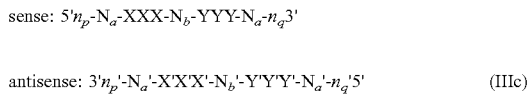

(IIIc)

wherein each $N_b$ and $N_b'$ independently represents an oligonucleotide sequence comprising 1-5 modified nucleotides.

In one embodiment, formula (III) is represented by formula (IIId):

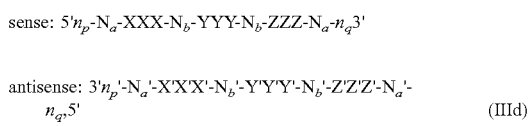

(IIId)

wherein each $N_b$ and $N_b'$ independently represents an oligonucleotide sequence comprising 1-5 modified nucleotides and each $N_a$ and $N_a'$ independently represents an oligonucleotide sequence comprising 2-10 modified nucleotides.

In one embodiment, the double-stranded region is 15-30 nucleotide pairs in length. In another embodiment, the double-stranded region is 17-23 nucleotide pairs in length. In yet another embodiment, the double-stranded region is 17-25 nucleotide pairs in length. In one embodiment, the double-stranded region is 23-27 nucleotide pairs in length. In another embodiment, the double-stranded region is 19-21 nucleotide pairs in length. In another embodiment, the double-stranded region is 21-23 nucleotide pairs in length. In one embodiment, each strand has 15-30 nucleotides. In another embodiment, each strand has 19-30 nucleotides.

In one embodiment, the modifications on the nucleotides are selected from the group consisting of LNA, HNA, CeNA, 2'-methoxyethyl, 2'-O-alkyl, 2'-O-allyl, 2'-C-allyl, 2'-fluoro, 2'-deoxy, 2'-hydroxyl, and combinations thereof. In another embodiment, the modifications on the nucleotides are 2'-O-methyl or 2'-fluoro modifications.

In one embodiment, the ligand is one or more GalNAc derivatives attached through a bivalent or trivalent branched linker. In another embodiment, the ligand is

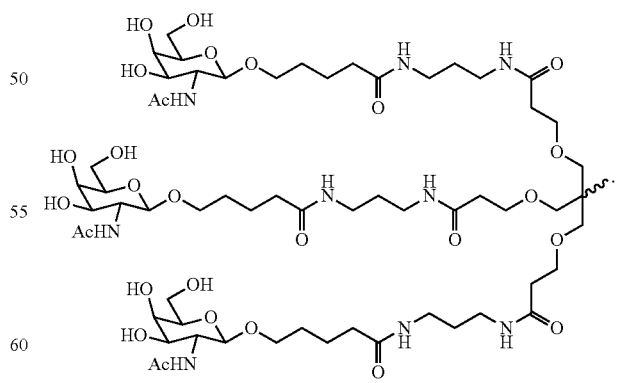

In one embodiment, the ligand is attached to the 3' end of the sense strand.

In one embodiment, the RNAi agent is conjugated to the ligand as shown in the following schematic

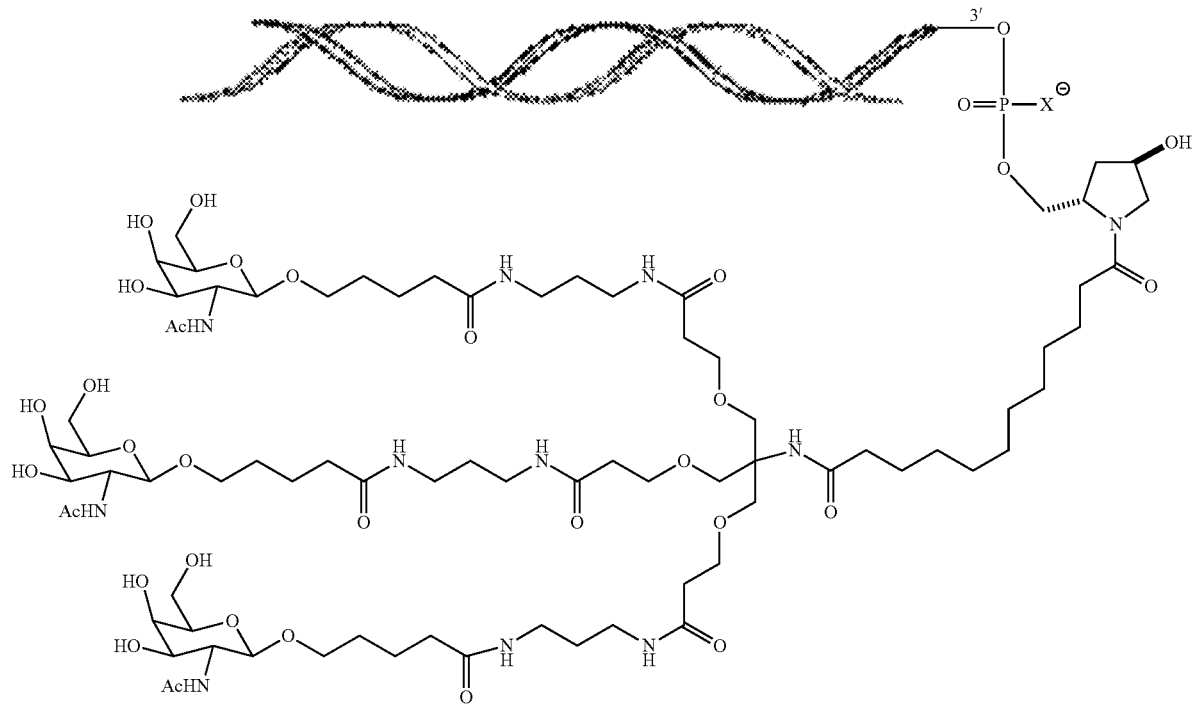

wherein X is O or S. In a specific embodiment, X is O.

In one embodiment, the agent further comprises at least one phosphorothioate or methylphosphonate internucleotide linkage.

In one embodiment, the phosphorothioate or methylphosphonate internucleotide linkage is at the 3'-terminus of one strand. In one embodiment, the strand is the antisense strand. In another embodiment, the strand is the sense strand.

In one embodiment, the phosphorothioate or methylphosphonate internucleotide linkage is at the 5'-terminus of one strand. In one embodiment, the strand is the antisense strand. In another embodiment, the strand is the sense strand.

In one embodiment, the phosphorothioate or methylphosphonate internucleotide linkage is at the both the 5'- and 3'-terminus of one strand. In one embodiment, the strand is the antisense strand.

In one embodiment, the RNAi agent comprises 6-8 phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the base pair at the 1 position of the 5'-end of the antisense strand of the duplex is an AU base pair.

In one embodiment, the Y nucleotides contain a 2'-fluoro modification.

In one embodiment, the Y' nucleotides contain a 2'-O-methyl modification.

In one embodiment, p'>0. In another embodiment, p'=2.

In one embodiment, q'=0, p=0, q=0, and p' overhang nucleotides are complementary to the target mRNA. In another embodiment, q'=0, p=0, q=0, and p' overhang nucleotides are non-complementary to the target mRNA.

In one embodiment, the sense strand has a total of 21 nucleotides and the antisense strand has a total of 23 nucleotides.

In one embodiment, at least one $n_p'$ is linked to a neighboring nucleotide via a phosphorothioate linkage.

In one embodiment, all $n_p'$ are linked to neighboring nucleotides via phosphorothioate linkages.

In one embodiment, the RNAi agent is selected from the group of RNAi agents listed in any one of Tables 1, 2, 5, 7, 8, and 9.

In one embodiment, the RNAi agent is selected from the group consisting of AD-58681, AD-59054, AD-61719, and AD-61444.

In another aspect, the present invention provides double stranded RNAi agent for inhibiting expression of Serpina1 in a cell. The double stranded RNAi agents comprise a sense strand and an antisense strand forming a double stranded region, wherein the sense strand comprises at least 15 contiguous nucleotides differing by no more than 3 nucleotides from any one of the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the antisense strand comprises at least 15 contiguous nucleotides differing by no more than 3 nucleotides from any one of the nucleotide sequences of SEQ ID NO: 15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In one embodiment, one of the 3 nucleotide differences in the nucleotide sequence of the antisense strand is a nucleotide mismatch in the seed region of the antisense strand. In one embodiment, the antisense strand comprises a universal base at the mismatched nucleotide.

In one embodiment, all of the nucleotides of said sense strand and all of the nucleotides of said antisense strand comprise a modification.

In another aspect, the present invention provides RNAi agents, e.g., double stranded RNAi agents, capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

sense: 5' $n_p$-$N_a$-(XXX)$_i$-$N_b$-YYY-$N_b$-(ZZZ)$_j$-$N_a$-$n_q$3' antisense: 3' $n_p$'-$N_a$'-(X'X'X')$_k$-$N_b$'-Y'Y'Y'-$N_b$'-(Z'Z'Z')-$N_a$'-$n_q$'5' (III)

wherein:
i, j, k, and l are each independently 0 or 1;
p, p', q, and q' are each independently 0-6;
each $N_a$ and $N_a$' independently represents an oligonucleotide sequence comprising 0-25 nucleotides which are either modified or unmodified or combinations thereof, each sequence comprising at least two differently modified nucleotides;
each $N_b$ and $N_b$' independently represents an oligonucleotide sequence comprising 0-10 nucleotides which are either modified or unmodified or combinations thereof;
each $n_p$, $n_p$', $n_q$, and $n_q$', each of which may or may not be present independently represents an overhang nucleotide;
XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;
modifications on $N_b$ differ from the modification on Y and modifications on $N_b$' differ from the modification on Y'; and
wherein the sense strand is conjugated to at least one ligand.

In yet another aspect, the present invention provides RNAi agents, e.g., double stranded RNAi agents, capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

sense: 5' $n_p$-$N_a$-(XXX)$_i$-$N_b$-YYY-$N_b$-(ZZZ)$_j$-$N_a$-$n_q$3' antisense: 3' $n_p$'-$N_a$'-(X'X'X')$_k$-$N_b$'-Y'Y'Y'-$N_b$'-(Z'Z'Z')-$N_a$'-$n_q$'5' (III)

wherein:
i, j, k, and l are each independently 0 or 1;
each $n_p$, $n_q$, and $n_q$', each of which may or may not be present, independently represents an overhang nucleotide;

p, q, and q' are each independently 0-6;
$n_p$'>0 and at least one $n_p$' is linked to a neighboring nucleotide via a phosphorothioate linkage;
each $N_a$ and $N_a$' independently represents an oligonucleotide sequence comprising 0-25 nucleotides which are either modified or unmodified or combinations thereof, each sequence comprising at least two differently modified nucleotides;
each $N_b$ and $N_b$' independently represents an oligonucleotide sequence comprising 0-10 nucleotides which are either modified or unmodified or combinations thereof;
XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;
modifications on $N_b$ differ from the modification on Y and modifications on $N_b$' differ from the modification on Y'; and
wherein the sense strand is conjugated to at least one ligand.

In a further aspect, the present invention provides RNAi agents, e.g., double stranded RNAi agents, capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

sense: 5' $n_p$-$N_a$-(XXX)$_i$-$N_b$-YYY-$N_b$-(ZZZ)$_j$-$N_a$-$n_q$3' antisense: 3' $n_p$'-$N_a$'-(X'X'X')$_k$-$N_b$'-Y'Y'Y'-$N_b$'-(Z'Z'Z')-$N_a$'-$n_q$'5' (III)

wherein:
i, j, k, and l are each independently 0 or 1;
each $n_p$, $n_q$, and $n_q$', each of which may or may not be present, independently represents an overhang nucleotide;
p, q, and q' are each independently 0-6;
$n_p$'>0 and at least one $n_p$' is linked to a neighboring nucleotide via a phosphorothioate linkage;
each $N_a$ and $N_a$' independently represents an oligonucleotide sequence comprising 0-25 nucleotides which are either modified or unmodified or combinations thereof, each sequence comprising at least two differently modified nucleotides;
each $N_b$ and $N_b$' independently represents an oligonucleotide sequence comprising 0-10 nucleotides which are either modified or unmodified or combinations thereof; XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;
modifications on $N_b$ differ from the modification on Y and modifications on $N_b$' differ from the modification on Y'; and
wherein the sense strand is conjugated to at least one ligand, wherein the ligand is one or more GalNAc derivatives attached through a bivalent or trivalent branched linker.

In another aspect, the present invention provides RNAi agents, e.g., double stranded RNAi agents capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

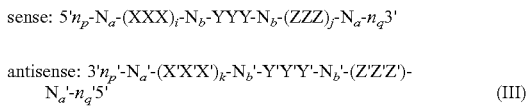

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In yet another aspect, the present invention provides RNAi agents, e.g., double stranded RNAi agents, capable of inhibiting the expression of Serpina1 in a cell, wherein the double stranded RNAi agent comprises a sense strand substantially complementary to an antisense strand, wherein the antisense strand comprises a region substantially complementary to part of an mRNA encoding Serpina1, wherein each strand is about 14 to about 30 nucleotides in length, wherein the double stranded RNAi agent is represented by formula (III):

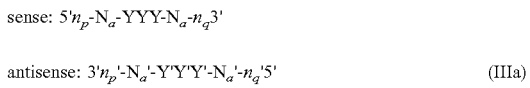

wherein:

each $n_p$, $n_q$, and $n_q'$, each of which may or may not be present, independently represents an overhang nucleotide;

p, q, and q' are each independently 0-6;

$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In one embodiment, Na' comprises 1-25 nucleotides, and wherein one of the 1-25 nucleotides at one of positions 2-9 from the 5' end is a nucleotide mismatch. In one embodiment, the mismatched base is a universal base.

The present invention also provides cells, vectors, host cells, and pharmaceutical compositions comprising the double stranded RNAi agents of the invention.

In one embodiment, the present invention provides RNAi agent selected from the group of RNAi agents listed in any one of Tables 1, 2, 5, 7, 8, and 9.

The present invention also provides a composition comprising a modified antisense polynucleotide agent. The agent is capable of inhibiting the expression of Serpina1 in a cell, and comprises a sequence complementary to a sense sequence selected from the group of the sequences listed in any one of Tables 1, 2, 5, 7, 8, and 9, wherein the polynucleotide is about 14 to about 30 nucleotides in length.

In another aspect, the present invention provides a cell containing the double stranded RNAi agent of the invention.

In some embodiments, the RNAi agent is administered using a pharmaceutical composition.

In preferred embodiments, the RNAi agent is administered in a solution. In some such embodiments, the siRNA is administered in an unbuffered solution. In one embodiment, the siRNA is administered in water. In other embodiments, the siRNA is administered with a buffer solution, such as an acetate buffer, a citrate buffer, a prolamine buffer, a carbonate buffer, or a phosphate buffer or any combination thereof. In some embodiments, the buffer solution is phosphate buffered saline (PBS).

In one embodiment, the pharmaceutical compositions further comprise a lipid formulation. In one aspect, the present invention provides methods of inhibiting Serpina1 expression in a cell. The methods include contacting the cell with an RNAi agent, e.g., a double stranded RNAi agent, composition, vector, or a pharmaceutical composition of the invention; and maintaining the cell produced in step (a) for a time sufficient to obtain degradation of the mRNA transcript of a Serpina1 gene, thereby inhibiting expression of the Serpina1 gene in the cell.

In one embodiment, the cell is within a subject.

In one embodiment, the subject is a human.

In one embodiment, the Serpina1 expression is inhibited by at least about 30% 35%, 40%, 45%, 50%, 55%, 60%, 65%, 70%, 75%, 80%, 85%, 90% or 95%.

In another aspect, the present invention provides methods of treating a subject having a Serpina1 associated disease. The methods include administering to the subject a therapeutically effective amount of an RNAi agent, e.g., a double stranded RNAi agent, composition, vector, or a pharmaceutical composition of the invention, thereby treating the subject.

In another aspect, the present invention provides methods of treating a subject having a Serpina1-associated disorder. The methods include subcutaneously administering to the subject a therapeutically effective amount of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from any one of the nucleotide sequences of SEQ ID NO: 1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the antisense strand comprises at least 15 contiguous nucleotides differing by no more than 3 nucleotides from any one of the nucleotide sequences of SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus and, wherein the sense strand is conjugated to one or more GalNAc derivatives attached through a branched bivalent or trivalent linker at the 3'-terminus, thereby treating the subject.

In one embodiment, one of the 3 nucleotide differences in the nucleotide sequence of the antisense strand is a nucleotide mismatch in the seed region of the antisense strand. In one embodiment, the antisense strand comprises a universal base at the mismatched nucleotide.

In one embodiment, all of the nucleotides of the sense strand and all of the nucleotides of the antisense strand comprise a modification.

In one embodiment, the Serpina1 associated disease is a liver disorder, e.g., chronic liver disease, liver inflammation, cirrhosis, liver fibrosis, and/or hepatocellular carcinoma In one embodiment, the administration of the RNAi agent to the subject results in a decrease in liver cirrhosis, fibrosis and/or Serpina1 protein accumulation in the liver. In another embodiment, the administration of the RNAi agent to the subject results, e.g., further results, in a decrease in lung inflammation.

In one embodiment, the subject is a human.

In one embodiment, the RNAi agent, e.g., double stranded RNAi agent, is administered at a dose of about 0.01 mg/kg to about 10 mg/kg, about 0.5 mg/kg to about 50 mg/kg, about 10 mg/kg to about 30 mg/kg, about 10 mg/kg to about 20 mg/kg, about 15 mg/kg to about 20 mg/kg, about 15 mg/kg to about 25 mg/kg, about 15 mg/kg to about 30 mg/kg, or about 20 mg/kg to about 30 mg/kg.

In one embodiment, the RNAi agent, e.g., double stranded RNAi agent, is administered subcutaneously or intravenously.

In yet another aspect, the present invention provides methods of inhibiting development of hepatocellular carcinoma in a subject having a Serpina1 deficiency variant. The methods include administering to the subject a therapeutically effective amount of an RNAi agent, e.g., a double stranded RNAi agent, composition, vector, or a pharmaceutical composition of the invention, thereby inhibiting the development of hepatocellular carcinoma in the subject.

In another aspect, the present invention provides methods of inhibiting development of hepatocellular carcinoma in a subject having a Serpina1 deficiency variant. The methods include subcutaneously administering to the subject a therapeutically effective amount of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from any one of the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the antisense strand comprises at least 15 contiguous nucleotides differing by no more than 3 nucleotides from any one of the nucleotide sequences of SEQ ID NO: 15, SEQ ID NO: 16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, wherein substantially all of the nucleotides of the sense strand comprise a modification selected from the group consisting of a 2'-O-methyl modification and a 2'-fluoromodification, wherein the sense strand comprises two phosphorothioate internucleotide linkages at the 5'-terminus and, wherein the sense strand is conjugated to one or more GalNAc derivatives attached through a branched bivalent or trivalent linker at the 3'-terminus, thereby inhibiting development of hepatocellular carcinoma in the subject having a Serpina1 deficiency variant.

In one embodiment, one of the 3 nucleotide differences in the nucleotide sequence of the antisense strand is a nucleotide mismatch in the seed region of the antisense strand. In one embodiment, the antisense strand comprises a universal base at the mismatched nucleotide.

In one embodiment, all of the nucleotides of the sense strand and all of the nucleotides of the antisense strand comprise a modification.

In one embodiment, the subject is a primate or rodent. In another embodiment, the subject is a human.

In one embodiment, the RNAi agent, e.g., double stranded RNAi agent, is administered at a dose of about 0.01 mg/kg to about 10 mg/kg or about 0.5 mg/kg to about 50 mg/kg. In another embodiment, the double stranded RNAi agent is administered at a dose of about 10 mg/kg to about 30 mg/kg.

In one embodiment, the RNAi agent, e.g., double stranded RNAi agent, is administered at a dose of about 3 mg/kg. In another embodiment, the double stranded RNAi agent is administered at a dose of about 10 mg/kg. In yet another other embodiment, the double stranded RNAi agent is administered at a dose of about 0.5 mg/kg twice per week. In yet another embodiment, the double stranded RNAi agent is administered at a dose of about 10 mg/kg every other week. In yet another embodiment, the double stranded RNAi agent is administered at a dose of about 0.5 to about 1 mg/kg once per week.

In one embodiment, the RNAi agent, e.g., double stranded RNAi agent, is administered twice per week. In another embodiment, the RNAi agent is administered every other week.

In one embodiment, the RNAi agent, e.g., double stranded RNAi agent, is administered subcutaneously or intravenously.

In another aspect, the present invention provides methods for reducing the accumulation of misfolded Serpina1 in the liver of a subject having a Serpina1 deficiency variant. The methods include administering to the subject a therapeutically effective amount of an RNAi agent, e.g., a double stranded RNAi agent, composition, vector, or a pharmaceutical composition of the invention, thereby reducing the accumulation of misfolded Serpina1 in the liver of the subject.

In another aspect, the present invention provides methods of reducing the accumulation of misfolded Serpina1 in the liver of a subject having a Serpina1 deficiency variant. The methods include subcutaneously administering to the subject a therapeutically effective amount of a double stranded RNAi agent, wherein the double stranded RNAi agent comprises a sense strand and an antisense strand forming a double stranded region, wherein the sense strand comprises at least 15 contiguous nucleotides differing by no more than 3 nucleotides from any one of the nucleotide sequences of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, or SEQ ID NO:11, and the antisense strand comprises at least 15 contiguous nucleotides differing by no more than 3 nucleotides from any one of the nucleotide sequences of SEQ ID NO: 15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, or SEQ ID NO:25, wherein substantially all of the nucleotides of the antisense strand comprise a modification selected from the group consisting of a 2'-O-methyl modification and a 2'-fluoromodification, wherein the antisense strand comprises two phosphorothioate internucleotide linkages at the 5'-terminus and two phosphorothioate internucleotide linkages at the 3'-terminus, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus and, wherein the sense strand is conjugated to one or more GalNAc derivatives attached through a branched bivalent or trivalent linker at the 3'-terminus, thereby reducing the accumulation of misfolded Serpina1 in the liver of the subject having a Serpina1 deficiency variant.

In one embodiment, one of the 3 nucleotide differences in the nucleotide sequence of the antisense strand is a nucleotide mismatch in the seed region of the antisense strand. In one embodiment, the antisense strand comprises a universal base at the mismatched nucleotide.

In one embodiment, all of the nucleotides of the sense strand and all of the nucleotides of the antisense strand comprise a modification.

In one embodiment, the subject is a primate or rodent. In another embodiment, the subject is a human.

In one embodiment, the RNAi agent, e.g., double stranded RNAi agent, is administered at a dose of about 0.01 mg/kg to about 10 mg/kg or about 0.5 mg/kg to about 50 mg/kg. In another embodiment, the double stranded RNAi agent is administered at a dose of about 10 mg/kg to about 30 mg/kg.

In one embodiment, the RNAi agent, e.g., double stranded RNAi agent, is administered subcutaneously or intravenously.

The present invention is further illustrated by the following detailed description and drawings.

BRIEF DESCRIPTION OF THE DRAWINGS

FIG. 2B depicts hAAT mRNA levels in liver normalized to GAPDH for each group. The bars reflect the average and the error bars reflect the standard deviation.

FIG. 3A specifically depicts the efficacy curve showing maximum knock-down of serum hAAT protein levels achieved at different doses of AD-59054 subcutaneously administered to transgenic mice. Each point is an average of three animals and the error bars represent the standard deviation. The duration of knock-down after a single dose of AAT siRNA at 0.3, 1, 3 or 10 mg/kg is shown in FIG. 3B. The hAAT levels were normalized to the average of three prebleeds for each animal. The PBS group serves as the control to reflect the variability in the serum hAAT levels. Each data point is an average of three animals and the error bars reflect the standard deviation. In FIG. 3C, animals were administered AD-59054 at a dose of 0.5 mg/kg twice a week. Each data point is an average relative serum hAAT from four animals and the error bars reflect the standard deviation.

FIG. 4A depicts the study design whereby aged mice with fibrotic livers were dosed subcutaneously once every other week (Q2W) with PBS or 10 mg/kg siRNA duplex AD58681 for 11 doses and sacrificed 7 days after the last dose. FIG. 4B shows liver levels of hAAT mRNA in control and treated groups. FIG. 4C shows liver levels of Colla2 mRNA in control and treated groups. FIG. 4D depicts liver levels of PtPrc mRNA in control and treated groups.

FIG. 5A depicts serum hAAT protein levels after the first dose. FIG. 5B and FIG. 5C depict PAS staining of liver sections from two littermates treated with either PBS or AAT siRNA. The darker colored dots represent the globules or Z-AAT aggregates.

FIG. 8A shows the nucleotide sequence of *Homo sapiens* Serpina1, transcript variant 1 (SEQ ID NO:1); FIG. 8B shows the nucleotide sequence of *Homo sapiens* Serpina1, transcript variant 3 (SEQ ID NO:2); FIG. 8C shows the nucleotide sequence of *Homo sapiens* Serpina1, transcript variant 2 (SEQ ID NO:3); FIG. 8D shows the nucleotide sequence of *Homo sapiens* Serpina1, transcript variant 4 (SEQ ID NO:4); FIG. 8E shows the nucleotide sequence of *Homo sapiens* Serpina1, transcript variant 5 (SEQ ID NO:5); FIG. 8F shows the nucleotide sequence of *Homo sapiens* Serpina1, transcript variant 6 (SEQ ID NO:6); FIG. 8G shows the nucleotide sequence of *Homo sapiens* Serpina1, transcript variant 7 (SEQ ID NO:7); FIG. 8H shows the nucleotide sequence of *Homo sapiens* Serpina1, transcript variant 8 (SEQ ID NO:8); FIG. 8I shows the nucleotide sequence of *Homo sapiens* Serpina1, transcript variant 9 (SEQ ID NO:9); FIG. 8J shows the nucleotide sequence of *Homo sapiens* Serpina1, transcript variant 10 (SEQ ID NO:10); FIG. 8K shows the nucleotide sequence of *Homo sapiens* Serpina1, transcript variant 11 (SEQ ID NO:11); FIG. 8L shows the nucleotide sequence of *Macaca mulatta* Serpina1 (SEQ ID NO:12); FIG. 8M shows the nucleotide sequence of *Macaca mulatta* Serpina1, transcript variant 6

(SEQ ID NO:13); FIG. 8N shows the nucleotide sequence of *Macaca mulatta* Serpina1, transcript variant 4 (SEQ ID NO: 14); FIG. 8O shows the reverse complement of SEQ ID NO:1 (SEQ ID NO:15); FIG. 8P shows the reverse complement of SEQ ID NO:2 (SEQ ID NO:16); FIG. 8Q shows the reverse complement of SEQ ID NO:3 (SEQ ID NO:17); FIG. 8R shows the reverse complement of SEQ ID NO:4 (SEQ ID NO:18); FIG. 8S shows the reverse complement of SEQ ID NO:5 (SEQ ID NO:19); FIG. 8T shows the reverse complement of SEQ ID NO:6 (SEQ ID NO:20); FIG. 8U shows the reverse complement of SEQ ID NO:7 (SEQ ID NO:21); FIG. 8V shows the reverse complement of SEQ ID NO:8 (SEQ ID NO:22); FIG. 8W shows the reverse complement of SEQ ID NO:9 (SEQ ID NO:23); FIG. 8X shows the reverse complement of SEQ ID NO:10 (SEQ ID NO:24); FIG. 8Y shows the reverse complement of SEQ ID NO:11 (SEQ ID NO:25); FIG. 8Z shows the reverse complement of SEQ ID NO:12 (SEQ ID NO:26); FIG. 8AA shows the reverse complement of SEQ ID NO: 13 (SEQ ID NO:27); and FIG. 8AB shows the reverse complement of SEQ ID NO: 14 (SEQ ID NO:28).

DETAILED DESCRIPTION OF THE INVENTION

Figure 1:
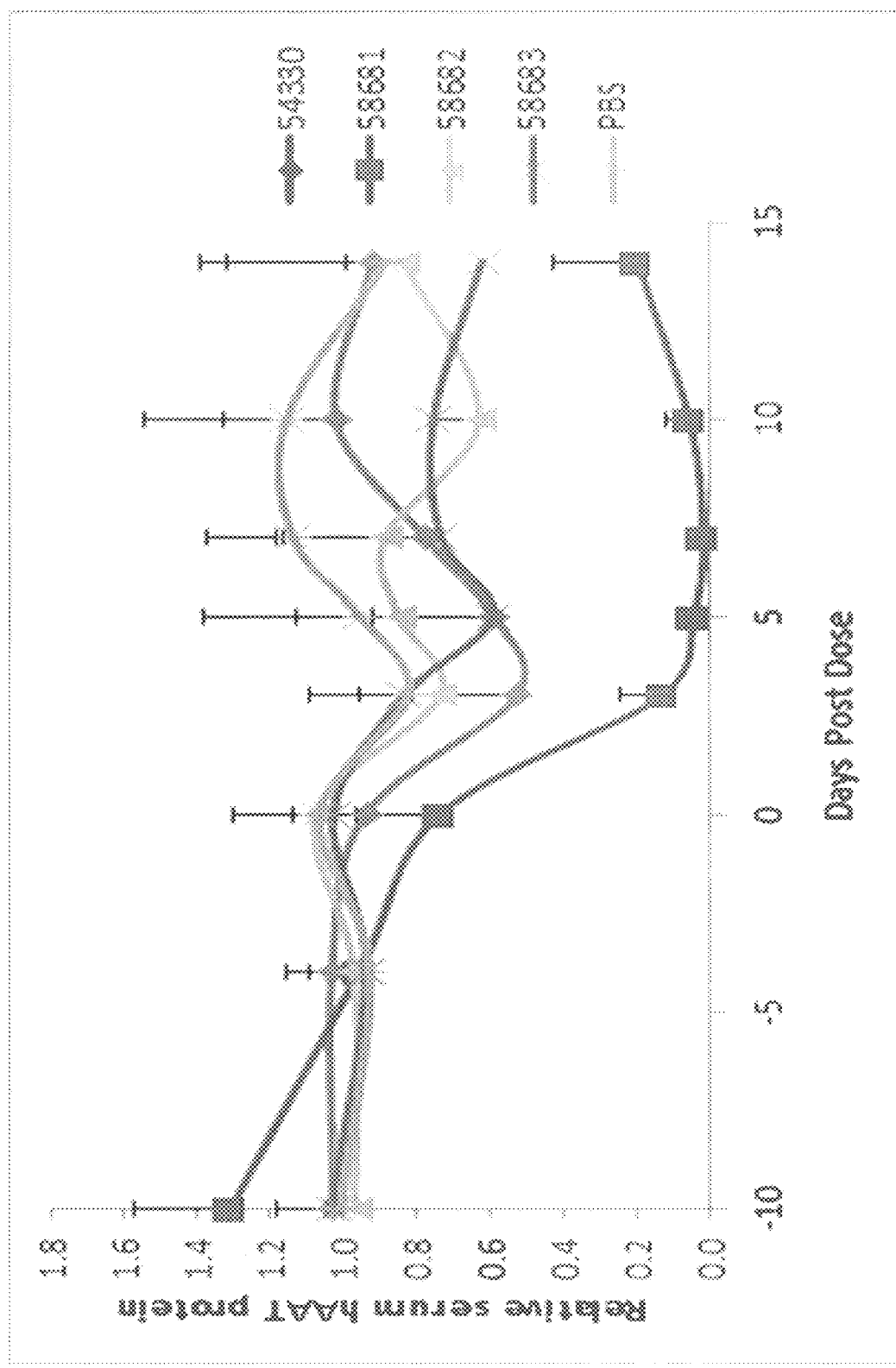
FIG. 1 is a graph depicting the in vivo efficacy and duration of response for the indicated siRNAs in transgenic mice expressing the Z-AAT form of human AAT.

The present invention provides compositions comprising agents, e.g., single-stranded and double-stranded oligonucleotides, e.g., RNAi agents, e.g., double-stranded iRNA agents, targeting Serpina1. Also disclosed are methods using the compositions of the invention for inhibiting Serpina1 expression and for treating Serpina1 associated diseases, such as liver disorders, e.g., chronic liver disease, liver inflammation, cirrhosis, liver fibrosis, and/or hepatocellular carcinoma.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

As used herein, "Serpina1" refers to the serpin peptidase inhibitor, clade A, member 1 gene or protein. Serpina1 is also known as alpha-1-antitrypsin, α-1-antitrypsin, AAT, protease inhibitor 1, PI, PI1, anti-elastase, and antitrypsin.

The term Serpina1 includes human Serpina1, the amino acid and nucleotide sequence of which may be found in, for example, GenBank Accession Nos. GI:189163524 (SEQ ID NO:1), GI:189163525 (SEQ ID NO:2), GI:189163526 (SEQ ID NO:3), GI:189163527 (SEQ ID NO:4), GI:189163529 (SEQ ID NO:5), GI:189163531 (SEQ ID NO:6), GI:189163533 (SEQ ID NO:7), GI:189163535 (SEQ ID NO:8), GI:189163537 (SEQ ID NO:9), GI:189163539 (SEQ ID NO:10), and/or GI:189163541 (SEQ ID NO:11); rhesus Serpina1, the amino acid and nucleotide sequence of which may be found in, for example, GenBank Accession Nos. GI:402766667 (SEQ ID NO:12), GI:297298519 (SEQ ID NO:13), and/or GI: 297298520 (SEQ ID NO:14); mouse Serpina1, the amino acid and nucleotide sequence of which may be found in, for example, GenBank Accession No. GI:357588423 and/or GI:357588426; and rat, the amino acid and nucleotide sequence of which may be found in, for example, GenBank Accession No. GI:77020249. Additional examples of Serpina1 mRNA sequences are readily available using, e.g., GenBank and OMIM.

Over 120 alleles of Serpina1 have been identified and the "M" alleles are considered the wild-type or "normal" allele (e.g., "PIM1-ALA213" (also known as PI, M1A), "PIM1-VAL213" (also known as PI, MIV), "PIM2", "PIM3", and PIM4"). Additional variants may be found in, for example, the A(1)ATVar database (see, e.g., Zaimidou, S., et al. (2009) Hum Mutat. 230(3):308-13 and www.goldenhelix.org/A1ATVar).

As used herein, the term "Serpina1 deficiency allele" refers to a variant allele that produces proteins which do not fold properly and may aggregate intracellularly and are, thus, not properly transported from the site of synthesis in the liver to the site of action within the body.

Exemplary Serpina1 deficiency alleles include, the "Z allele", the "S allele", the "PIM(Malton) allele", and the "PIM(Procida) allele".

As used herein, the terms "Z allele", "PIZ" and "Z-AAT" refer to a variant allele of Serpina1 in which the amino acid at position 342 of the protein is changed from a glutamine to a lysine as a result of the relevant codon being changed from GAG to AAG. A subject homozygous for a Z allele can be referred to as "PIZZ." Z-AAT mutations account for 95% of Serpina1 deficiency patients and are estimated to be present in 100,000 Americans and about 3 million individuals worldwide. The Z allele reaches polymorphic frequencies in Caucasians and is rare or absent in Asians and blacks. The homozygous ZZ phenotype is associated with a high risk of both emphysema and liver disease. Z-AAT protein does not fold correctly in the endoplasmic reticulum, leading to loop-sheet polymers which aggregate and reduce secretion, elicitation of the unfolded protein response, apoptosis, endoplasmic reticulum overload response, autophagy, mitochondrial stress, and altered hepatocyte function.

As used herein, the terms "PIM(Malton)" and "M(Malton)-AAT" refer to a variant allele of Serpina1 in which one of the adjacent phenylalanine residues at position 51 or 52 of the mature protein is deleted. Deletion of this one amino acid shortens one strand of the beta-sheet, B6, preventing normal processing and secretion in the liver which is associated with hepatocyte inclusions and impaired secretion of the protein from the liver.

As used herein, the term "PIS" refers to a variant allele of Serpina1 in which a glutamic acid at position 264 is substituted with valine. Although the majority of this variant protein is degraded intracellularly, there is a high frequency of the PIS allele in the Caucasian population and, thus, compound heterozygotes with a Z or null allele are frequent.

As used herein, "target sequence" refers to a contiguous portion of the nucleotide sequence of an mRNA molecule formed during the transcription of a Serpina1 gene, including mRNA that is a product of RNA processing of a primary transcription product.

As used herein, the term "strand comprising a sequence" refers to an oligonucleotide comprising a chain of nucleotides that is described by the sequence referred to using the standard nucleotide nomenclature.

"G," "C," "A" and "U" each generally stand for a nucleotide that contains guanine, cytosine, adenine, and uracil as a base, respectively. "T" and "dT" are used interchangeably herein and refer to a deoxyribonucleotide wherein the nucleobase is thymine, e.g., deoxyribothymine, 2'-deoxythymidine or thymidine. However, it will be understood that the term "ribonucleotide" or "nucleotide" or "deoxyribonucleotide" can also refer to a modified nucleotide, as further detailed below, or a surrogate replacement moiety. The skilled person is well aware that guanine, cytosine, adenine, and uracil may be replaced by other moieties without substantially altering the base pairing properties of an oligonucleotide comprising a nucleotide bearing such replacement moiety. For example, without limitation, a nucleotide comprising inosine as its base may base pair with nucleotides containing adenine, cytosine, or uracil. Hence, nucleotides containing uracil, guanine, or adenine may be replaced in the nucleotide sequences of the invention by a nucleotide containing, for example, inosine. Sequences comprising such replacement moieties are embodiments of the invention. The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of Serpina1 in a cell, e.g., a cell within a subject, such as a mammalian subject.

In one embodiment, an RNAi agent of the invention includes a single stranded RNA that interacts with a target RNA sequence, e.g., a Serpina1 target mRNA sequence, to direct the cleavage of the target RNA. Without wishing to be bound by theory, it is believed that long double stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188). Thus, in one aspect the invention relates to a single stranded RNA (siRNA) generated within a cell and which promotes the formation of a RISC complex to effect silencing of the target gene, i.e., a Serpina1 gene. Accordingly, the term "siRNA" is also used herein to refer to an RNAi as described above.

In another embodiment, the RNAi agent may be a single-stranded siRNA that is introduced into a cell or organism to inhibit a target mRNA. Single-stranded RNAi agents bind to the RISC endonuclease Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) *Cell* 150: 883-894, the entire contents of each of which are hereby incorporated herein by reference. Any of the antisense nucleotide sequences described herein may be used as a single-stranded siRNA as described herein or as chemically modified by the methods described in Lima et al., (2012) *Cell* 150; 883-894.

In yet another embodiment, the present invention provides single-stranded antisense oligonucleotide molecules targeting Serpina1. A "single-stranded antisense oligonucleotide molecule" is complementary to a sequence within the target mRNA (i.e., Serpina1). Single-stranded antisense oligonucleotide molecules can inhibit translation in a stoichiometric manner by base pairing to the mRNA and physically obstructing the translation machinery, see Dias, N. et al., (2002) *Mol Cancer Ther* 1:347-355. Alternatively, the single-stranded antisense oligonucleotide molecules inhibit a target mRNA by hydridizing to the target and cleaving the target through an RNaseH cleavage event. The single-stranded antisense oligonucleotide molecule may be about 10 to about 30 nucleotides in length and have a sequence that is complementary to a target sequence. For example, the single-stranded antisense oligonucleotide molecule may comprise a sequence that is at least about 10, 11, 12, 13, 14, 15, 16, 17, 18, 19, 20, or more contiguous nucleotides from any one of the antisense nucleotide sequences described herein, e.g., the sequences provided in any one of Tables, 1, 2, 5, 7, 8, or 9 or bind any of the target sites described herein. The single-stranded antisense oligonucleotide molecules may comprise modified RNA, DNA, or a combination thereof.

In another embodiment, an "iRNA" for use in the compositions, uses, and methods of the invention is a double-stranded RNA and is referred to herein as a "double stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., a Serpina1 gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi agent may comprise one or more nucleotide overhangs.

In one embodiment, an RNAi agent of the invention is a dsRNA of 24-30 nucleotides that interacts with a target RNA sequence, e.g., a Serpina1 target mRNA sequence, to direct the cleavage of the target RNA. Without wishing to be bound by theory, long double stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188).

As used herein, a "nucleotide overhang" refers to the unpaired nucleotide or nucleotides that protrude from the duplex structure of an RNAi agent when a 3'-end of one strand of the RNAi agent extends beyond the 5'-end of the other strand, or vice versa. "Blunt" or "blunt end" means that there are no unpaired nucleotides at that end of the double stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" refers to the strand of a double stranded RNAi agent which includes a region that is substantially complementary to a target sequence (e.g., a human Serpina1 mRNA). As used herein, the term "region complementary to part of an mRNA encoding Serpina1" refers to a region on the antisense strand that is substantially complementary to part of a Serpina1 mRNA sequence. Where the region of complementarity is not fully complementary to the target sequence, the mismatches are most tolerated in the terminal regions and, if present, are generally in a terminal region or regions, e.g., within 8, 7, 6, 5, 4, 3, or 2 nucleotides of the 5' and/or 3' terminus.

As demonstrated in the working examples below, it has been surpringly discovered that a single nucleotide mismatch in the seed region of the antisense strand of the RNAi agents disclosed herein was tolerated for all bases except C. The "seed region" is the region in the antisense strand of an RNAi agent responsible for recognition of the target mRNA and corresponds to, for example, nucleotides 2-8 from the 5' end of the antisense strand. After the seed region anneals, Argonaute then subjects complementary mRNA sequences 10 nucleotides from the 5' end of the incorporated antisense strand to nucleolytic degradation, resulting in the cleavage of the target mRNA. Accordingly, in one embodiment, the antisense strand of an RNAi agent of the invention comprises a one nucleotide mismatch in the seed region of the antisense strand, e.g., a mismatch at any one of positions 2-8 from the 5'-end of the antisense strand.

The term "sense strand," as used herein, refers to the strand of a dsRNA that includes a region that is substantially complementary to a region of the antisense strand.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12 and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions may include: 400 mM NaCl, 40 mM PIPES pH 6.4, 1 mM EDTA, 50° C. or 70° C. for 12-16 hours followed by washing. Other conditions, such as physiologically relevant conditions as may be encountered inside an organism, can apply. For example, a complementary sequence is sufficient to allow the relevant function of the nucleic acid to proceed, e.g., RNAi. The skilled person will be able to determine the set of conditions most appropriate for a test of complementarity of two sequences in accordance with the ultimate application of the hybridized nucleotides.

Sequences can be "fully complementary" with respect to each when there is base-pairing of the nucleotides of the first nucleotide sequence with the nucleotides of the second nucleotide sequence over the entire length of the first and second nucleotide sequences. However, where a first sequence is referred to as "substantially complementary" with respect to a second sequence herein, the two sequences can be fully complementary, or they may form one or more, but generally not more than 4, 3 or 2 mismatched base pairs upon hybridization, while retaining the ability to hybridize under the conditions most relevant to their ultimate application. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, may yet be referred to as "fully complementary" for the purposes described herein.

"Complementary" sequences, as used herein, may also include, or be formed entirely from, non-Watson-Crick base pairs and/or base pairs formed from non-natural and modified nucleotides, in as far as the above requirements with respect to their ability to hybridize are fulfilled. Such non-Watson-Crick base pairs includes, but not limited to, G:U Wobble or Hoogstein base pairing.

The terms "complementary," "fully complementary" and "substantially complementary" herein may be used with respect to the base matching between the sense strand and the antisense strand of a dsRNA, or between the antisense strand of a dsRNA and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding Serpina1) including a 5' UTR, an open reading frame (ORF), or a 3' UTR. For example, a polynucleotide is complementary to at least a part of a Serpina1 mRNA if the sequence is substantially complementary to a non-interrupted portion of an mRNA encoding Serpina1.

The term "inhibiting," as used herein, is used interchangeably with "reducing," "silencing," "downregulating," "suppressing" and other similar terms, and includes any level of inhibition.

The phrase "inhibiting expression of a Serpina1," as used herein, includes inhibition of expression of any Serpina1 gene (such as, e.g., a mouse Serpina1 gene, a rat Serpina1 gene, a monkey Serpina1 gene, or a human Serpina1 gene) as well as variants, (e.g., naturally occurring variants), or mutants of a Serpina1 gene. Thus, the Serpina1 gene may be a wild-type Serpina1 gene, a variant Serpina1 gene, a mutant Serpina1 gene, or a transgenic Serpina1 gene in the context of a genetically manipulated cell, group of cells, or organism.

"Inhibiting expression of a Serpina1 gene" includes any level of inhibition of a Serpina1 gene, e.g., at least partial suppression of the expression of a Serpina1 gene, such as an inhibition of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

The expression of a Serpina1 gene may be assessed based on the level of any variable associated with Serpina1 gene expression, e.g., Serpina1 mRNA level, Serpina1 protein level, or serum AAT levels. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

The phrase "contacting a cell with a double stranded RNAi agent," as used herein, includes contacting a cell by any possible means. Contacting a cell with a double stranded RNAi agent includes contacting a cell in vitro with the RNAi agent or contacting a cell in vivo with the RNAi agent. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, the bloodstream or the subcutaneous space, such that the agent will subsequently reach the tissue where the cell to be contacted is located. For example, the RNAi agent may contain and/or be coupled to a ligand, e.g., a GalNAc3 ligand, that directs the RNAi agent to a site of interest, e.g., the liver. Combinations of in vitro and in vivo methods of contacting are also possible. In connection with the methods of the invention, a cell might also be contacted in vitro with an RNAi agent and subsequently transplanted into a subject.

A "patient" or "subject," as used herein, is intended to include either a human or non-human animal, preferably a mammal, e.g., a monkey. Most preferably, the subject or patient is a human.

A "Serpina1 associated disease," as used herein, is intended to include any disease, disorder, or condition associated with the Serpina1 gene or protein. Such a disease may be caused, for example, by misfolding of a Serpina1 protein, intracellular accumulation of Serpina1 protein (e.g., misfolded Serpina1 protein), excess production of the Serpina1 protein, by Serpina1 gene variants, Serpina1 gene mutations, by abnormal cleavage of the Serpina1 protein, by abnormal interactions between Serpina1 and other proteins or other endogenous or exogenous substances. A Serpina1 associated disease may be a liver disease and/or a lung disease.

A "liver disease", as used herein, includes a disease, disorder, or condition affecting the liver and/or its function. A liver disorder can be the result of accumulation of Serpina1 protein in the liver and/or liver cells. Examples of liver disorders include liver disorders resulting from, viral infections, parasitic infections, genetic predisposition, autoimmune diseases, exposure to radiation, exposure to hepatotoxic compounds, mechanical injuries, various environmental toxins, alcohol, acetaminophen, a combination of alcohol and acetaminophen, inhalation anesthetics, niacin, chemotherapeutics, antibiotics, analgesics, antiemetics and the herbal supplement kava, and combinations thereof.

For example, a liver disorder associated with Serpina1 deficiency may occur more often in subjects with one or more copies of certain alleles (e.g., the PIZ, PiM(Malton), and/or PIS alleles). Without wishing to be bound by theory, it is thought that alleles associated with a greater risk of developing an alpha-1 anti-trypsin liver disease encode forms of Serpina1 which are subject to misfolding and are not properly secreted from the hepatocytes. The cellular responses to these misfolded proteins can include the unfolded protein response (UPR), endoplasmic reticulum-associated degradation (ERAD), apoptosis, ER overload response, autophagy, mitochondrial stress and altered hepatocyte function. The injuries to the hepatocytes can lead to symptoms such as, but not limited to, inflammation, cholestosis, fibrosis, cirrhosis, prolonged obstructive jaundice, increased transaminases, portal hypertension and/or hepatocellular carcinoma. Without wishing to be bound by theory, the highly variable clinical course of this disease is suggestive of modifiers or "second hits" as contributors to developing symptoms or progressing in severity.

For example, subjects with a PIZ allele can be more sensitive to Hepatitis C infections or alcohol abuse and more likely to develop a liver disorder if exposed to such factors. Additionally cystic fibrosis (CF) subjects carrying the PIZ allele are at greater risk of developing severe liver disease with portal hypertension. A deficiency of Serpina1 can also cause or contribute to the development of early onset emphysema, necrotizing panniculitis, bronchiectasis, and/or prolonged neonatal jaundice. Some patients having or at risk of having a deficiency of alpha-1-antitrypsin are identified by screening when they have family members affected by an alpha-1-antitrypsin deficiency.

Exemplary liver disorders include, but are not limited to, liver inflammation, chronic liver disease, cirrhosis, liver fibrosis, hepatocellular carcinoma, liver necrosis, steatosis, cholestatis and/or reduction and/or loss of hepatocyte function.

"Cirrhosis" is a pathological condition associated with chronic liver damage that includes extensive fibrosis and regenerative nodules in the liver.

"Fibrosis" is the proliferation of fibroblasts and the formation of scar tissue in the liver.

The phrase "liver function" refers to one or more of the many physiological functions performed by the liver. Such functions include, but are not limited to, regulating blood sugar levels, endocrine regulation, enzyme systems, interconversion of metabolites (e.g., ketone bodies, sterols and steroids and amino acids); manufacturing blood proteins such as fibrinogen, serum albumin, and cholinesterase, erythropoietic function, detoxification, bile formation, and vitamin storage. Several tests to examine liver function are known in the art, including, for example, measuring alanine amino transferase (ALT), alkaline phosphatase, bilirubin, prothrombin, and albumin.

"Therapeutically effective amount," as used herein, is intended to include the amount of an RNAi agent that, when administered to a patient for treating a Serpina1-associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, stage of pathological processes mediated by Serpina1 expression, the types of preceding or concomitant treatments, if any, and other individual characteristics of the patient to be treated.

"Prophylactically effective amount," as used herein, is intended to include the amount of an RNAi agent that, when administered to a subject who does not yet experience or display symptoms of an Serpina1-associated disease, but who may be predisposed to the disease, is sufficient to prevent or ameliorate the disease or one or more symptoms of the disease.

Ameliorating the disease includes slowing the course of the disease or reducing the severity of later-developing disease. The "prophylactically effective amount" may vary depending on the RNAi agent, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. RNAi gents employed in the methods of the present invention may be administered in a sufficient amount to produce a reasonable benefit/risk ratio applicable to such treatment.

The term "sample," as used herein, includes a collection of similar fluids, cells, or tissues isolated from a subject, as well as fluids, cells, or tissues present within a subject. Examples of biological fluids include blood, serum and serosal fluids, plasma, urine, lymph, cerebrospinal fluid, ocular fluids, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue (or subcomponents thereof) derived from the subject.

II. iRNAs of the Invention

Described herein are improved double-stranded RNAi agents which inhibit the expression of a Serpina1 gene in a cell, such as a cell within a subject, e.g., a mammal, such as a human having a Serpina1 associated disease, e.g., a liver disease, e.g., chronic liver disease, liver inflammation, cirrhosis, liver fibrosis, and/or hepatocellular carcinoma.

Accordingly, the invention provides double-stranded RNAi agents with chemical modifications capable of inhibiting the expression of a target gene (i.e., a Serpina1 gene) in vivo.

In certain aspects of the invention, substantially all of the nucleotides of an iRNA of the invention are modified. In other embodiments of the invention, all of the nucleotides of an iRNA of the invention are modified. iRNAs of the invention in which "substantially all of the nucleotides are modified" are largely but not wholly modified and can include not more than 5, 4, 3, 2, or 1 unmodified nucleotides.

The RNAi agent comprises a sense strand and an antisense strand. Each strand of the RNAi agent may range from 12-30 nucleotides in length. For example, each strand may be between 14-30 nucleotides in length, 17-30 nucleotides in length, 19-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-O-methyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

Any of the nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289; 5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., *Science*, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N(CH$_3$)—CH$_2$—CH$_2$—[wherein the native phosphodiester backbone is represented as —O—P—O—CH$_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted C$_1$ to C$_{10}$ alkyl or C$_2$ to C$_{10}$ alkenyl and alkynyl. Exemplary suitable modifications include O[(CH$_2$)$_n$O]$_m$CH$_3$, O(CH$_2$)$_n$OCH$_3$, O(CH$_2$)$_n$NH$_2$, O(CH$_2$)$_n$CH$_3$, O(CH$_2$)$_n$ONH$_2$, and O(CH$_2$)$_n$ON[(CH$_2$)$_n$CH$_3$)]$_2$, where n and m are from 1 to about 10. In other embodiments, dsRNAs include one of the following at the 2' position: C$_1$ to C$_{10}$ lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—CH$_2$CH$_2$OCH$_3$, also known as 2'-O-(2-methoxyethyl) or 2'-MOE) (Martin et al., *Helv. Chim. Acta*, 1995, 78:486-504) i.e., an alkoxy-alkoxy group. Another exemplary modification is 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—CH$_2$—O—CH$_2$—N(CH$_2$)$_2$.

Other modifications include 2'-methoxy (2'-OCH$_3$), 2'-aminopropoxy (2'-OCH$_2$CH$_2$CH$_2$NH$_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

Representative U.S. Patents that teach the preparation of locked nucleic acid nucleotides include, but are not limited to, the following: U.S. Pat. Nos. 6,268,490; 6,670,461; 6,794,499; 6,998,484; 7,053,207; 7,084,125; and 7,399,845, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

A. Modified iRNAs Comprising Motifs of the Invention

In certain aspects of the invention, the double-stranded RNAi agents of the invention include agents with chemical modifications as disclosed, for example, in U.S. Provisional Application No. 61/561,710, filed on Nov. 18, 2011, or in PCT/US2012/065691, filed on Nov. 16, 2012, the entire contents of each of which are incorporated herein by reference.

As shown herein and in Provisional Application No. 61/561,710, a superior result may be obtained by introducing one or more motifs of three identical modifications on three consecutive nucleotides into a sense strand and/or antisense strand of a RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are modified to have one or more motifs of three identical modifications on three consecutive nucleotides at or near the cleavage site of at least one strand of an RNAi agent, the gene silencing activity of the RNAi agent was superiorly enhanced.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5' end. The antisense strand contains at least one motif of three 2'-O-methyl modifications on three consecutive nucleotides at positions 11, 12, 13 from the 5' end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5' end. The antisense strand contains at least one motif of three 2'-O-methyl modifications on three consecutive nucleotides at positions 11, 12, 13 from the 5' end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5' end. The antisense strand contains at least one motif of three 2'-O-methyl modifications on three consecutive nucleotides at positions 11, 12, 13 from the 5' end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5' end; the antisense strand contains at least one motif of three 2'-O-methyl modifications on three consecutive nucleotides at positions 11, 12, 13 from the 5' end, wherein one end of the RNAi agent is blunt, while the other end comprises a 2 nucleotide overhang. Preferably, the 2 nucleotide overhang is at the 3'-end of the antisense strand. When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotides in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand.

A modification may occur in a double strand region, a single strand region, or in both. A modification may occur only in the double strand region of an RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAA-BAAABAAAB . . . ," "AAABBBAAABBB . . . ," or "ABCABCABCABC . . . ," etc.

The type of modifications contained in the alternating motif may be the same or different.

For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisense strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " ... $N_a$YYY$N_b$ ... ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5' end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. A "mismatch" may be non-canonical base pairing or other than canonical pairing of nucleotides. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings. A "universal base" is a base that exhibits the ability to replace any of the four normal bases (G, C, A, and U) without significantly destabilizing neighboring base-pair interactions or disrupting the expected functional biochemical utility of the modified oligonucleotide. Non-limiting examples of universal bases include 2'-deoxyinosine (hypoxanthine deoxynucleotide) or its derivatives, nitroazole analogues, and hydrophobic aromatic non-hydrogen-bonding bases.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

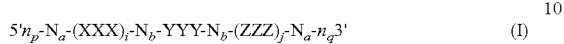   (I)

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;
each $N_b$ independently represents an oligonucleotide sequence comprising 0-10 modified nucleotides;
each $n_p$ and $n_q$ independently represent an overhang nucleotide;
wherein $N_b$ and Y do not have the same modification; and
XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand.

For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the 1$^{st}$ nucleotide, from the 5'-end; or optionally, the count starting at the 1$^{st}$ paired nucleotide within the duplex region, from the 5'-end.

In one embodiment, i is 1 and j is 0, or i is 0 and j is 1, or both i and j are 1. The sense strand can therefore be represented by the following formulas:

   (Ib);

   (Ic); or

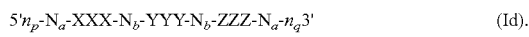   (Id).

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides.

Each of X, Y and Z may be the same or different from each other.

In other embodiments, i is 0 and j is 0, and the sense strand may be represented by the formula:

   (Ia).

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

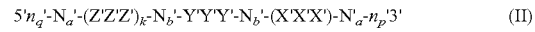   (II)

wherein:
k and l are each independently 0 or 1;
p' and q' are each independently 0-6;
each $N_a'$ independently represents an oligonucleotide sequence comprising 0-25 modified nucleotides, each sequence comprising at least two differently modified nucleotides;
each $N_b'$ independently represents an oligonucleotide sequence comprising 0-10 modified nucleotides;
each $n_p'$ and $n_q'$ independently represent an overhang nucleotide;
wherein $N_b'$ and Y' do not have the same modification; and
X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23 nucleotide in length, the Y'Y'Y' motif can occur at positions 9, 10, 11; 10, 11, 12; 11, 12, 13; 12, 13, 14; or 13, 14, 15 of the antisense strand, with the count starting from the 1$^{st}$ nucleotide, from the 5'-end; or optionally, the count starting at the 1$^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

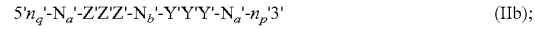   (IIb);

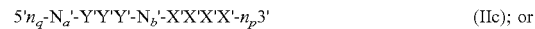   (IIc); or

   (IId).

When the antisense strand is represented by formula (IIb), $N_b$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

   (Ia).

When the antisense strand is represented as formula (IIa), each $N_a'$ independently represents an oligonucleotide sequence comprising 2-20, 2-15, or 2-10 modified nucleotides.

Each of X', Y' and Z' may be the same or different from each other.

Each nucleotide of the sense strand and antisense strand may be independently modified with LNA, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y' and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

sense: 5'$n_p$-$N_a$-(XXX)$_i$-$N_b$-YYY-$N_b$-(ZZZ)$_j$-$N_a$-$n_q$3' antisense: 3'$n_p'$-$N_a'$-(X'X'X')$_k$-$N_b$-Y'Y'Y'-$N_b$-(Z'Z'Z')$_l$-$N_a'$-$n_q'$5'    (III)

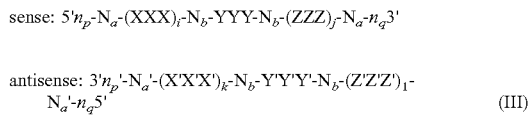

wherein:
i, j, k, and l are each independently 0 or 1;
p, p', q, and q' are each independently 0-6;
each $N_a$ and $N_a'$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein
each $n_p'$, $n_p$, $n_q'$, and $n_q$, each of which may or may not be present, independently represents an overhang nucleotide; and
XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and l is 0; or k is 1 and l is 0; k is 0 and l is 1; or both k and l are 0; or both k and l are 1.

Exemplary combinations of the sense strand and antisense strand forming a RNAi duplex include the formulas below:

5'$n_p$-$N_a$-YYY-$N_a$-$n_q$3'

3'$n_p'$-$N_a$-Y'Y'Y'-$N_a'$$n_q'$5'    (IIIa)

5'$n_p$-$N_a$-YYY-$N_b$-ZZZ-$N_a$-$n_q$3'

3'$n_p'$-$N_a'$-Y'Y'Y'-$N_b$-Z'Z'Z'-$N_a'$$n_q'$5'    (IIIb)

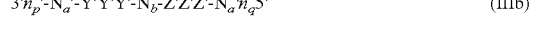

5'$n_p$-$N_a$-XXX-$N_b$YYY-$N_a$$n_q$3'

3'$n_p'$-$N_a'$-X'X'X'-$N_b$-Y'Y'Y'-$N_a'$-$n_q'$5'    (IIIc)

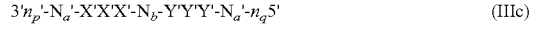

5'$n$-$N_a$-XXX-$N_b$-YYY-$N_b$-ZZZ-$N_a$-$n_q$3'

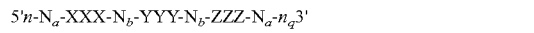

3'$n_p'$-$N_a'$-X'X'X'-$N_b$-Y'Y'Y'-$N_b$-Z'Z'Z'-$N_a$-$n_q$5'    (IIId)

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a$ independently represents an oligonucleotide sequence comprising 2-20, 2-15, or 2-10 modified nucleotides. Each of $N_a$, $N_a'$, $N_b$ and $N_b'$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker. In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

The RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is an agent selected from the group of agents listed in any one of Tables 1, 2, 5, and 7.

These agents may further comprise a ligand.

A. Ligands

The double-stranded RNA (dsRNA) agents of the invention may optionally be conjugated to one or more ligands. The ligand can be attached to the sense strand, antisense strand or both strands, at the 3'-end, 5'-end or both ends. For instance, the ligand may be conjugated to the sense strand. In preferred embodiments, the ligand is conjugated to the 3'-end of the sense strand. In one preferred embodiment, the ligand is a GalNAc ligand. In particularly preferred embodiments, the ligand is GalNAc$_3$:

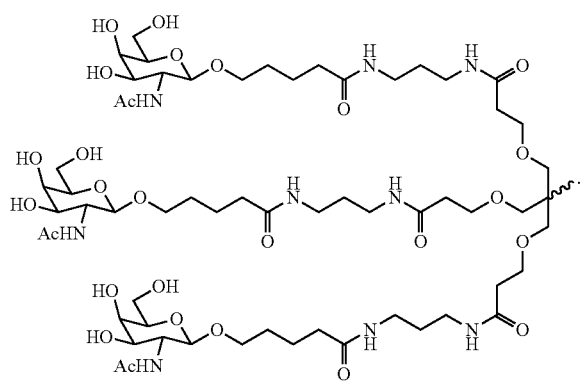 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

In some embodiments, the ligand, e.g., GalNAc ligand, is attached to the 3' end of the RNAi agent. In one embodiment, the RNAi agent is conjugated to the ligand, e.g., GalNAc ligand, as shown in the following schematic

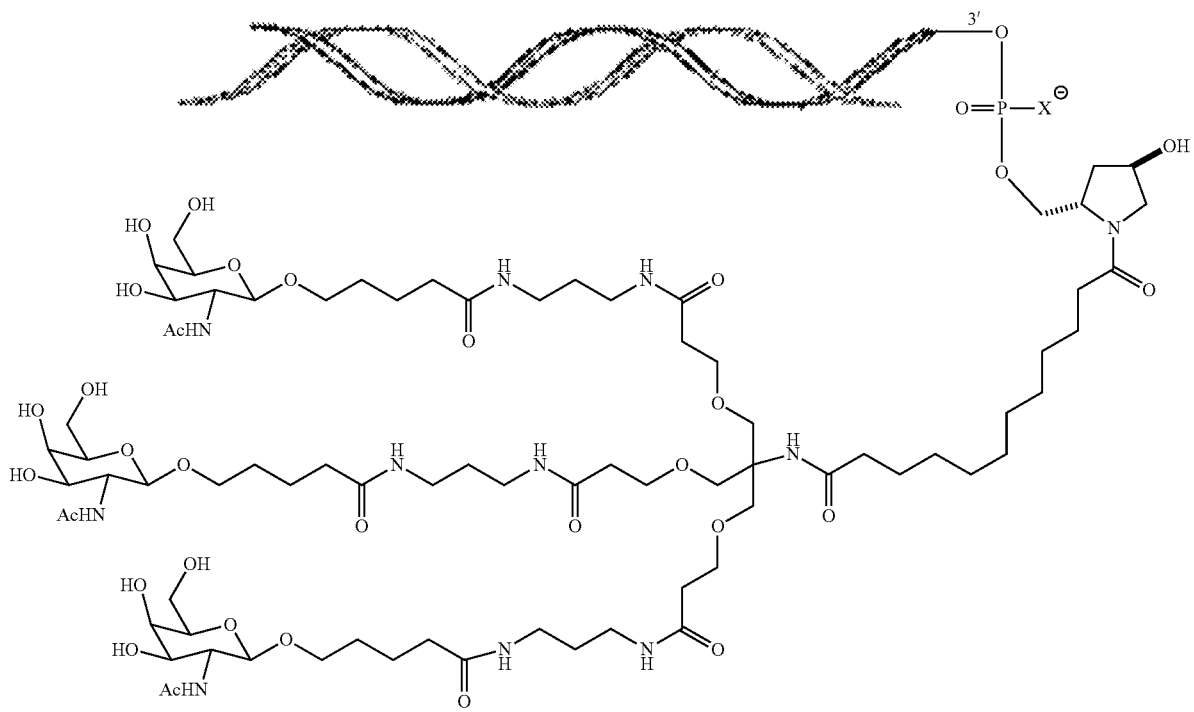

wherein X is O or S. In one embodiment, X is O.

A wide variety of entities can be coupled to the RNAi agents of the present invention.

Preferred moieties are ligands, which are coupled, preferably covalently, either directly or indirectly via an intervening tether.

In preferred embodiments, a ligand alters the distribution, targeting or lifetime of the molecule into which it is incorporated. In preferred embodiments a ligand provides an enhanced affinity for a selected target, e.g., molecule, cell or cell type, compartment, receptor e.g., a cellular or organ compartment, tissue, organ or region of the body, as, e.g., compared to a species absent such a ligand. Ligands providing enhanced affinity for a selected target are also termed targeting ligands.

Some ligands can have endosomolytic properties. The endosomolytic ligands promote the lysis of the endosome and/or transport of the composition of the invention, or its components, from the endosome to the cytoplasm of the cell. The endosomolytic ligand may be a polyanionic peptide or peptidomimetic which shows pH-dependent membrane activity and fusogenicity. In one embodiment, the endosomolytic ligand assumes its active conformation at endosomal pH.

The "active" conformation is that conformation in which the endosomolytic ligand promotes lysis of the endosome and/or transport of the composition of the invention, or its components, from the endosome to the cytoplasm of the cell. Exemplary endosomolytic ligands include the GALA peptide (Subbarao et al., *Biochemistry*, 1987, 26: 2964-2972), the EALA peptide (Vogel et al., *J. Am. Chem. Soc.*, 1996, 118: 1581-1586), and their derivatives (Turk et al., *Biochem. Biophys. Acta*, 2002, 1559: 56-68). In one embodiment, the endosomolytic component may contain a chemical group (e.g., an amino acid) which will undergo a change in charge or protonation in response to a change in pH. The endosomolytic component may be linear or branched.

Ligands can improve transport, hybridization, and specificity properties and may also improve nuclease resistance of the resultant natural or modified oligoribonucleotide, or a polymeric molecule comprising any combination of monomers described herein and/or natural or modified ribonucleotides.

Ligands in general can include therapeutic modifiers, e.g., for enhancing uptake; diagnostic compounds or reporter groups e.g., for monitoring distribution; cross-linking agents; and nuclease-resistance conferring moieties. General examples include lipids, steroids, vitamins, sugars, proteins, peptides, polyamines, and peptide mimics.

Ligands can include a naturally occurring substance, such as a protein (e.g., human serum albumin (HSA), low-density lipoprotein (LDL), high-density lipoprotein (HDL), or globulin); a carbohydrate (e.g., a dextran, pullulan, chitin, chitosan, inulin, cyclodextrin or hyaluronic acid); or a lipid. The ligand may also be a recombinant or synthetic molecule, such as a synthetic polymer, e.g., a synthetic polyamino acid, an oligonucleotide (e.g., an aptamer). Examples of polyamino acids include polyamino acid is a polylysine (PLL), poly L-aspartic acid, poly L-glutamic acid, styrenemaleic acid anhydride copolymer, poly(L-lactide-co-glycolide) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacrylic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-glucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, biotin, an RGD peptide, an RGD peptide mimetic or an aptamer.

Other examples of ligands include dyes, intercalating agents (e.g., acridines), cross-linkers (e.g., psoralene, mitomycin C), porphyrins (TPPC4, texaphyrin, Sapphyrin), polycyclic aromatic hydrocarbons (e.g., phenazine, dihydrophenazine), artificial endonucleases or a chelator (e.g., EDTA), lipophilic molecules, e.g., cholesterol, cholic acid, adamantane acetic acid, 1-pyrene butyric acid, dihydrotestosterone, 1,3-Bis-O(hexadecyl)glycerol, geranyloxyhexyl group, hexadecylglycerol, borneol, menthol, 1,3-propanediol, heptadecyl group, palmitic acid, myristic acid, O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a cancer cell, endothelial cell, or bone cell. Ligands may also include hormones and hormone receptors. They can also include non-peptidic species, such as lipids, lectins, carbohydrates, vitamins, cofactors, multivalent lactose, multivalent galactose, N-acetyl-galactosamine, N-acetyl-glucosamine multivalent mannose, multivalent fucose, or aptamers. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, jasplakinolide, latrunculin A, phalloidin, swinholide A, indanocine, or myoservin.

The ligand can increase the uptake of the oligonucleotide into the cell by, for example, activating an inflammatory response. Exemplary ligands that would have such an effect include tumor necrosis factor alpha (TNFalpha), interleukin-1 beta, or gamma interferon.

In one aspect, the ligand is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to modulate, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells.

Exemplary vitamins include vitamin A, E, and K. Other exemplary vitamins include B vitamins, e.g., folic acid, B12, riboflavin, biotin, pyridoxal or other vitamins or nutrients taken up by cancer cells. Also included are HAS, low density lipoprotein (LDL) and high-density lipoprotein (HDL).

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The peptide or peptidomimetic moiety can be about 5-50 amino acids long, e.g., about 5, 10, 15, 20, 25, 30, 35, 40, 45, or 50 amino acids long. A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVL-LALLAP (SEQ ID NO:29). An RFGF analogue (e.g., amino acid sequence AALLPVLLAAP (SEQ ID NO:30)) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ; SEQ ID NO:31) and the *Drosophila* Antennapedia protein (RQIKIWFQNRRMKWKK; SEQ ID NO:32) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., *Nature,* 354:82-84, 1991). Preferably the peptide or peptidomimetic tethered to an iRNA agent via an incorporated monomer unit is a cell targeting peptide such as an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized. An RGD peptide moiety can be used to target a tumor cell, such as an endothelial tumor cell or a breast cancer tumor cell (Zitzmann et al., *Cancer Res.,* 62:5139-43, 2002). An RGD peptide can facilitate targeting of an iRNA agent to tumors of a variety of other tissues, including the lung, kidney, spleen, or liver (Aoki et al., *Cancer Gene Therapy* 8:783-787, 2001). Preferably, the RGD peptide will facilitate targeting of an iRNA agent to the kidney. The RGD peptide can be linear or cyclic, and can be modified, e.g., glycosylated or methylated to facilitate targeting to specific tissues. For example, a glycosylated RGD peptide can deliver an iRNA agent to a tumor cell expressing $\alpha_v\beta_3$ (Haubner et al., *Jour. Nucl. Med.,* 42:326-336, 2001). Peptides that target markers enriched in proliferating cells can be used. For example, RGD containing peptides and peptidomimetics can target cancer cells, in particular cells that exhibit an integrin. Thus, one could use RGD peptides, cyclic peptides containing RGD, RGD peptides that include D-amino acids, as well as synthetic RGD mimics. In addition to RGD, one can use other moieties that target the integrin ligand. Generally, such ligands can be used to control proliferating cells and angiogeneis. Preferred conjugates of this type of ligand target PECAM-1, VEGF, or other cancer gene, e.g., a cancer gene described herein.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

In one embodiment, a targeting peptide can be an amphipathic α-helical peptide. Exemplary amphipathic α-helical peptides include, but are not limited to, cecropins, lycotoxins, paradaxins, buforin, CPF, bombinin-like peptide (BLP), cathelicidins, ceratotoxins, *S. clava* peptides, hagfish intestinal antimicrobial peptides (HFIAPs), magainines, brevinins-2, dermaseptins, melittins, pleurocidin, $H_2A$ peptides, *Xenopus* peptides, esculentinis-1, and caerins. A number of factors will preferably be considered to maintain the integrity of helix stability. For example, a maximum number of helix stabilization residues will be utilized (e.g., leu, ala, or lys), and a minimum number helix destabilization residues will be utilized (e.g., proline, or cyclic monomeric units. The capping residue will be considered (for example Gly is an exemplary N-capping residue and/or C-terminal amidation can be used to provide an extra H-bond to stabilize the helix. Formation of salt bridges between residues with opposite charges, separated by i±3, or i±4 positions can provide stability. For example, cationic residues such as lysine, arginine, homo-arginine, ornithine or histidine can form salt bridges with the anionic residues glutamate or aspartate.

Peptide and peptidomimetic ligands include those having naturally occurring or modified peptides, e.g., D or L peptides; α, β, or γ peptides; N-methyl peptides; azapeptides; peptides having one or more amide, i.e., peptide, linkages replaced with one or more urea, thiourea, carbamate, or sulfonyl urea linkages; or cyclic peptides.

The targeting ligand can be any ligand that is capable of targeting a specific receptor.

Examples are: folate, GalNAc, galactose, mannose, mannose-6P, clusters of sugars such as GalNAc cluster, mannose cluster, galactose cluster, or an apatamer. A cluster is a combination of two or more sugar units. The targeting ligands also include integrin receptor ligands, Chemokine receptor ligands, transferrin, biotin, serotonin receptor ligands, PSMA, endothelin, GCPII, somatostatin, LDL and HDL ligands. The ligands can also be based on nucleic acid, e.g., an aptamer. The aptamer can be unmodified or have any combination of modifications disclosed herein.

Endosomal release agents include imidazoles, poly or oligoimidazoles, PEIs, peptides, fusogenic peptides, polycaboxylates, polyacations, masked oligo or poly cations or anions, acetals, polyacetals, ketals/polyketyals, orthoesters, polymers with masked or unmasked cationic or anionic charges, dendrimers with masked or unmasked cationic or anionic charges.

PK modulator stands for pharmacokinetic modulator. PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple phosphorothioate linkages in the backbone are also amenable to the present invention as ligands (e.g., as PK modulating ligands).

In addition, aptamers that bind serum components (e.g., serum proteins) are also amenable to the present invention as PK modulating ligands.

Other ligand conjugates amenable to the invention are described in U.S. patent application Ser. No. 10/916,185, filed Aug. 10, 2004; U.S. Ser. No. 10/946,873, filed Sep. 21, 2004; U.S. Ser. No. 10/833,934, filed Aug. 3, 2007; U.S. Ser.

No. 11/115,989 filed Apr. 27, 2005 and U.S. Ser. No. 11/944,227 filed Nov. 21, 2007, which are incorporated by reference in their entireties for all purposes.

When two or more ligands are present, the ligands can all have same properties, all have different properties or some ligands have the same properties while others have different properties. For example, a ligand can have targeting properties, have endosomolytic activity or have PK modulating properties. In a preferred embodiment, all the ligands have different properties.

Ligands can be coupled to the oligonucleotides at various places, for example, 3'-end, 5'-end, and/or at an internal position. In preferred embodiments, the ligand is attached to the oligonucleotides via an intervening tether, e.g., a carrier described herein. The ligand or tethered ligand may be present on a monomer when the monomer is incorporated into the growing strand.

In some embodiments, the ligand may be incorporated via coupling to a "precursor" monomer after the "precursor" monomer has been incorporated into the growing strand. For example, a monomer having, e.g., an amino-terminated tether (i.e., having no associated ligand), e.g., TAP-(CH$_2$)$_n$NH$_2$ may be incorporated into a growing oligonucleotide strand. In a subsequent operation, i.e., after incorporation of the precursor monomer into the strand, a ligand having an electrophilic group, e.g., a pentafluorophenyl ester or aldehyde group, can subsequently be attached to the precursor monomer by coupling the electrophilic group of the ligand with the terminal nucleophilic group of the precursor monomer's tether.

In another example, a monomer having a chemical group suitable for taking part in Click Chemistry reaction may be incorporated, e.g., an azide or alkyne terminated tether/linker. In a subsequent operation, i.e., after incorporation of the precursor monomer into the strand, a ligand having complementary chemical group, e.g. an alkyne or azide can be attached to the precursor monomer by coupling the alkyne and the azide together.

For double-stranded oligonucleotides, ligands can be attached to one or both strands. In some embodiments, a double-stranded iRNA agent contains a ligand conjugated to the sense strand. In other embodiments, a double-stranded iRNA agent contains a ligand conjugated to the antisense strand.

In some embodiments, ligand can be conjugated to nucleobases, sugar moieties, or internucleosidic linkages of nucleic acid molecules. Conjugation to purine nucleobases or derivatives thereof can occur at any position including, endocyclic and exocyclic atoms. In some embodiments, the 2-, 6-, 7-, or 8-positions of a purine nucleobase are attached to a conjugate moiety. Conjugation to pyrimidine nucleobases or derivatives thereof can also occur at any position. In some embodiments, the 2-, 5-, and 6-positions of a pyrimidine nucleobase can be substituted with a conjugate moiety. Conjugation to sugar moieties of nucleosides can occur at any carbon atom. Example carbon atoms of a sugar moiety that can be attached to a conjugate moiety include the 2', 3', and 5' carbon atoms. The 1' position can also be attached to a conjugate moiety, such as in an abasic residue. Internucleosidic linkages can also bear conjugate moieties.

For phosphorus-containing linkages (e.g., phosphodiester, phosphorothioate, phosphorodithiotate, phosphoroamidate, and the like), the conjugate moiety can be attached directly to the phosphorus atom or to an O, N, or S atom bound to the phosphorus atom. For amine- or amide-containing internucleosidic linkages (e.g., PNA), the conjugate moiety can be attached to the nitrogen atom of the amine or amide or to an adjacent carbon atom.

Any suitable ligand in the field of RNA interference may be used, although the ligand is typically a carbohydrate e.g. monosaccharide (such as GalNAc), disaccharide, trisaccharide, tetrasaccharide, polysaccharide.

Linkers that conjugate the ligand to the nucleic acid include those discussed above. For example, the ligand can be one or more GalNAc (N-acetylglucosamine) derivatives attached through a bivalent or trivalent branched linker.

In one embodiment, the dsRNA of the invention is conjugated to a bivalent and trivalent branched linkers include the structures shown in any of formula (IV)-(VII):

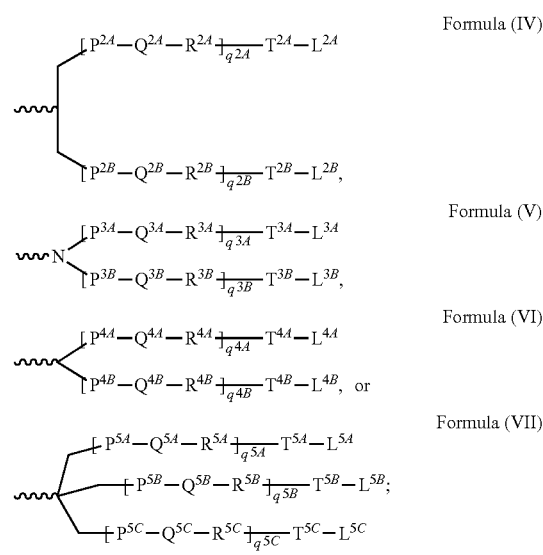

wherein:
$q^{2A}$, $q^{2B}$, $q^{3A}$, $q^{3B}$, $q^{4A}$, $q^{4B}$, $q^{5A}$, $q^{5B}$, $q^{5C}$ represent independently for each occurrence 0-20 and wherein the repeating unit can be the same or different;

$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{5A}$, $T^{5B}$, $T^{5C}$ are each independently for each occurrence absent, CO, NH, O, S, OC(O), NHC(O), CH$_2$, CH$_2$NH or CH$_2$O;

$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R''), C≡C or C(O);

$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—O,

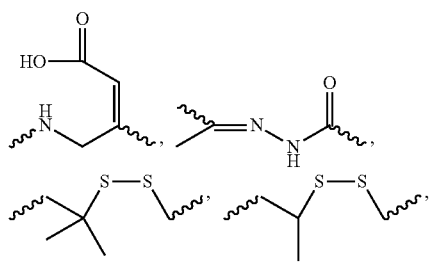

-continued

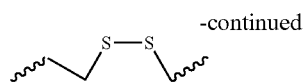

heterocyclyl;

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and $R^a$ is H or amino acid side chain.

Trivalent conjugating GalNAc derivatives are particularly useful for use with RNAi agents for inhibiting the expression of a target gene, such as those of formula (VII):

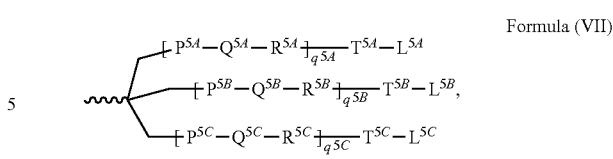

Formula (VII)

wherein $L^{5A}$, $L^{5B}$ and $L^{5C}$ represent a monosaccharide, such as GalNAc derivative. Examples of suitable bivalent and trivalent branched linker groups conjugating GalNAc derivatives include, but are not limited to, the following compounds:

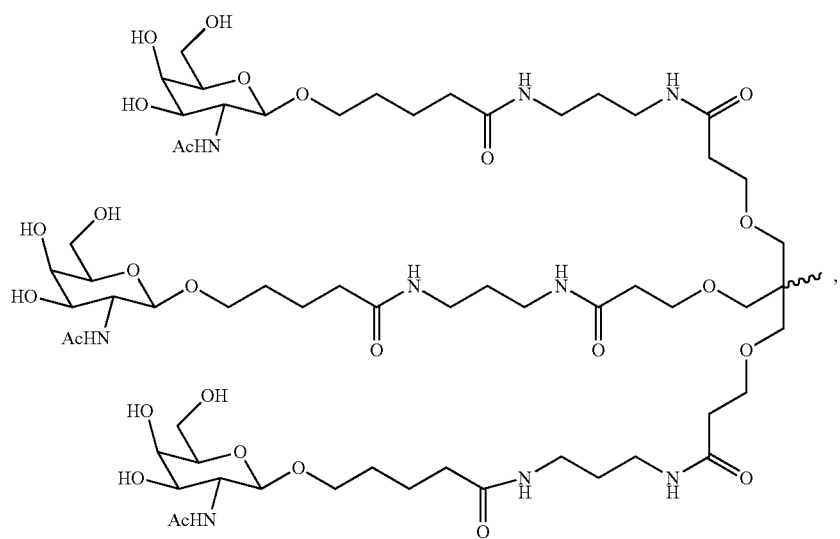

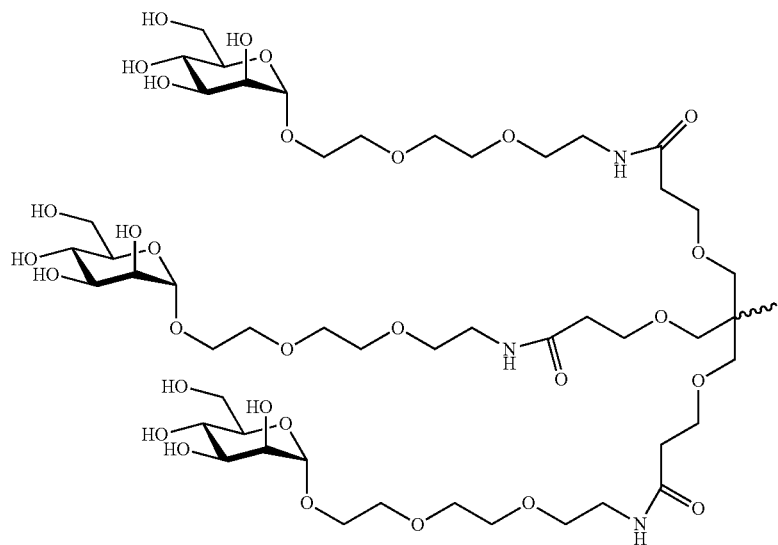

-continued
51
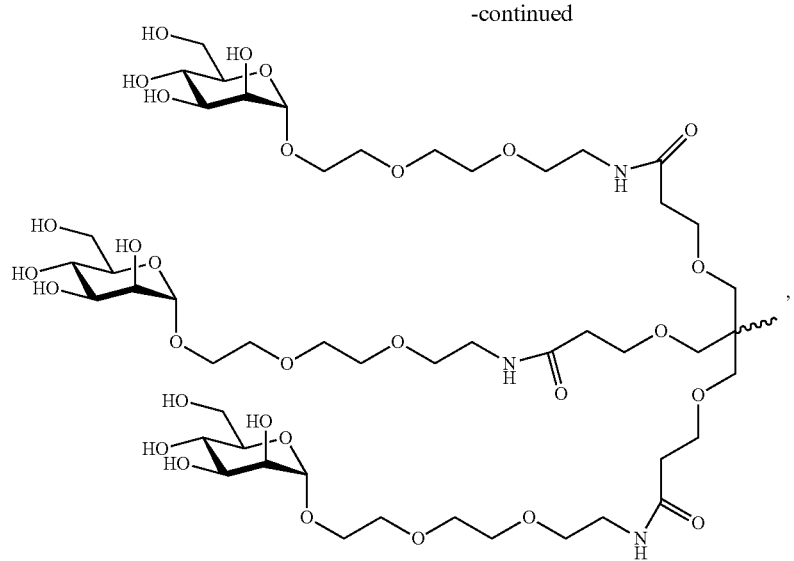
52
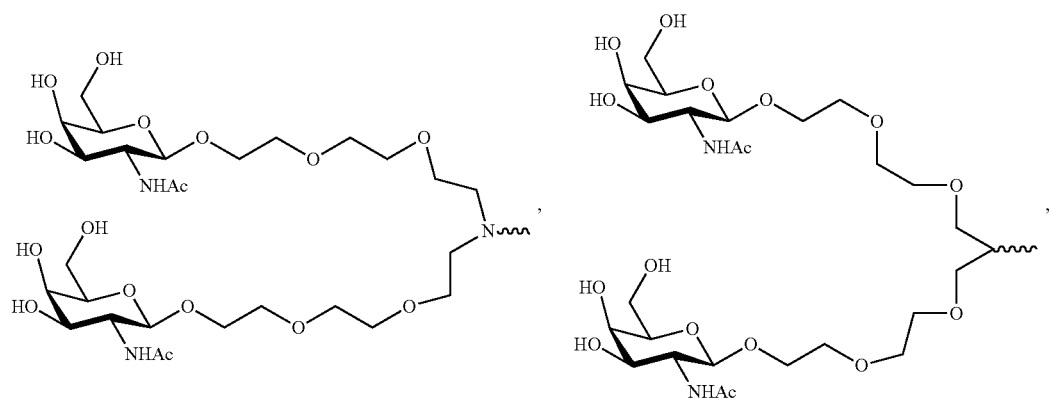
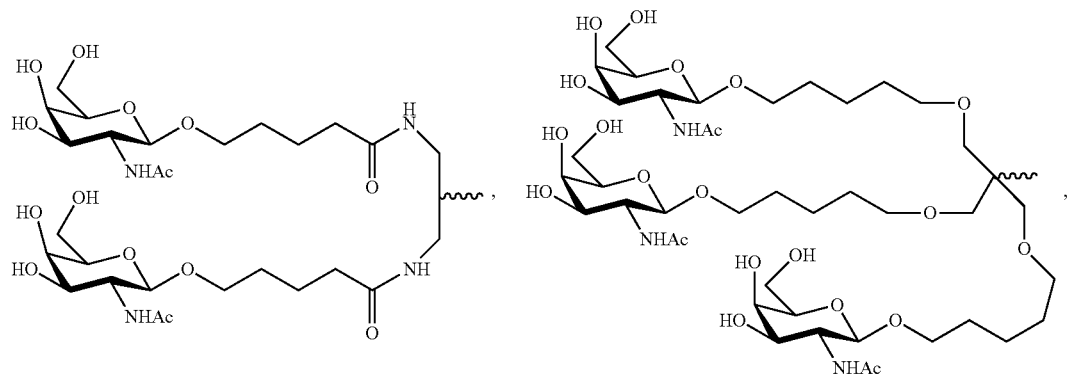

-continued

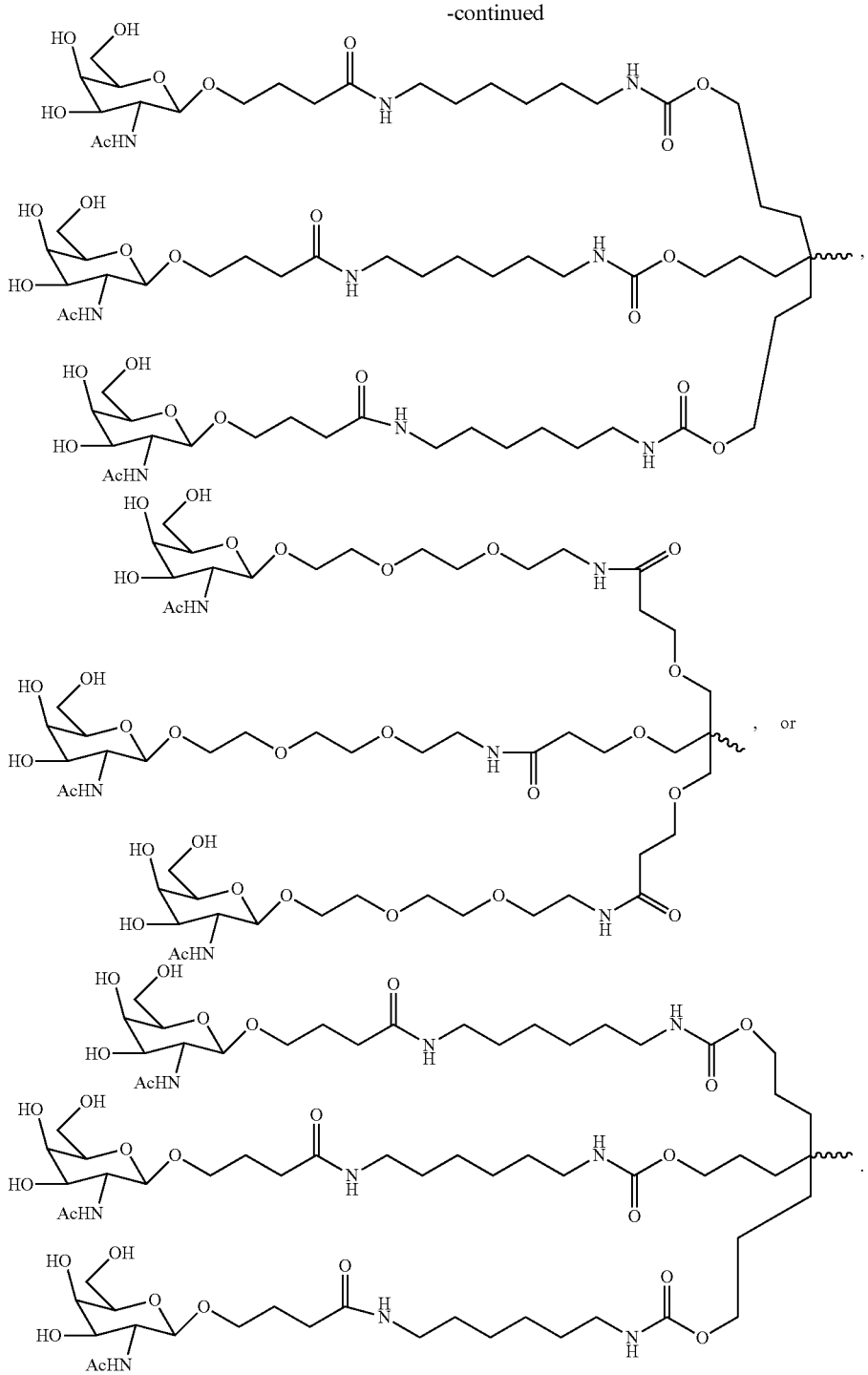

Representative U.S. patents that teach the preparation of RNA conjugates include, but are not limited to, U.S. Pat. Nos. 4,828,979; 4,948,882; 5,218,105; 5,525,465; 5,541, 313; 5,545,730; 5,552,538; 5,578,717; 5,580,731; 5,591, 584; 5,109,124; 5,118,802; 5,138,045; 5,414,077; 5,486, 603; 5,512,439; 5,578,718; 5,608,046; 4,587,044; 4,605, 735; 4,667,025; 4,762,779; 4,789,737; 4,824,941; 4,835, 263; 4,876,335; 4,904,582; 4,958,013; 5,082,830; 5,112, 963; 5,214,136; 5,082,830; 5,112,963; 5,214,136; 5,245, 022; 5,254,469; 5,258,506; 5,262,536; 5,272,250; 5,292, 873; 5,317,098; 5,371,241, 5,391,723; 5,416,203, 5,451, 463; 5,510,475; 5,512,667; 5,514,785; 5,565,552; 5,567, 810; 5,574,142; 5,585,481; 5,587,371; 5,595,726; 5,597, 696; 5,599,923; 5,599,928 and 5,688,941; 6,294,664; 6,320, 017; 6,576,752; 6,783,931; 6,900,297; 7,037,646; 8,106, 022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.,* 2007, 365(1):54-61; Letsinger et al., *Proc. Natl. Acad. Sci. USA,* 1989, 86:6553), cholic acid (Manoharan et al., *Bioorg. Med. Chem. Lett.,* 1994, 4:1053), a thioether, e.g., hexyl-S-tritylthiol (Manoharan et al., *Ann. N. Y. Acad. Sci.,* 1992, 660:306; Manoharan et al., *Bioorg. Med. Chem. Let.,* 1993, 3:2765), a thiocholesterol (Oberhauser et al., *Nucl. Acids Res.,* 1992, 20:533), an aliphatic chain, e.g., dodecandiol or undecyl residues (Saison-Behmoaras et al., *EMBO J.,* 1991, 10:111; Kabanov et al., *FEBS Lett.,* 1990, 259:327; Svinarchuk et al., *Biochimie,* 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.,* 1995, 36:3651; Shea et al., *Nucl. Acids Res.,* 1990, 18:3777), a polyamine or a polyethylene glycol chain (Manoharan et al., *Nucleosides & Nucleotides,* 1995, 14:969), or adamantane acetic acid (Manoharan et al., *Tetrahedron Lett.,* 1995, 36:3651), a palmityl moiety (Mishra et al., *Biochim. Biophys. Acta,* 1995, 1264:229), or an octadecylamine or hexylamino-carbonyl-oxycholesterol moiety (Crooke et al., *J. Pharmacol. Exp. Ther.,* 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

In some embodiments, method double-stranded RNAi agent of the invention is selected from the group consisting of AD-58681, AD-59054, AD-61719, and AD-61444.

III. Delivery of an iRNA of the Invention

The delivery of an iRNA agent of the invention to a cell e.g., a cell within a subject, such as a human subject (e.g., a subject in need thereof, such as a subject having a Serpinal deficiency-associated disorder, e.g., a Serpinal deficiency liver disorder) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knock-down of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim S H., et al (2008) *Journal of Controlled Release* 129(2):107-116) that encases an iRNA. The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) Clin. *Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res.* August 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the Serpina1 gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., *Blood* 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., *Proc. Soc. Exp. Biol. Med.* 204:289-300 (1993); U.S. Pat. No. 5,436,146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol*, 70: 520-532; Samulski R et al. (1989), *J. Virol.* 63: 3822-3826; U.S. Pat. Nos. 5,252,479; 5,139,941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like. AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

III. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of a Serpina1 gene, e.g., a Serpina1 deficiency-associated disorder, e.g., a Serpina1 deficiency liver disorder. Such pharmaceutical compositions are formulated based on the mode of delivery. One example is compositions that are formulated for systemic administration via parenteral delivery, e.g., by intravenous (IV) delivery. Another example is compositions that are formulated for direct delivery into the brain parenchyma, e.g., by infusion into the brain, such as by continuous pump infusion.

The pharmaceutical compositions comprising RNAi agents of the invention may be, for example, solutions with or without a buffer, or compositions containing pharmaceutically acceptable carriers. Such compositions include, for example, aqueous or crystalline compositions, liposomal formulations, micellar formulations, emulsions, and gene therapy vectors.

In the methods of the invention, the RNAi agent may be administered in a solution. A free RNAi agent may be administered in an unbuffered solution, e.g., in saline or in water. Alternatively, the free siRNA may also be administered in a suitable buffer solution. The buffer solution may comprise acetate, citrate, prolamine, carbonate, or phosphate, or any combination thereof. In a preferred embodiment, the buffer solution is phosphate buffered saline (PBS). The pH and osmolarity of the buffer solution containing the RNAi agent can be adjusted such that it is suitable for administering to a subject.

In some embodiments, the buffer solution further comprises an agent for controlling the osmolarity of the solution, such that the osmolarity is kept at a desired value, e.g., at the physiologic values of the human plasma. Solutes which can be added to the buffer solution to control the osmolarity include, but are not limited to, proteins, peptides, amino acids, non-metabolized polymers, vitamins, ions, sugars, metabolites, organic acids, lipids, or salts. In some embodiments, the agent for controlling the osmolarity of the solution is a salt. In certain embodiments, the agent for controlling the osmolarity of the solution is sodium chloride or potassium chloride.

The pharmaceutical compositions of the invention may be administered in dosages sufficient to inhibit expression of a Serpina1 gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the RNAi agent, e.g., dsRNA, may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.1 to about 50 mg/kg, about 0.25 to about 50 mg/kg, about 0.5 to about 50 mg/kg, about 0.75 to about 50 mg/kg, about 1 to about 50 mg/mg, about 1.5 to about 50 mg/kb, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/mg, about 1.5 to about 45 mg/kb, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kb, about 2 to about 30 mg/mg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the RNAi agent, e.g., dsRNA, may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the RNAi agent, e.g., dsRNA, is administered at a dose of about 0.5 to about 50 mg/kg, about 0.75 to about 50 mg/kg, about 1 to about 50 mg/mg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/mg, about 1.5 to about 45 mg/kg, about 2 to about 45 mg/kb, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/mg, about 1.5 to about 40 mg/kb, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/mg, about 1.5 to about 30 mg/kb, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/mg, about 1.5 to about 20 mg/kb, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered a therapeutic amount of iRNA, such as about 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention. For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In certain embodiments of the invention, for example, when a double-stranded RNAi agent includes modifications (e.g., one or more motifs of three identical modifications on three consecutive nucleotides, including one such motif at or near the cleavage site of the agent), six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments, a single dose of the pharmaceutical compositions of the invention is administered once per week. In other embodiments of the invention, a single dose of the pharmaceutical compositions of the invention is administered bi-monthly.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

Advances in mouse genetics have generated a number of mouse models for the study of various human diseases, such as a liver disorder that would benefit from reduction in the expression of Serpina1. Such models can be used for in vivo testing of iRNA, as well as for determining a therapeutically effective dose. Suitable mouse models are known in the art and include, for example, a mouse containing a transgene expressing human Serpina1.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate RNAi. In some cases the liposomes are also specifically targeted, e.g., to direct the iRNA to particular cell types.

A liposome containing a RNAi agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The RNAi agent preparation is then added to the micelles that include the lipid component. The cationic groups on the lipid interact with the RNAi agent and condense around the RNAi agent to form a liposome. After condensation, the detergent is removed, e.g., by dialysis, to yield a liposomal preparation of RNAi agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. Nos. 4,897,355; 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta*

858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging RNAi agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. Nos. 5,283,185; 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside GM1, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside GM1, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside GM1 or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver RNAi agents to macrophages.

Further advantages of liposomes include: liposomes obtained from natural phospholipids are biocompatible and biodegradable; liposomes can incorporate a wide range of water and lipid soluble drugs; liposomes can protect encapsulated RNAi agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of RNAi agent (see, e.g., Felgner, P. L. et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoylphosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., Biochim. Biophys. Res. Commun. 179:280, 1991). Lipopolylysine, made by conjugating polylysine to DOPE, has been reported to be effective for transfection in the presence of serum (Zhou, X. et al., Biochim. Biophys. Acta 1065:8, 1991). For certain cell lines, these liposomes containing conjugated cationic lipids, are said to exhibit lower toxicity and provide more efficient transfection than the DOTMA-containing compositions. Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer RNAi agent into the skin. In some implementations, liposomes are used for delivering RNAi agent to epidermal cells and also to enhance the penetration of RNAi agent into dermal tissues, e.g., into skin. For example, the liposomes can be applied topically. Topical delivery of drugs formulated as liposomes to the skin has been documented (see, e.g., Weiner et al., Journal of Drug Targeting, 1992, vol. 2,405-410 and du Plessis et al., Antiviral Research, 18, 1992, 259-265; Mannino, R. J. and Fould-Fogerite, S., Biotechniques 6:682-690, 1988; Itani, T. et al. Gene 56:267-276. 1987; Nicolau, C. et al. Meth. Enz. 149:157-176, 1987; Straubinger, R. M. and Papahadjopoulos, D. Meth. Enz. 101:512-527, 1983; Wang, C. Y. and Huang, L., Proc. Natl. Acad. Sci. USA 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with RNAi agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include RNAi agent can be delivered, for example, subcutaneously by infection in order to deliver RNAi agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018, 616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in Pharmaceutical Dosage Forms, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in Pharmaceutical Dosage Forms, Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N, N-dimethylammonium bromide (DDAB), N-(1-(2,3-dioleyloxy)propyl)-N,N,N-trimethylammonium chloride (DOTAP), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN 100), (6Z,9Z, 28Z,31Z)-heptatriaconta-6,9,28,31-tetraen-19-yl 4-(dimethylamino)butanoate (MC3), 1,1'-(2-(4-(2-((2-(bis (2-hydroxydodecyl)amino)ethyl)(2-hydroxydodecyl)amino) ethyl)piperazin-1-yl)ethylazanediyl)didodecan-2-ol (Tech GI), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference. In one embodiment, the lipid-siRNA particle includes 40% 2,2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylpho sphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylpho sphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof.

The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HCl (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

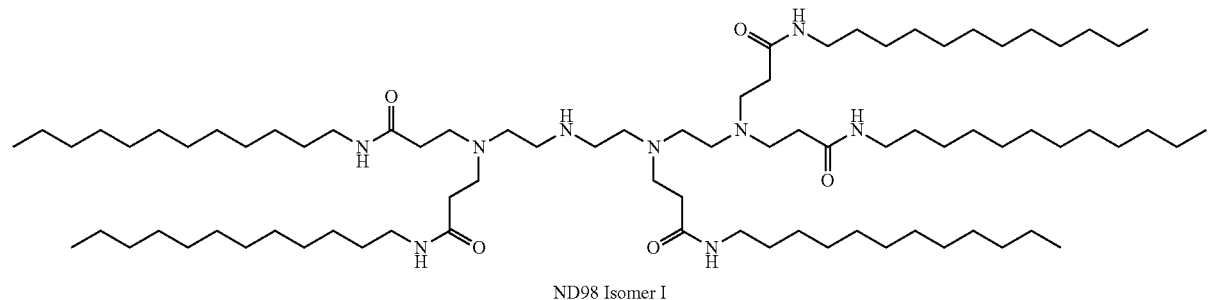

ND98 Isomer I

LNP01 formulations are described, e.g., in International Application Publication No. WO 2008/042973, which is hereby incorporated by reference.

Additional exemplary lipid-dsRNA formulations are described in Table A.

TABLE A

| | Ionizable/Cationic Lipid | cationic lipid/non-cationic lipid/cholesterol/PEG-lipid conjugate Lipid:siRNA ratio |
|---|---|---|
| LNP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA ~7:1 |

TABLE A-continued

| | Ionizable/Cationic Lipid | cationic lipid/non-cationic lipid/cholesterol/PEG-lipid conjugate Lipid:siRNA ratio |
|---|---|---|
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA ~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA ~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA ~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |
| LNP22 | XTC | XTC/DSPC/Chol/PEG-DSG 50/10/38.5/1.5 Lipid:siRNA: 10:1 |

DSPC: distearoylphosphatidylcholine

DPPC: dipalmitoylpho sphatidylcho line

PEG-DMG: PEG-didimyristoyl glycerol (C14-PEG, or PEG-C14) (PEG with avg mol wt of 2000)

PEG-DSG: PEG-distyryl glycerol (C18-PEG, or PEG-C18) (PEG with avg mol wt of 2000)

PEG-cDMA: PEG-carbamoyl-1,2-dimyristyloxypropylamine (PEG with avg mol wt of 2000)

LNP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Ser. No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference. ALNY-100 comprising formulations are described, e.g., International patent application number PCT/US09/

63933, filed on Nov. 10, 2009, which is hereby incorporated by reference. C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like.

Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom.

Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O) NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

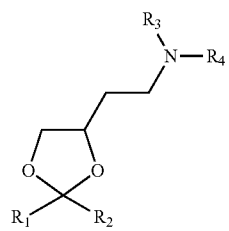

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

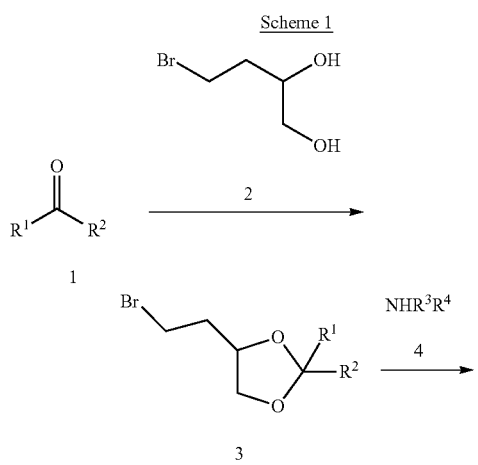

-continued

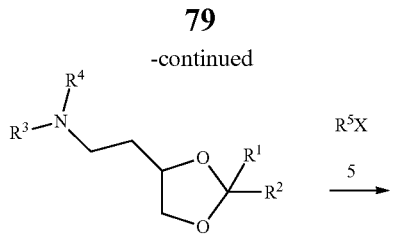

Formula A

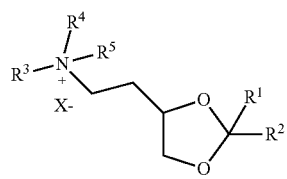

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

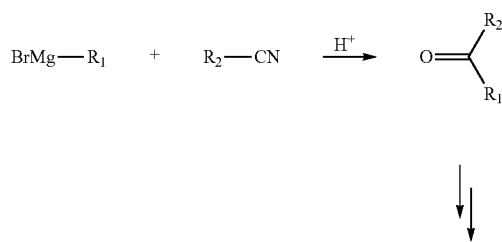

-continued

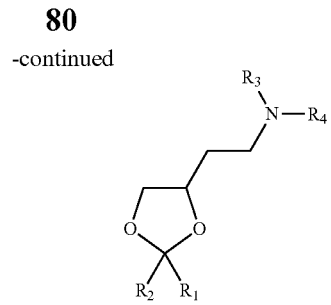

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g). Synthesis of ALNY-100

Synthesis of ketal 519 [ALNY-100] was performed using the following scheme 3:

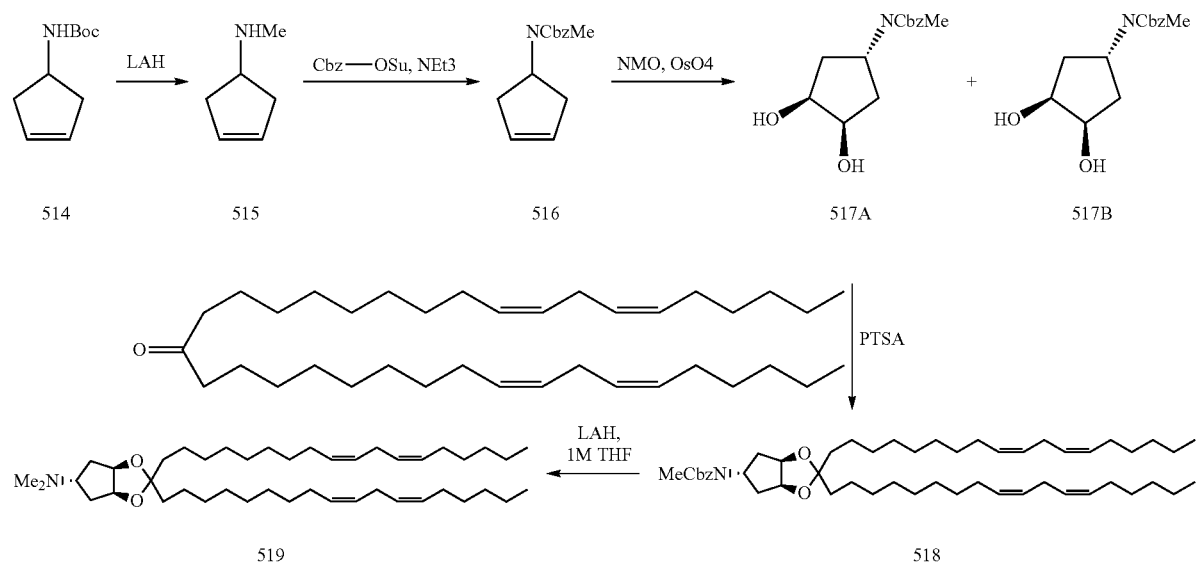

Synthesis of 515

To a stirred suspension of LiAlH4 (3.74 g, 0.09852 mol) in 200 ml anhydrous THF in a two neck RBF (IL), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): $\delta$=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with 1N HCl solution (1×100 mL) and saturated NaHCO$_3$ solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): $\delta$=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO$_3$ (1×50 mL) solution, water (1×30 mL) and finally with brine (1×50 mL). Organic phase was dried over an.Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): $\delta$=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS—[M+H]—266.3, [M+NH4+]—283.5 present, HPLC—97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): $\delta$=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC—98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 400° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR $\delta$=130.2, 130.1 (×2), 127.9 (×3), 112.3, 79.3, 64.4, 44.7, 38.3, 35.4, 31.5, 29.9 (×2), 29.7, 29.6 (×2), 29.5 (×3), 29.3 (×2), 27.2 (×3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For LNP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles.

DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and anti-oxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.;

Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V, Popovich N G, and Ansel H C, 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (M0310), hexaglycerol monooleate (PO310), hexaglycerol pentaoleate (PO500), decaglycerol monocaprate (MCA750), decaglycerol monooleate (MO750), decaglycerol sesquioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191, 105; 7,063,860; 7,070,802; 7,157,099; Constantinides et al., *Pharmaceutical Research*, 1994, 11, 1385-1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., *Pharmaceutical Research*, 1994, 11, 1385; Ho et al., *J. Pharm. Sci.*, 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

iii. Microparticles

An RNAi agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p. 92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p. 92); and perfluorochemical emulsions, such as FC-43. Takahashi et al., *J. Pharm. Pharmacol.*, 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-20}$ alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p. 92; Muranishi, Critical Reviews in Therapeutic Drug Carrier Systems, 1990, 7, 1-33; El Hariri et al., *J. Pharm. Pharmacol.*, 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-*Hill*, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., *J. Pharm. Exp. Ther.*, 1992, 263, 25; Yamashita et al., *J. Pharm. Sci.*, 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. *Chromatogr.*, 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., *J. Control Rel.*, 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., *J. Pharm. Pharmacol.*, 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen; Carlsbad, Calif.), Lipofectamine 2000™ (Invitrogen; Carlsbad, Calif.), 293Fectin™ (Invitrogen; Carlsbad, Calif.), Cellfectin™ (Invitrogen; Carlsbad, Calif.), DMRIE-C™ (Invitrogen; Carlsbad, Calif.), FreeStyle™ MAX (Invitrogen; Carlsbad, Calif.), Lipofectamine™ 2000 CD (Invitrogen; Carlsbad, Calif.), Lipofectamine™ (Invitrogen; Carlsbad, Calif.), RNAiMAX (Invitrogen; Carlsbad, Calif.), Oligofectamine™ (Invitrogen; Carlsbad, Calif.), Optifect™ (Invitrogen; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega; Madison, Wis.), TransFast™ Transfection Reagent (Promega; Madison, Wis.), Tfx™-20 Reagent (Promega; Madison, Wis.), Tfx™-50 Reagent (Promega; Madison, Wis.), DreamFect™ (OZ Biosciences; Marseille, France), EcoTransfect (OZ Biosciences; Marseille, France), TransPass$^a$ D1 Transfection Reagent (New England Biolabs; Ipswich, Mass., USA), LyoVec™/LipoGen™ (Invitrogen; San Diego, Calif., USA), PerFectin Transfection Reagent (Genlantis; San Diego, Calif., USA), NeuroPORTER Transfection Reagent (Genlantis; San Diego, Calif., USA), GenePORTER Transfection reagent (Genlantis; San Diego, Calif., USA), GenePORTER 2 Transfection reagent (Genlantis; San Diego, Calif., USA), Cytofectin Transfection Reagent (Genlantis; San Diego, Calif., USA), BaculoPORTER Transfection Reagent (Genlantis; San Diego, Calif., USA), TroganPORTER™ transfection Reagent (Genlantis; San Diego, Calif., USA), RiboFect (Bioline; Taunton, Mass., USA), PlasFect (Bioline; Taunton, Mass., USA), UniFECTOR (B-Bridge International; Mountain View, Calif., USA), SureFECTOR (B-Bridge International; Mountain View, Calif., USA), or HiFect™ (B-Bridge International, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4' isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-RNAi mechanism and which are useful in treating a bleeding disorder. Examples of such agents include, but are not limited to an anti-inflammatory agent, anti-steatosis agent, anti-viral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by Serpina1 expression. In any event, the administering physician can adjust the amount and timing of iRNA administration on the basis of results observed using standard measures of efficacy known in the art or described herein.

IV. Methods for Inhibiting Serpina1 Expression

The present invention provides methods of inhibiting expression of a Serpina1 in a cell. The methods include contacting a cell with an RNAi agent, e.g., a double stranded RNAi agent, in an amount effective to inhibit expression of the Serpina1 in the cell, thereby inhibiting expression of the Serpina1 in the cell.

Contacting of a cell with a double stranded RNAi agent may be done in vitro or in vivo. Contacting a cell in vivo with the RNAi agent includes contacting a cell or group of cells within a subject, e.g., a human subject, with the RNAi agent. Combinations of in vitro and in vivo methods of contacting are also possible. Contacting may be direct or indirect, as discussed above. Furthermore, contacting a cell may be accomplished via a targeting ligand, including any ligand described herein or known in the art. In preferred embodiments, the targeting ligand is a carbohydrate moiety, e.g., a GalNAc$_3$ ligand, or any other ligand that directs the RNAi agent to a site of interest, e.g., the liver of a subject.

The term "inhibiting," as used herein, is used interchangeably with "reducing," "silencing," "downregulating" and other similar terms, and includes any level of inhibition.

The phrase "inhibiting expression of a Serpina1" is intended to refer to inhibition of expression of any Serpina1 gene (such as, e.g., a mouse Serpina1 gene, a rat Serpina1 gene, a monkey Serpina1 gene, or a human Serpina1 gene) as well as variants or mutants of a Serpina1 gene. Thus, the Serpina1 gene may be a wild-type Serpina1 gene, a mutant Serpina1 gene, or a transgenic Serpina1 gene in the context of a genetically manipulated cell, group of cells, or organism.

"Inhibiting expression of a Serpina1 gene" includes any level of inhibition of a Serpina1 gene, e.g., at least partial suppression of the expression of a Serpina1 gene. The expression of the Serpina1 gene may be assessed based on the level, or the change in the level, of any variable associated with Serpina1 gene expression, e.g., Serpina1 mRNA level, Serpina1 protein level, or lipid levels. This level may be assessed in an individual cell or in a group of cells, including, for example, a sample derived from a subject.

Inhibition may be assessed by a decrease in an absolute or relative level of one or more variables that are associated with Serpina1 expression compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In some embodiments of the methods of the invention, expression of a Serpina1 gene is inhibited by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%. at least about 95%, at least about 96%, at least about 97%, at least about 98%, or at least about 99%.

Inhibition of the expression of a Serpina1 gene may be manifested by a reduction of the amount of mRNA expressed by a first cell or group of cells (such cells may be present, for example, in a sample derived from a subject) in which a Serpina1 gene is transcribed and which has or have been treated (e.g., by contacting the cell or cells with an RNAi agent of the invention, or by administering an RNAi agent of the invention to a subject in which the cells are or were present) such that the expression of a Serpina1 gene is inhibited, as compared to a second cell or group of cells substantially identical to the first cell or group of cells but which has not or have not been so treated (control cell(s)). In preferred embodiments, the inhibition is assessed by expressing the level of mRNA in treated cells as a percentage of the level of mRNA in control cells, using the following formula:

$$\frac{(mRNA \text{ in control cells}) - (mRNA \text{ in treated cells})}{(mRNA \text{ in control cells})} \bullet 100\%$$

Alternatively, inhibition of the expression of a Serpina1 gene may be assessed in terms of a reduction of a parameter that is functionally linked to Serpina1 gene expression, e.g., Serpina1 protein expression, such as ALT, alkaline phosphatase, bilirubin, prothrombin and albumin. Serpina1 gene silencing may be determined in any cell expressing Serpina1, either constitutively or by genomic engineering, and by any assay known in the art. The liver is the major site of Serpina1 expression. Other significant sites of expression include the lung and intestines.

Inhibition of the expression of a Serpina1 protein may be manifested by a reduction in the level of the Serpina1 protein that is expressed by a cell or group of cells (e.g., the level of protein expressed in a sample derived from a subject). As explained above for the assessment of mRNA suppression, the inhibition of protein expression levels in a treated cell or group of cells may similarly be expressed as a percentage of the level of protein in a control cell or group of cells.

A control cell or group of cells that may be used to assess the inhibition of the expression of a Serpina1 gene includes a cell or group of cells that has not yet been contacted with an RNAi agent of the invention. For example, the control cell or group of cells may be derived from an individual subject (e.g., a human or animal subject) prior to treatment of the subject with an RNAi agent.

The level of Serpina1 mRNA that is expressed by a cell or group of cells may be determined using any method known in the art for assessing mRNA expression. In one embodiment, the level of expression of Serpina1 in a sample is determined by detecting a transcribed polynucleotide, or portion thereof, e.g., mRNA of the Serpina1 gene. RNA may be extracted from cells using RNA extraction techniques including, for example, using acid phenol/guanidine isothiocyanate extraction (RNAzol B; Biogenesis), RNeasy RNA preparation kits (Qiagen) or PAXgene (PreAnalytix, Switzerland). Typical assay formats utilizing ribonucleic acid hybridization include nuclear run-on assays, RT-PCR, RNase protection assays (Melton et al., *Nuc. Acids Res.* 12:7035), Northern blotting, in situ hybridization, and microarray analysis.

In one embodiment, the level of expression of Serpina1 is determined using a nucleic acid probe. The term "probe", as used herein, refers to any molecule that is capable of selectively binding to a specific Serpina1. Probes can be synthesized by one of skill in the art, or derived from appropriate biological preparations. Probes may be specifically designed to be labeled. Examples of molecules that can be utilized as probes include, but are not limited to, RNA, DNA, proteins, antibodies, and organic molecules.

Isolated mRNA can be used in hybridization or amplification assays that include, but are not limited to, Southern or Northern analyses, polymerase chain reaction (PCR) analyses and probe arrays. One method for the determination of mRNA levels involves contacting the isolated mRNA with a nucleic acid molecule (probe) that can hybridize to Serpina1 mRNA. In one embodiment, the mRNA is immobilized on a solid surface and contacted with a probe, for example by running the isolated mRNA on an agarose gel and transferring the mRNA from the gel to a membrane, such as nitrocellulose. In an alternative embodiment, the probe(s) are immobilized on a solid surface and the mRNA is contacted with the probe(s), for example, in an Affymetrix gene chip array. A skilled artisan can readily adapt known mRNA detection methods for use in determining the level of Serpina1 mRNA.

An alternative method for determining the level of expression of Serpina1 in a sample involves the process of nucleic acid amplification and/or reverse transcriptase (to prepare cDNA) of for example mRNA in the sample, e.g., by RT-PCR (the experimental embodiment set forth in Mullis, 1987, U.S. Pat. No. 4,683,202), ligase chain reaction (Barany (1991) *Proc. Natl. Acad. Sci. USA* 88:189-193), self sustained sequence replication (Guatelli et al. (1990) *Proc. Natl. Acad. Sci. USA* 87:1874-1878), transcriptional amplification system (Kwoh et al. (1989) *Proc. Natl. Acad. Sci. USA* 86:1173-1177), Q-Beta Replicase (Lizardi et al. (1988) *Bio/Technology* 6:1197), rolling circle replication (Lizardi et al., U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. In particular aspects of the invention, the level of expression of Serpina1 is determined by quantitative fluorogenic RT-PCR (i.e., the TaqMan™ System).

The expression levels of Serpina1 mRNA may be monitored using a membrane blot (such as used in hybridization analysis such as Northern, Southern, dot, and the like), or microwells, sample tubes, gels, beads or fibers (or any solid support comprising bound nucleic acids). See U.S. Pat. Nos. 5,770,722, 5,874,219, 5,744,305, 5,677,195 and 5,445,934, which are incorporated herein by reference. The determination of Serpina1 expression level may also comprise using nucleic acid probes in solution.

In preferred embodiments, the level of mRNA expression is assessed using branched DNA (bDNA) assays or real time PCR (qPCR). The use of these methods is described and exemplified in the Examples presented herein.

The level of Serpina1 protein expression may be determined using any method known in the art for the measurement of protein levels. Such methods include, for example, electrophoresis, capillary electrophoresis, high performance liquid chromatography (HPLC), thin layer chromatography (TLC), hyperdiffusion chromatography, fluid or gel precipitin reactions, absorption spectroscopy, a colorimetric assays, spectrophotometric assays, flow cytometry, immunodiffusion (single or double), immunoelectrophoresis, Western blotting, radioimmunoassay (RIA), enzyme-linked immunosorbent assays (ELISAs), immunofluorescent assays, electrochemiluminescence assays, and the like.

The term "sample" as used herein refers to a collection of similar fluids, cells, or tissues isolated from a subject, as well as fluids, cells, or tissues present within a subject. Examples of biological fluids include blood, serum and serosal fluids, plasma, lymph, urine, cerebrospinal fluid, saliva, ocular fluids, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In preferred embodiments, a "sample derived from a subject" refers to blood or plasma drawn from the subject. In further embodiments, a "sample derived from a subject" refers to liver tissue derived from the subject.

In some embodiments of the methods of the invention, the RNAi agent is administered to a subject such that the RNAi agent is delivered to a specific site within the subject. The inhibition of expression of Serpina1 may be assessed using measurements of the level or change in the level of Serpina1 mRNA or Serpina1 protein in a sample derived from fluid or tissue from the specific site within the subject. In preferred embodiments, the site is the liver. The site may also be a subsection or subgroup of cells from any one of the aforementioned sites. The site may also include cells that express a particular type of receptor.

V. Methods for Treating or Preventing a Serpina1 Associated Disease

The present invention also provides methods for treating or preventing diseases and conditions that can be modulated by down regulating Serpina1 gene expression. For example, the compositions described herein can be used to treat Serpina1 associated diseases, such as liver diseases, e.g., chronic liver disease, liver inflammation, cirrhosis, liver fibrosis, and/or hepatocellular carcinoma, and other pathological conditions that may be associated with these disorders, such as lung inflammation, emphysema, and COPD.

The present invention also provides methods for inhibiting the development of hepatocellular carcinoma in a subject, e.g., a subject having a Serpina1 deficiency variant. The methods include administering a therapeutically effective amount of a composition of the invention to the subject, thereby inhibiting the development of hepatocellular carcinoma in the subject.

Methods and uses of the compositions of the invention for reducing the accumulation of misfolded Serpina1 in the liver of a subject, e.g., a subject having a Serpina1 deficiency variant, are also provided by the present invention. The methods include administering a therapeutically effective amount of a composition of the invention to the subject, thereby reducing the accumulation of misfolded Serpina1 in the liver of the subject.

As used herein, a "subject" includes a human or non-human animal, preferably a vertebrate, and more preferably a mammal. A subject may include a transgenic organism. Most preferably, the subject is a human, such as a human suffering from or predisposed to developing a Serpina1-associated disease. In one embodiment, the subject suffering or predisposed to developing a Serpina1-associated disease has one or more Serpina1 deficient alleles, e.g., a PIZ, PIS, or PIM(Malton) allele.

In further embodiments of the invention, an iRNA agent of the invention is administered in combination with an additional therapeutic agent. The iRNA agent and an additional therapeutic agent can be administered in combination in the same composition, e.g., parenterally, or the additional therapeutic agent can be administered as part of a separate composition or by another method described herein.

Examples of additional therapeutic agents suitable for use in the methods of the invention include those agents known to treat liver disorders, such as liver cirhosis. For example, an iRNA agent featured in the invention can be administered with, e.g., ursodeoxycholic acid (UDCA), immunosuppressive agents, methotrexate, corticosteroids, cyclosporine, colchicine, antipruritic treatments, such as antihistamines, cholestyramine, colestipol, rifampin, dronabinol (Marinol), and plasmaphesesis, prophylactic antibiotics, ultraviolet light, zinc supplements, and hepatitis A, influenza and pneumococci vaccination.

In some embodiments of the methods of the invention, Serpina1 expression is decreased for an extended duration, e.g., at least one week, two weeks, three weeks, or four weeks or longer. For example, in certain instances, expression of the Serpina1 gene is suppressed by at least about 5%, 10%, 15%, 20%, 25%, 30%, 35%, 40%, 45%, 50%, or 55% by administration of an iRNA agent described herein. In some embodiments, the Serpina1 gene is suppressed by at least about 60%, 70%, or 80% by administration of the iRNA agent. In some embodiments, the Serpina1 gene is suppressed by at least about 85%, 90%, or 95% by administration of the iRNA agent.

The iRNA agents of the invention may be administered to a subject using any mode of administration known in the art, including, but not limited to subcutaneous, intravenous, intramuscular, intraocular, intrabronchial, intrapleural, intraperitoneal, intraarterial, lymphatic, cerebrospinal, and any combinations thereof. In preferred embodiments, the iRNA agents are administered subcutaneously.

In some embodiments, the administration is via a depot injection. A depot injection may release the iRNA agents in a consistent way over a prolonged time period. Thus, a depot injection may reduce the frequency of dosing needed to obtain a desired effect, e.g., a desired inhibition of Serpina1, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the RNAi agent to the liver.

Other modes of administration include epidural, intracerebral, intracerebroventricular, nasal administration, intraarterial, intracardiac, intraosseous infusion, intrathecal, and intravitreal, and pulmonary. The mode of administration may be chosen based upon whether local or systemic treatment is desired and based upon the area to be treated. The route and site of administration may be chosen to enhance targeting.

The methods of the invention include administering an iRNA agent at a dose sufficient to suppress/decrease levels of Serpina1 mRNA for at least 5, more preferably 7, 10, 14, 21, 25, 30 or 40 days; and optionally, administering a second single dose of the iRNA agent, wherein the second single dose is administered at least 5, more preferably 7, 10, 14, 21, 25, 30 or 40 days after the first single dose is administered, thereby inhibiting the expression of the Serpina1 gene in a subject.

In one embodiment, doses of an iRNA agent of the invention are administered not more than once every four weeks, not more than once every three weeks, not more than once every two weeks, or not more than once every week. In another embodiment, the administrations can be maintained for one, two, three, or six months, or one year or longer.

In general, the iRNA agent does not activate the immune system, e.g., it does not increase cytokine levels, such as TNF-alpha or IFN-alpha levels. For example, when measured by an assay, such as an in vitro PBMC assay, such as described herein, the increase in levels of TNF-alpha or IFN-alpha, is less than 30%, 20%, or 10% of control cells treated with a control iRNA agent, such as an iRNA agent that does not target Serpina1.

For example, a subject can be administered a therapeutic amount of an iRNA agent, such as 0.5 mg/kg, 1.0 mg/kg, 1.5 mg/kg, 2.0 mg/kg, or 2.5 mg/kg dsRNA. The iRNA agent can be administered by intravenous infusion over a period of time, such as over a 5 minute, 10 minute, 15 minute, 20 minute, or 25 minute period. The administration is repeated, for example, on a regular basis, such as biweekly (i.e., every two weeks) for one month, two months, three months, four months or longer.

After an initial treatment regimen, the treatments can be administered on a less frequent basis. For example, after administration biweekly for three months, administration can be repeated once per month, for six months or a year or longer. Administration of the iRNA agent can reduce Serpina1 levels, e.g., in a cell, tissue, blood, urine, organ (e.g., the liver), or other compartment of the patient by at least 10%, at least 15%, at least 20%, at least 25%, at least 30%, at least 40%, at least 50%, at least 60%, at least 70%, at least 80% or at least 90% or more.

Before administration of a full dose of the iRNA agent, patients can be administered a smaller dose, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels. An exemplary smaller dose is one that results in an incidence of infusion reaction of less than or equal to 5%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of liver fibrosis or amelioration of liver fibrosis can be assessed, for example by periodic monitoring of liver fibrosis markers: a-2-macroglobulin (a-MA), transferrin, apolipoproteinA1, hyaluronic acid (HA), laminin, N-terminal procollagen III (PIIINP), 7S collagen IV (7S-IV), total bilirubin, indirect bilirubin, alanine aminotransferase (ALT), aspartate aminotransferase (AST), AST/ALT, g-glutamyl transpeptidase (GGT), alkaline phosphatase (ALP), albumin, albumin/globulin, blood urea nitrogen (BUN), creatinine (Cr), triglyceride, cholersterol, high density lipoprotein and low density lipoprotein and liver puncture biopsy. Liver fibrosis markers can be measured and/or liver puncture biopsy can be performed before treatment (initial readings) and subsequently (later readings) during the treatment regimen.

Comparisons of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA agent targeting Serpina1 or pharmaceutical composition thereof, "effective against" a Serpina1 associate disease, such as a liver disease, e.g., a hepatic fibrosis condition, indicates that administration of an iRNA agent of the invention in a clinically appropriate manner results in a beneficial effect for at least a statistically significant fraction of patients, such as an improvement of symptoms, a cure, a reduction in disease load, reduction in tumor mass or cell numbers, extension of life, improvement in quality of life, or other effect generally recognized as positive by medical doctors familiar with treating liver diseases.

In the methods of the invention, an iRNA agent as described herein can be used to treat individuals having the signs, symptoms and/or markers of, or being diagnosed with, or being a risk of having an Serpina1 associate disease, such as a liver disease, e.g., liver inflammation, cirrhosis, liver fibrosis, and/or hepatoceullar carcinoma. One of skill in the art can easily monitor the signs, symptoms, and/or makers of such disorders in subjects receiving treatment with an iRNA agent as described herein and assay for a reduction in these signs, symptoms and/or makers of at least 10% and preferably to a clinical level representing a low risk of liver disease.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease (such as a liver function described supra), and preferably at least 20%, 30%, 40%, 50% or more can be indicative of effective treatment.

Efficacy for a given iRNA agent of the invention or formulation of that iRNA agent can also be judged using an experimental animal model for the given disease as known in the art. When using an experimental animal model, efficacy of treatment is evidenced when a statistically significant reduction in a marker or symptom is observed.

A treatment or preventive effect is also evident when one or more symptoms are reduced or alleviated. For example, a treatment or preventive is effective when one or more of weakness, fatigue, weight loss, nausea, vomiting, abdominal swelling, extremity swelling, excessive itching, and jaundice of the eyes and/or skin is reduced or alleviated.

For certain indications, the efficacy can be measured by an increase in serum levels of Serpina1 protein. As an example, an increase of serum levels of properly folded Serpina1 of at least 10%, at least 20%, at least 50%, at least 100%, at least 200% more can be indicative of effective treatment.

Alternatively, the efficacy can be measured by a reduction in the severity of disease as determined by one skilled in the art of diagnosis based on a clinically accepted disease severity grading scale, as but one example the Child-Pugh score (sometimes the Child-Turcotte-Pugh score). In this example, prognosis of chronic liver disease, mainly cirrhosis, is measured by an aggregate score of five clinical measures, bilirubin, serum albumin, INR, ascites, and hepatic encephalopathy. Each marker is assigned a value from 1-3, and the total value is used to provide a score categorized as A (5-6 points), B (7-9 points), or C (10-15 points), which can be correlated with one and two year survival rates. Methods for determination and analysis of Child-Pugh scores are well known in the art (Farnsworth et al, Am J Surgery 2004 188:580-583; Child and Turcotte. Surgery and portal hypertension. In: The liver and portal hypertension. Edited by CG Child. Philadelphia: Saunders 1964:50-64; Pugh et al, Br J Surg 1973; 60:648-52). Efficacy can be measured in this example by the movement of a patient from e.g., a "B" to an "A." Any positive change resulting in e.g., lessening of severity of disease measured using the appropriate scale, represents adequate treatment using an iRNA or iRNA formulation as described herein.

In one embodiment, the RNAi agent is administered at a dose of between about 0.25 mg/kg to about 50 mg/kg, e.g., between about 0.25 mg/kg to about 0.5 mg/kg, between about 0.25 mg/kg to about 1 mg/kg, between about 0.25 mg/kg to about 5 mg/kg, between about 0.25 mg/kg to about 10 mg/kg, between about 1 mg/kg to about 10 mg/kg, between about 5 mg/kg to about 15 mg/kg, between about 10 mg/kg to about 20 mg/kg, between about 15 mg/kg to about 25 mg/kg, between about 20 mg/kg to about 30 mg/kg, between about 25 mg/kg to about 35 mg/kg, or between about 40 mg/kg to about 50 mg/kg.

In some embodiments, the RNAi agent is administered at a dose of about 0.25 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 11 mg/kg, about 12 mg/kg, about 13 mg/kg, about 14 mg/kg, about 15 mg/kg, about 16 mg/kg, about 17 mg/kg, about 18 mg/kg, about 19 mg/kg, about 20 mg/kg, about 21 mg/kg, about 22 mg/kg, about 23 mg/kg, about 24 mg/kg, about 25 mg/kg, about 26 mg/kg, about 27 mg/kg, about 28 mg/kg, about 29 mg/kg, 30 mg/kg, about 31 mg/kg, about 32 mg/kg, about 33 mg/kg, about 34 mg/kg, about 35 mg/kg, about 36 mg/kg, about 37 mg/kg, about 38 mg/kg, about 39 mg/kg, about 40 mg/kg, about 41 mg/kg, about 42 mg/kg, about 43 mg/kg, about 44 mg/kg, about 45 mg/kg, about 46 mg/kg, about 47 mg/kg, about 48 mg/kg, about 49 mg/kg or about 50 mg/kg.

In certain embodiments of the invention, for example, when a double-stranded RNAi agent includes modifications (e.g., one or more motifs of three identical modifications on three consecutive nucleotides, including one such motif at or near the cleavage site of the agent), six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/mg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The dose of an RNAi agent that is administered to a subject may be tailored to balance the risks and benefits of a particular dose, for example, to achieve a desired level of Serpina1 gene suppression (as assessed, e.g., based on Serpina1 mRNA suppression, Serpina1 protein expression) or a desired therapeutic or prophylactic effect, while at the same time avoiding undesirable side effects.

In some embodiments, the RNAi agent is administered in two or more doses. If desired to facilitate repeated or frequent infusions, implantation of a delivery device, e.g., a pump, semi-permanent stent (e.g., intravenous, intraperitoneal, intracisternal or intracapsular), or reservoir may be advisable. In some embodiments, the number or amount of subsequent doses is dependent on the achievement of a desired effect, e.g., the suppression of a Serpina1 gene, or the achievement of a therapeutic or prophylactic effect, e.g., reducing a symptom of a liver disease. In some embodiments, the RNAi agent is administered according to a schedule. For example, the RNAi agent may be administered once per week, twice per week, three times per week, four times per week, or five times per week. In some embodiments, the schedule involves regularly spaced administrations, e.g., hourly, every four hours, every six hours, every eight hours, every twelve hours, daily, every 2 days, every 3 days, every 4 days, every 5 days, weekly, biweekly, or monthly. In other embodiments, the schedule involves closely spaced administrations followed by a longer period of time during which the agent is not administered. For example, the schedule may involve an initial set of doses that are administered in a relatively short period of time (e.g., about every 6 hours, about every 12 hours, about every 24 hours, about every 48 hours, or about every 72 hours) followed by a longer time period (e.g., about 1 week, about 2 weeks, about 3 weeks, about 4 weeks, about 5 weeks, about 6 weeks, about 7 weeks, or about 8 weeks) during which the RNAi agent is not administered. In one embodiment, the RNAi agent is initially administered hourly and is later administered at a longer interval (e.g., daily, weekly, biweekly, or monthly). In another embodiment, the RNAi agent is initially administered daily and is later administered at a longer interval (e.g., weekly, biweekly, or monthly). In certain embodiments, the longer interval increases over time or is determined based on the achievement of a desired effect. In a specific embodiment, the RNAi agent is administered once daily during a first week, followed by weekly dosing starting on the eighth day of administration. In another specific embodiment, the RNAi agent is administered every other day during a first week followed by weekly dosing starting on the eighth day of administration.

In some embodiments, the RNAi agent is administered in a dosing regimen that includes a "loading phase" of closely spaced administrations that may be followed by a "maintenance phase", in which the RNAi agent is administered at longer spaced intervals. In one embodiment, the loading phase comprises five daily administrations of the RNAi agent during the first week.

In another embodiment, the maintenance phase comprises one or two weekly administrations of the RNAi agent. In a further embodiment, the maintenance phase lasts for 5 weeks. In one embodiment, the loading phase comprises administration of a dose of 2 mg/kg, 1 mg/kg or 0.5 mg/kg five times a week. In another embodiment, the maintenance phase comprises administration of a dose of 2 mg/kg, 1 mg/kg or 0.5 mg/kg once or twice weekly.

Any of these schedules may optionally be repeated for one or more iterations. The number of iterations may depend on the achievement of a desired effect, e.g., the suppression of a Serpina1 gene, and/or the achievement of a therapeutic or prophylactic effect, e.g., reducing a symptom of a Serpina1 associated disease, e.g., a liver disease.

In another aspect, the invention features, a method of instructing an end user, e.g., a caregiver or a subject, on how to administer an iRNA agent described herein. The method includes, optionally, providing the end user with one or more doses of the iRNA agent, and instructing the end user to administer the iRNA agent on a regimen described herein, thereby instructing the end user.

Genetic predisposition plays a role in the development of target gene associated diseases, e.g., liver disease. Therefore, a patient in need of a siRNA can be identified by taking a family history, or, for example, screening for one or more genetic markers or variants. Accordingly, in one aspect, the invention provides a method of treating a patient by selecting a patient on the basis that the patient has one or more of a Serpina1 deficiency or a Serpina1 deficiency gene variant, e.g., a PIZ, PIS, or PIM(Malton) allele. The method includes administering to the patient an iRNA agent in a therapeutically effective amount.

A healthcare provider, such as a doctor, nurse, or family member, can take a family history before prescribing or administering an iRNA agent of the invention. In addition, a test may be performed to determine a genotype or phenotype. For example, a DNA test may be performed on a sample from the patient, e.g., a blood sample, to identify the Serpina1 genotype and/or phenotype before a Serpina1 dsRNA is administered to the patient.

VI. Kits

The present invention also provides kits for using any of the iRNA agents and/or performing any of the methods of the invention. Such kits include one or more RNAi agent(s) and instructions for use, e.g., instructions for inhibiting expression of a Serpina1 in a cell by contacting the cell with the RNAi agent(s) in an amount effective to inhibit expression of the Serpina1. The kits may optionally further comprise means for contacting the cell with the RNAi agent (e.g., an injection device), or means for measuring the inhibition of Serpina1 (e.g., means for measuring the inhibition of Serpina1 mRNA). Such means for measuring the inhibition of Serpina1 may comprise a means for obtaining a sample from a subject, such as, e.g., a plasma sample. The kits of the invention may optionally further comprise means for administering the RNAi agent(s) to a subject or means for determining the therapeutically effective or prophylactically effective amount.

Unless otherwise defined, all technical and scientific terms used herein have the same meaning as commonly understood by one of ordinary skill in the art to which this invention belongs. Although methods and materials similar or equivalent to those described herein can be used in the practice or testing of the iRNAs and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Materials and Methods

The following materials and methods were used in the Examples.

siRNA Design

The Serpina1 gene has multiple, alternate transcripts. siRNA design was carried out to identify siRNAs targeting all human and Cynomolgus monkey (*Macaca fascicularis*; henceforth "cyno") Serpina1 transcripts annotated in the NCBI Gene database (http://www.ncbi.nlm.nih.gov/gene/). The following human transcripts from the NCBI RefSeq collection were used: Human—NM_000295.4, NM_001002235.2, NM_001002236.2, NM_001127700.1, NM_001127701.1, NM_001127702.1, NM_001127703.1, NM_001127704.1, NM_001127705.1, NM_001127706.1, NM_001127707.1. To identify a cyno transcript, the rhesus monkey (*Macaca mulatta*) transcript, XM_001099255.2, was aligned to the *M. fascicularis* genome using the Spidey alignment tool (www.ncbi.nlim,nih.gov/spidey/). The overall percent identity of rhesus and cyno transcripts was 99.6%. The cyno transcript was hand-assembled to preserve consensus splice sites and full-length coding and untranslated regions. The resulting transcript was 2064 nucleotides long.

All siRNA duplexes were designed that shared 100% identity with all listed human and cyno transcripts.

Five hundred eighty-five candidate siRNAs were used in a comprehensive search against the human transcriptome (defined as the set of NM_ and XM_records within the human NCBI Refseq set). A total of 48 sense (21 mers) and 48 antisense (23 mers) derived siRNA oligos were synthesized and formed into duplexes. A detailed list of Serpina1 sense and antisense strand sequences is shown in Tables 1 and 2.

siRNA Synthesis

I. General Small and Medium Scale RNA Synthesis Procedure

RNA oligonucleotides were synthesized at scales between 0.2-500 µmol using commercially available 5'-O-(4,4'-dimethoxytrityl)-2'-O-t-butyldimethylsilyl-3'-O-(2-cyanoethyl-N,N-diisopropyl)phosphoramidite monomers of uridine, 4-N-acetylcytidine, 6-N-benzoyladenosine and 2-N-isobutyrylguanosine and the corresponding 2'-O-methyl and 2'-fluoro phosphoramidites according to standard solid phase oligonucleotide synthesis protocols. The amidite solutions were prepared at 0.1-0.15 M concentration and 5-ethylthio-1H-tetrazole (0.25-0.6 M in acetonitrile) was used as the activator. Phosphorothioate backbone modifications were introduced during synthesis using 0.2 M phenylacetyl disulfide (PADS) in lutidine:acetonitrile (1:1) (v;v) or 0.1 M 3-(dimethylaminomethylene) amino-3H-1,2,4-dithiazole-5-thione (DDTT) in pyridine for the oxidation step. After completion of synthesis, the sequences were cleaved from the solid support and deprotected using methylamine followed by triethylamine. 3HF to remove any 2'-O-t-butyldimethylsilyl protecting groups present.

For synthesis scales between 5-500 µmol and fully 2' modified sequences (2'-fluoro and/or 2'-O-methyl or combinations thereof) the oligonucleotides where deprotected using 3:1 (v/v) ethanol and concentrated (28-32%) aqueous ammonia either at 35° C. 16 h or 55° C. for 5.5 h. Prior to ammonia deprotection the oligonucleotides where treated with 0.5 M piperidine in acetonitrile for 20 min on the solid support. The crude oligonucleotides were analyzed by LC-MS and anion-exchange HPLC (IEX-HPLC). Purification of the oligonucleotides was carried out by IEX HPLC using: 20 mM phosphate, 10%-15% ACN, pH=8.5 (buffer A) and 20 mM phosphate, 10%-15% ACN, 1 M NaBr, pH=8.5 (buffer B). Fractions were analyzed for purity by analytical HPLC. The product-containing fractions with suitable purity were pooled and concentrated on a rotary evaporator prior to desalting. The samples were desalted by size exclusion chromatography and lyophilized to dryness. Equal molar amounts of sense and antisense strands were annealed in 1×PBS buffer to prepare the corresponding siRNA duplexes.

For small scales (0.2-1 µmol), synthesis was performed on a MerMade 192 synthesizer in a 96 well format. In case of fully 2'-modified sequences (2'-fluoro and/or 2'-O-methyl or combinations thereof) the oligonucleotides where deprotected using methylamine at room temperature for 30-60 min followed by incubation at 60° C. for 30 min or using 3:1 (v/v) ethanol and concentrated (28-32%) aqueous ammonia at room temperature for 30-60 min followed by incubation at 40° C. for 1.5 hours. The crude oligonucleotides were then precipitated in a solution of acetonitrile:acetone (9:1) and isolated by centrifugation and decanting the supernatant. The crude oligonucleotide pellet was re-suspended in 20 mM NaOAc buffer and analyzed by LC-MS and anion exchange HPLC. The crude oligonucleotide sequences were desalted in 96 deep well plates on a 5 mL HiTrap Sephadex G25 column (GE Healthcare). In each well about 1.5 mL samples corresponding to an individual sequence was collected. These purified desalted oligonucleotides were analyzed by LC-MS and anion exchange chromatography. Duplexes were prepared by annealing equimolar amounts of sense and antisense sequences on a Tecan robot. Concentration of duplexes was adjusted to 10 µM in 1×PBS buffer.

II. Synthesis of GalNAc-Conjugated Oligonucleotides for In Vivo Analysis

Oligonucleotides conjugated with GalNAc ligand at their 3'-terminus were synthesized at scales between 0.2-500 µmol using a solid support pre-loaded with a Y-shaped linker bearing a 4,4'-dimethoxytrityl (DMT)-protected primary hydroxy group for oligonucleotide synthesis and a GalNAc ligand attached through a tether.

For synthesis of GalNAc conjugates in the scales between 5-500 µmol, the above synthesis protocol for RNA was followed with the following adaptions: For polystyrene-based synthesis supports 5% dichloroacetic acid in toluene was used for DMT-cleavage during synthesis. Cleavage from the support and deprotection was performed as described above. Phosphorothioate-rich sequences (usually >5 phosphorothioates) were synthesized without removing the final 5'-DMT group ("DMT-on") and, after cleavage and deprotection as described above, purified by reverse phase HPLC using 50 mM ammonium acetate in water (buffer A) and 50 mM ammoniumacetate in 80% acetonitrile (buffer B). Fractions were analyzed for purity by analytical HPLC and/or LC-MS. The product-containing fractions with suitable purity were pooled and concentrated on a rotary evaporator. The DMT-group was removed using 20%-25% acetic acid in water until completion. The samples were desalted by size exclusion chromatography and lyophilized to dryness. Equal molar amounts of sense and antisense strands were annealed in 1×PBS buffer to prepare the corresponding siRNA duplexes.

For small scale synthesis of GalNAc conjugates (0.2-1 µmol), including sequences with multiple phosphorothioate linkages, the protocols described above for synthesis of RNA or fully 2'-F/2'-OMe-containing sequences on Mer- Made platform were applied. Synthesis was performed on pre-packed columns containing GalNAc-functionalized controlled pore glass support.

cDNA Synthesis Using ABI High Capacity cDNA Reverse Transcription Kit (Applied Biosystems, Foster City, Calif., Cat #4368813)

A master mix of 2 µl 10× Buffer, 0.8 µl 25×dNTPs, 2 µl Random primers, 1 µl Reverse Transcriptase, 1 µl RNase inhibitor and 3.2 µl of $H_2O$ per reaction was added into 10 µl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Cell Culture and Transfections

Hep3B, HepG2 or HeLa cells (ATCC, Manassas, Va.) were grown to near confluence at 37° C. in an atmosphere of 5% $CO_2$ in recommended media (ATCC) supplemented with 10% FBS and glutamine (ATCC) before being released from the plate by trypsinization. For duplexes screened in 96-well format, transfection was carried out by adding 44.75 µl of Opti-MEM plus 0.25 µl of Lipofectamine RNAiMax per well (Invitrogen, Carlsbad Calif. cat #13778-150) to 5 µl of each siRNA duplex to an individual well in a 96-well plate. The mixture was then incubated at room temperature for 15 minutes. Fifty µl of complete growth media without antibiotic containing ~$2\times10^4$ cells were then added to the siRNA mixture. For duplexes screened in 384-well format, 5 µl of Opti-MEM plus 0.1 µl of Lipofectamine RNAiMax (Invitrogen, Carlsbad Calif. cat #13778-150) was mixed with 5 µl of each siRNA duplex per an individual well. The mixture was then incubated at room temperature for 15 minutes followed by addition of 40 µl of complete growth media without antibiotic containing ~$8\times10^3$ cells. Cells were incubated for 24 hours prior to RNA purification. Single dose experiments were performed at 10 nM and 0.1 nM final duplex concentration and dose response experiments were done at 10, 1.67, 0.27, 0.046, 0.0077, 0.0013, 0.00021, 0.00004 nM final duplex concentration.

Free Uptake Transfection

Five µl of each GalNac conjugated siRNA in PBS was combined with $3\times10^4$ freshly thawed cryopreserved Cynomolgus monkey hepatocytes (In Vitro Technologies-Celsis, Baltimore, Md.; lot#JQD) resuspended in 95 µl of In Vitro Gro CP media (In Vitro Technologies-Celsis, Baltimore, Md.) in each well of a 96-well plate or 5 ul siRNA and 45 µl media containing $1.2\times10^3$ cells for 384 well plate format. The mixture was incubated for about 24 hours at 37° C. in an atmosphere of 5% $CO_2$. siRNAs were tested at final concentrations of 500 nM and O1 nM.

Total RNA Isolation Using DYNABEADS mRNA Isolation Kit (Invitrogen, Part #: 610-12) Cells were harvested and lysed in 150 µl of Lysis/Binding Buffer then mixed for 5 minutes at 850 rpm using an Eppendorf Thermomixer (the mixing speed was the same throughout the process). Ten microliters of magnetic beads and 80l1 Lysis/Binding Buffer mixture were added to a round bottom plate and mixed for 1 minute. Magnetic beads were captured using magnetic stand and the supernatant was removed without disturbing the beads. After removing the supernatant, the lysed cells were added to the remaining beads and mixed for 5 minutes. After removing the supernatant, magnetic beads were washed 2 times with 150 µl Wash Buffer A and mixed for 1 minute. Beads were captured again and the supernatant removed. Beads were then washed with 150 µl Wash Buffer B, captured and the supernatant was removed. Beads were next washed with 150 µl Elution Buffer, captured and the supernatant removed. Beads were allowed to dry for 2 minutes. After drying, 50 µl of Elution Buffer was added and mixed for 5 minutes at 70° C. Beads were captured on a magnet for 5 minutes. Fifty µl of supernatant was removed and added to another 96-well plate.

For 384-well format, the cells were lysed for one minute by addition of 50 µl Lysis/Binding buffer. Two µl of magnetic beads per well was used. The required volume of beads was aliquoted, captured on a magnetic stand, and the bead storage solution was removed. The beads were then resuspended in the required volume of Lysis/Binding buffer (25 µl per well) and 25 µl of bead suspension was added to the lysed cells. The lysate-bead mixture was incubated for 10 minutes on VibraTransaltor at setting #7 (UnionScientific Corp., Randallstown, Md.). Subsequently beads were captured using a magnetic stand, the supernatant removed and the beads are washed once with 90 µl Buffer A, followed by single washing steps with 90 µl Buffer B and 100l of Elution buffer. The beads were soaked in each washing buffer for ~1 minute (no mixing involved). After the final wash step, the beads were resuspended in 15 µl of elution buffer for 5 minutes at 70° C., followed by bead capture and the removal of the supernatant (up to 8 µl) for cDNA synthesis and/or purified RNA storage (−20° C.).

Real Time PCR

Two µl of cDNA were added to a master mix containing 0.5 µl GAPDH TaqMan Probe (Applied Biosystems Cat #4326317E), 0.5 µl SERPINA1 TaqMan probe (Applied Biosystems cat #Hs00165475_ml) for Hep3B experiments or with custom designed GAPDH and SERPINA1 taqman assays for PCH experiments and 5 µl Lightcycler 480 probe master mix (Roche Cat #04887301001) per well in a 384 well plates (Roche cat #04887301001). Real time PCR was done in a Roche LC480 Real Time PCR system (Roche). Each duplex was tested in at least two independent transfections with two biological replicates each, and each transfection was assayed in duplicate.

To calculate relative fold change, real time data were analyzed using the ΔΔCt method and normalized to assays performed with cells transfected with 10 nM AD-1955, or mock transfected cells. For free uptake assays the data were normalized to PBS or GalNAc-1955 (highest concentration used for experimental compounds) treated cells. $IC_{50}$s were calculated using a 4 parameter fit model using XLFit and normalized to cells transfected with AD-1955 over the same dose range, or to its own lowest dose.

The sense and antisense sequences of AD-1955 are: SENSE: 5'-cuuAcGcuGAGuAcuucGAdTsdT-3'(SEQ ID NO: 33); and ANTISENSE: 5'-UCGAAGuA-CUcAGCGuAAGdTsdT-3'(SEQ ID NO: 40).

The Taqman primers and probes used are as follows:
Cynomolgus Serpina1 and Gapdh TaqMan Primers and Probes:

```
Serpina1:
Forward Primer:
                                       (SEQ ID NO: 34)
ACTAAGGTCTTCAGCAATGGG;

Reverse Primer:
                                       (SEQ ID NO: 35)
GCTTCAGTCCCTTTCTCATCG;

Taqman Probe:
                                       (SEQ ID NO: 36)
TGGTCAGCACAGCCTTATGCACG
```

Gapdh:
Forward Primer:
(SEQ ID NO: 37)
GCATCCTGGGCTACACTGA;

Reverse Primer:
(SEQ ID NO: 38)
TGGGTGTCGCTGTTGAAGTC;

Taqman Probe:
(SEQ ID NO: 39)
CCAGGTGGTCTCCTCC

TABLE B

Abbreviations of nucleotide monomers used in nucleic acid sequence representation.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| dT | 2'-deoxythymidine |
| dTs | 2'-deoxythymidine-3'-phosphorothioate |
| dU | 2'-deoxyuridine |
| s | phosphorothioate linkage |
| L96 | N-[tris(GalNAc-alkyl)-amidodecanoyl)]-4-hydroxyprolinol Hyp-(GalNAc-alkyl)3 |
| I | inosine-3'-phosphate |
| Is | inosine-3'-phosphorothioate |
| dI | 2'-deoxyriboinosine |
| dIs | 2'-deoxyinosine-3'-phosphorothioate |
| Y34 | 2-hydroxymethyl-tetrahydrofurane-4-methoxy-3-phosphate (abasic 2'-OMe furanose) |
| Y34s | 2-hydroxymethyl-tetrahydrofurane-4-methoxy-3-phosphorothioate (abasic 2'-OMe furanose) |
| P | 5'-phosphate |

Example 1. Synthesis of GalNAc-Conjugated Oligonucleotides

A series of siRNA duplexes spanning the sequence of Serpina1 mRNA were designed, synthesized, and conjugated with a trivalent GalNAc at the 3-end of the sense strand using the techniques described above. The sequences of these duplexes are shown in Table 1. These same sequences were also synthesized with various nucleotide modifications and conjugated with a trivalent GalNAc. The sequences of the modified duplexes are shown in Table 2.

TABLE 1

Serpinal unmodified sequences

| Duplex Name | Sense Oligo Name | Sense Trans Seq | SEQ ID NO: | Position in NM_000295.4 | Antisense Oligo Name | Antisense Trans Sequence | SEQ ID NO: | Position in NM_000295.4 |
|---|---|---|---|---|---|---|---|---|
| AD-58681.1 | A-119065.1 | GUCCAACAGCACCAAUAUCUU | 41 | 469-489 | A-119066.1 | AAGAUAUUGGUGCUGUUGGACUG | 129 | 467-489 |
| AD-59084.1 | A-119065.2 | GUCCAACAGCACCAAUAUCUU | 42 | 469-489 | A-119941.1 | AAGAUAUUGGUGCUGUUGGACUG | 130 | 467-489 |
| AD-59060.2 | A-119933.1 | UAAUGAUUGAACAAAAUACCA | 43 | 1455-1475 | A-119934.1 | UGGUAUUUUGUUCAAUCAUUAAG | 131 | 1453-1475 |
| AD-59060.1 | A-119933.1 | UAAUGAUUGAACAAAAUACCA | 44 | 1455-1475 | A-119934.1 | UGGUAUUUUGUUCAAUCAUUAAG | 132 | 1453-1475 |
| AD-59054.2 | A-119931.1 | CUUCUUAAUGAUUGAACAAAA | 45 | 1450-1470 | A-119932.1 | UUUUGUUCAAUCAUUAAGAAGAC | 133 | 1448-1470 |
| AD-59054.1 | A-119931.1 | CUUCUUAAUGAUUGAACAAAA | 46 | 1450-1470 | A-119932.1 | UUUUGUUCAAUCAUUAAGAAGAC | 134 | 1448-1470 |
| AD-59072.2 | A-119937.1 | AUUGAACAAAAUACCAAGUCU | 47 | 1460-1480 | A-119938.1 | AGACUUGGUAUUUUGUUCAAUCA | 135 | 1458-1480 |
| AD-59072.1 | A-119937.1 | AUUGAACAAAAUACCAAGUCU | 48 | 1460-1480 | A-119938.1 | AGACUUGGUAUUUUGUUCAAUCA | 136 | 1458-1480 |
| AD-59048.2 | A-119929.1 | UUCUUAAUGAUUGAACAAAAU | 49 | 1451-1471 | A-119930.1 | AUUUUGUUCAAUCAUUAAGAAGA | 137 | 1449-1471 |
| AD-59048.1 | A-119929.1 | UUCUUAAUGAUUGAACAAAAU | 50 | 1451-1471 | A-119930.1 | AUUUUGUUCAAUCAUUAAGAAGA | 138 | 1449-1471 |
| AD-59062.2 | A-119964.1 | CAAACCCUUUGUCUUCUUAAU | 51 | 1438-1458 | A-119965.1 | AUUAAGAAGACAAAGGGUUUGUU | 139 | 1436-1458 |
| AD-59062.1 | A-119964.1 | CAAACCCUUUGUCUUCUUAAU | 52 | 1438-1458 | A-119965.1 | AUUAAGAAGACAAAGGGUUUGUU | 140 | 1436-1458 |
| AD-59078.2 | A-119939.1 | UGUCUUCUUAAUGAUUGAACA | 53 | 1447-1467 | A-119940.1 | UGUUCAAUCAUUAAGAAGACAAA | 141 | 1445-1467 |
| AD-59078.1 | A-119939.1 | UGUCUUCUUAAUGAUUGAACA | 54 | 1447-1467 | A-119940.1 | UGUUCAAUCAUUAAGAAGACAAA | 142 | 1445-1467 |
| AD-59056.2 | A-119962.1 | CACCUGGAAAAUGAACUCACC | 55 | 1121-1141 | A-119963.1 | GGUGAGUUCAUUUUCCAGGUGCU | 143 | 1119-1141 |
| AD-59056.1 | A-119962.1 | CACCUGGAAAAUGAACUCACC | 56 | 1121-1141 | A-119963.1 | GGUGAGUUCAUUUUCCAGGUGCU | 144 | 1119-1141 |
| AD-59091.2 | A-119958.1 | UUUUGCUCUGGUGAAUUACAU | 57 | 880-900 | A-119959.1 | AUGUAAUUCACCAGAGCAAAAC | 145 | 878-900 |
| AD-59091.1 | A-119958.1 | UUUUGCUCUGGUGAAUUACAU | 58 | 880-900 | A-119959.1 | AUGUAAUUCACCAGAGCAAAAC | 146 | 878-900 |
| AD-59083.2 | A-120018.1 | ACCCUUUGUCUUCUUAAUGAU | 59 | 1441-1461 | A-120019.1 | AUCAUUAAGAAGACAAAGGGUUU | 147 | 1439-1461 |
| AD-59083.1 | A-120018.1 | ACCCUUUGUCUUCUUAAUGAU | 60 | 1441-1461 | A-120019.1 | AUCAUUAAGAAGACAAAGGGUUU | 148 | 1439-1461 |
| AD-59073.2 | A-119952.1 | UUGAACAAAAUACCAAGUCUC | 61 | 1461-1481 | A-119953.1 | GAGACUUGGUAUUUUGUUCAUC | 149 | 1459-1481 |
| AD-59073.1 | A-119952.1 | UUGAACAAAAUACCAAGUCUC | 62 | 1461-1481 | A-119953.1 | GAGACUUGGUAUUUUGUUCAUC | 150 | 1459-1481 |
| AD-59066.2 | A-119935.1 | GUUCAACAAACCCUUUGUCUU | 63 | 1432-1452 | A-119936.1 | AAGACAAAGGGUUUGUUGAACUU | 151 | 1430-1452 |

TABLE 1-continued

Serpinal unmodified sequences

| Duplex Name | Sense Oligo Name | Sense Trans Seq | SEQ ID NO: | Position in NM_000295.4 | Antisense Oligo Name | Antisense Trans Sequence | SEQ ID NO: | Position in NM_000295.4 |
|---|---|---|---|---|---|---|---|---|
| AD-59066.1 | A-119935.1 | GUUCAACAAACCCUUGUCUU | 64 | 1432-1452 | A-119936.1 | AAGACAAAGGGUUUGUUGAACUU | 152 | 1430-1452 |
| AD-59059.2 | A-120010.1 | AAAUACCAAGUCUCCCCUCUU | 65 | 1468-1488 | A-120011.1 | AAGAGGGGAGACUUGGUAUUUUG | 153 | 1466-1488 |
| AD-59059.1 | A-120010.1 | AAAUACCAAGUCUCCCCUCUU | 66 | 1468-1488 | A-120011.1 | AAGAGGGGAGACUUGGUAUUUUG | 154 | 1466-1488 |
| AD-59070.2 | A-119998.1 | UUUUUGCUCUGGUGAAUUACA | 67 | 879-899 | A-119999.1 | UGUAAUUCACCAGAGCAAAAACU | 155 | 877-899 |
| AD-59070.1 | A-119998.1 | UUUUUGCUCUGGUGAAUUACA | 68 | 879-899 | A-119999.1 | UGUAAUUCACCAGAGCAAAAACU | 156 | 877-899 |
| AD-59063.2 | A-119980.1 | AGUUCAACAAACCCUUUGUCU | 69 | 1431-1451 | A-119981.1 | AGACAAAGGGUUUGUUGAACUUG | 157 | 1429-1451 |
| AD-59063.1 | A-119980.1 | AGUUCAACAAACCCUUUGUCU | 70 | 1431-1451 | A-119981.1 | AGACAAAGGGUUUGUUGAACUUG | 158 | 1429-1451 |
| AD-59069.2 | A-119982.1 | AAUGAUUGAACAAAAAUACCAA | 71 | 1456-1476 | A-119983.1 | UUGGUAUUUUGUUCAUCAUUAA | 159 | 1454-1476 |
| AD-59069.1 | A-119982.1 | AAUGAUUGAACAAAAAUACCAA | 72 | 1456-1476 | A-119983.1 | UUGGUAUUUUGUUCAUCAUUAA | 160 | 1454-1476 |
| AD-59082.2 | A-120002.1 | UACUGGAACCUAUGAUCUGAA | 73 | 1216-1236 | A-120003.1 | UUCAGAUCAUAGGUUCCAGUAAU | 161 | 1214-1236 |
| AD-59082.1 | A-120002.1 | UACUGGAACCUAUGAUCUGAA | 74 | 1216-1236 | A-120003.1 | UUCAGAUCAUAGGUUCCAGUAAU | 162 | 1214-1236 |
| AD-59088.2 | A-120004.1 | ACAUUAAAGAAGGGUUGAGCU | 75 | 1576-1596 | A-120005.1 | AGCUCAACCCUUCUUUAAUGUCA | 163 | 1574-1596 |
| AD-59088.1 | A-120004.1 | ACAUUAAAGAAGGGUUGAGCU | 76 | 1576-1596 | A-120005.1 | AGCUCAACCCUUCUUUAAUGUCA | 164 | 1574-1596 |
| AD-59080.2 | A-119970.1 | AAAAUGUGGAUUUGGUCAAG | 77 | 839-859 | A-119971.1 | CUUGACCAAAUCCACAAUUUCC | 165 | 837-859 |
| AD-59080.1 | A-119970.1 | AAAAUGUGGAUUUGGUCAAG | 78 | 839-859 | A-119971.1 | CUUGACCAAAUCCACAAUUUCC | 166 | 837-859 |
| AD-59058.2 | A-119994.1 | AUUACUGGAACCUAUGAUCUG | 79 | 1214-1234 | A-119995.1 | CAGAUCAUAGGUUCCAGUAAUGG | 167 | 1212-1234 |
| AD-59058.1 | A-119994.1 | AUUACUGGAACCUAUGAUCUG | 80 | 1214-1234 | A-119995.1 | CAGAUCAUAGGUUCCAGUAAUGG | 168 | 1212-1234 |
| AD-59090.2 | A-119942.1 | CACAGUUUUUGCUCUGGUGAA | 81 | 874-894 | A-119943.1 | UUCACCAGAGCAAAAACUGUGUC | 169 | 872-894 |
| AD-59090.1 | A-119942.1 | CACAGUUUUUGCUCUGGUGAA | 82 | 874-894 | A-119943.1 | UUCACCAGAGCAAAAACUGUGUC | 170 | 872-894 |
| AD-59057.2 | A-119978.1 | UUAAAGAAGGGUUGAGCUGGU | 83 | 1579-1599 | A-119979.1 | ACCAGCUCAACCCUUCUUUAAUG | 171 | 1577-1599 |
| AD-59057.1 | A-119978.1 | UUAAAGAAGGGUUGAGCUGGU | 84 | 1579-1599 | A-119979.1 | ACCAGCUCAACCCUUCUUUAAUG | 172 | 1577-1599 |
| AD-59051.2 | A-119976.1 | AGUGAGCAUCGCUACAGCCUU | 85 | 499-519 | A-119977.1 | AAGGCUGUAGCGAUGCUCACUGG | 173 | 497-519 |
| AD-59051.1 | A-119976.1 | AGUGAGCAUCGCUACAGCCUU | 86 | 499-519 | A-119977.1 | AAGGCUGUAGCGAUGCUCACUGG | 174 | 497-519 |

TABLE 1-continued

Serpinal unmodified sequences

| Duplex Name | Sense Oligo Name | Sense Trans Seq | SEQ ID NO: | Position in NM_000295.4 | Antisense Oligo Name | Antisense Trans Sequence | SEQ ID NO: | Position in NM_000295.4 |
|---|---|---|---|---|---|---|---|---|
| AD-59065.2 | A-120012.1 | AAGGAGCUUGACAGAGACACA | 87 | 857-877 | A-120013.1 | UGUGUCUCUGUCAAGCUCCUUGA | 175 | 855-877 |
| AD-59065.1 | A-120012.1 | AAGGAGCUUGACAGAGACACA | 88 | 857-877 | A-120013.1 | UGUGUCUCUGUCAAGCUCCUUGA | 176 | 855-877 |
| AD-59087.2 | A-119988.1 | GUGGAUAAGUUUUUGGAGGAU | 89 | 716-736 | A-119989.1 | AUCCUCCAAAAACUUAUCCACUA | 177 | 714-736 |
| AD-59087.1 | A-119988.1 | GUGGAUAAGUUUUUGGAGGAU | 90 | 716-736 | A-119989.1 | AUCCUCCAAAAACUUAUCCACUA | 178 | 714-736 |
| AD-59075.2 | A-119984.1 | GAUUGAACAAAAUACCAAGUC | 91 | 1459-1479 | A-119985.1 | GACUUGGUAUUUUGUUCAAUCAU | 179 | 1457-1479 |
| AD-59075.1 | A-119984.1 | GAUUGAACAAAAUACCAAGUC | 92 | 1459-1479 | A-119985.1 | GACUUGGUAUUUUGUUCAAUCAU | 180 | 1457-1479 |
| AD-59092.2 | A-119974.1 | GCUCUCCAAGGCCGUGCAUAA | 93 | 1321-1341 | A-119975.1 | UUAUGCACGGCCUUGGAGAGCUU | 181 | 1319-1341 |
| AD-59092.1 | A-119974.1 | GCUCUCCAAGGCCGUGCAUAA | 94 | 1321-1341 | A-119975.1 | UUAUGCACGGCCUUGGAGAGCUU | 182 | 1319-1341 |
| AD-59081.2 | A-119986.1 | ACCUGGAAAAUGAACUCACCC | 95 | 1122-1142 | A-119987.1 | GGGUGAGUUCAUUUUCCAGGUGC | 183 | 1120-1142 |
| AD-59081.1 | A-119986.1 | ACCUGGAAAAUGAACUCACCC | 96 | 1122-1142 | A-119987.1 | GGGUGAGUUCAUUUUCCAGGUGC | 184 | 1120-1142 |
| AD-59064.2 | A-119996.1 | GGGACCAAGGCUGACACUCAC | 97 | 536-556 | A-119997.1 | GUGAGUGUCAGCCUUGGUCCCA | 185 | 534-556 |
| AD-59064.1 | A-119996.1 | GGGACCAAGGCUGACACUCAC | 98 | 536-556 | A-119997.1 | GUGAGUGUCAGCCUUGGUCCCA | 186 | 534-556 |
| AD-59052.2 | A-119992.1 | GCCAUGUUUUUAGAGGCCAUA | 99 | 1385-1405 | A-119993.1 | UAUGGCCUCUAAAAACAUGGCCC | 187 | 1383-1405 |
| AD-59052.1 | A-119992.1 | GCCAUGUUUUUAGAGGCCAUA | 100 | 1385-1405 | A-119993.1 | UAUGGCCUCUAAAAACAUGGCCC | 188 | 1383-1405 |
| AD-59076.2 | A-120000.1 | CCUGGAAAAUGAACUCACCCA | 101 | 1123-1143 | A-120001.1 | UGGGUGAGUUCAUUUUCCAGGUG | 189 | 1121-1143 |
| AD-59076.1 | A-120000.1 | CCUGGAAAAUGAACUCACCCA | 102 | 1123-1143 | A-120001.1 | UGGGUGAGUUCAUUUUCCAGGUG | 190 | 1121-1143 |
| AD-59068.2 | A-119966.1 | AAGAGGCCAAGAAACAGAUCA | 103 | 789-809 | A-119967.1 | UGAUCUGUUUCUUGGCCUCUUCG | 191 | 787-809 |
| AD-59068.1 | A-119966.1 | AAGAGGCCAAGAAACAGAUCA | 104 | 789-809 | A-119967.1 | UGAUCUGUUUCUUGGCCUCUUCG | 192 | 787-809 |
| AD-59089.2 | A-120020.1 | GGCAAAUGGGAGAGAACCUUU | 105 | 911-931 | A-120021.1 | AAAGGGUCUUCUCCCAUUGCCUU | 193 | 909-931 |
| AD-59089.1 | A-120020.1 | GGCAAAUGGGAGAGAACCUUU | 106 | 911-931 | A-120021.1 | AAAGGGUCUUCUCCCAUUGCCUU | 194 | 909-931 |
| AD-59093.2 | A-119990.1 | UGGGAAAAGUGGUGAAUCCCA | 107 | 1491-1511 | A-119991.1 | UGGGAUUCACCACUUUUCCAUG | 195 | 1489-1511 |
| AD-59093.1 | A-119990.1 | UGGGAAAAGUGGUGAAUCCCA | 108 | 1491-1511 | A-119991.1 | UGGGAUUCACCACUUUUCCAUG | 196 | 1489-1511 |
| AD-59061.2 | A-119948.1 | GGGGACCAAGGCUGACACUCA | 109 | 535-555 | A-119949.1 | UGAGUGUCAGCCUUGGUCCCCA | 197 | 533-555 |
| AD-59061.1 | A-119948.1 | GGGGACCAAGGCUGACACUCA | 110 | 535-555 | A-119949.1 | UGAGUGUCAGCCUUGGUCCCCAG | 198 | 533-555 |

TABLE 1-continued

Serpina1 unmodified sequences

| Duplex Name | Sense Oligo Name | Sense Trans Seq | SEQ ID NO: | Position in NM_000295.4 | Antisense Oligo Name | Antisense Trans Sequence | SEQ ID NO: | Position in NM_000295.4 |
|---|---|---|---|---|---|---|---|---|
| AD-59074.2 | A-119968.1 | GACAUUAAAGAAGGUUGAGC | 111 | 1575-1595 | A-119969.1 | GCUCAACCCUUCUUUAAUGUCAU | 199 | 1573-1595 |
| AD-59074.1 | A-119968.1 | GACAUUAAAGAAGGUUGAGC | 112 | 1575-1595 | A-119969.1 | GCUCAACCCUUCUUUAAUGUCAU | 200 | 1573-1595 |
| AD-59079.2 | A-119954.1 | GGCCAUGUUUUUAGAGGCCAU | 113 | 1384-1404 | A-119955.1 | AUGGCCUCUAAAAACAUGGCCCC | 201 | 1382-1404 |
| AD-59079.1 | A-119954.1 | GGCCAUGUUUUUAGAGGCCAU | 114 | 1384-1404 | A-119955.1 | AUGGCCUCUAAAAACAUGGCCCC | 202 | 1382-1404 |
| AD-59071.2 | A-120014.1 | UUCCUGCCUGAUGAGGGAAA | 115 | 1094-1114 | A-120015.1 | UUUCCCCUCAUCAGGCAGGAAGA | 203 | 1092-1114 |
| AD-59071.1 | A-120014.1 | UUCCUGCCUGAUGAGGGAAA | 116 | 1094-1114 | A-120015.1 | UUUCCCCUCAUCAGGCAGGAAGA | 204 | 1092-1114 |
| AD-59086.2 | A-119972.1 | CUCUCCAAGGCCGUGCAUAAG | 117 | 1322-1342 | A-119973.1 | CUUAUGCACGGCCUUGGAGAGCU | 205 | 1320-1342 |
| AD-59086.1 | A-119972.1 | CUCUCCAAGGCCGUGCAUAAG | 118 | 1322-1342 | A-119973.1 | CUUAUGCACGGCCUUGGAGAGCU | 206 | 1320-1342 |
| AD-59094.2 | A-120006.1 | AGCUCUCCAAGGCCGUGCAUA | 119 | 1320-1340 | A-120007.1 | UAUGCACGGCCUUGGAGAGCUUC | 207 | 1318-1340 |
| AD-59094.1 | A-120006.1 | AGCUCUCCAAGGCCGUGCAUA | 120 | 1320-1340 | A-120007.1 | UAUGCACGGCCUUGGAGAGCUUC | 208 | 1318-1340 |
| AD-59085.2 | A-119956.1 | UCCUGGAGGGCCUGAAUUUCA | 121 | 564-584 | A-119957.1 | UGAAAUUCAGGCCCUCCAGGAUU | 209 | 562-584 |
| AD-59085.1 | A-119956.1 | UCCUGGAGGGCCUGAAUUUCA | 122 | 564-584 | A-119957.1 | UGAAAUUCAGGCCCUCCAGGAUU | 210 | 562-584 |
| AD-59067.2 | A-119950.1 | UUGGUCAAGGAGCUUGACAGA | 123 | 851-871 | A-119951.1 | UCUGUCAAGCUCCUUGACCAAAU | 211 | 849-871 |
| AD-59067.1 | A-119950.1 | UUGGUCAAGGAGCUUGACAGA | 124 | 851-871 | A-119951.1 | UCUGUCAAGCUCCUUGACCAAAU | 212 | 849-871 |
| AD-59053.2 | A-120008.1 | UUUGGUCAAGGAGCUUGACAG | 125 | 850-870 | A-120009.1 | CUGUCAAGCUCCUUGACCAAAUC | 213 | 848-870 |
| AD-59053.1 | A-120008.1 | UUUGGUCAAGGAGCUUGACAG | 126 | 850-870 | A-120009.1 | CUGUCAAGCUCCUUGACCAAAUC | 214 | 848-870 |
| AD-59077.2 | A-120016.1 | UCCCCAGUGAGCAUCGCUACA | 127 | 494-514 | A-120017.1 | UGUAGCGAUGCUCACUGGGGAGA | 215 | 492-514 |
| AD-59077.1 | A-120016.1 | UCCCCAGUGAGCAUCGCUACA | 128 | 494-514 | A-120017.1 | UGUAGCGAUGCUCACUGGGGAGA | 216 | 492-514 |

TABLE 2

Serpina1- modified sequences

| Duplex Name | Sense Oligo Name | Sense Oligo Sequence | SEQ ID NO: | Antisense Oligo Name | Antisense Oligo Sequence | SEQ ID NO: |
|---|---|---|---|---|---|---|
| AD-58681.1 | A-119065.1 | GfsusCfAfaCfaGfcCfAfcCfaAfuAfuCfuUfL96 | 217 | A-119066.1 | asAfsgAfuAfuUfgGfugcUfgUfuGfgAfcsUfsg | 305 |
| AD-59084.1 | A-119065.2 | GfsusCfAfaCfaGfcCfAfcCfaAfuAfuCfuUfL96 | 218 | A-119941.1 | asAfsgAfuAfuUfgGfugcUfgUfuGfgAfcsusg | 306 |
| AD-59060.2 | A-119933.1 | UfsasAfuGfaUfuGfAfAfcAfaAfaAfuAfCfcAfL96 | 219 | A-119934.1 | usGfsgUfaUfuGfuGfuuCfaAfuCfAfuUfasasg | 307 |
| AD-59060.1 | A-119933.1 | UfsasAfuGfaUfuGfAfAfcAfaAfaAfuAfCfcAfL96 | 220 | A-119934.1 | usGfsgUfaUfuGfuGfuuCfaAfuCfAfuUfasasg | 308 |
| AD-59054.2 | A-119931.1 | CfsusUfcUfuAfaUfGfAfuUfgAfAfucAfUfaAfL96 | 221 | A-119932.1 | usUfsuUfgUfuCfaAfucaUfuAfaGfaAfgsasc | 309 |
| AD-59054.1 | A-119931.1 | CfsusUfcUfuAfaUfGfAfuUfgAfAfucAfUfaAfL96 | 222 | A-119932.1 | usUfsuUfgUfuCfaAfucaUfuAfaGfaAfgsasc | 310 |
| AD-59072.2 | A-119937.1 | AfsusUfgAfaCfaAfAfAfuAfcCfaAfgUfcUfL96 | 223 | A-119938.1 | asGfsaCfuUfgGfuAfuuuUfguUfcCfaAfuscsa | 311 |
| AD-59072.1 | A-119937.1 | AfsusUfgAfaCfaAfAfAfuAfcCfaAfgUfcUfL96 | 224 | A-119938.1 | asGfsaCfuUfgGfuAfuuuUfguUfcCfaAfuscsa | 312 |
| AD-59048.2 | A-119929.1 | UfsusCfcUfuAfaUfgAfAfuGfAfAfcAfcAfL96 | 225 | A-119930.1 | asUfsUfuGfuUfcAfaucAfuUfaAfgAfasgsa | 313 |
| AD-59048.1 | A-119929.1 | UfsusCfcUfuAfaUfgAfAfuGfAfAfcAfcAfL96 | 226 | A-119930.1 | asUfsUfuGfuUfcAfaucAfuUfaAfgAfasgsa | 314 |
| AD-59062.2 | A-119964.1 | CfsasAfaCfcCfcUfuUfGfgAfuCfuUfcUfUfAfaUfL96 | 227 | A-119965.1 | asUfsuAfaGfaAfgAfcaaAfgGfgUfuUfgsusu | 315 |
| AD-59062.1 | A-119964.1 | CfsasAfaCfcCfcUfuUfGfgAfuCfuUfcUfUfAfaUfL96 | 228 | A-119965.1 | asUfsuAfaGfaAfgAfcaaAfgGfgUfuUfgsusu | 316 |
| AD-59078.2 | A-119939.1 | UfsgsUfCfuUfAfAfuGfaUfuGfaAfcAfCfaAfL96 | 229 | A-119940.1 | usGfsuUfcAfaUfcAfuuaAfgAfaGfaCfasasa | 317 |
| AD-59078.1 | A-119939.1 | UfsgsUfCfuUfAfAfuGfaUfuGfaAfcAfCfaAfL96 | 230 | A-119940.1 | usGfsuUfcAfaUfcAfuuaAfgAfaGfaCfasasa | 318 |
| AD-59056.2 | A-119962.1 | CfsasCfcUfgGfaAfAfAfuGfaAfcUfcAfccCfL96 | 231 | A-119963.1 | gsGfsuAfgUfuCfAfuuuUfcCfaGfgUfgscsu | 319 |
| AD-59056.1 | A-119962.1 | CfsasCfcUfgGfaAfAfAfuGfaAfcUfcAfccCfL96 | 232 | A-119963.1 | gsGfsuAfgUfuCfAfuuuUfcCfaGfgUfgscsu | 320 |
| AD-59091.2 | A-119958.1 | UfsusUfuGfcUfcUfgGfuGfaAfuUfaCfaUfaCfL96 | 233 | A-119959.1 | asAfsgUfaAfuUfcAfccaGfaGfcAfaAfasasc | 321 |
| AD-59091.1 | A-119958.1 | UfsusUfuGfcUfcUfgGfuGfaAfuUfaCfaUfaCfL96 | 234 | A-119959.1 | asAfsgUfaAfuUfcAfccaGfaGfcAfaAfasasc | 322 |
| AD-59083.2 | A-120018.1 | AfscsCfuUfuGfcUfcUfuUfaAfuGfaAfuGfL96 | 235 | A-120019.1 | asUfsAfuUfaAfgAfagaCfaAfaGfgGfususu | 323 |
| AD-59083.1 | A-120018.1 | AfscsCfuUfuGfcUfcUfuUfaAfuGfaAfuGfL96 | 236 | A-120019.1 | asUfsAfuUfaAfgAfagaCfaAfaGfgGfususu | 324 |
| AD-59073.2 | A-119952.1 | UfsusGfaAfcAfaAfuAfcCfaAfgUfcUfcCfL96 | 237 | A-119953.1 | gsAfsgAfcUfuGfgUfauuUfgUfuUfcAfasusc | 325 |
| AD-59073.1 | A-119952.1 | UfsusGfaAfcAfaAfuAfcCfaAfgUfcUfcCfL96 | 238 | A-119953.1 | gsAfsgAfcUfuGfgUfauuUfgUfuUfcAfasusc | 326 |
| AD-59066.2 | A-119935.1 | GfsusUfcAfaCfaAfcCfcCfuAfgGfuCfuUfL96 | 239 | A-119936.1 | asAfsgAfcAfaAfggGfguUfgUfuGfaAfcsusu | 327 |

TABLE 2-continued

Serpina1- modified sequences

| Duplex Name | Sense Oligo Name | Sense Oligo Sequence | SEQ ID NO: | Antisense Oligo Name | Antisense Oligo Sequence | SEQ ID NO: |
|---|---|---|---|---|---|---|
| AD-59066.1 | A-119935.1 | GfsusUfCafaCfaAfAfCfccCfuUfugUfucCfuUfcUfuUfL96 | 240 | A-119936.1 | asAfsgAfcAfaAfgGfguuUfgUfuGfaAfcsusu | 328 |
| AD-59059.2 | A-120010.1 | AfsasAfuAfcCfaAfgCfuUfcCfcCfcCfucCfuUfL96 | 241 | A-120011.1 | asAfsgAfgCfgGfaGfacuUfgGfuAfuUfususg | 329 |
| AD-59059.1 | A-120010.1 | AfsasAfuAfcCfaAfgCfuUfcCfcCfcCfucCfuUfL96 | 242 | A-120011.1 | asAfsgAfgGfGfaGfacuUfgGfuAfuUfususg | 330 |
| AD-59070.2 | A-119998.1 | UfsusUfuUfgCfucCfuUfgCfuUfgAfaUfuAfcAfL96 | 243 | A-119999.1 | usGfsuAfaUfuCfaCfcagAfgCfaAfaAfascsu | 331 |
| AD-59070.1 | A-119998.1 | UfsusUfuUfgCfucCfuUfgCfuUfgAfaUfuAfcAfL96 | 244 | A-119999.1 | usGfsuAfaUfuCfaCfcagAfgCfaAfaAfascsu | 332 |
| AD-59063.2 | A-119980.1 | AfsgsUfuCfaAfcAfAfAfccCfcUfuUfgUfcUfL96 | 245 | A-119981.1 | asGfsaCfaAfaGfgGfuuuuGfuUfgAfaCfusug | 333 |
| AD-59063.1 | A-119980.1 | AfsgsUfuCfaAfcAfAfAfccCfcUfuUfgUfcUfL96 | 246 | A-119981.1 | asGfsaCfaAfaGfgGfuuuGfuUfgAfaCfususg | 334 |
| AD-59069.2 | A-119982.1 | AfsasUfgAfuUfgAfaCfaAfaAfuAfcCfaAfL96 | 247 | A-119983.1 | usUfsgGfuAfuUfgfuuCfaAfuCfaUfusasa | 335 |
| AD-59069.1 | A-119982.1 | AfsasUfgAfuUfgAfaCfaAfaAfuAfcCfaAfL96 | 248 | A-119983.1 | usUfsgGfuAfuUfgfuuCfaAfuCfaUfusasg | 336 |
| AD-59082.2 | A-120002.1 | UfsasCfuGfgAfaCfCfcUfuAfaUfuAfcUfL96 | 249 | A-120003.1 | usUfscAfgAfuCfaUfaggUfuCfCfgUfasasu | 337 |
| AD-59082.1 | A-120002.1 | UfsasCfuGfgAfaCfCfcUfuAfaUfuAfcUfL96 | 250 | A-120003.1 | usUfscAfgAfuCfaUfaggUfuCfCfgUfasasu | 338 |
| AD-59088.2 | A-120004.1 | AfcsAfaUfAfaAfaGfAfAfgGfgUfuUfaGfL96 | 251 | A-120005.1 | asGfscUfcAfaCfcCfuucUfuUfaAfuGfuscsa | 339 |
| AD-59088.1 | A-120004.1 | AfcsAfaUfAfaAfaGfAfAfgGfgUfuUfaGfL96 | 252 | A-120005.1 | asGfscUfcAfaCfcCfuucUfuUfaAfuGfuscsa | 340 |
| AD-59080.2 | A-119970.1 | AfsasAfaUfuGfuGfAfAfgGfAfCfcUfaAfgGfL96 | 253 | A-119971.1 | csUfsuGfaCfcAfaAfuccAfcAfaUfuUfuscsc | 341 |
| AD-59080.1 | A-119970.1 | AfsasAfaUfuGfuGfAfAfgGfAfCfcUfaAfgGfL96 | 254 | A-119971.1 | csUfsuGfaCfcAfaAfuccAfcAfaUfuUfuscsc | 342 |
| AD-59058.2 | A-119994.1 | AfsusUfaCfuGfgAfAfCfcUfuAfuGfAfuUfgUfL96 | 255 | A-119995.1 | csAfsgAfuCfaUfaGfguuCfcAfgUfaAfusgsg | 343 |
| AD-59058.1 | A-119994.1 | AfsusUfaCfuGfgAfAfCfcUfuAfuGfAfuUfgUfL96 | 256 | A-119995.1 | csAfsgAfuCfaUfaGfguuCfcAfgUfaAfusgsg | 344 |
| AD-59090.2 | A-119942.1 | CfsasCfaGfuUfuUfgCfuCfuGfuGfaAfL96 | 257 | A-119943.1 | usUfscAfcCfaGfaGfcaaAfaAfcUfgUfgsusc | 345 |
| AD-59090.1 | A-119942.1 | CfsasCfaGfuUfuUfgCfuCfuGfuGfaAfL96 | 258 | A-119943.1 | usUfscAfcCfaGfaGfcaaAfaAfcUfgUfgsusc | 346 |
| AD-59057.2 | A-119978.1 | UfsusAfaAfgAfgGffuUfgAfgCfuGfuGfuUfL96 | 259 | A-119979.1 | asCfscAfgCfuCfaAfcccUfuCfuUfuAfasusg | 347 |
| AD-59057.1 | A-119978.1 | UfsusAfaAfgAfgGffuUfgAfgCfuGfuGfuUfL96 | 260 | A-119979.1 | asCfscAfgCfuCfaAfcccUfuCfuUfuAfasusg | 348 |
| AD-59051.2 | A-119976.1 | AfsgsUfgAfgCfuUfCfgUfcAfuCfagcfgcCfuUfL96 | 261 | A-119977.1 | asAfsgGfgCfUfugAfgCfgaUfgCfcCfusgsg | 349 |
| AD-59051.1 | A-119976.1 | AfsgsUfgAfgCfuUfCfgUfcAfuCfagcfgcCfuUfL96 | 262 | A-119977.1 | asAfsgGfgCfUfugAfgCfgaUfgCfcCfusgsg | 350 |
| AD-59065.2 | A-120012.1 | AfsasGfAfgCfuUfgAfcAfgAfgAfcAfcAfL96 | 263 | A-120013.1 | usGfsuGfucCfuGfucaAfgCfucCfuUfsgsa | 351 |

TABLE 2-continued

Serpina1- modified sequences

| Duplex Name | Sense Oligo Name | Sense Oligo Sequence | SEQ ID NO: | Antisense Oligo Name | Antisense Oligo Sequence | SEQ ID NO: |
|---|---|---|---|---|---|---|
| AD-59065.1 | A-120012.1 | AfsasGfgAfgCfuUfGfeAfcAfgAfcAfcAfLL96 | 264 | A-120013.1 | usGfsuGfuCfuCfuGfucaAfgCfuCfcCfusgsa | 352 |
| AD-59087.2 | A-119988.1 | GfsusGfgAfuAfaGfUfUfuUfuGfgAfgGfauFl96 | 265 | A-119989.1 | asUfscCfucCfAfaAfaacUfuAfcCfAfcsusa | 353 |
| AD-59087.1 | A-119988.1 | GfsusGfgAfuAfaGfUfUfuUfuGfgAfgGfauFl96 | 266 | A-119989.1 | asUfscCfucCfAfaAfaacUfuAfcCfAfcsusa | 354 |
| AD-59075.2 | A-119984.1 | GfsasUfuGfaAfcAfaAfaUfauCfcAfaGfucCfL96 | 267 | A-119985.1 | gsAfscUfuGfgUfaUfuuuGfuUfcAfaUfcsasu | 355 |
| AD-59075.1 | A-119984.1 | GfsasUfuGfaAfcAfaAfaUfauCfcAfaGfucCfL96 | 268 | A-119985.1 | gsAfscUfuGfgUfaUfuuuGfuUfcAfaUfcsasu | 356 |
| AD-59092.2 | A-119974.1 | GfcsUfcUfcCfaAfGfGfcCfgUfgCfaUfaAfL96 | 269 | A-119975.1 | usUfsaUfgCfaCfgGfccuGfgAfGfaGfcsusu | 357 |
| AD-59092.1 | A-119974.1 | GfcsUfcUfcCfaAfGfGfcCfgUfgCfaUfaAfL96 | 270 | A-119975.1 | usUfsaUfgCfaCfgGfccuGfgAfGfaGfcsusu | 358 |
| AD-59081.1 | A-119986.1 | AfscsCfuGfgAfaAfaUfGfccCfuCfaCfcCfL96 | 271 | A-119987.1 | gsGfsgUfgAfgGfufcUfauuUfuCfcAfgGfusgsc | 359 |
| AD-59081.2 | A-119986.1 | AfscsCfuGfgAfaAfaUfGfccCfuCfaCfcCfL96 | 272 | A-119987.1 | gsGfsgUfgAfgGfufcUfauuUfuCfcAfgGfusgsc | 360 |
| AD-59064.1 | A-119996.1 | GfsgsGfaCfcAfcAfGfGfcCfuGfacCfaCfuCfL96 | 273 | A-119997.1 | gsUfsgAfgGfuGfgUfgCfcCfuGfuCfcCfscsa | 361 |
| AD-59064.2 | A-119996.1 | GfsgsGfaCfcAfcAfGfGfcCfuGfacCfaCfuCfL96 | 274 | A-119997.1 | gsUfsgAfgGfuGfgUfgCfcCfuGfuCfcCfscsa | 362 |
| AD-59052.1 | A-119992.1 | GfscsCfaUfgUfuUfuUfaGfaGfaGfcfCfAtuAfL96 | 275 | A-119993.1 | usAfsuGfcCfcUfcCfuAfaaAfaCfaUfgGfcscsc | 363 |
| AD-59052.2 | A-119992.1 | GfscsCfaUfgUfuUfuUfaGfaGfaGfcfCfAtuAfL96 | 276 | A-119993.1 | usAfsuGfcCfcUfcCfuAfaaAfaCfaUfgGfcscsc | 364 |
| AD-59076.1 | A-120000.1 | CfscsUfgGfaAfaAfUfGfaAfcUfcAfcCfcCfAfL96 | 277 | A-120001.1 | usGfsgGfuGfaGfuUfcauUfuUfcCfaGfgsusg | 365 |
| AD-59076.2 | A-120000.1 | CfscsUfgGfaAfaAfUfGfaAfcUfcAfcCfcCfAfL96 | 278 | A-120001.1 | usGfsgGfuGfaGfuUfcauUfuUfcCfaGfgsusg | 366 |
| AD-59068.2 | A-119966.1 | AfsasGfaGfgCfcAfAfGfaAfaCfaGfaUfcAfL96 | 279 | A-119967.1 | usGfsaUfcUfgUfuUfcuuGffcCfuCfUfuscsg | 367 |
| AD-59068.1 | A-119966.1 | AfsasGfaGfgCfcAfAfGfaAfaCfaGfaUfcAfL96 | 280 | A-119967.1 | usGfsaUfcUfgUfuUfcuuGffcCfuCfUfuscsg | 368 |
| AD-59089.2 | A-120020.1 | GfsgsCfaAfaUfgGfAfaGfGfcCfcUfiuUfL96 | 281 | A-120021.1 | asAfsaGfgGfucCffaUfuUfgCfcsusu | 369 |
| AD-59089.1 | A-120020.1 | GfsgsCfaAfaUfgGfAfaGfGfcCfcUfiuUfL96 | 282 | A-120021.1 | asAfsaGfgGfucCffaUfuUfgCfcsusu | 370 |
| AD-59093.2 | A-119990.1 | UfsgsGfaAfaAfGfUfGfgUfgAfaUfcCfcAfL96 | 283 | A-119991.1 | usGfsgGfaUfuCfcacUfuUfcCfCfasusg | 371 |
| AD-59093.1 | A-119990.1 | UfsgsGfaAfaAfGfUfGfgUfgAfaUfcCfcAfL96 | 284 | A-119991.1 | usGfsgGfaUfuCfcacUfuUfcCfCfasusg | 372 |
| AD-59061.2 | A-119948.1 | GfsgsGfafcCfaAfcCfaCfcAfcUfcAfL96 | 285 | A-119949.1 | usGfsaGfuGfuCfaGfccuUfgGfuCfcCfasag | 373 |
| AD-59061.1 | A-119948.1 | GfsgsGfafcCfaAfcCfaCfcAfcUfcAfL96 | 286 | A-119949.1 | usGfsaGfuGfuCfaGfccuUfgGfuCfcCfasag | 374 |
| AD-59074.2 | A-119968.1 | GfsasCfaUfuAfaAfGfgGfuUfgAfgcCfL96 | 287 | A-119969.1 | gsCfsuCfaAfcCfcCfucuUfaAfgUfcsasu | 375 |

TABLE 2-continued

Serpinal- modified sequences

| Duplex Name | Sense Oligo Name | Sense Oligo Sequence | SEQ ID NO: | Antisense Oligo Name | Antisense Oligo Sequence | SEQ ID NO: |
|---|---|---|---|---|---|---|
| AD-59074.1 | A-119968.1 | GfsasCfaUfuAfaAfGfAfaGfGfuUfgAfgCfL96 | 288 | A-119969.1 | gsCfsuCfaAfcCfcUfucuUfuAfaUfgUfcsasu | 376 |
| AD-59079.2 | A-119954.1 | GfsgsCfCfAfuGfuUfUfUfuAfgAfgGfcCfaUfL96 | 289 | A-119955.1 | asUfsgGfcCfcCfuCfuAfaaaAfcAfcGfgCfcscsc | 377 |
| AD-59079.1 | A-119954.1 | GfsgsCfAfuGfuUfUfUfuAfgAfgGfcCfaUfL96 | 290 | A-119955.1 | asUfsgGfcCfuCfuAfaaaAfcAfuGfgCfcscsc | 378 |
| AD-59071.2 | A-120014.1 | UfsusCfcUfgCfcUfgCfAfuGfaGfgCfaGfAfaAfL96 | 291 | A-120015.1 | usUfsuCfcCfcUfcAfucaGfgCfaGfgAfasgsa | 379 |
| AD-59071.1 | A-120014.1 | UfsusCfcUfgCfcUfgCfAfuGfaGfgCfGfgAfaAfL96 | 292 | A-120015.1 | usUfsuCfcCfcUfcAfucaGfgCfaGfgAfasgsa | 380 |
| AD-59086.2 | A-119972.1 | CfsusCfuCfcAfaGfCfcGfuGfcAfuAfaGfL96 | 293 | A-119973.1 | csUfsuAfuGfcAfcGfgccUfuGfgAfgAfgscsu | 381 |
| AD-59086.1 | A-119972.1 | CfsusCfuCfcAfaGfCfcGfuGfcAfuAfaGfL96 | 294 | A-119973.1 | csUfsuAfuGfcAfcGfgccUfuGfgAfgAfgscsu | 382 |
| AD-59094.2 | A-120006.1 | AfgsCfuCfuCfcAfAfGfgcCfcGfuGfcAfuAfL96 | 295 | A-120007.1 | usAfsuGfcAfcGfgCfcuuGfgAfgAfgCfususc | 383 |
| AD-59094.1 | A-120006.1 | AfsgsCfuCfuCfcAfAfGfgcCfcGfuGfcAfuAfL96 | 296 | A-120007.1 | usAfsuGfcAfcGfgCfcuuGfgAfgAfgCfususc | 384 |
| AD-59085.2 | A-119956.1 | UfscsCfuGfgAfgGfGfcCfuGfaAfuUfcAfL96 | 297 | A-119957.1 | usGfsaAfaUfuCfaGfgccCfuCfcAfgGfasusu | 385 |
| AD-59085.1 | A-119956.1 | UfscsCfuGfgAfgGfGfcCfuGfaAfuUfcAfL96 | 298 | A-119957.1 | usGfsaAfaUfuCfaGfgccCfuCfcAfgGfasusu | 386 |
| AD-59067.2 | A-119950.1 | UfsgsGfgUfcAfaGfGfaAfgCfuuUfgAfcAfgAfL96 | 299 | A-119951.1 | usCfsuGfuCfaAfgCfuuccUfuGfaCfcAfasasu | 387 |
| AD-59067.1 | A-119950.1 | UfsgsGfgUfcAfaGfGfaAfgCfuuUfgAfcAfgAfL96 | 300 | A-119951.1 | usCfsuGfuCfaAfgCfuuccUfuGfaCfcAfasasu | 388 |
| AD-59053.2 | A-120008.1 | UfsusUfgGfuCfaAfGfGfaAfGfcUfccuUfgAfcCfaAfasusc | 301 | A-120009.1 | csUfsgUfcAfaGfcUfccuUfgAfcCfaAfasusc | 389 |
| AD-59053.1 | A-120008.1 | UfsusUfgGfuCfaAfGfGfaAfGfcUfccuUfgAfcCfaAfasusc | 302 | A-120009.1 | csUfsgUfcAfaGfcUfccuUfgAfcCfaAfasusc | 390 |
| AD-59077.2 | A-120016.1 | UfscsCfcCfaGfuGfAfGfcAfuCfgCfuAfcAfL96 | 303 | A-120017.1 | usGfsuAfgCfgAfuGfcucAfcUfgGfgGfasgsa | 391 |
| AD-59077.1 | A-120016.1 | UfscsCfcCfaGfuGfAfGfcAfuCfgCfuAfcAfL96 | 304 | A-120017.1 | usGfsuAfgCfgAfuGfcucAfcUfgGfgGfasgsa | 392 |

Example 2. In Vitro and In Vivo Screening

A subset of these duplexes was evaluated for efficacy in single dose assays as described above. Table 3 shows the results of a single dose screen in primary mouse hepatocytes (Hep3b) transfected with the indicated GalNAC conjugated modified iRNAs and the results of a single dose free uptake screen in primary *Cynomolgus* hepatocytes (PCH) with the indicated GalNAC conjugated modified iRNAs. Data are expressed as fraction of message remaining relative to cells treated with AD-1955, a non-targeting control for Hep3B experiments, or relative to naïve cells for PCH experiments.

TABLE 3

Serpina1 efficacy screen by free uptake in primary Hep3b cells and in primary Cynomolgous monkey hepatocytes (PCH).

| | Transfection (Hep3b) | | | | Free Uptake (PCH) | | | |
|---|---|---|---|---|---|---|---|---|
| | 10 nM | | 0.1 nM | | 10 nM | | 500 nM | |
| | Avg | SD | Avg | SD | Avg | SD | Avg | SD |
| AD-58681 | 2.7 | 0.8 | 4.2 | 0.5 | 72.7 | 9.8 | 42.1 | 4.6 |
| AD-59084 | 2.1 | 0.2 | 6.2 | 0.6 | 74.5 | 10.1 | 54.2 | 13.3 |
| AD-59060 | 1.2 | 0.4 | 6.5 | 0.3 | 87.4 | 8.7 | 69.5 | 4.5 |
| AD-59054 | 2.2 | 1.4 | 7.2 | 0.7 | 59.1 | 10.8 | 50.3 | 5.0 |
| AD-59072 | 1.3 | 0.3 | 7.7 | 0.2 | 87.6 | 6.4 | 86.2 | 9.9 |
| AD-59048 | 1.1 | 0.4 | 8.1 | 0.4 | 72.9 | 19.5 | 46.4 | 5.8 |
| AD-59062 | 1.4 | 0.0 | 9.2 | 0.6 | 77.9 | 11.6 | 64.9 | 11.0 |
| AD-59078 | 1.8 | 0.0 | 12.1 | 0.2 | 89.2 | 9.3 | 71.1 | 3.2 |
| AD-59056 | 1.8 | 0.1 | 20.2 | 1.8 | 88.9 | 13.4 | 83.7 | 8.5 |
| AD-59091 | 3.8 | 0.5 | 26.6 | 4.1 | 89.7 | 15.0 | 75.6 | 7.5 |
| AD-59083 | 2.3 | 0.6 | 27.2 | 2.5 | 94.5 | 9.1 | 74.5 | 11.9 |
| AD-59073 | 3.7 | 0.7 | 27.3 | 2.3 | 101.5 | 15.7 | 85.1 | 18.9 |
| AD-59066 | 5.9 | 1.7 | 31.5 | 3.4 | 106.2 | 25.3 | 28.2 | 27.1 |
| AD-59059 | 2.9 | 0.7 | 32.9 | 3.4 | 101.3 | 10.4 | 84.9 | 18.0 |
| AD-59070 | 7.4 | 1.0 | 33.9 | 6.6 | 87.5 | 9.3 | 80.1 | 13.2 |
| AD-59063 | 3.0 | 0.3 | 35.0 | 3.9 | 99.3 | 4.9 | 91.1 | 7.9 |
| AD-59069 | 5.6 | 0.5 | 39.6 | 3.5 | 90.5 | 19.6 | 100.4 | 7.3 |
| AD-59082 | 5.0 | 2.3 | 41.3 | 1.8 | 89.2 | 27.3 | 87.8 | 3.9 |
| AD-59088 | 5.2 | 0.2 | 41.5 | 2.1 | 96.4 | 17.1 | 96.2 | 18.2 |
| AD-59080 | 8.2 | 1.8 | 41.8 | 2.1 | 94.3 | 4.9 | 93.4 | 15.0 |
| AD-59058 | 6.4 | 0.7 | 43.9 | 0.3 | 112.1 | 12.7 | 92.5 | 8.6 |
| AD-59090 | 5.8 | 0.5 | 44.8 | 0.8 | 119.3 | 14.6 | 100.2 | 26.7 |
| AD-59057 | 6.2 | 0.3 | 47.5 | 0.9 | 95.2 | 7.8 | 76.1 | 5.8 |
| AD-59051 | 7.0 | 0.3 | 52.2 | 4.4 | 89.4 | 2.8 | 82.0 | 13.6 |
| AD-59065 | 12.7 | 1.4 | 60.1 | 4.4 | 94.1 | 9.7 | 90.6 | 5.9 |
| AD-59087 | 7.7 | 1.0 | 62.1 | 4.7 | 92.3 | 6.8 | 72.6 | 10.4 |
| AD-59075 | 9.3 | 2.3 | 62.9 | 2.0 | 101.7 | 10.6 | 99.0 | 18.8 |
| AD-59092 | 14.6 | 4.0 | 65.5 | 1.7 | 87.4 | 17.3 | 94.1 | 21.2 |
| AD-59081 | 10.9 | 2.3 | 68.2 | 2.4 | 115.1 | 18.4 | 106.1 | 11.8 |
| AD-59064 | 11.0 | 0.1 | 71.6 | 4.5 | 91.3 | 14.7 | 87.2 | 10.3 |
| AD-59052 | 21.8 | 2.6 | 78.6 | 2.4 | 99.9 | 9.2 | 88.9 | 17.5 |
| AD-59076 | 14.5 | 4.2 | 79.4 | 1.5 | 84.9 | 27.2 | 101.7 | 10.8 |
| AD-59068 | 48.1 | 1.6 | 81.8 | 2.5 | 100.2 | 19.7 | 107.1 | 25.8 |
| AD-59089 | 30.4 | 0.6 | 82.6 | 9.0 | 87.3 | 11.9 | 89.1 | 3.7 |
| AD-59093 | 23.5 | 0.2 | 85.2 | 5.4 | 72.1 | 48.5 | 103.0 | 13.2 |

TABLE 3-continued

Serpina1 efficacy screen by free uptake in primary Hep3b cells and in primary Cynomolgous monkey hepatocytes (PCH).

| | Transfection (Hep3b) | | | | Free Uptake (PCH) | | | |
|---|---|---|---|---|---|---|---|---|
| | 10 nM | | 0.1 nM | | 10 nM | | 500 nM | |
| | Avg | SD | Avg | SD | Avg | SD | Avg | SD |
| AD-59061 | 38.1 | 2.2 | 86.5 | 4.4 | 100.3 | 13.3 | 102.3 | 9.0 |
| AD-59074 | 38.9 | 5.4 | 86.6 | 3.0 | 106.5 | 10.3 | 100.6 | 14.7 |
| AD-59079 | 45.1 | 0.8 | 87.6 | 4.8 | 100.5 | 17.4 | 92.1 | 33.3 |
| AD-59071 | 58.6 | 1.0 | 96.2 | 7.1 | 82.3 | 25.8 | 110.7 | 2.2 |
| AD-59086 | 78.3 | 1.1 | 96.3 | 4.1 | 93.1 | 7.3 | 97.1 | 17.0 |
| AD-59094 | 96.6 | 2.7 | 102.1 | 0.8 | 75.2 | 52.7 | 76.9 | 7.9 |
| AD-59085 | 99.3 | 3.7 | 102.5 | 4.4 | 94.1 | 10.0 | 102.4 | 16.3 |
| AD-59067 | 88.7 | 0.8 | 103.7 | 0.9 | 118.5 | 17.2 | 108.9 | 30.3 |
| AD-59053 | 98.5 | 4.7 | 103.7 | 1.9 | 98.7 | 14.8 | 96.4 | 8.1 |
| AD-59077 | 100.5 | 8.2 | 104.8 | 1.6 | 88.0 | 32.5 | 88.1 | 4.1 |

The $IC_{50}$ values for selected duplexes by transfection in primary Hep3B are shown in Table 4.

TABLE 4

Serpina1 $IC_{50}$ values for selected duplexes by transfection in the Hep3B human cell line.

| Duplex | IC50 (nM) |
|---|---|
| AD-58681 | 0.031 |
| AD-59054 | 0.128 |
| AD-59062 | 0.130 |
| AD-59084 | 0.143 |
| AD-59048 | 0.146 |
| AD-59072 | 0.197 |
| AD-59056 | 0.408 |
| AD-59078 | 0.600 |
| AD-59066 | 0.819 |
| AD-59060 | 1.883 |

A subset of these duplexes was evaluated for in vivo efficacy in transgenic mice expressing the Z-AAT form of human Serpina1 (see, e.g., Dycaico, et al. (1988) *Science* 242:1409-12; Carlson, et al. (1989) *J Clin Invest* 83:1183-90; Perfumo, et al. (1994) *Ann Hum Genet*. 58:305-20. This is an established model of AAT-deficiency associated liver disease. Briefly, transgenic mice were injected subcutaneously with a single 20 mg/kg dose of the iRNAs listed in Table 5 at Day 0. Serum was collected at Days −10, −5, 0, 3, 5, 7, 10, and 17 and the amount of circulating Serpina1 protein was determined using a human-specific ELISA assay. The results of these analyses are depicted in FIG. 1. As indicated in FIG. 1, AD-58681-6PS was the most effective in reducing serum Serpina1 protein levels in these mice.

TABLE 5

```
AD-54330.2  A-111587.3  sense      GfuCfcAfaCfaGfCfAfcCfaAfuAfuCfuUfL96
                                   (SEQ ID NO: 393)

A-111588.3  antisense  aAfgAfuAfuUfgGfugcUfgUfuGfgAfcsUfsg
                                   (SEQ ID NO: 394)

AD-58681.1  A-119065.1  sense      GfsusCfcAfaCfaGfCfAfcCfaAfuAfuCfuUfL96
                                   (SEQ ID NO: 395)

A-119066.1  antisense  asAfsgAfuAfuUfgGfugcUfgUfuGfgAfcsUfsg
                                   (SEQ ID NO: 396)
```

TABLE 5-continued

```
AD-58682.1   A-119065.1   sense       GfsusCfcAfaCfaGfCfAfcCfaAfuAfuCfuUfL96
                                      (SEQ ID NO: 397)

A-119067.1   antisense   asAfsgAfsuAfsuUfgGfugcUfgUfsuGfgAfcsUfsg
                                      (SEQ ID NO: 398)

AD-58683.1   A-119068.1   sense       GsusccAAcAGcAccAAuAucuuL96
                                      (SEQ ID NO: 399)

A-119067.1   antisense   asAfsgAfsuAfsuUfgGfugcUfgUfsuGfgAfcsUfsg
                                      (SEQ ID NO: 400).
```

Example 3. Efficacy of Si-AAT in Transgenic Mice

Figure 2A:
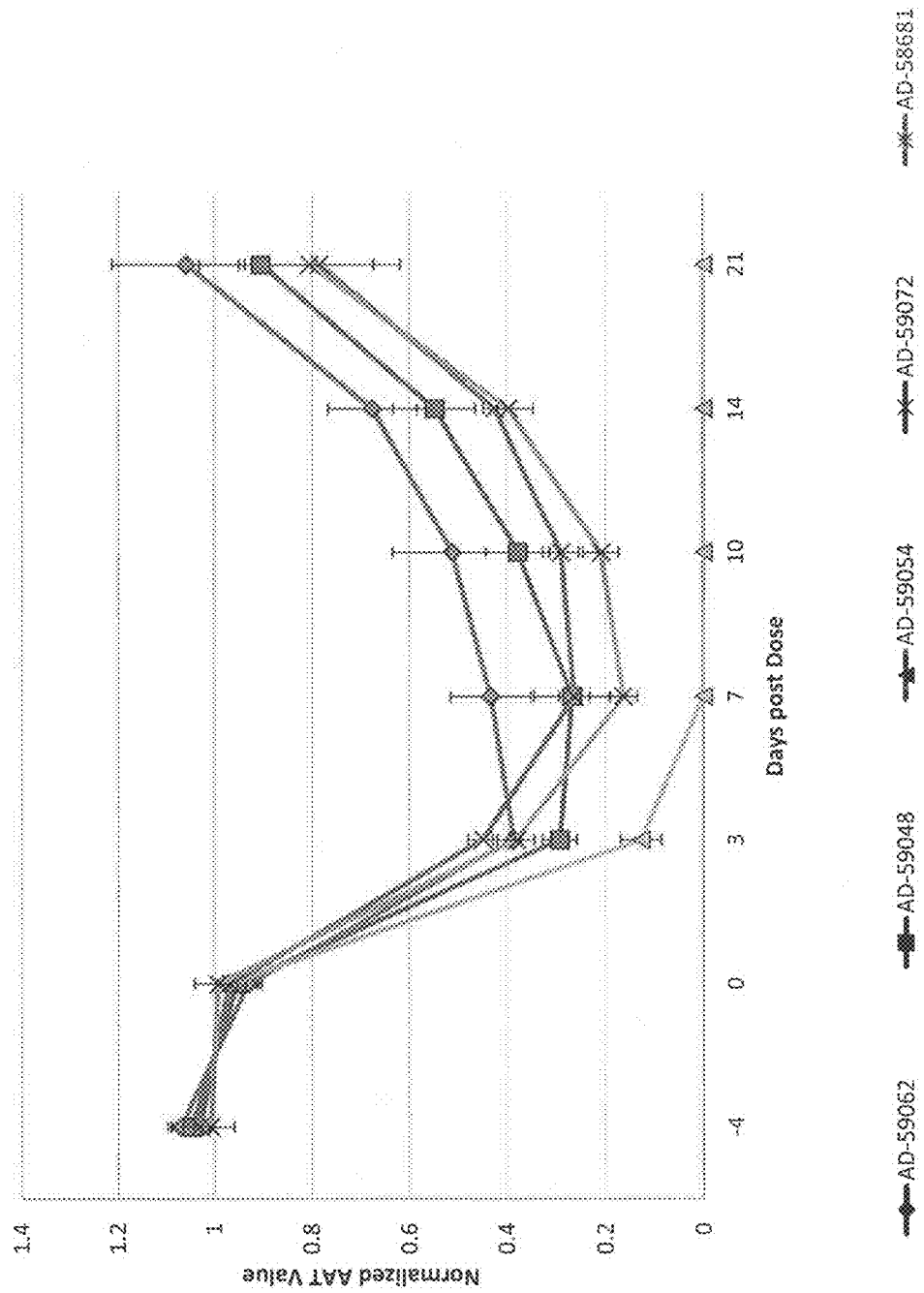
FIGS. 2A-2B depict in vivo efficacy of five siRNAs with low IC50 values. Transgenic mice expressing the human Z-AAT allele were injected with 10 mg/kg siRNA duplex on day 0 and serum human AAT was followed for 21 days post dose (FIG. 2A). Each point represents an average of three mice and the error bars reflect the standard deviation.
Figure 2B:
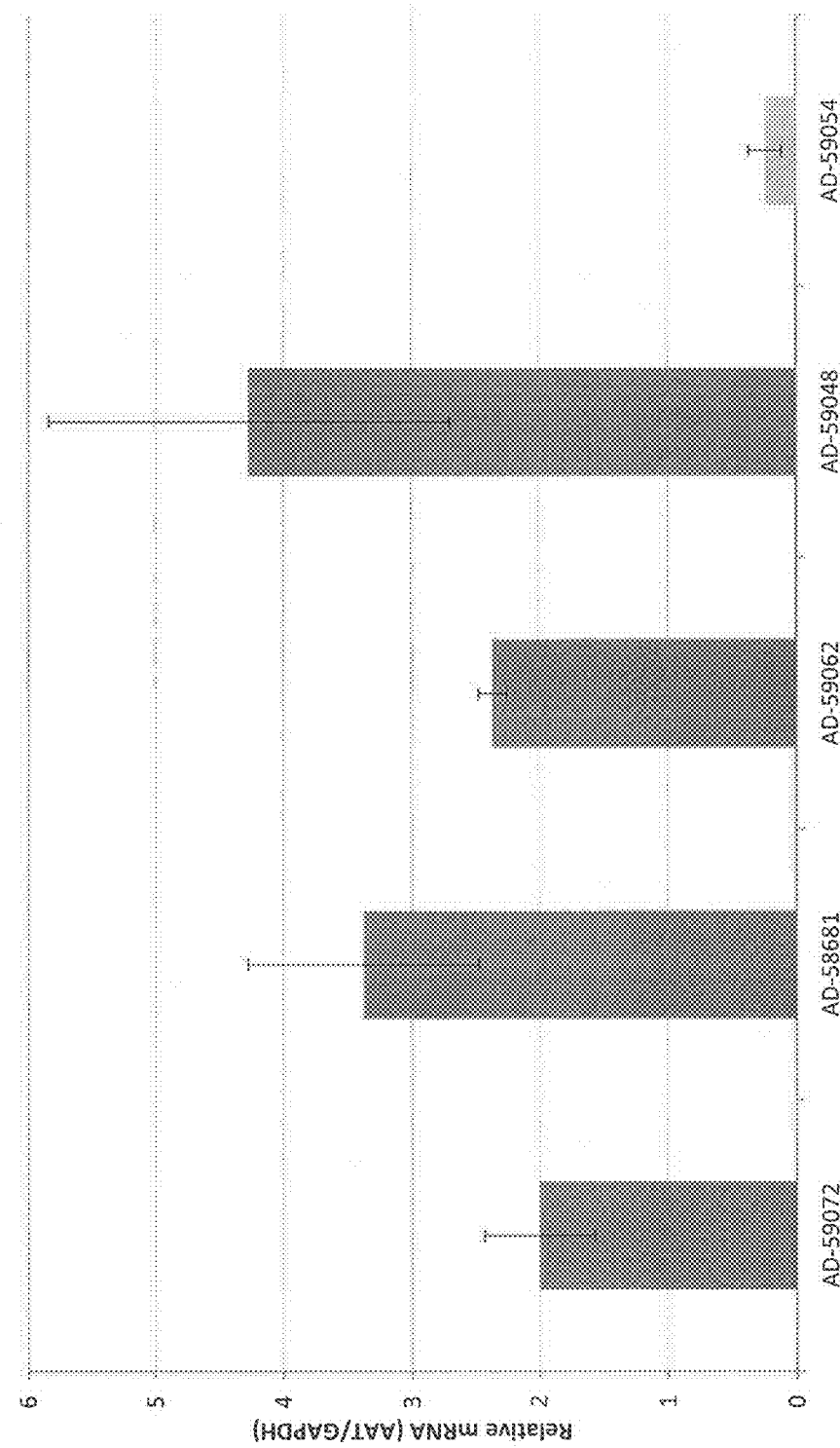

Five siRNA duplexes, as described in the preceding examples, with low IC50 values were tested in vivo for efficacy. The siRNA duplexes were injected at 10 mg/kg into transgenic mice expressing the human Z-AAT allele, an established model of AAT-deficiency associated liver disease. The mice were dosed on day 0 and serum human AAT was followed for 21 days post dose (FIG. 2A). Each point represents an average of three mice and the error bars reflect the standard deviation. The mice were sacrificed on day 21 and their livers were processed to measure mRNA levels. The graph shows hAAT mRNA normalized to GAPDH for each group (FIG. 2B). The bars reflect the average and the error bars reflect the standard deviation. As indicated in FIGS. 2A and 2B, AD59054 was the most effective in reducing hAAT mRNA levels in the mice.

Example 4. Durable AAT Suppression in a Dose Responsive Manner

Figure 3A:
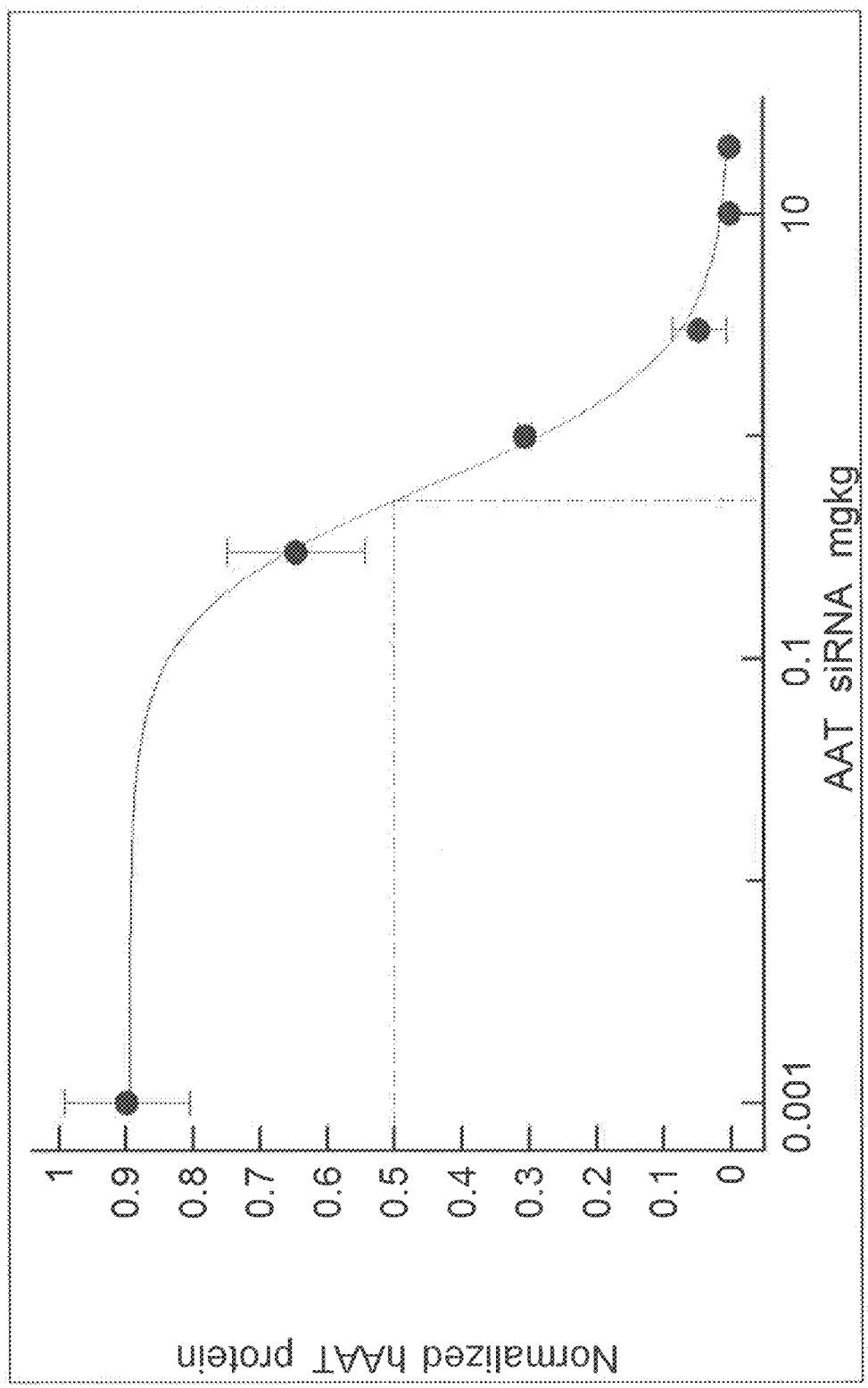
FIGS. 3A-3C depict durable AAT suppression in a dose responsive manner.
Figure 3B:
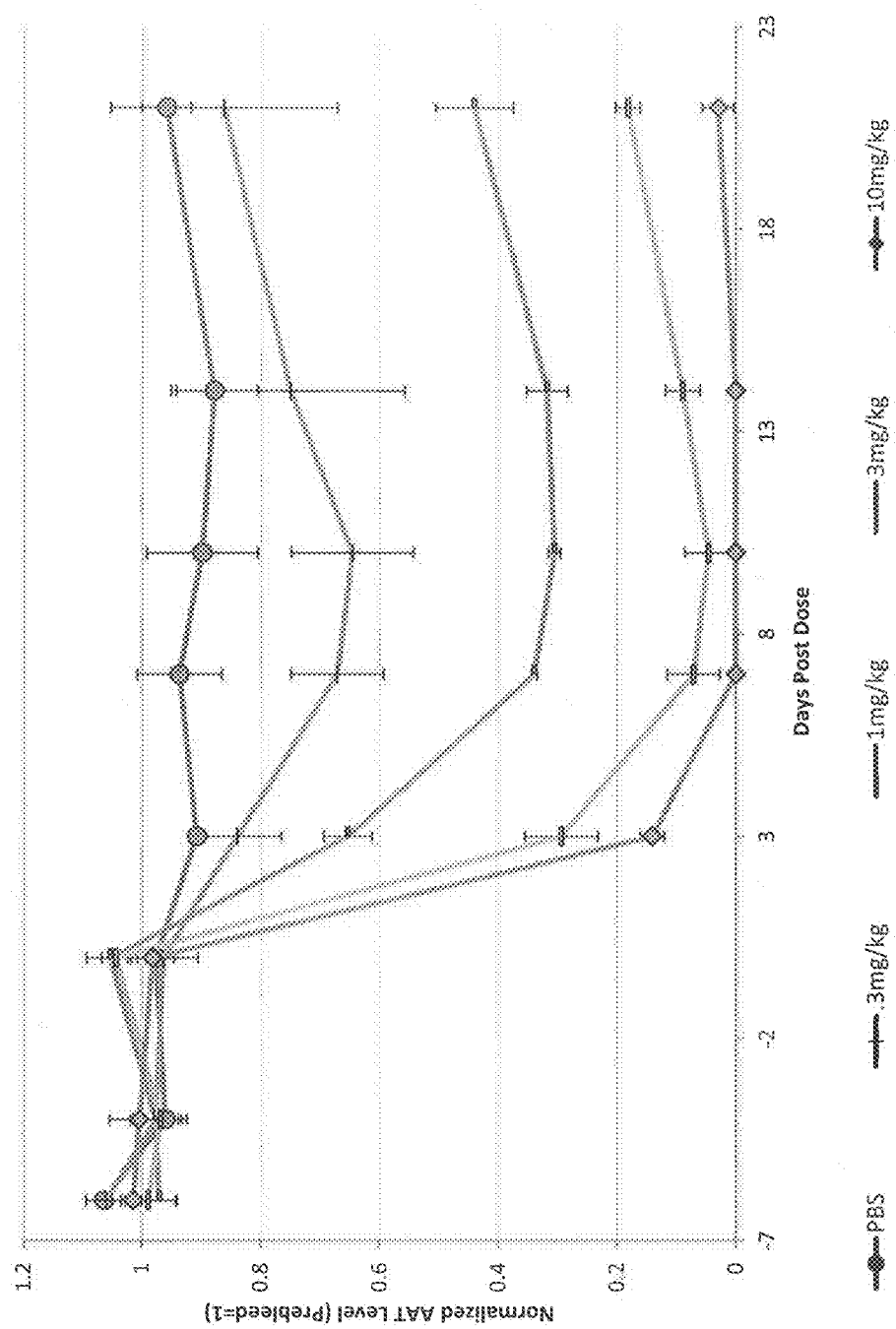
Figure 3C:
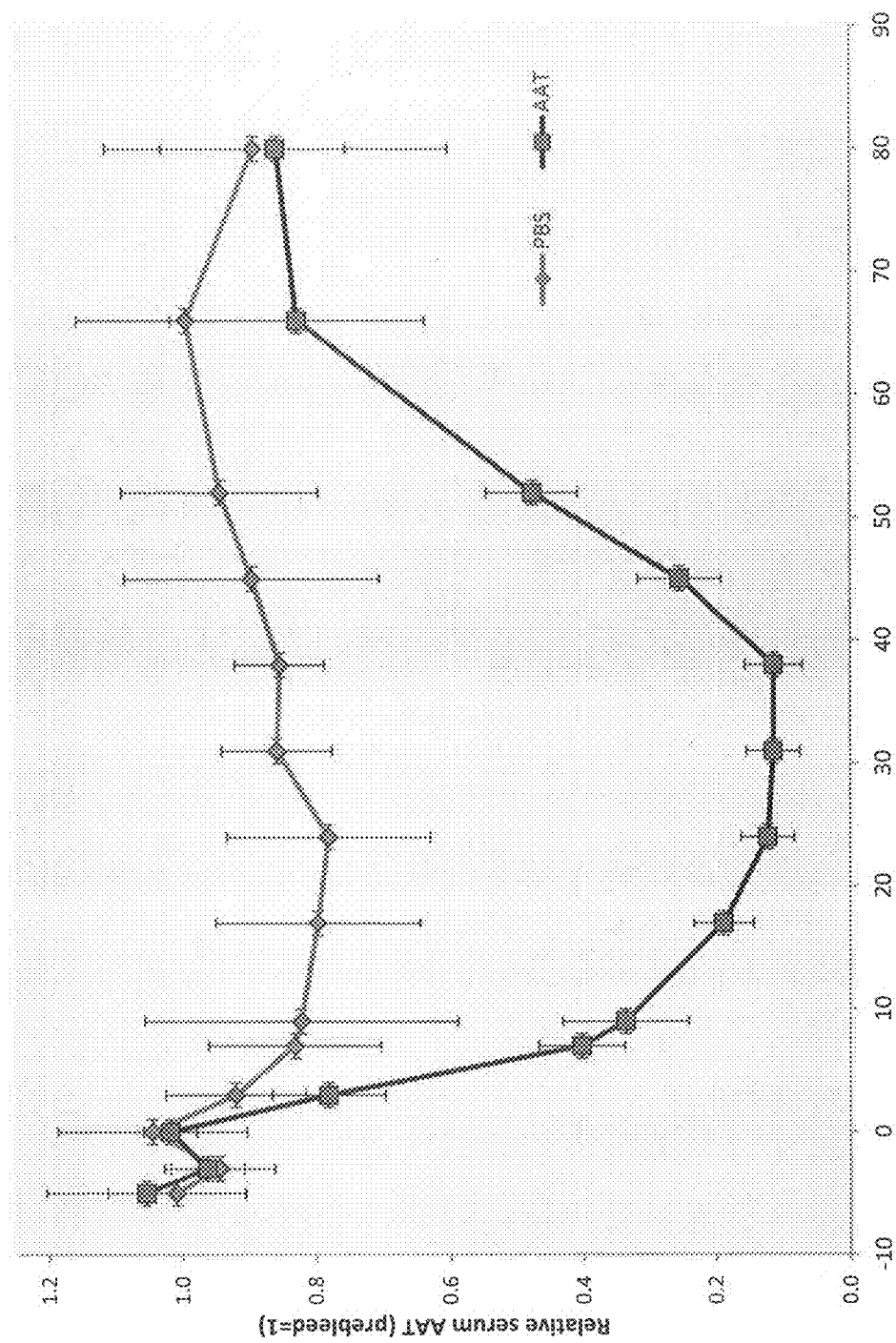

The efficacy of siRNA duplex AD-59054 in the transgenic animal model of AAT-deficiency associated liver disease was measured by administration of different doses of siRNA duplex AD-59054 subcutaneously. Serum was drawn at different time intervals to measure the serum hAAT protein levels using human AAT specific ELISA. The efficacy curve showing maximum knock-down achieved at different doses tested in mice is depicted in FIG. 3A. Each point is an average of three animals and the error bars represent the standard deviation. The duration of knock-down after a single dose of AAT siRNA at 0.3, 1, 3 or 10 mg/kg is shown in FIG. 3B. Each data point is an average of three animals and the error bars reflect the standard deviation. The hAAT levels were normalized to the average of three prebleeds for each animal. The siRNA was administered in PBS, hence the PBS group serves as the control to reflect the variability in the serum hAAT levels. Subcutaneous administration of the AAT siRNA led to dose-dependent inhibition of serum hATT, with maximum inhibition of >95% observed at a dose of 3 mg/kg. A single dose of 1 mg/kg maintained 40% levels of hAAT for at least 15 days. Animals were also administered AD-59054 at a dose of 0.5 mg/kg twice a week (FIG. 3C). The repeat dosing leads to a cumulative response and more than 90% protein suppression. Each data point is an average of four animals and the error bars reflect the standard deviation.

Example 5. Decreased Tumor Incidence with Reduction in Z-AAT

Figure 4A:
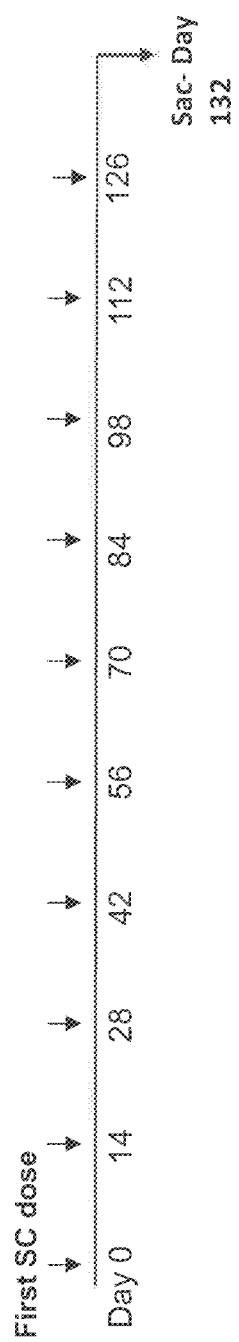
FIGS. 4A-4D depict decreased tumor incidence with reduction in Z-AAT.
Figure 4B:
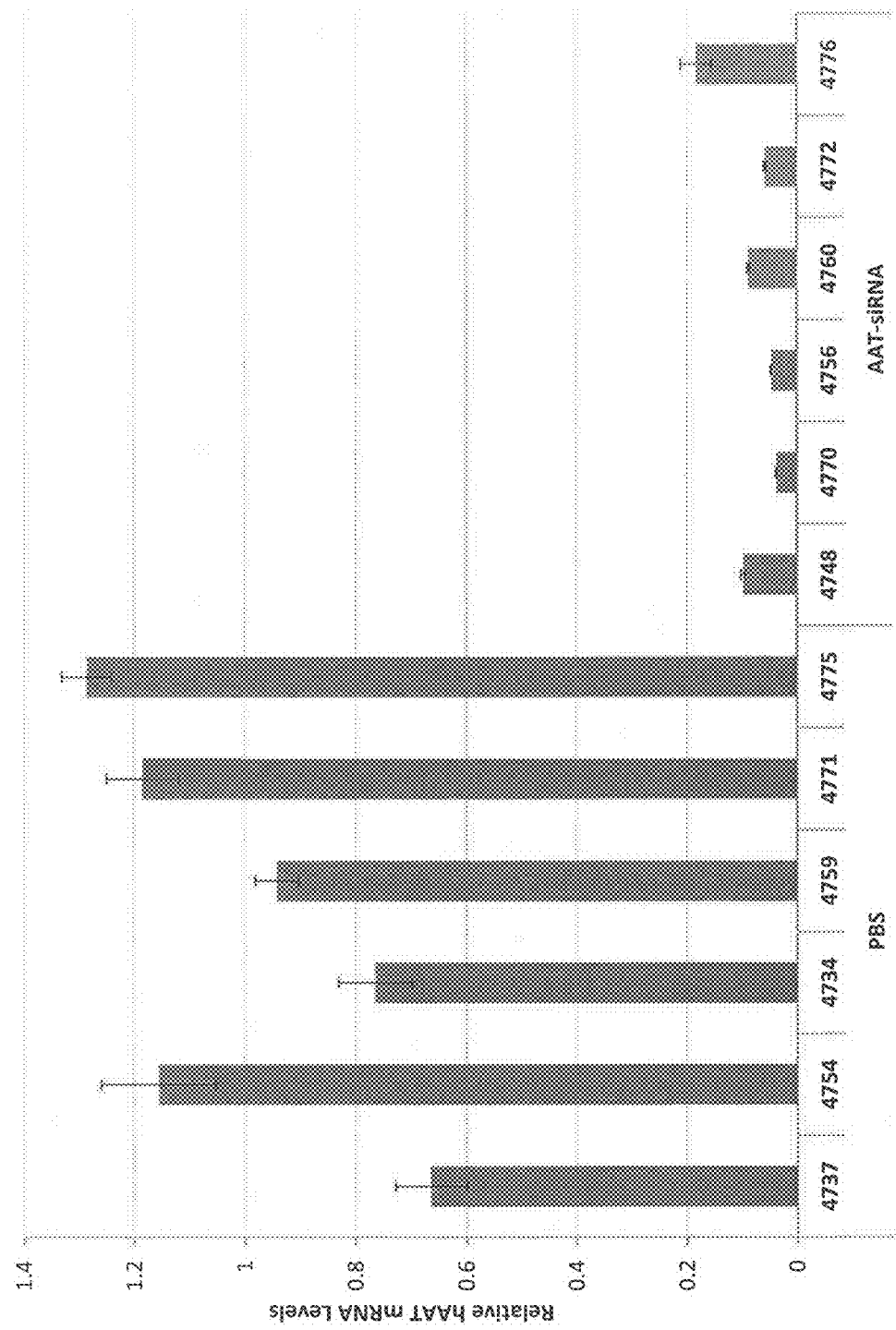
Figure 4C:
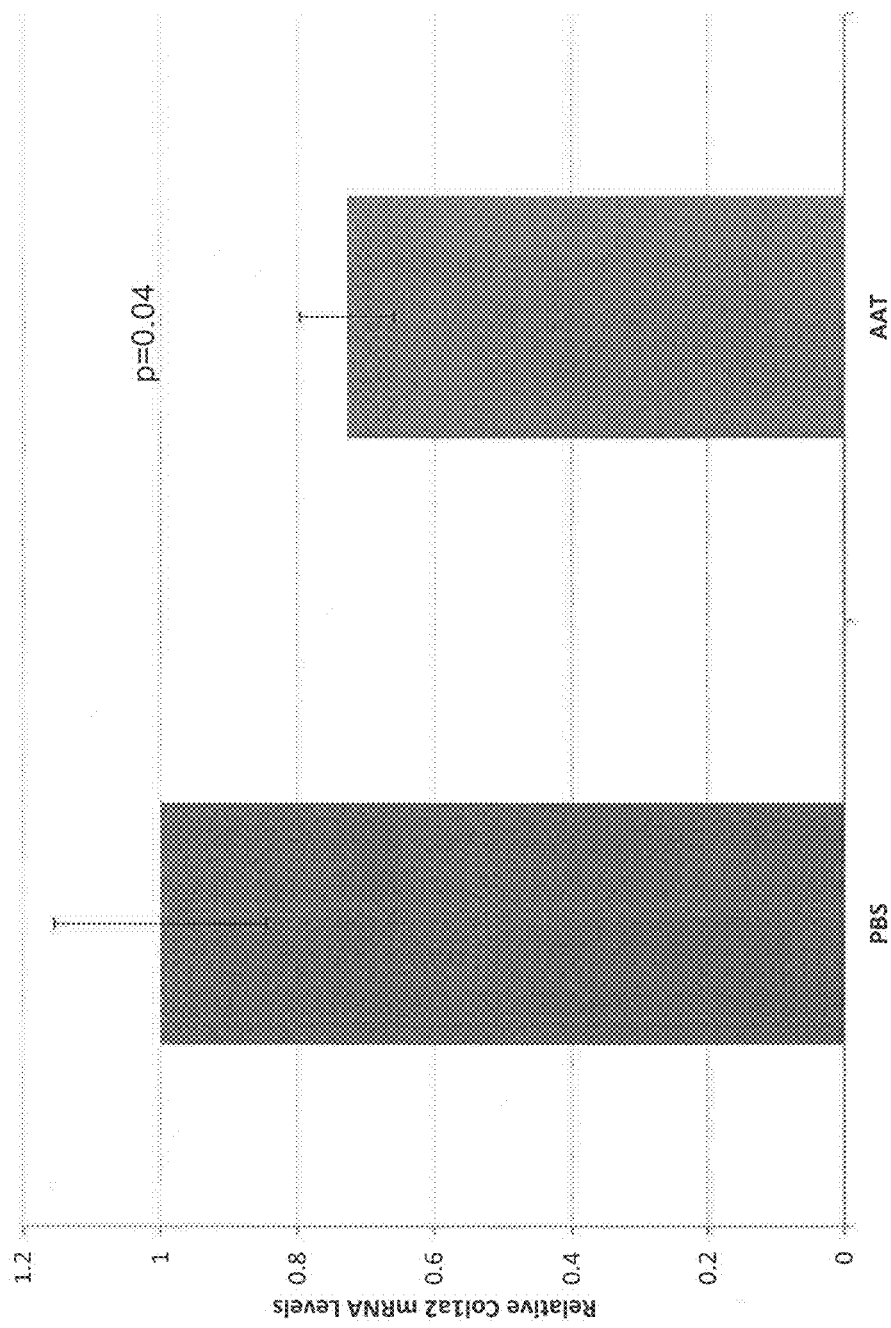
Figure 4D:
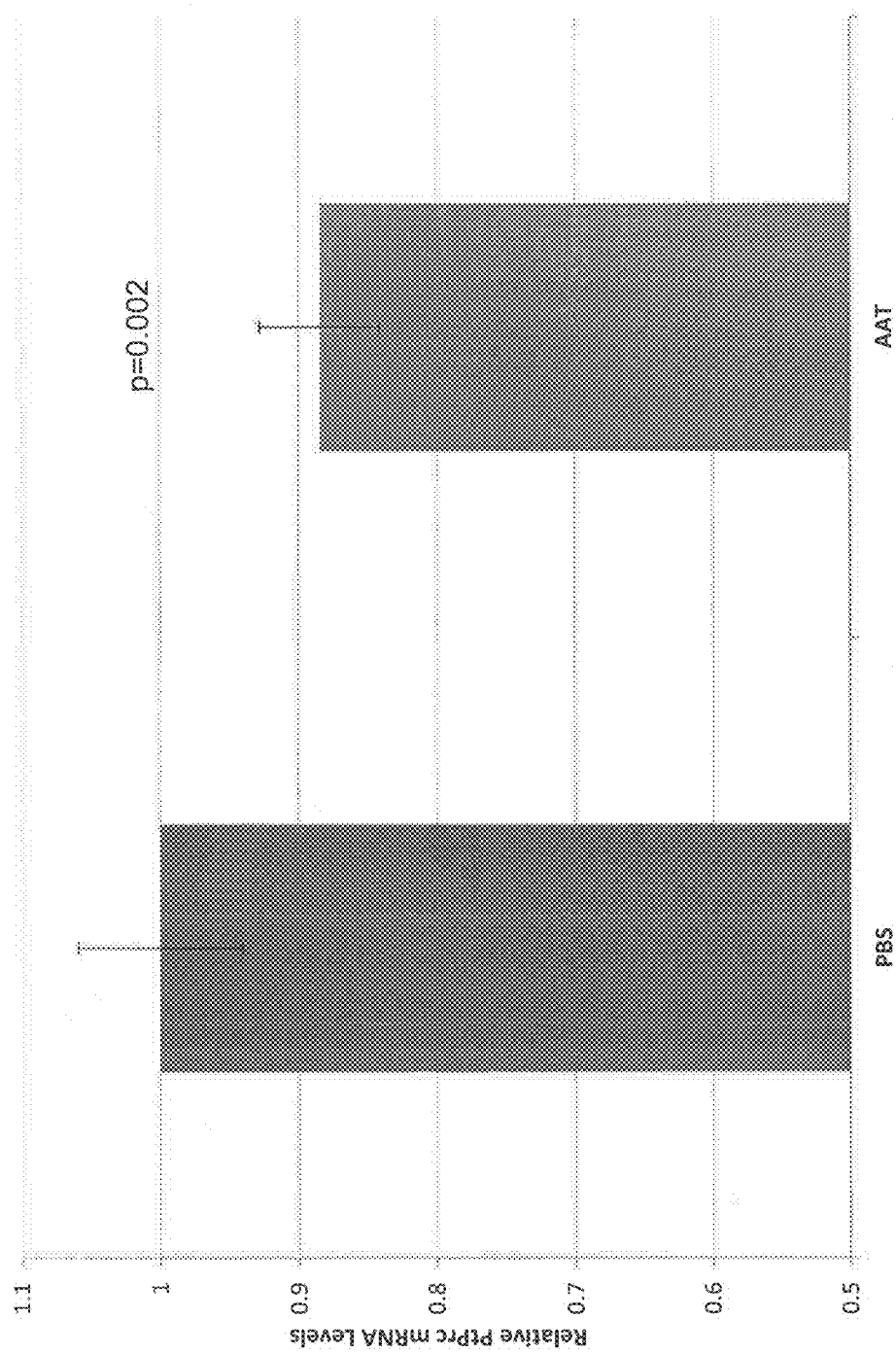

Transgenic human Z-AAT expressing mice develop tumors with age. This experiment was designed to determine whether chronic dosing of these aged mice with an siRNA of the invention can decrease the tumor incidence in the mice. Specifically, aged mice (25-46 weeks of age) with fibrotic livers were chronically dosed with siRNA duplex AD-58681 to decrease liver tumor incidence. Animals were dosed subcutaneously once every other week (Q2W) with PBS or 10 mg/kg AAT siRNA for 11 doses and sacrificed 7 days after the last dose (FIG. 4A). The liver levels of hAAT mRNA, Colla2 mRNA and PtPrc mRNA in control and treated groups were measured. The AAT siRNA treated animals showed a higher than 90% decrease in hAAT mRNA levels (FIG. 4B). Colla2 mRNA was measured as a marker of fibrosis and the levels of this marker decreased in AAT siRNA treated animals (FIG. 4C). PtPrc (CD45) mRNA was measured as a marker for the presence of immune cells (FIG. 4D). There is more immune cell infiltration in diseased livers and, as shown in FIG. 4D, the PtPrc mRNA levels decreased significantly when animals were treated with AAT siRNA.

Figure 5A:
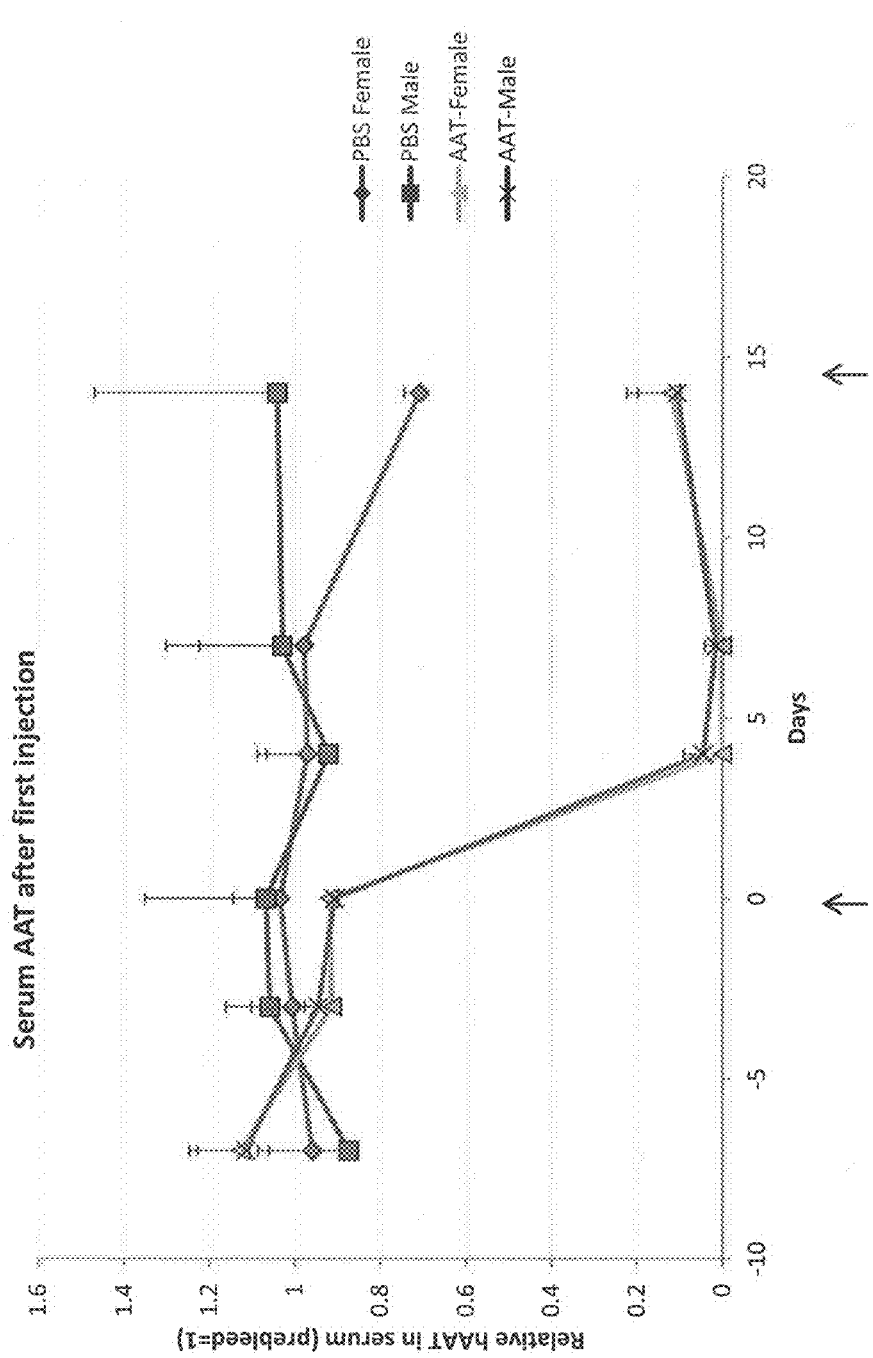
FIGS. 5A-5C depict decreased tumor incidence with reduction in Z-AAT. Serum samples were collected from mice treated according to the study design of FIG. 4A to monitor the extent of hAAT suppression.
Figure 5C:
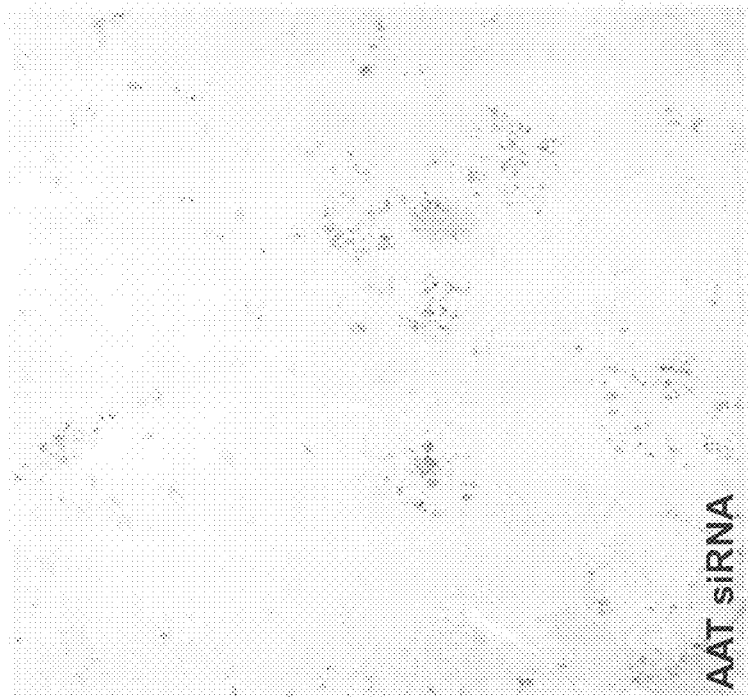
Figure 5B:
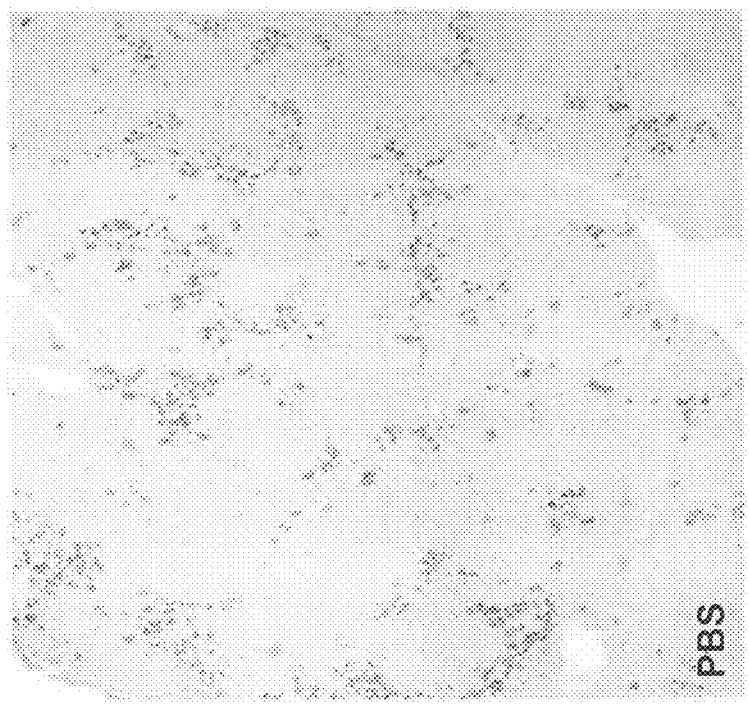

Serum samples were collected after the first dose to monitor the extent of AAT suppression. All AAT siRNA treated animals showed less than 5% residual AAT protein and a single dose maintained the AAT levels below 80% for 14 days before the next dose was administered (FIG. 5A). Table 6 provides observations from the animals at the time of sacrifice (day 132). Transgenic animals administered the siRNA duplex exhibited decreased tumor incidence when compared to untreated control animals. Specifically, four out of six animals treated with PBS showed tumors in the livers, whereas only one out of six animals treated with AAT siRNA showed a liver tumor. The p value for the difference in tumor incidence was calculated by t-test to be 0.045. FIG. 5B and FIG. 5C show PAS staining of liver sections from two littermates treated with either PBS or AAT siRNA. The darker colored dots represent the globules or Z-AAT aggregates. These data indicate that siRNA duplex is effective in decreasing Z-AAT levels in transgenic mice and the decreased levels of Z-AAT show a physiological benefit in the form of healthier livers.

TABLE 6

| Treatment | Animal # | Observation |
|---|---|---|
| PBS | 4734 | pale liver |
|  | 4737 | large tumor in left lateral lobe, ~5 mm diameter |
|  | 4754 | pale liver, 2 mm tumor in caudate lobe, many lesions in 2nd aux lobe |
|  | 4759 | dark liver, 1.5 mm tumor in caudate lobe, 1 mm lesion in right medial lobe, multiple 1 mm lesions in 1st aux lobe |
|  | 4771 | 3 mm tumor in left lateral lobe |
|  | 4775 | dark liver |

TABLE 6-continued

| Treatment | Animal # | Observation |
|---|---|---|
| AAT-siRNA | 4748 | dark liver |
| | 4756 | pale liver, 3 mm tumor in caudate lobe |
| | 4760 | dark liver |
| | 4770 | nothing abnormal |
| | 4772 | nothing abnormal |
| | 4776 | nothing abnormal |

Example 6. Lead Optimization of AD-59054

As described above, AD-59054 was demonstrated to durably suppress AAT in a dose-responsive manner in vivo. However, the nucleotide sequence of AD-59054 spans a region in AAT mRNA that includes a prevalent single nucleotide polymorphism (SNP) (Reference SNP Accession No.: rs1303 (see, e.g., www.ncbi.nlm.nih.gov/projects/SNP)). Specifically, the SNP location corresponds to the nucleotide at position 6 (5' to 3') in the antisense strand of AD-59054 (i.e., within the seed region of AD-59054). Accordingly, as mismatches within the seed region may lead to off-target effects and/or loss of efficacy, additional duplexes having various bases at position 6 (5' to 3') of the antisense strand were prepared based on the sequence of AD-59054. The target mRNA carries an A corresponding to position 6 (5' to 3') of the antisense strand of AD-59054. The sequences of these duplexes are provided in Table 7. Table 8 provides the sequences of these same duplexes having various chemical modifications and conjugated with a tri-valent GalNAc.

These modified duplexes were evaluated for efficacy in a single dose free uptake screen in primary mouse hepatocytes (Hep3B), as described above. Hep3B cell mRNA carries a C at the position corresponding to position 6 (5' to 3') of the antisense strand of AD-59054. The $IC_{50}$ values for the duplexes are shown in Table 8. Surprisingly, as demonstrated therein, a single mismatch within the seed region at position 6 was tolerated for all bases except C.

Figure 6:
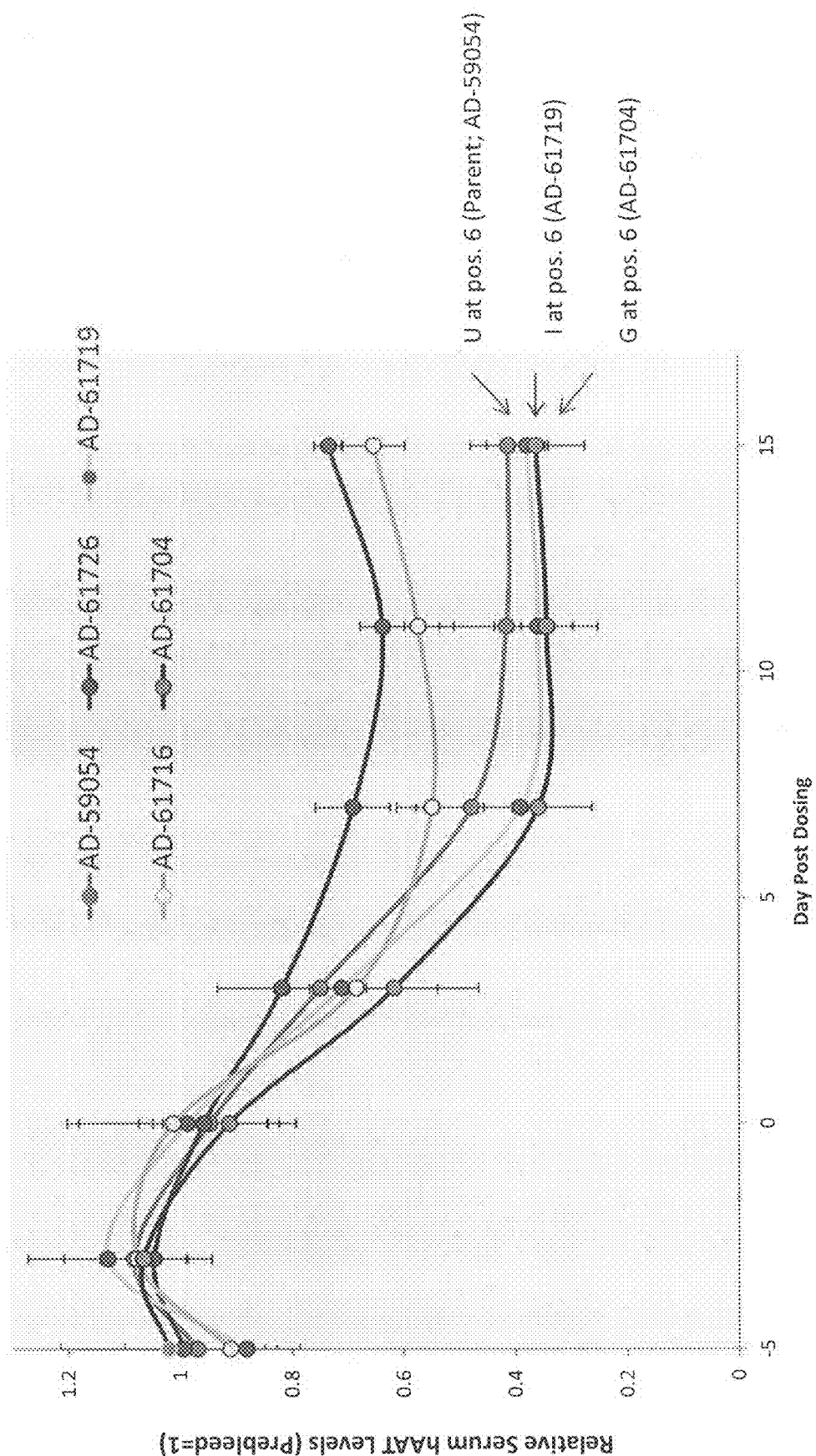
FIG. 6 depicts the in vivo efficacy of the indicated compounds.

A subset of these duplexes was also evaluated for in vivo efficacy. Transgenic mice expressing the human Z-AAT allele (and having an A in the mRNA corresponding to position 6 (5' to 3') of the antisense strand of AD-59054) were injected with 1.0 mg/kg of AD-59054, AD-61719, AD-61700, AD-61726, or AD-61704 on day 0 and serum human AAT, measured as described above, was followed for 14 days post dose (FIG. 6). Each point represents an average of three mice and the error bars reflect the standard of deviation. As demonstrated in FIG. 6, AD-61719 and AD-61704 perform as well as the parent AD-59054.

TABLE 7

| Duplex Name | Sense (5'→3') | SEQ ID NO: | Antisense (5'→3') | SEQ ID NO: |
|---|---|---|---|---|
| AD-59054 | CUUCUUAAUGAUUGAACAAAA | 401 | UUUUGUUCAAUCAUUAAGAAGAC | 409 |
| AD-61704 | CUUCUUAAUGAUUGACCAAAA | 402 | UUUUGGUCAAUCAUUAAGAAGAC | 410 |
| AD-61708 | CUUCUUAAUGAUUGAUCAAAA | 403 | UUUUGAUCAAUCAUUAAGAAGAC | 411 |
| AD-61712 | CUUCUUAAUGAUUGAGCAAAA | 404 | UUUUGCUCAAUCAUUAAGAAGAC | 412 |
| AD-61719 | CUUCUUAAUGAUUGACCAAAA | 405 | UUUUGIUCAAUCAUUAAGAAGAC | 413 |
| AD-61700 | CUUCUUAAUGAUUGACCAAAA | 406 | UUUUGNUCAAUCAUUAAGAAGAC | 414 |
| AD-61726 | CUUCUUAAUGAUUGAACAAAA | 407 | UUUUGNUCAAUCAUUAAGAAGAC | 415 |
| AD-61716 | CUUCUUAAUGAUUGAACAAAA | 408 | UUUUGNUCAAUCAUUAAGAAGAC | 416 |

Example 7. Lead Optimization of AD-59054

Additional duplexes were prepared based on the sequence of AD-59054, including AD-61444. The modified and unmodified sense and antisense sequences of AD-61444 are provided in Table 9.

TABLE 9

| Duplex Name | Unmodified Sense (5'→3') | Unmodified Antisense (5'→3') |
|---|---|---|
| AD-61444 | CUUCUUAAUGAUUGAACAAAA (SEQ ID NO: 417) | UUUUGUUCAAUCAUUAAGAAGAC (SEQ ID NO: 419) |
| | Modified Sense (5'→3') | Modified Antisense (5'→3') |
| | csusucuuaauGfAfuugaacaaaaL96 (SEQ ID NO: 418) | usUfsuUfgUfuCfaAfucaUfuAfaGfaAfgsasc (SEQ ID NO: 420) |

TABLE 8

| Duplex Name | Base at position 6 | Sense (5'→3') | SEQ ID NO: | Antisense (5'→3') | SEQ ID NO: | IC$_{50}$ mean |
|---|---|---|---|---|---|---|
| AD-59054 | U (parent compound) | CfsusUfcUfuAfaUfGfAfuUfgAfaCfaAfaAfL96 | 421 | usUfsuUfgUfucUfaAfucaUfuAfaGfaAfgsasc | 429 | 0.098 |
| AD-61704 | G | CfsusUfcUfuAfaUfGfAfuUfgAfaCfaAfaAfL96 | 422 | usUfsuUfgGfucUfaAfucaUfuAfaGfaAfgsasc | 430 | 0.102 |
| AD-61708 | A | CfsusUfcUfuAfaUfGfAfuUfgAfuCfaAfaAfL96 | 423 | usUfsuUfgAfucUfaAfucaUfuAfaGfaAfgsasc | 431 | 0.147 |
| AD-61712 | C | CfsusUfcUfuAfaUfGfAfuUfgAfgCfaAfaAfL96 | 424 | usUfsuUfgCfucUfaAfucaUfuAfaGfaAfgsasc | 432 | 1.499 |
| AD-61719 | I (inosine) | CfsusUfcUfuAfaUfGfAfuUfgAfcCfaAfaAfL96 | 425 | usUfsuUfgiuCfaAfucaUfuAfaGfaAfgsasc | 433 | 0.088 |
| AD-61700 | dI (deoxyinosine) (S/AS¹: C/dI) | CfsusUfcUfuAfaUfGfAfuUfgAfcCfaAfaAfL96 | 426 | usUfsuUfgdIucCfaAfucaUfuAfaGfaAfgsasc | 434 | 0.097 |
| AD-61726 | dI (deoxyinosine) (S/AS: A/dI) | CfsusUfcUfuAfaUfGfAfuUfgAfuCfaAfaAfL96 | 427 | usUfsuUfgdIucCfaAfucaUfuAfaGfaAfgsasc | 435 | 0.059 |
| AD-61716 | abasic 2'-OMe | CfsusUfcUfuAfaUfGfAfuUfgAfcCfaAfaAfL96 | 428 | usUfsuUfgY34ucCfaAfucaUfuAfaGfaAfgsasc | 436 | 0.333 |

[1] S/AS: Sense/Antisense.

Example 8. Non-Human Primate Dosing of AD-59054, AD-61719, and AD-61444

Figures 7A, 7B:
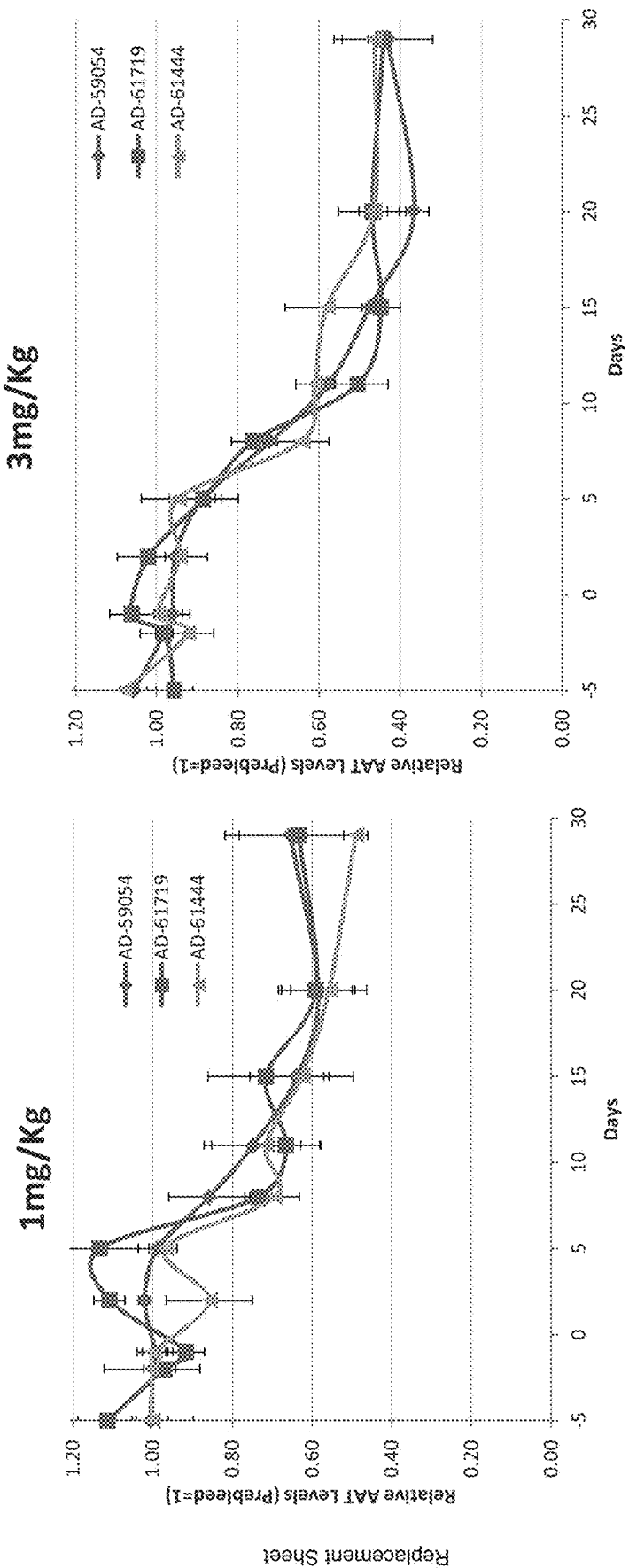
FIGS. 7A and 7B are graphs depicting the duration of knock-down of AAT in non-human primates after a single dose of AD-59054, AD-61719, or AD-61444 at a dose of 1 mg/kg (7A) or 3 mg/kg (7B). Each data point is an average of three animals and the error bars reflect the standard deviation.

AD-59054, AD-61719, and AD-61444 were tested for efficacy in non-human primates by administering to the primates a single dose of 1 mg/kg or 3 mg/kg of AD-59054, AD-61719, or AD-61444. Serum samples were collected five days prior to administration, at day 0, and at days 3, 7, 10, 15, 20, and 30 after administration to monitor the extent of AAT suppression by measuring serum hAAT protein levels using human AAT specific ELISA. There were no changes in cytokine or chemokine levels in the serum of the animals administered any of the compounds, and no injection site reactions or drug related health concerns were associated with administration of the compounds. FIG. 7 shows that a single dose of 1 mg/kg of AD-59054, AD-61719, or AD-61444 (7A) or a single dose of 3 mg/kg of AD-59054, AD-61719, or AD-61444 (7B) results in a dose dependent and durable lowering of AAT protein.

SEQUENCE LISTING

<160> NUMBER OF SEQ ID NOS: 436

<210> SEQ ID NO 1
<211> LENGTH: 3220
<212> TYPE: DNA
<213> ORGANISM: Homo sapiens

<400> SEQUENCE: 1

```
acaatgactc ctttcggtaa gtgcagtgga agctgtacac tgcccaggca aagcgtccgg      60
gcagcgtagg cgggcgactc agatcccagc cagtggactt agccctgtt tgctcctccg     120 ataactgggg tgaccttggt taatattcac cagcagcctc ccccgttgcc cctctggatc     180
cactgcttaa atacggacga ggacagggcc ctgtctcctc agcttcaggc accaccactg     240
acctgggaca gtgaatcgac aatgccgtct tctgtctcgt ggggcatcct cctgctggca     300
ggcctgtgct gcctggtccc tgtctccctg gctgaggatc cccagggaga tgctgcccag     360
aagacagata catcccacca tgatcaggat cacccaacct tcaacaagat caccccaac      420 ctggctgagt tcgccttcag cctataccgc cagctggcac accagtccaa cagcaccaat     480
atcttcttct ccccagtgag catcgctaca gcctttgcaa tgctctccct ggggaccaag     540
gctgacactc acgatgaaat cctggagggc ctgaatttca acctcacgga gattccggag     600
gctcagatcc atgaaggctt ccaggaactc ctccgtaccc tcaaccagcc agacagccag     660
ctccagctga ccaccggcaa tggcctgttc ctcagcgagg gcctgaagct agtggataag     720
tttttggagg atgttaaaaa gttgtaccac tcagaagcct tcactgtcaa cttcggggac     780
accgaagagg ccaagaaaca gatcaacgat tacgtggaga agggtactca agggaaaatt     840
gtggatttgg tcaaggagct tgacagagac acagtttttg ctctggtgaa ttacatcttc     900
tttaaaggca aatgggagag acccttgaa gtcaaggaca ccgaggaaga ggacttccac     960
gtggaccagg tgaccaccgt gaaggtgcct atgatgaagc gtttaggcat gtttaacatc    1020
cagcactgta agaagctgtc cagctgggtg ctgctgatga aatacctggg caatgccacc    1080
gccatcttct tcctgcctga tgagggggaaa ctacagcacc tggaaaatga actcacccac    1140
gatatcatca ccaagttcct ggaaaatgaa gacagaaggt ctgccagctt acatttaccc    1200
aaactgtcca ttactggaac ctatgatctg aagagcgtcc tgggtcaact gggcatcact    1260
aaggtcttca gcaatgggc tgacctctcc ggggtcacag aggaggcacc cctgaagctc    1320
tccaaggccg tgcataaggc tgtgctgacc atcgacgaga aagggactga agctgctggg    1380
gccatgtttt tagaggccat acccatgtct atccccccg aggtcaagtt caacaaaccc    1440
tttgtcttct taatgattga acaaaatacc aagtctcccc tcttcatggg aaaagtggtg    1500
aatcccaccc aaaaataact gcctctcgct cctcaacccc tccctccat ccctggcccc    1560 ctccctggat gacattaaag aagggttgag ctggtccctg cctgcatgtg actgtaaatc    1620
cctcccatgt tttctctgag tctcccttg cctgctgagg ctgtatgtgg gctccaggta    1680
```

```
acagtgctgt cttcgggccc cctgaactgt gttcatggag catctggctg ggtaggcaca    1740
tgctgggctt gaatccaggg gggactgaat cctcagctta cggacctggg cccatctgtt    1800
tctggagggc tccagtcttc cttgtcctgt cttggagtcc ccaagaagga atcacagggg    1860
aggaaccaga taccagccat gaccccaggc tccaccaagc atcttcatgt cccccctgctc   1920
atcccccact ccccccccacc cagagttgct catcctgcca gggctggctg tgcccacccc   1980
aaggctgccc tcctggggc cccagaactg cctgatcgtg ccgtggccca gttttgtggc     2040
atctgcagca acacaagaga aggacaatg tcctcctctt gacccgctgt cacctaacca    2100
gactcgggcc ctgcacctct caggcacttc tggaaaatga ctgaggcaga ttcttcctga   2160
agcccattct ccatggggca acaaggacac ctattctgtc cttgtccttc catcgctgcc   2220
ccagaaagcc tcacatatct ccgtttagaa tcaggtccct tctccccaga tgaagaggag    2280
ggtctctgct ttgttttctc tatctcctcc tcagacttga ccaggcccag caggcccag     2340
aagaccatta ccctatatcc cttctcctcc ctagtcacat ggccataggc ctgctgatgg   2400
ctcaggaagg ccattgcaag gactcctcag ctatgggaga ggaagcacat cacccattga   2460
cccccgcaac ccctcccttt cctcctctga gtcccgactg gggccacatg cagcctgact   2520
tctttgtgcc tgttgctgtc cctgcagtct tcagagggcc accgcagctc cagtgccacg    2580
gcaggaggct gttcctgaat agccctgtg gtaaggccca ggagagtcct tccatcctcc    2640
aaggccctgc taaaggacac agcagccagg aagtcccctg ggcccctagc tgaaggacag    2700
cctgctccct ccgtctctac caggaatggc cttgtcctat ggaaggcact gccccatccc   2760
aaactaatct aggaatcact gtctaaccac tcactgtcat gaatgtgtac ttaaaggatg    2820
aggttgagtc ataccaaata gtgatttcga tagttcaaaa tggtgaaatt agcaattcta   2880
catgattcag tctaatcaat ggataccgac tgtttcccac acaagtctcc tgttctctta   2940
agcttactca ctgacagcct ttcactctcc acaaatacat taaagatatg gccatcacca    3000
agccccctag gatgacacca gacctgagag tctgaagacc tggatccaag ttctgacttt    3060
tcccctgac agctgtgtga ccttcgtgaa gtcgccaaac ctctctgagc ccagtcatt    3120
gctagtaaga cctgcctttg agttggtatg atgttcaagt tagataacaa aatgtttata    3180
cccattagaa cagagaataa atagaactac atttcttgca                          3220
```

<210> SEQ ID NO 2
<211> LENGTH: 3199
<212> TYPE: DNA
<213> ORGANISM: Homo sapiens

<400> SEQUENCE: 2

```
tgggcaggaa ctgggcactg tgcccagggc atgcactgcc tccacgcagc aaccctcaga     60
gtcctgagct gaaccaagaa ggaggagggg gtcgggcctc cgaggaaggc ctagccgctg    120
ctgctgccag gaattccagg ttggagggc ggcaacctcc tgccagcctt caggccactc     180
tcctgtgcct gccagaagag acagagcttg aggagagctt gaggagagca ggaaaggaca    240
atgccgtctt ctgtctcgtg gggcatcctc ctgctggcag gcctgtgctg cctggtccct    300
gtctccctgg ctgaggatcc ccaggagat gctgcccaga agacagatac atcccaccat     360
gatcaggatc acccaacctt caacaagatc accccaacc tggctgagtt cgccttcagc     420
ctataccgcc agctggcaca ccagtccaac agcaccaata tcttcttctc cccagtgagc    480
atcgctacag cctttgcaat gctctcccctg gggaccaagg ctgacactca cgatgaaatc    540
```

```
ctggagggcc tgaatttcaa cctcacggag attccggagg ctcagatcca tgaaggcttc    600
caggaactcc tccgtaccct caaccagcca gacagccagc tccagctgac caccggcaat    660
ggcctgttcc tcagcgaggg cctgaagcta gtggataagt ttttggagga tgttaaaaag    720
ttgtaccact cagaagcctt cactgtcaac ttcggggaca ccgaagaggc caagaaacag    780
atcaacgatt acgtggagaa gggtactcaa gggaaaattg tggatttggt caaggagctt    840
gacagagaca cagttttttgc tctggtgaat tacatcttct ttaaaggcaa atgggagaga    900
ccctttgaag tcaaggacac cgaggaagag gacttccacg tggaccaggt gaccaccgtg    960
aaggtgccta tgatgaagcg tttaggcatg tttaacatcc agcactgtaa gaagctgtcc   1020
agctgggtgc tgctgatgaa atacctgggc aatgccaccg ccatcttctt cctgcctgat   1080
gaggggaaac tacagcacct ggaaaatgaa ctcacccacg atatcatcac caagttcctg   1140
gaaaatgaag acagaaggtc tgccagctta catttaccca aactgtccat tactggaacc   1200
tatgatctga gagcgtcctc gggtcaactg gcatcacta aggtcttcag caatggggct   1260
gacctctccg gggtcacaga ggaggcaccc ctgaagctct ccaaggccgt gcataaggct   1320
gtgctgacca tcgacgagaa agggactgaa gctgctgggg ccatgttttt agaggccata   1380
cccatgtcta tccccccga ggtcaagttc aacaaaccct tgtcttctt aatgattgaa   1440
caaaatacca agtctcccct cttcatggga aaagtggtga atcccaccca aaaataactg   1500
cctctcgctc ctcaaccct ccctccatc cctggcccc tccctggatg acattaaaga   1560
agggttgagc tggtccctgc ctgcatgtga ctgtaaatcc ctcccatgtt ttctctgagt   1620
ctccctttgc ctgctgaggc tgtatgtggg ctccaggtaa cagtgctgtc ttcgggcccc   1680
ctgaactgtg ttcatggagc atctggctgg gtaggcacat gctgggcttg aatccagggg   1740
ggactgaatc ctcagcttac ggacctgggc ccatctgttt ctggagggct ccagtcttcc   1800
ttgtcctgtc ttggagtccc caagaaggaa tcacagggga ggaaccagat accagccatg   1860
accccaggct ccaccaagca tcttcatgtc ccctgctca tccccactc cccccaccc    1920
agagttgctc atcctgccag ggctggctgt gcccacccca aggctgccct cctggggggcc   1980
ccagaactgc ctgatcgtgc cgtggcccag ttttgtggca tctgcagcaa cacaagagag   2040
aggacaatgt cctcctcttg acccgctgtc acctaaccag actcgggccc tgcacctctc   2100
aggcacttct ggaaaatgac tgaggcagat tcttcctgaa gcccattctc catggggcaa   2160
caaggacacc tattctgtcc ttgtccttcc atcgctgccc cagaaagcct cacatatctc   2220
cgtttagaat caggtccctt ctccccagat gaagaggagg gtctctgctt tgttttctct   2280
atctcctcct cagacttgac caggcccagc aggccccaga agaccattac cctatatccc   2340
ttctcctccc tagtcacatg gccataggcc tgctgatggc tcaggaaggc cattgcaagg   2400
actcctcagc tatgggagag gaagcacatc acccattgac ccccgcaacc cctcccttt c   2460
ctcctctgag tccgactgg ggccacatgc agcctgactt ctttgtgcct gttgctgtcc   2520
ctgcagtctt cagagggcca ccgcagctcc agtgccacgg caggaggctg ttcctgaata   2580
gccctgtgg taagggccag gagagtcctt ccatcctcca aggccctgct aaaggacaca   2640
gcagccagga gtcccctgg gcccctagct gaaggacagc ctgctccctc cgtctctacc   2700
aggaatggcc ttgtcctatg gaaggcactg ccccatccca aactaatcta ggaatcactg   2760
tctaaccact cactgtcatg aatgtgtact taaaggatga ggttgagtca taccaaatag   2820
tgatttcgat agttcaaaat ggtgaaatta gcaattctac atgattcagt ctaatcaatg   2880
gataccgact gtttcccaca caagtctcct gttctcttaa gcttactcac tgacagcctt   2940
```

```
tcactctcca caaatacatt aaagatatgg ccatcaccaa gcccctagg atgacaccag    3000 acctgagagt ctgaagacct ggatccaagt tctgactttt ccccctgaca gctgtgtgac    3060
cttcgtgaag tcgccaaacc tctctgagcc ccagtcattg ctagtaagac ctgcctttga    3120
gttggtatga tgttcaagtt agataacaaa atgtttatac ccattagaac agagaataaa    3180
tagaactaca tttcttgca                                                 3199

<210> SEQ ID NO 3
<211> LENGTH: 3513
<212> TYPE: DNA
<213> ORGANISM: Homo sapiens

<400> SEQUENCE: 3
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggagggggc ggcaacctcc tgccagcctt caggccactc    180
```

|  |  |  |  | |
|---|---|---|---|---|
| cccaaaaata | actgcctctc | gctcctcaac | ccctcccctc | catccctggc | ccctccctg | 1860 |
| gatgacatta | aagaagggtt | gagctggtcc | ctgcctgcat | gtgactgtaa | atccctccca | 1920 |
| tgttttctct | gagtctccct | ttgcctgctg | aggctgtatg | tgggctccag | gtaacagtgc | 1980 |
| tgtcttcggg | cccctgaac | tgtgttcatg | gagcatctgg | ctgggtaggc | acatgctggg | 2040 |
| cttgaatcca | gggggactg | aatcctcagc | ttacggacct | gggcccatct | gtttctggag | 2100 |
| ggctccagtc | ttccttgtcc | tgtcttggag | tccccaagaa | ggaatcacag | gggaggaacc | 2160 |
| agataccagc | catgaccca | ggctccacca | agcatcttca | tgtcccctg | ctcatccccc | 2220 |
| actcccccc | acccagagtt | gctcatcctg | ccagggctgg | ctgtgccac | ccaaggctg | 2280 |
| ccctcctggg | ggcccagaa | ctgcctgatc | gtgccgtggc | ccagttttgt | ggcatctgca | 2340 |
| gcaacacaag | agagaggaca | atgtcctcct | cttgacccgc | tgtcacctaa | ccagactcgg | 2400 |
| gccctgcacc | tctcaggcac | ttctggaaaa | tgactgaggc | agattcttcc | tgaagcccat | 2460 |
| tctccatggg | gcaacaagga | cacctattct | gtccttgtcc | ttccatcgct | gccccagaaa | 2520 |
| gcctcacata | tctccgttta | gaatcaggtc | ccttctcccc | agatgaagag | gagggtctct | 2580 |
| gctttgtttt | ctctatctcc | tcctcagact | tgaccaggcc | cagcaggccc | cagaagacca | 2640 |
| ttaccctata | tcccttctcc | tccctagtca | catggccata | ggcctgctga | tggctcagga | 2700 |
| aggccattgc | aaggactcct | cagctatggg | agaggaagca | catcacccat | tgacccccgc | 2760 |
| aacccctccc | tttcctcctc | tgagtcccga | ctggggccac | atgcagcctg | acttctttgt | 2820 |
| gcctgttgct | gtccctgcag | tcttcagagg | gccaccgcag | ctccagtgcc | acggcaggag | 2880 |
| gctgttcctg | aatagcccct | gtggtaaggg | ccaggagagt | ccttccatcc | tccaaggccc | 2940 |
| tgctaaagga | cacagcagcc | aggaagtccc | ctgggcccct | agctgaagga | cagcctgctc | 3000 |
| cctccgtctc | taccaggaat | ggccttgtcc | tatggaaggc | actgccccat | cccaaactaa | 3060 |
| tctaggaatc | actgtctaac | cactcactgt | catgaatgtg | tacttaaagg | atgaggttga | 3120 |
| gtcataccaa | atagtgattt | cgatagttca | aaatggtgaa | attagcaatt | ctacatgatt | 3180 |
| cagtctaatc | aatggatacc | gactgtttcc | cacacaagtc | tcctgttctc | ttaagcttac | 3240 |
| tcactgacag | cctttcactc | tccacaaata | cattaaagat | atggccatca | ccaagccccc | 3300 |
| taggatgaca | ccagacctga | gagtctgaag | acctggatcc | aagttctgac | ttttcccct | 3360 |
| gacagctgtg | tgaccttcgt | gaagtcgcca | aacctctctg | agcccagtc | attgctagta | 3420 |
| agacctgcct | ttgagttggt | atgatgttca | agttagataa | caaaatgttt | atacccatta | 3480 |
| gaacagagaa | taaatagaac | tacatttctt | gca |  |  | 3513 |

<210> SEQ ID NO 4
<211> LENGTH: 3236
<212> TYPE: DNA
<213> ORGANISM: Homo sapiens

<400> SEQUENCE: 4

|  |  |  |  |  |  | |
|---|---|---|---|---|---|---|
| tgggcaggaa | ctgggcactg | tgcccagggc | atgcactgcc | tccacgcagc | aaccctcaga | 60 |
| gtcctgagct | gaaccaagaa | ggaggagggg | gtcgggcctc | cgaggaaggc | ctagccgctg | 120 |
| ctgctgccag | gaattccagg | ttggaggggc | ggcaacctcc | tgccagcctt | caggccactc | 180 |
| tcctgtgcct | gccagaagag | acagagcttg | aggagagctt | gaggagagca | ggaaaggtgg | 240 |
| gacattgctg | ctgctgctca | ctcagttcca | caggacaatg | ccgtcttctg | tctcgtgggg | 300 |
| catcctcctg | ctggcaggcc | tgtgctgcct | ggtccctgtc | tccctggctg | aggatcccca | 360 |
| gggagatgct | gcccagaaga | cagatacatc | ccaccatgat | caggatcacc | caaccttcaa | 420 |

```
caagatcacc cccaacctgg ctgagttcgc cttcagccta taccgccagc tggcacacca    480
gtccaacagc accaatatct tcttctcccc agtgagcatc gctacagcct ttgcaatgct    540
ctccctgggg accaaggctg acactcacga tgaaatcctg gagggcctga atttcaacct    600
cacggagatt ccggaggctc agatccatga aggcttccag gaactcctcc gtaccctcaa    660
ccagccagac agccagctcc agctgaccac cggcaatggc ctgttcctca gcgagggcct    720
gaagctagtg dataagtttt tggaggatgt taaaaagttg taccactcag aagccttcac    780
tgtcaacttc ggggacaccg aagaggccaa gaaacagatc aacgattacg tggagaaggg    840
tactcaaggg aaaattgtgg atttggtcaa ggagcttgac agagacacag tttttgctct    900
ggtgaattac atcttcttta aaggcaaatg ggagagaccc tttgaagtca aggacaccga    960
ggaagaggac ttccacgtgg accaggtgac caccgtgaag gtgcctatga tgaagcgttt    1020
aggcatgttt aacatccagc actgtaagaa gctgtccagc tgggtgctgc tgatgaaata    1080
cctgggcaat gccaccgcca tcttcttcct gcctgatgag gggaaactac agcacctgga    1140
aaatgaactc acccacgata tcatcaccaa gttcctggaa aatgaagaca aaggtctgc     1200 cagcttacat ttacccaaac tgtccattac tggaacctat gatctgaaga gcgtcctggg    1260
tcaactgggc atcactaagg tcttcagcaa tggggctgac ctctccgggg tcacagagga    1320
ggcacccctg aagctctcca aggccgtgca taaggctgtg ctgaccatcg acgagaaagg    1380
gactgaagct gctggggcca tgttttttaga ggccataccc atgtctatcc cccccgaggt    1440
caagttcaac aaaccctttg tcttcttaat gattgaacaa ataccaagt ctcccctctt     1500 catgggaaaa gtggtgaatc ccacccaaaa ataactgcct ctcgctcctc aacccctccc    1560
ctccatccct ggccccctcc ctggatgaca ttaaagaagg gttgagctgg tccctgcctg    1620
catgtgactg taaatccctc ccatgttttc tctgagtctc cctttgcctg ctgaggctgt    1680
atgtgggctc caggtaacag tgctgtcttc gggccccctg aactgtgttc atggagcatc    1740
tggctgggta ggcacatgct gggcttgaat ccaggggдga ctgaatcctc agcttacgga    1800
cctgggccca tctgtttctg gagggctcca gtcttccttg tcctgtcttg gagtccccaa    1860
gaaggaatca caggggagga accagatacc agccatgacc ccaggctcca ccaagcatct    1920
tcatgtcccc ctgctcatcc cccactcccc cccacccaga gttgctcatc ctgccagggc    1980
tggctgtgcc caccccaagg ctgccctcct gggggcccca gaactgcctg atcgtgccgt    2040
ggcccagttt tgtggcatct gcagcaacac aagagagagg acaatgtcct cctcttgacc    2100
cgctgtcacc taaccagact cggggccctgc acctctcagg cacttctgga aaatgactga    2160
ggcagattct tcctgaagcc cattctccat ggggcaacaa ggacacctat tctgtccttg    2220
tccttccatc gctgccccag aaagcctcac atatctccgt ttagaatcag gtcccttctc    2280
cccagatgaa gaggagggtc tctgctttgt tttctctatc tcctcctcag acttgaccag    2340
gcccagcagg ccccagaaga ccattaccct atatcccttc tcctccctag tcacatggcc    2400
ataggcctgc tgatggctca ggaaggccat tgcaaggact cctcagctat gggagaggaa    2460
gcacatcacc cattgacccc cgcaacccct ccctttcctc ctctgagtcc cgactggggc    2520
cacatgcagc ctgacttctt tgtgcctgtt gctgtccctg cagtcttcag agggccaccg    2580
cagctccagt gccacggcag gaggctgttc ctgaatagcc cctgtggtaa gggccaggag    2640
agtccttcca tcctccaagg ccctgctaaa ggacacagca gccaggaagt cccctgggcc    2700
cctagctgaa ggacagcctg ctccctccgt ctctaccagg aatggccttg tcctatggaa    2760
```

-continued

| | |
|---|---|
| ggcactgccc catcccaaac taatctagga atcactgtct aaccactcac tgtcatgaat | 2820 |
| gtgtacttaa aggatgaggt tgagtcatac caaatagtga tttcgatagt tcaaaatggt | 2880 |
| gaaattagca attctacatg attcagtcta atcaatggat accgactgtt tcccacacaa | 2940 |
| gtctcctgtt ctcttaagct tactcactga cagcctttca ctctccacaa atacattaaa | 3000 |
| gatatggcca tcaccaagcc ccctaggatg acaccagacc tgagagtctg aagacctgga | 3060 |
| tccaagttct gacttttccc cctgacagct gtgtgacctt cgtgaagtcg ccaaacctct | 3120 |
| ctgagcccca gtcattgcta gtaagacctg cctttgagtt ggtatgatgt tcaagttaga | 3180 |
| taacaaaatg tttatacccca ttagaacaga gaataaatag aactacatttt cttgca | 3236 |

<210> SEQ ID NO 5
<211> LENGTH: 3532
<212> TYPE: DNA
<213> ORGANISM: Homo sapiens

<400> SEQUENCE: 5

| | |
|---|---|
| tgggcaggaa ctgggcactg tgcccagggc atgcactgcc tccacgcagc aaccctcaga | 60 |
| gtcctgagct gaaccaagaa ggaggagggg gtcgggcctc cgaggaaggc ctagccgctg | 120 |
| ctgctgccag gaattccagg ttggaggggc ggcaacctcc tgccagcctt caggccactc | 180 |
| tcctgtgcct gccagaagag acagagcttg aggagagctt gaggagagca ggaaaggtgg | 240 |
| gacattgctg ctgctgctca ctcagttcca cagggcggca gtaagtcttc agcatcaggc | 300 |
| attttggggt gactcagtaa atggtagatc ttgctaccag tggaacagcc actaaggatt | 360 |
| ctgcagtgag agcagagggc cagctaagtg gtactctccc agagactgtc tgactcacgc | 420 |
| cacccccctcc accttggaca caggacgctg tggtttctga gccagcagcc tcccccgttg | 480 |
| cccctctgga tccactgctt aaatacggac gaggacaggg ccctgtctcc tcagcttcag | 540 |
| gcaccaccac tgacctggga cagtgaatcg acaatgccgt cttctgtctc gtgggcatc | 600 |
| ctcctgctgg caggcctgtg ctgcctggtc cctgtctccc tggctgagga tccccaggga | 660 |
| gatgctgccc agaagacaga tacatcccac catgatcagg atcacccaac cttcaacaag | 720 |
| atcacccccca acctggctga gttcgccttc agcctatacc gccagctggc acaccagtcc | 780 |
| aacagcacca atatcttctt ctccccagtg agcatcgcta cagccttttgc aatgctctcc | 840 |
| ctggggacca aggctgacac tcacgatgaa atcctggagg gcctgaattt caacctcacg | 900 |
| gagattccgg aggctcagat ccatgaaggc ttccaggaac tcctccgtac cctcaaccag | 960 |
| ccagacagcc agtccagct gaccaccggc aatggcctgt tcctcagcga gggcctgaag | 1020 |
| ctagtggata agttttttgga ggatgttaaa aagttgtacc actcagaagc cttcactgtc | 1080 |
| aacttcgggg acaccgaaga ggccaagaaa cagatcaacg attacgtgga aagggtact | 1140 |
| caagggaaaa ttgtggattt ggtcaaggag cttgacagag acacagtttt tgctctggtg | 1200 |
| aattacatct tctttaaagg caaatgggag agaccctttg aagtcaagga caccgaggaa | 1260 |
| gaggacttcc acgtggacca ggtgaccacc gtgaaggtgc ctatgatgaa gcgtttaggc | 1320 |
| atgtttaaca tccagcactg taagaagctg tccagctggg tgctgctgat gaaatacctg | 1380 |
| ggcaatgcca ccgccatctt cttcctgcct gatgaggga actacagca cctggaaaat | 1440 |
| gaactcaccc acgatatcat caccaagttc ctggaaaatg aagacagaag gtctgccagc | 1500 |
| ttacatttac ccaaactgtc cattactgga acctatgatc tgaagagcgt cctgggtcaa | 1560 |
| ctgggcatca ctaaggtctt cagcaatggg gctgacctct ccggggtcac agaggaggca | 1620 |
| cccctgaagc tctccaaggc cgtgcataag gctgtgctga ccatcgacga gaagggact | 1680 |

```
gaagctgctg gggccatgtt tttagaggcc atacccatgt ctatccccc cgaggtcaag    1740 ttcaacaaac cctttgtctt cttaatgatt gaacaaaata ccaagtctcc cctcttcatg    1800
ggaaaagtgg tgaatcccac ccaaaaataa ctgcctctcg ctcctcaacc cctcccctcc    1860
atccctggcc ccctccctgg atgacattaa agaagggttg agctggtccc tgcctgcatg    1920
tgactgtaaa tccctcccat gttttctctg agtctccctt tgcctgctga ggctgtatgt    1980
gggctccagg taacagtgct gtcttcgggc cccctgaact gtgttcatgg agcatctggc    2040
tgggtaggca catgctgggc ttgaatccag ggggactga atcctcagct acggacctg    2100 ggcccatctg tttctggagg ctccagtct tccttgtcct gtcttggagt ccccaagaag    2160
gaatcacagg ggaggaacca gataccagcc atgccccag gctccaccaa gcatcttcat    2220 gtcccctgc tcatccccca ctcccccca cccagagttg ctcatcctgc cagggctggc    2280
tgtgcccacc ccaaggctgc cctcctgggg gccccagaac tgcctgatcg tgccgtggcc    2340
cagttttgtg gcatctgcag caacacaaga gagaggacaa tgtcctcctc ttgacccgct    2400
gtcacctaac cagactcggg ccctgcacct ctcaggcact tctggaaaat gactgaggca    2460
gattcttcct gaagcccatt tccatgggg caacaaggac acctattctg tccttgtcct    2520
tccatcgctg ccccagaaag cctcacatat ctccgtttag aatcaggtcc cttctcccca    2580
gatgaagagg agggtctctg ctttgttttc tctatctcct cctcagactt gaccaggccc    2640
agcaggcccc agaagaccat taccctatat cccttctcct ccctagtcac atggccatag    2700
gcctgctgat ggctcaggaa ggccattgca aggactcctc agctatggga gaggaagcac    2760
atcacccatt gaccccgca acccctccct ttcctcctct gagtcccgac tggggccaca    2820
tgcagcctga cttctttgtg cctgttgctg tccctgcagt cttcagaggg ccaccgcagc    2880
tccagtgcca cggcaggagg ctgttcctga atagcccctg tggtaagggc caggagagtc    2940
cttccatcct ccaaggccct gctaaaggac acagcagcca ggaagtcccc tgggcccta    3000 gctgaaggac agcctgctcc ctccgtctct accaggaatg gccttgtcct atggaaggca    3060
ctgccccatc ccaaactaat ctaggaatca ctgtctaacc actcactgtc atgaatgtgt    3120
acttaaagga tgaggttgag tcataccaaa tagtgatttc gatagttcaa aatggtgaaa    3180
ttagcaattc tacatgattc agtctaatca atggataccg actgttccc acacaagtct    3240 cctgttctct taagcttact cactgacagc ctttcactct ccacaaatac attaaagata    3300
tggccatcac caagcccct aggatgacac cagacctgag agtctgaaga cctggatcca    3360
agttctgact tttcccctg acagctgtgt gaccttcgtg aagtcgccaa acctctctga    3420
gccccagtca ttgctagtaa gacctgcctt tgagttggta tgatgttcaa gttagataac    3480
aaaatgttta tacccattag aacagagaat aaatagaact acatttcttg ca           3532

<210> SEQ ID NO 6
<211> LENGTH: 3340
<212> TYPE: DNA
<213> ORGANISM: Homo sapiens

<400> SEQUENCE: 6
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggagggc ggcaacctcc tgccagcctt caggccactc     180
tcctgtgcct gccagaagag acagagcttg aggagagctt gaggagagca ggaaaggtgg     240
```

-continued

```
gacattgctg ctgctgctca ctcagttcca cagcagcctc ccccgttgcc cctctggatc    300
cactgcttaa atacggacga ggacagggcc ctgtctcctc agcttcaggc accaccactg    360
acctgggaca gtgaatcgac aatgccgtct tctgtctcgt ggggcatcct cctgctggca    420
ggcctgtgct gcctggtccc tgtctccctg gctgaggatc cccagggaga tgctgcccag    480
aagacagata catcccacca tgatcaggat cacccaacct tcaacaagat caccccaac    540 ctggctgagt tcgccttcag cctataccgc cagctggcac accagtccaa cagcaccaat    600
atcttcttct ccccagtgag catcgctaca gcctttgcaa tgctctccct ggggaccaag    660
gctgacactc acgatgaaat cctggagggc ctgaatttca acctcacgga gattccggag    720
gctcagatcc atgaaggctt ccaggaactc ctccgtaccc tcaaccagcc agacagccag    780
ctccagctga ccaccggcaa tggcctgttc tcagcgagg gcctgaagct agtggataag    840
tttttggagg atgttaaaaa gttgtaccac tcagaagcct tcactgtcaa cttcggggac    900
accgaagagg ccaagaaaca gatcaacgat tacgtggaga agggtactca agggaaaatt    960
gtggatttgg tcaaggagct tgacagagac acagttttg ctctggtgaa ttacatcttc    1020
tttaaaggca aatgggagag acccttgaa gtcaaggaca ccgaggaaga ggacttccac    1080
gtggaccagg tgaccaccgt gaaggtgcct atgatgaagc gtttaggcat gtttaacatc    1140
cagcactgta agaagctgtc cagctgggtg ctgctgatga ataccctggg caatgccacc    1200
gccatcttct tcctgcctga tgaggggaaa ctacagcacc tggaaaatga actcacccac    1260
gatatcatca ccaagttcct ggaaaatgaa gacagaaggt ctgccagctt acatttaccc    1320
aaactgtcca ttactggaac ctatgatctg aagagcgtcc tgggtcaact gggcatcact    1380
aaggtcttca gcaatggggc tgacctctcc ggggtcacag aggaggcacc cctgaagctc    1440
tccaaggccg tgcataaggc tgtgctgacc atcgacgaga aagggactga agctgctggg    1500
gccatgtttt tagaggccat acccatgtct atcccccccg aggtcaagtt caacaaaccc    1560
tttgtcttct taatgattga acaaaatacc aagtctcccc tcttcatggg aaaagtggtg    1620
aatcccaccc aaaaataact gcctctcgct cctcaaccc tcccctccat ccctggcccc    1680
ctccctggat gacattaaag aagggttgag ctggtccctg cctgcatgtg actgtaaatc    1740
cctcccatgt tttctctgag tctcccttg cctgctgagg ctgtatgtgg gctccaggta    1800
acagtgctgt cttcgggccc cctgaactgt gttcatggag catctggctg ggtaggcaca    1860
tgctgggctt gaatccaggg gggactgaat cctcagctta cggacctggg cccatctgtt    1920
tctggagggc tccagtcttc cttgtcctgt cttggagtcc ccaagaagga atcacagggg    1980
aggaaccaga taccagccat gaccccaggc tccaccaagc atcttcatgt cccctgctc    2040 atcccccact ccccccacc cagagttgct catcctgcca gggctggctg tgcccacccc    2100
aaggctgccc tcctggggc cccagaactg cctgatcgtg ccgtggccca gttttgtggc    2160
atctgcagca acacaagaga gaggacaatg tcctcctctt gacccgctgt cacctaacca    2220
gactcgggcc ctgcacctct caggcacttc tggaaaatga ctgaggcaga ttcttcctga    2280
agcccattct ccatggggca acaaggacac ctattctgtc cttgtccttc catcgctgcc    2340
ccagaaagcc tcacatatct ccgtttagaa tcaggtccct tctccccaga tgaagaggag    2400
ggtctctgct ttgttttctc tatctcctcc tcagacttga ccaggcccag caggcccag    2460 aagaccatta ccctatatcc cttctcctcc ctagtcacat ggccataggc tgctgatgg    2520 ctcaggaagg ccattgcaag gactcctcag ctatgggaga ggaagcacat cacccattga    2580 ccccgcaac ccctcccttt cctcctctga gtcccgactg gggccacatg cagcctgact    2640
```

| | |
|---|---|
| tctttgtgcc tgttgctgtc cctgcagtct tcagagggcc accgcagctc cagtgccacg | 2700 |
| gcaggaggct gttcctgaat agcccctgtg gtaagggcca ggagagtcct tccatcctcc | 2760 |
| aaggccctgc taaaggacac agcagccagg aagtcccctg ggccctagc tgaaggacag | 2820 |
| cctgctccct ccgtctctac caggaatggc cttgtcctat ggaaggcact gccccatccc | 2880 |
| aaactaatct aggaatcact gtctaaccac tcactgtcat gaatgtgtac ttaaaggatg | 2940 |
| aggttgagtc ataccaaata gtgatttcga tagttcaaaa tggtgaaatt agcaattcta | 3000 |
| catgattcag tctaatcaat ggataccgac tgtttcccac acaagtctcc tgttctctta | 3060 |
| agcttactca ctgacagcct ttcactctcc acaaatacat taaagatatg gccatcacca | 3120 |
| agcccctag gatgacacca gacctgagag tctgaagacc tggatccaag ttctgacttt | 3180 |
| tccccctgac agctgtgtga ccttcgtgaa gtcgccaaac ctctctgagc ccagtcatt | 3240 |
| gctagtaaga cctgcctttg agttggtatg atgttcaagt tagataacaa aatgtttata | 3300 |
| cccattagaa cagagaataa atagaactac atttcttgca | 3340 |

<210> SEQ ID NO 7
<211> LENGTH: 3495
<212> TYPE: DNA
<213> ORGANISM: Homo sapiens

<400> SEQUENCE: 7

| | |
|---|---|
| tgggcaggaa ctgggcactg tgcccagggc atgcactgcc tccacgcagc aaccctcaga | 60 |
| gtcctgagct gaaccaagaa ggaggagggg gtcgggcctc cgaggaaggc ctagccgctg | 120 |
| ctgctgccag gaattccagg ttggaggggc ggcaacctcc tgccagcctt caggccactc | 180 |
| tcctgtgcct gccagaagag acagagcttg aggagagctt gaggagagca ggaaagggcg | 240 |
| gcagtaagtc ttcagcatca ggcattttgg ggtgactcag taaatggtag atcttgctac | 300 |
| cagtggaaca gccactaagg attctgcagt gagagcagag ggccagctaa gtggtactct | 360 |
| cccagagact gtctgactca cgccaccccc tccaccttgg acacaggacg ctgtggtttc | 420 |
| tgagccagca gcctccccg ttgcccctct ggatccactg cttaaatacg gacgaggaca | 480 |
| gggccctgtc tcctcagctt caggcaccac cactgacctg ggacagtgaa tcgacaatgc | 540 |
| cgtcttctgt ctcgtggggc atcctcctgc tggcaggcct gtgctgcctg gtccctgtct | 600 |
| ccctggctga ggatccccag ggagatgctg cccagaagac agatacatcc caccatgatc | 660 |
| aggatcaccc aaccttcaac aagatcaccc ccaacctggc tgagttcgcc ttcagcctat | 720 |
| accgccagct ggcacaccag tccaacagca ccaatatctt cttctcccca gtgagcatcg | 780 |
| ctacagcctt tgcaatgctc tccctgggga ccaaggctga cactcacgat gaaatcctgg | 840 |
| agggcctgaa tttcaacctc acggagattc cggaggctca gatccatgaa ggcttccagg | 900 |
| aactcctccg taccctcaac cagccagaca gccagctcca gctgaccacc ggcaatggcc | 960 |
| tgttcctcag cgagggcctg aagctagtgg ataagttttt ggaggatgtt aaaaagttgt | 1020 |
| accactcaga agccttcact gtcaacttcg ggacaccga agaggccaag aaacagatca | 1080 |
| acgattacgt ggagaagggt actcaaggga aaattgtgga tttggtcaag gagcttgaca | 1140 |
| gagacacagt ttttgctctg gtgaattaca tcttctttaa aggcaaatgg gagagaccct | 1200 |
| ttgaagtcaa ggacaccgag gaagaggact ccacgtggga ccaggtgacc accgtgaagg | 1260 |
| tgcctatgat gaagcgttta ggcatgttta acatccagca ctgtaagaag ctgtccagct | 1320 |
| gggtgctgct gatgaaatac ctgggcaatg ccaccgccat cttcttcctg cctgatgagg | 1380 |

-continued

```
ggaaactaca gcacctggaa aatgaactca cccacgatat catcaccaag ttcctggaaa    1440
atgaagacag aaggtctgcc agcttacatt tacccaaact gtccattact ggaacctatg    1500
atctgaagag cgtcctgggt caactgggca tcactaaggt cttcagcaat ggggctgacc    1560
tctccggggt cacagaggag gcaccctga agctctccaa ggccgtgcat aaggctgtgc    1620
tgaccatcga cgagaaaggg actgaagctg ctggggccat gttttagag gccatacca    1680 tgtctatccc ccccgaggtc aagttcaaca aacccttgt cttcttaatg attgaacaaa    1740
ataccaagtc tcccctcttc atgggaaaag tggtgaatcc cacccaaaaa taactgcctc    1800
tcgctcctca accctcccc tccatccctg gccccctccc tggatgacat aaagaaggg    1860 ttgagctggt ccctgcctgc atgtgactgt aaatccctcc catgttttct ctgagtctcc    1920
ctttgcctgc tgaggctgta tgtgggctcc aggtaacagt gctgtcttcg ggcccctga    1980 actgtgttca tggagcatct ggctgggtag gcacatgctg ggcttgaatc caggggggac    2040
tgaatcctca gcttacggac ctgggcccat ctgtttctgg agggctccag tcttccttgt    2100
cctgtcttgg agtccccaag aaggaatcac aggggaggaa ccagatacca gccatgaccc    2160
caggctccac caagcatctt catgtccccc tgctcatccc ccactccccc ccacccagag    2220
ttgctcatcc tgccagggct ggctgtgccc accccaaggc tgccctcctg ggggcccag    2280 aactgcctga tcgtgccgtg gcccagtttt gtggcatctg cagcaacaca agagagagga    2340
caatgtcctc ctcttgaccc gctgtcacct aaccagactc gggccctgca cctctcaggc    2400
acttctggaa aatgactgag gcagattctt cctgaagccc attctccatg gggcaacaag    2460
gacacctatt ctgtccttgt ccttccatcg ctgccccaga aagcctcaca tatctccgtt    2520
tagaatcagg tcccttctcc ccagatgaag aggagggtct ctgctttgtt ttctctatct    2580
cctcctcaga cttgaccagg cccagcaggc cccagaagac cattacccta tatcccttct    2640
cctccctagt cacatggcca taggcctgct gatggctcag gaaggccatt gcaaggactc    2700
ctcagctatg ggagaggaag cacatcaccc attgaccccc gcaacccctc cctttcctcc    2760
tctgagtccc gactggggcc acatgcagcc tgacttcttt gtgcctgttg ctgtccctgc    2820
agtcttcaga gggccaccgc agctccagtg ccacggcagg aggctgttcc tgaatagccc    2880
ctgtggtaag ggccaggaga gtccttccat cctccaaggc cctgctaaag gacacagcag    2940
ccaggaagtc ccctgggccc ctagctgaag gacagcctgc tccctccgtc tctaccagga    3000
atggccttgt cctatggaag gcactgcccc atcccaaact aatctaggaa tcactgtcta    3060
accactcact gtcatgaatg tgtacttaaa ggatgaggtt gagtcatacc aaatagtgat    3120
ttcgatagtt caaaatggtg aaattagcaa ttctacatga ttcagtctaa tcaatggata    3180
ccgactgttt cccacacaag tctcctgttc tcttaagctt actcactgac agcctttcac    3240
tctccacaaa tacattaaag atatggccat caccaagccc cctaggatga caccagacct    3300
gagagtctga agacctggat ccaagttctg acttttcccc ctgacagctg tgtgaccttc    3360
gtgaagtcgc caaacctctc tgagccccag tcattgctag taagacctgc ctttgagttg    3420
gtatgatgtt caagttagat aacaaaatgt ttatacccat tagaacagag aataaataga    3480
actacatttc ttgca                                                    3495
```

<210> SEQ ID NO 8
<211> LENGTH: 3492
<212> TYPE: DNA
<213> ORGANISM: Homo sapiens

<400> SEQUENCE: 8

```
tgggcaggaa ctgggcactg tgcccagggc atgcactgcc tccacgcagc aaccctcaga    60
gtcctgagct gaaccaagaa ggaggagggg gtcgggcctc cgaggaaggc ctagccgctg   120
ctgctgccag gaattccagg ttggaggggc ggcaacctcc tgccagcctt caggccactc   180
tcctgtgcct gccagaagag acagagcttg aggagagctt gaggagagca ggaaagggcg   240
gcagtaagtc ttcagcatca ggcattttgg ggtgactcag taaatggtag atcttgctac   300
cagtggaaca gccactaagg attctgcagt gagagcagag ggccagctaa gtggtactct   360
cccagagact gtctgactca cgccaccccc tccaccttgg acacaggacg ctgtggtttc   420
tgagccagcc tcccccgttg ccctctgga tccactgctt aaatacggac gaggacaggg   480
ccctgtctcc tcagcttcag gcaccaccac tgacctggga cagtgaatcg acaatgccgt   540
cttctgtctc gtggggcatc ctcctgctgg caggcctgtg ctgcctggtc cctgtctccc   600
tggctgagga tccccaggga gatgctgccc agaagacaga tacatcccac catgatcagg   660
atcacccaac cttcaacaag atcaccccca acctggctga gttcgccttc agcctatacc   720
gccagctggc acaccagtcc aacagcacca atatcttctt ctccccagtg agcatcgcta   780
cagcctttgc aatgctctcc ctggggacca aggctgacac tcacgatgaa atcctggagg   840
gcctgaattt caacctcacg gagattccgg aggctcagat ccatgaaggc ttccaggaac   900
tcctccgtac cctcaaccag ccagacagcc agctccagct gaccaccggc aatggcctgt   960
tcctcagcga gggcctgaag ctagtggata gttttttgga ggatgttaaa aagttgtacc  1020
actcagaagc cttcactgtc aacttcgggg acaccgaaga ggccaagaaa cagatcaacg  1080
attacgtgga gaagggtact caagggaaaa ttgtggattt ggtcaaggag cttgacagag  1140
acacagtttt tgctctggtg aattacatct tctttaaagg caaatgggag agacccttttg  1200
aagtcaagga caccgaggaa gaggacttcc acgtggacca ggtgaccacc gtgaaggtgc  1260
ctatgatgaa gcgtttaggc atgtttaaca tccagcactg taagaagctg tccagctggg  1320
tgctgctgat gaaatacctg ggcaatgcca ccgccatctt cttcctgcct gatgagggga  1380
aactacagca cctggaaaat gaactcaccc acgatatcat caccaagttc ctggaaaatg  1440
aagacagaag gtctgccagc ttacatttac ccaaactgtc cattactgga acctatgatc  1500
tgaagagcgt cctgggtcaa ctgggcatca ctaaggtctt cagcaatggg gctgacctct  1560
ccgggggtcac agaggaggca ccctgaagc tctccaaggc cgtgcataag gctgtgctga  1620
ccatcgacga aaagggact gaagctgctg gggccatgtt tttagaggcc atacccatgt  1680
ctatccccc cgaggtcaag ttcaacaaac cctttgtctt cttaatgatt gaacaaaata  1740
ccaagtctcc cctcttcatg ggaaaagtgg tgaatcccac ccaaaaataa ctgcctctcg  1800
ctcctcaacc cctcccctcc atccctggcc cctcctggg atgacattaa agaagggttg  1860
agctggtccc tgcctgcatg tgactgtaaa tccctcccat gttttctctg agtctcccctt  1920
tgcctgctga ggctgtatgt gggctccagg taacagtgct gtcttcgggc cccctgaact  1980
gtgttcatgg agcatctggc tgggtaggca catgctgggc ttgaatccag ggggactga   2040
atcctcagct tacggacctg ggcccatctg tttctggagg gctccagtct tccttgtcct  2100
gtcttggagt cccaagaag gaatcacagg ggaggaacca gataccagcc atgacccag   2160
gctccaccaa gcatcttcat gtccccctgc tcatccccca ctccccccca cccagagttg  2220
ctcatcctgc cagggctggc tgtgcccacc ccaaggctgc cctcctgggg ccccagaac   2280
tgcctgatcg tgccgtggcc cagttttgtg gcatctgcag caacacaaga gagaggacaa  2340
```

```
tgtcctcctc ttgacccgct gtcacctaac cagactcggg ccctgcacct ctcaggcact    2400
tctggaaaat gactgaggca gattcttcct gaagcccatt ctccatgggg caacaaggac    2460
acctattctg tccttgtcct tccatcgctg ccccagaaag cctcacatat ctccgtttag    2520
aatcaggtcc cttctcccca gatgaagagg agggtctctg ctttgttttc tctatctcct    2580
cctcagactt gaccaggccc agcaggcccc agaagaccat taccctatat cccttctcct    2640
ccctagtcac atggccatag gcctgctgat ggctcaggaa ggccattgca aggactcctc    2700
agctatggga gaggaagcac atcacccatt gaccccgca acccctccct ttcctcctct     2760
gagtcccgac tggggccaca tgcagcctga cttctttgtg cctgttgctg tccctgcagt    2820
cttcagaggg ccaccgcagc tccagtgcca cggcaggagg ctgttcctga atagcccctg    2880
tggtaagggc caggagagtc cttccatcct ccaaggccct gctaaaggac acagcagcca    2940
ggaagtcccc tgggccccta gctgaaggac agcctgctcc ctccgtctct accaggaatg    3000
gccttgtcct atggaaggca ctgccccatc ccaaactaat ctaggaatca ctgtctaacc    3060
actcactgtc atgaatgtgt acttaaagga tgaggttgag tcataccaaa tagtgatttc    3120
gatagttcaa aatggtgaaa ttagcaattc tacatgattc agtctaatca atggataccg    3180
actgtttccc acacaagtct cctgttctct taagcttact cactgacagc ctttcactct    3240
ccacaaatac attaaagata tggccatcac caagccccct aggatgacac cagacctgag    3300
agtctgaaga cctggatcca agttctgact tttcccctg acagctgtgt gaccttcgtg      3360
aagtcgccaa acctctctga gccccagtca ttgctagtaa gacctgcctt tgagttggta    3420
tgatgttcaa gttagataac aaaatgttta tacccattag aacagagaat aaatagaact    3480
acatttcttg ca                                                        3492
```

<210> SEQ ID NO 9
<211> LENGTH: 3510
<212> TYPE: DNA
<213> ORGANISM: Homo sapiens

<400> SEQUENCE: 9

```
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaagggcg     240
gcagtaagtc ttcagcatca ggcattttgg ggtgactcag taaatggtag atcttgctac     300
cagtggaaca gccactaagg attctgcagt gagagcagag ggccagctaa gtggtactct     360
cccagagact gtctgactca cgccaccccc tccaccttgg acacaggacg ctgtggtttc     420
tgagccaggt acaatgactc ctttcgcctc cccgttgcc cctctggatc cactgcttaa      480
atacggacga ggacagggcc ctgtctcctc agcttcaggc accaccactg acctgggaca    540
gtgaatcgac aatgccgtct tctgtctcgt ggggcatcct cctgctggca ggcctgtgct    600
gcctggtccc tgtctccctg gctgaggatc cccagggaga tgctgcccag aagacagata    660
catcccacca tgatcaggat cacccaacct tcaacaagat caccccaac ctggctgagt      720 tcgccttcag cctataccgc cagctggcac accagtccaa cagcaccaat atcttcttct    780
ccccagtgag catcgctaca gcctttgcaa tgctctccct ggggaccaag gctgacactc    840
acgatgaaat cctggagggc ctgaatttca acctcacgga gattccggag gctcagatcc    900
atgaaggctt ccaggaactc ctccgtaccc tcaaccagcc agacagccag ctccagctga    960
```

```
ccaccggcaa tggcctgttc ctcagcgagg gcctgaagct agtggataag ttttttggagg   1020
atgttaaaaa gttgtaccac tcagaagcct tcactgtcaa cttcgggac accgaagagg    1080
ccaagaaaca gatcaacgat tacgtggaga agggtactca agggaaaatt gtggatttgg   1140
tcaaggagct tgacagagac acagttttg ctctggtgaa ttacatcttc tttaaaggca    1200
aatgggagag accctttgaa gtcaaggaca ccgaggaaga ggacttccac gtggaccagg   1260
tgaccaccgt gaaggtgcct atgatgaagc gtttaggcat gtttaacatc cagcactgta   1320
agaagctgtc cagctgggtg ctgctgatga aatacctggg caatgccacc gccatcttct   1380
tcctgcctga tgaggggaaa ctacagcacc tggaaaatga actcacccac gatatcatca   1440
ccaagttcct ggaaaatgaa gacagaaggt ctgccagctt acatttaccc aaactgtcca   1500
ttactggaac ctatgatctg aagagcgtcc tgggtcaact gggcatcact aaggtcttca   1560
gcaatggggc tgacctctcc ggggtcacag aggaggcacc cctgaagctc tccaaggccg   1620
tgcataaggc tgtgctgacc atcgacgaga aagggactga agctgctggg gccatgtttt   1680
tagaggccat acccatgtct atcccccccg aggtcaagtt caacaaaccc tttgtcttct   1740
taatgattga acaaaatacc aagtctcccc tcttcatggg aaaagtggtg aatcccaccc   1800
aaaaataact gcctctcgct cctcaacccc tcccctccat ccctggcccc ctccctggat   1860
gacattaaag aagggttgag ctggtccctg cctgcatgtg actgtaaatc cctcccatgt   1920
tttctctgag tctcccttttg cctgctgagg ctgtatgtgg gctccaggta acagtgctgt   1980
cttcgggccc cctgaactgt gttcatggag catctggctg ggtaggcaca tgctgggctt   2040
gaatccaggg gggactgaat cctcagctta cggacctggg cccatctgtt tctggagggc   2100
tccagtcttc cttgtcctgt cttggagtcc caagaagga atcacagggg aggaaccaga   2160
taccagccat gaccccaggc tccaccaagc atcttcatgt cccctgctc atcccccact    2220
cccccccacc cagagttgct catcctgcca gggctggctg tgcccacccc aaggctgccc   2280
tcctggggc cccagaactg cctgatcgtg ccgtggccca gttttgtggc atctgcagca   2340
acacaagaga gaggacaatg tcctcctctt gacccgctgt cacctaacca gactcgggcc   2400
ctgcacctct caggcactttc tggaaaatga ctgaggcaga ttcttcctga gcccattct    2460
ccatggggca acaaggacac ctattctgtc cttgtccttc catcgctgcc ccagaaagcc   2520
tcacatatct ccgtttagaa tcaggtccct tctccccaga tgaagaggag ggtctctgct   2580
ttgttttctc tatctcctcc tcagacttga ccaggcccag caggcccag aagaccatta    2640
ccctatatcc cttctcctcc ctagtcacat ggccataggc ctgctgatgg ctcaggaagg   2700
ccattgcaag gactcctcag ctatgggaga ggaagcacat cacccattga cccccgcaac   2760
ccctccctt cctcctctga gtcccgactg gggccacatg cagcctgact ctttgtgcc    2820
tgttgctgtc cctgcagtct tcagagggcc accgcagctc cagtgccacg gcaggaggct   2880
gttcctgaat agcccctgtg gtaagggcca ggagagtcct tccatcctcc aaggccctgc   2940
taaaggacac agcagccagg aagtccctg ggcccctagc tgaaggacag cctgctccct    3000
ccgtctctac caggaatggc cttgtcctat ggaaggcact gccccatccc aaactaatct   3060
aggaatcact gtctaaccac tcactgtcat gaatgtgtac ttaaaggatg aggttgagtc   3120
ataccaaata gtgatttcga tagttcaaaa tggtgaaatt agcaattcta catgattcag   3180
tctaatcaat ggataccgac tgtttcccac acaagtctcc tgttctctta agcttactca   3240
ctgacagcct ttcactctcc acaaatacat taaagatatg gccatcacca agccccctag   3300
```

```
gatgacacca gacctgagag tctgaagacc tggatccaag ttctgacttt tccccctgac    3360
agctgtgtga ccttcgtgaa gtcgccaaac ctctctgagc cccagtcatt gctagtaaga    3420
cctgcctttg agttggtatg atgttcaagt tagataacaa aatgtttata cccattagaa    3480
cagagaataa atagaactac atttcttgca                                     3510

<210> SEQ ID NO 10
<211> LENGTH: 3303
<212> TYPE: DNA
<213> ORGANISM: Homo sapiens

<400> SEQUENCE: 10
tgggcaggaa ctgggcactg tgcccagggc atgcactgcc tccacgcagc aaccctcaga      60
gtcctgagct gaaccaagaa ggaggagggg gtcgggcctc cgaggaaggc ctagccgctg     120
ctgctgccag gaattccagg ttggaggggc ggcaacctcc tgccagcctt caggccactc     180
tcctgtgcct gccagaagag acagagcttg aggagagctt gaggagagca ggaaagcagc     240
ctcccccgtt gcccctctgg atccactgct taaatacgga cgaggacagg gccctgtctc     300
ctcagcttca ggcaccacca ctgacctggg acagtgaatc gacaatgccg tcttctgtct     360
cgtggggcat cctcctgctg gcaggcctgt gctgcctggt ccctgtctcc ctggctgagg     420
atccccaggg agatgctgcc cagaagacag atacatccca ccatgatcag gatcacccaa     480
ccttcaacaa gatcaccccc aacctggctg agttcgcctt cagcctatac cgccagctgg     540
cacaccagtc caacagcacc aatatcttct ctccccagt gagcatcgct acagcctttg     600
caatgctctc cctggggacc aaggctgaca ctcacgatga atcctggag ggcctgaatt     660 tcaacctcac ggagattccg gaggctcaga tccatgaagg cttccaggaa ctcctccgta     720
ccctcaacca gccagacagc cagctccagc tgaccaccgg caatggcctg ttcctcagcg     780
agggcctgaa gctagtggat aagttttttgg aggatgttaa aaagttgtac cactcagaag     840
ccttcactgt caacttcggg gacaccgaag aggccaagaa acagatcaac gattacgtgg     900
agaagggtac tcaagggaaa attgtggatt tggtcaagga gcttgacaga gacacagttt     960
ttgctctggt gaattacatc ttctttaaag gcaaatggga gagaccctt gaagtcaagg    1020 acaccgagga agaggacttc cacgtggacc aggtgaccac cgtgaaggtg cctatgatga    1080
agcgtttagg catgtttaac atccagcact gtaagaagct gtccagctgg gtgctgctga    1140
tgaaatacct gggcaatgcc accgccatct tcttcctgcc tgatgagggg aaactacagc    1200
acctggaaaa tgaactcacc cacgatatca tcaccaagtt cctggaaaat gaagacagaa    1260
ggtctgccag cttacattta cccaaactgt ccattactgg aacctatgat ctgaagagcg    1320
tcctgggtca actgggcatc actaaggtct tcagcaatgg ggctgacctc tccgggtca    1380 cagaggaggc acccctgaag ctctccaagg ccgtgcataa ggctgtgctg accatcgacg    1440
agaaagggac tgaagctgct ggggccatgt ttttagaggc catacccatg tctatccccc    1500
ccgaggtcaa gttcaacaaa ccctttgtct tcttaatgat tgaacaaaat accaagtctc    1560
ccctcttcat gggaaaagtg gtgaatccca cccaaaaata actgcctctc gctcctcaac    1620
ccctcccctc catccctggc ccctcccctg gatgacatta agaagggtt gagctggtcc    1680 ctgcctgcat gtgactgtaa atccctccca tgttttctct gagtctccct ttgcctgctg    1740
aggctgtatg tgggctccag gtaacagtgc tgtcttcggg ccccctgaac tgtgttcatg    1800
gagcatctgg ctgggtaggc acatgctggg cttgaatcca gggggactg aatcctcagc    1860 ttacggacct gggcccatct gtttctggag ggctccagtc ttccttgtcc tgtcttggag    1920
```

| | |
|---|---|
| tccccaagaa ggaatcacag gggaggaacc agataccagc catgacccca ggctccacca | 1980 |
| agcatcttca tgtccccctg ctcatccccc actccccccc acccagagtt gctcatcctg | 2040 |
| ccagggctgg ctgtgcccac cccaaggctg ccctcctggg ggcccagaa ctgcctgatc | 2100 |
| gtgccgtggc ccagttttgt ggcatctgca gcaacacaag agagaggaca atgtcctcct | 2160 |
| cttgacccgc tgtcacctaa ccagactcgg gccctgcacc tctcaggcac ttctggaaaa | 2220 |
| tgactgaggc agattcttcc tgaagcccat tctccatggg gcaacaagga cacctattct | 2280 |
| gtccttgtcc ttccatcgct gccccagaaa gcctcacata tctccgttta gaatcaggtc | 2340 |
| ccttctcccc agatgaagag gagggtctct gctttgtttt ctctatctcc tcctcagact | 2400 |
| tgaccaggcc cagcaggccc cagaagacca ttaccctata tcccttctcc tccctagtca | 2460 |
| catggccata ggcctgctga tggctcagga aggccattgc aaggactcct cagctatggg | 2520 |
| agaggaagca catcacccat tgacccccgc aacccctccc tttcctcctc tgagtcccga | 2580 |
| ctggggccac atgcagcctg acttctttgt gcctgttgct gtccctgcag tcttcagagg | 2640 |
| gccaccgcag ctccagtgcc acggcaggag gctgttcctg aatagcccct gtggtaaggg | 2700 |
| ccaggagagt ccttccatcc tccaaggccc tgctaaagga cacagcagcc aggaagtccc | 2760 |
| ctgggcccct agctgaagga cagcctgctc cctccgtctc taccaggaat ggccttgtcc | 2820 |
| tatggaaggc actgccccat cccaaaactaa tctaggaatc actgtctaac cactcactgt | 2880 |
| catgaatgtg tacttaaagg atgaggttga gtcataccaa atagtgattt cgatagttca | 2940 |
| aaatggtgaa attagcaatt ctacatgatt cagtctaatc aatggatacc gactgtttcc | 3000 |
| cacacaagtc tcctgttctc ttaagcttac tcactgacag cctttcactc tccacaaata | 3060 |
| cattaaagat atggccatca ccaagccccc taggatgaca ccagacctga gagtctgaag | 3120 |
| acctggatcc aagttctgac ttttccccct gacagctgtg tgaccttcgt gaagtcgcca | 3180 |
| aacctctctg agccccagtc attgctagta agacctgcct ttgagttggt atgatgttca | 3240 |
| agttagataa caaatgtttt atacccatta gaacagagaa taaatagaac tacatttctt | 3300 |
| gca | 3303 |

<210> SEQ ID NO 11
<211> LENGTH: 3300
<212> TYPE: DNA
<213> ORGANISM: Homo sapiens

<400> SEQUENCE: 11

| | |
|---|---|
| tgggcaggaa ctgggcactg tgcccagggc atgcactgcc tccacgcagc aaccctcaga | 60 |
| gtcctgagct gaaccaagaa ggaggagggg gtcgggcctc cgaggaaggc ctagccgctg | 120 |
| ctgctgccag gaattccagg ttggaggggc ggcaacctcc tgccagcctt caggccactc | 180 |
| tcctgtgcct gccagaagag acagagcttg aggagagctt gaggagagca ggaaagcctc | 240 |
| ccccgttgcc cctctggatc cactgcttaa atacggacga ggacagggcc ctgtctcctc | 300 |
| agcttcaggc accaccactg acctgggaca gtgaatcgac aatgccgtct tctgtctcgt | 360 |
| ggggcatcct cctgctggca ggcctgtgct gcctggtccc tgtctccctg gctgaggatc | 420 |
| cccagggaga tgctgcccag aagacagata catcccacca tgatcaggat cacccaacct | 480 |
| tcaacaagat cacccccaac ctggctgagt cgccttcag cctataccgc cagctggcac | 540 |
| accagtccaa cagcaccaat atcttcttct ccccagtgag catcgctaca gcctttgcaa | 600 |
| tgctctccct ggggaccaag gctgacactc acgatgaaat cctggagggc ctgaatttca | 660 |

```
acctcacgga gattccggag gctcagatcc atgaaggctt ccaggaactc ctccgtaccc    720
tcaaccagcc agacagccag ctccagctga ccaccggcaa tggcctgttc ctcagcgagg    780
gcctgaagct agtggataag tttttggagg atgttaaaaa gttgtaccac tcagaagcct    840
tcactgtcaa cttcggggac accgaagagg ccaagaaaca gatcaacgat tacgtggaga    900
agggtactca agggaaaatt gtggatttgg tcaaggagct tgacagagac acagtttttg    960
ctctggtgaa ttacatcttc tttaaaggca aatgggagag accctttgaa gtcaaggaca   1020
ccgaggaaga ggacttccac gtggaccagg tgaccaccgt gaaggtgcct atgatgaagc   1080
gtttaggcat gtttaacatc cagcactgta agaagctgtc cagctgggtg ctgctgatga   1140
aatacctggg caatgccacc gccatcttct tcctgcctga tgaggggaaa ctacagcacc   1200
tggaaaatga actcacccac gatatcatca ccaagttcct ggaaaatgaa gacagaaggt   1260
ctgccagctt acatttaccc aaactgtcca ttactggaac ctatgatctg aagagcgtcc   1320
tgggtcaact gggcatcact aaggtcttca gcaatgggtc tgacctctcc ggggtcacag   1380
aggaggcacc cctgaagctc tccaaggccg tgcataaggc tgtgctgacc atcgacgaga   1440
aagggactga agctgctggg gccatgtttt tagaggccat acccatgtct atccccccg    1500 aggtcaagtt caacaaaccc tttgtcttct taatgattga acaaaatacc aagtctcccc   1560
tcttcatggg aaaagtggtg aatcccaccc aaaataact gcctctcgct cctcaacccc    1620 tccccctccat ccctggcccc ctccctggat gacattaaag aagggttgag ctggtccctg   1680
cctgcatgtg actgtaaatc cctcccatgt tttctctgag tctcccttg cctgctgagg    1740 ctgtatgtgg gctccaggta acagtgctgt cttcgggccc cctgaactgt gttcatggag   1800
catctggctg ggtaggcaca tgctgggctt gaatccaggg gggactgaat cctcagctta   1860
cggacctggg cccatctgtt tctggagggc tccagtcttc cttgtcctgt cttggagtcc   1920
ccaagaagga atcacagggg aggaaccaga taccagccat gaccccaggc tccaccaagc   1980
atcttcatgt cccctgctc atccccact cccccccacc cagagttgct catcctgcca    2040
gggctggctg tgcccacccc aaggctgccc tcctgggggc cccagaactg cctgatcgtg   2100
ccgtggccca gttttgtggc atctgcagca acacaagaga gaggacaatg tcctcctctt   2160
gacccgctgt cacctaacca gactcgggcc ctgcacctct caggcacttc tggaaaatga   2220
ctgaggcaga ttcttcctga agcccattct ccatggggca acaaggacac ctattctgtc   2280
cttgtccttc catcgctgcc ccagaaagcc tcacatatct ccgtttagaa tcaggtccct   2340
tctccccaga tgaagaggag ggtctctgct ttgttttctc tatctcctcc tcagacttga   2400
ccaggcccag caggcccag aagaccatta ccctatatcc cttctcctcc ctagtcacat    2460
ggccataggc ctgctgatgg ctcaggaagg ccattgcaag gactcctcag ctatgggaga   2520
ggaagcacat cacccattga cccccgcaac ccctcccttt cctcctctga gtcccgactg   2580
gggccacatg cagcctgact tctttgtgcc tgttgctgtc cctgcagtct tcagagggcc   2640
accgcagctc cagtgccacg gcaggaggct gttcctgaat agcccctgtg gtaagggcca   2700
ggagagtcct tccatcctcc aaggccctgc taaaggacac agcagccagg aagtcccctg   2760
ggcccctagc tgaaggacag cctgctccct ccgtctctac caggaatggc cttgtcctat   2820
ggaaggcact gccccatccc aaactaatct aggaatcact gtctaaccac tcactgtcat   2880
gaatgtgtac ttaaaggatg aggttgagtc ataccaaata gtgatttcga tagttcaaaa   2940
tggtgaaatt agcaattcta catgattcag tctaatcaat ggataccgac tgtttcccac   3000
acaagtctcc tgttctctta agcttactca ctgacagcct ttcactctcc acaaatacat   3060
```

-continued

| | |
|---|---|
| taaagatatg gccatcacca agcccccctag gatgacacca gacctgagag tctgaagacc | 3120 |
| tggatccaag ttctgacttt tccccctgac agctgtgtga ccttcgtgaa gtcgccaaac | 3180 |
| ctctctgagc cccagtcatt gctagtaaga cctgcctttg agttggtatg atgttcaagt | 3240 |
| tagataacaa aatgtttata cccattagaa cagagaataa atagaactac atttcttgca | 3300 |

<210> SEQ ID NO 12
<211> LENGTH: 1321
<212> TYPE: DNA
<213> ORGANISM: Macaca mulatta

<400> SEQUENCE: 12

| | |
|---|---|
| caggacaatg ccatcttctg tctcatgggg cgtcctcctg ctggcaggcc tgtgctgcct | 60 |
| gctccccggc tctctggctg aggatcccca gggagatgct gcccagaaga cggatacatc | 120 |
| ccaccatgat caggaccacc caaccctcaa caagatcacc cccagcctgg ctgagttcgg | 180 |
| cttcagccta taccgccagc tggcacacca gtccaacagc accatatatct tcttctcccc | 240 |
| agtgagcatc gctacagcct ttgcaatgct ctccctgggg accaaggctg acactcacag | 300 |
| tgaaatcctg gagggcctga atttcaacgt cacggagatt ccggaggctc aggtccatga | 360 |
| aggcttccag gaactcctcc ataccctcaa caagccagac agccagctcc agctgaccac | 420 |
| cggcaacggc ctgttcctca caagagcct gaaggtagtg gataagtttt tggaggatgt | 480 |
| caaaaaactg taccactcag aagccttctc tgtcaacttt gaggacaccg aagaggccaa | 540 |
| gaaacagatc aacaattacg tggagaagga aactcaaggg aaaattgtgg atttggtcaa | 600 |
| ggagcttgac agagacacag ttttgctct ggtgaattac atcttcttta aaggcaaatg | 660 |
| ggagagaccc tttgacgttg aggccaccaa ggaagaggac ttccacgtgg accaggcgac | 720 |
| caccgtgaag gtgcccatga tgaggcgttt aggcatgttt aacatctacc actgtgagaa | 780 |
| gctgtccagc tgggtgctgc tgatgaaata cctgggcaat gccaccgcca tcttcttcct | 840 |
| gcctgatgag gggaaactgc agcacctgga aaatgaactc acccatgata tcatcaccaa | 900 |
| gttcctggaa aatgaaaaca gcaggtctgc caacttacat ttacccagac tggccattac | 960 |
| tggaacctat gatctgaaga cagtcctggg ccacctgggt atcactaagg tcttcagcaa | 1020 |
| tggggctgac ctctcgggga tcacggagga ggcacccctg aagctctcca aggccgtgca | 1080 |
| taaggctgtg ctgaccatcg atgagaaagg gactgaagct gctggggcca tgttttagaa | 1140 |
| ggccataccc atgtctattc cccccgaggt caagttcaac aaacccttg tcttcttaat | 1200 |
| gattgaacaa aataccaagt ctcccctctt catggggaaa gtggtgaatc ccacccagaa | 1260 |
| ataactgcct gtcactcctc agcccctccc ctccatccct ggcccctcc ctgaatgaca | 1320 |
| t | 1321 |

<210> SEQ ID NO 13
<211> LENGTH: 2064
<212> TYPE: DNA
<213> ORGANISM: Macaca mulatta

<400> SEQUENCE: 13

| | |
|---|---|
| gcccagtctt gtgtctgcct ggcaatgggc aaggccccctt cctgcccaag ctccccgccc | 60 |
| ctcccccaacc tattgcctcc gccacccgcc acccgaggcc aacttcctgg gtgggcagga | 120 |
| actgggccct gtgcccaggg cgtgcactgc ctgcacgcag caaccctcag agtactgagc | 180 |
| tgagcaaagg aggaggaggg gatcagcact ctgaggaagg cctagccact gctgctgcca | 240 |

```
ggaattccag ggcggcatca gtcttcagca tcaggcattt cggggtgaat tagtaaatgg      300
tagatcttgc taccagtgga acagccgcta aggattctgc agtgagagca gagggccagc      360
aaagtggtac tctcccagcg actggctgac tcacgccacc ccctccacct tggacgcagg      420
acactgtggt ttctgagcca ggtacaatga ctccttttgg tacgtgcagt ggaggctgta      480
tgctgctcag gcagagcgtc cggacagcgt gggcgggcga ctcagcgccc agcctgtgaa      540
cttagtccct gtttgctcct ccggtaactg gggtgatctt ggttaatatt caccagcagc      600
ctcccccgtt gcccctctgc acccactgct taaatacgga caaggacagg gctctgtctc      660
ctcagcctca ggcaccacca ctgacctggg acggtgaatc gacaatgcca tcttctgtct      720
catgggcgt cctcctgctg gcaggcctgt gctgcctgct ccccggctct ctggctgagg      780
atccccaggg agatgctgcc cagaagacgg atacatccca ccatgatcag gaccacccaa      840
ccctcaacaa gatcaccccc agcctggctg agttcggctt cagcctatac cgccagctgg      900
cacaccagtc caacagcacc aatatcttct ctccccagt gagcatcgct acagcctttg      960
caatgctctc cctggggacc aaggctgaca ctcacagtga aatcctggag ggcctgaatt     1020
tcaacgtcac ggagattccg gaggctcagg tccatgaagg cttccaggaa ctcctccata     1080
ccctcaacaa gccagacagc cagctccagc tgaccaccgg caacggcctg ttcctcaaca     1140
agagcctgaa ggtagtggat aagttttgg aggatgtcaa aaactgtac cactcagaag      1200
ccttctctgt caactttgag gacaccgaag aggccaagaa acagatcaac aattacgtgg     1260
agaaggaaac tcaagggaaa attgtggatt tggtcaagga gcttgacaga gacacagttt     1320
ttgctctggt gaattacatc ttctttaaag gcaaatggga gagaccctt gacgttgagg      1380
ccaccaagga agaggacttc cacgtggacc aggcgaccac cgtgaaggtg cccatgatga     1440
ggcgtttagg catgtttaac atctaccact gtgagaagct gtccagctgg gtgctgctga     1500
tgaaatacct gggcaatgcc accgccatct tcttcctgcc tgatgagggg aaactgcagc     1560
acctggaaaa tgaactcacc catgatatca tcaccaagtt cctggaaaat gaaacagca      1620
ggtctgccaa cttacattta cccagactgg ccattactgg aacctatgat ctgaagacag     1680
tcctgggcca cctgggtatc actaaggtct tcagcaatgg ggctgacctc tcggggatca     1740
cggaggaggc accctgaag ctctccaagg ccgtgcataa ggctgtgctg accatcgatg      1800
agaaagggac tgaagctgct ggggccatgt ttttagaggc catacccatg tctattcccc     1860
ccgaggtcaa gttcaacaaa ccctttgtct tcttaatgat tgaacaaaat accaagtctc     1920
ccctcttcat gggaaaagtg gtgaatccca cccagaaata actgcctgtc actcctcagc     1980
ccctcccctc catccctggc cccctccctg aatgacatta agaagggtt gagctggtcc     2040
ctgcctgcgt gtgtgactgc aaac                                            2064
```

<210> SEQ ID NO 14
<211> LENGTH: 1608
<212> TYPE: DNA
<213> ORGANISM: Macaca mulatta

<400> SEQUENCE: 14

```
tcttgtgtct gcctggcaat gggcaaggcc ccttcctgcc caagctcccc gcccctcccc       60
aacctattgc ctccgccacc cgccacccga ggccaacttc ctgggtgggc aggaactggg      120
ccctgtgccc agggcgtgca ctgcctccac gcagcaaccc tcagagtact gagctgagca      180
aaggaggagg aggggatcag cactctgagg aaggcctagc cactgctgct gccaggaatt      240
ccaggacaat gccatcttct gtctcatggg gcgtcctcct gctggcaggc ctgtgctgcc      300
```

```
tgctccccgg ctctctggct gaggatcccc agggagatgc tgcccagaag acggatacat    360
cccaccatga tcaggaccac ccaaccctca acaagatcac ccccagcctg gctgagttcg    420
gcttcagcct ataccgccag ctggcacacc agtccaacag caccaatatc ttcttctccc    480
cagtgagcat cgctacagcc tttgcaatgc tctccctggg gaccaaggct gacactcaca    540
gtgaaatcct ggagggcctg aatttcaacg tcacggagat tccggaggct caggtccatg    600
aaggcttcca ggaactcctc catccctca acaagccaga cagccagctc cagctgacca    660
ccggcaacgg cctgttcctc aacaagagcc tgaaggtagt ggataagttt ttggaggatg    720
tcaaaaaact gtaccactca gaagccttct ctgtcaactt tgaggacacc gaagaggcca    780
agaaacagat caacaattac gtggagaagg aaactcaagg gaaaattgtg gatttggtca    840
aggagcttga cagagacaca gttttgctc tggtgaatta catcttcttt aaaggcaaat    900
gggagagacc ctttgacgtt gaggccacca aggaagagga cttccacgtg gaccaggcga    960
ccaccgtgaa ggtgcccatg atgaggcgtt taggcatgtt taacatctac cactgtgaga   1020
agctgtccag ctgggtgctg ctgatgaaat acctgggcaa tgccaccgcc atcttcttcc   1080
tgcctgatga ggggaaactg cagcacctgg aaaatgaact cacccatgat atcatcacca   1140
agttcctgga aaatgaaaac agcaggtctg ccaacttaca tttacccaga ctggccatta   1200
ctggaaccta tgatctgaag acagtcctgg gccacctggg tatcactaag gtcttcagca   1260
atggggctga cctctcgggg atcacggagg aggcaccccct gaagctctcc aaggccgtgc   1320
ataaggctgt gctgaccatc gatgagaaag ggactgaagc tgctgggggcc atgttttag   1380 aggccatacc catgtctatt ccccccgagg tcaagttcaa caaaccctt gtcttcttaa   1440 tgattgaaca aaataccaag tctccctct tcatgggaaa agtggtgaat cccacccaga   1500
aataactgcc tgtcactcct cagcccctcc cctccatccc tggcccctc cctgaatgac   1560 attaaagaag ggttgagctg gtccctgcct gcgtgtgtga ctgcaaac                1608
```

<210> SEQ ID NO 15
<211> LENGTH: 3220
<212> TYPE: DNA
<213> ORGANISM: Homo sapiens

<400> SEQUENCE: 15

```
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcaggggga aaagtcagaa cttggatcca    180
ggtcttcaga ctctcaggtc tggtgtcatc ctaggggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg agctgcggt    660 ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
```

-continued

| | |
|---|---|
| tctcccatag ctgaggagtc cttgcaatgg ccttcctgag ccatcagcag gcctatggcc | 840 |
| atgtgactag ggaggagaag ggatataggg taatggtctt ctggggcctg ctgggcctgg | 900 |
| tcaagtctga ggaggagata gagaaaacaa agcagagacc ctcctcttca tctggggaga | 960 |
| agggacctga ttctaaacgg agatatgtga ggctttctgg ggcagcgatg gaaggacaag | 1020 |
| gacagaatag gtgtccttgt tgccccatgg agaatgggct tcaggaagaa tctgcctcag | 1080 |
| tcattttcca gaagtgcctg agaggtgcag ggcccgagtc tggttaggtg acagcgggtc | 1140 |
| aagaggagga cattgtcctc tctcttgtgt tgctgcagat gccacaaaac tgggccacgg | 1200 |
| cacgatcagg cagttctggg gcccccagga gggcagcctt ggggtgggca cagccagccc | 1260 |
| tggcaggatg agcaactctg ggtgggggg agtgggggat gagcaggggg acatgaagat | 1320 |
| gcttggtgga gcctgggtc atggctggta tctggttcct ccctgtgat tccttcttgg | 1380 |
| ggactccaag acaggacaag gaagactgga gccctccaga aacagatggg cccaggtccg | 1440 |
| taagctgagg attcagtccc ccctggattc aagcccagca tgtgcctacc cagccagatg | 1500 |
| ctccatgaac acagttcagg gggcccgaag acagcactgt tacctggagc ccacatacag | 1560 |
| cctcagcagg caaagggaga ctcagagaaa acatgggagg gatttacagt cacatgcagg | 1620 |
| cagggaccag ctcaacccttt ctttaatgtc atccaggag ggggcaggg atggaggga | 1680 |
| ggggttgagg agcgagaggc agttattttt gggtgggatt caccactttt cccatgaaga | 1740 |
| ggggagactt ggtattttgt tcaatcatta agaagacaaa gggtttgttg aacttgacct | 1800 |
| cggggggat agacatgggt atggcctcta aaaacatggc cccagcagct tcagtcccctt | 1860 |
| tctcgtcgat ggtcagcaca gccttatgca cggccttgga gagcttcagg ggtgcctcct | 1920 |
| ctgtgacccc ggagaggtca gccccattgc tgaagacctt agtgatgccc agttgaccca | 1980 |
| ggacgctctt cagatcatag gttccagtaa tggacagttt gggtaaatgt aagctggcag | 2040 |
| accttctgtc ttcattttcc aggaacttgg tgatgatatc gtgggtgagt tcattttcca | 2100 |
| ggtgctgtag tttcccctca tcaggcagga agaaagatggc ggtggcattg cccaggtatt | 2160 |
| tcatcagcag cacccagctg gacagcttct tacagtgctg gatgttaaac atgcctaaac | 2220 |
| gcttcatcat aggccacctttc acggtggtca cctggtccac gtggaagtcc tcttcctcgg | 2280 |
| tgtccttgac ttcaaagggt ctctcccatt tgccttttaaa gaagatgtaa ttcaccagag | 2340 |
| caaaaactgt gtctctgtca agctccttga ccaaatccac aattttccct tgagtaccct | 2400 |
| tctccacgta atcgttgatc tgtttcttgg cctcttcggt gtccccgaag ttgacagtga | 2460 |
| aggcttctga gtggtacaac tttttaacat cctccaaaaa cttatccact agcttcaggc | 2520 |
| cctcgctgag gaacaggcca ttgccggtgg tcagctggag ctggctgtct ggctggttga | 2580 |
| gggtacggag gagttcctgg aagccttcat ggatctgagc ctccggaatc tccgtgaggt | 2640 |
| tgaaattcag gccctccagg atttcatcgt gagtgtcagc cttggtcccc agggagagca | 2700 |
| ttgcaaaggc tgtagcgatg ctcactgggg agaagaagat attggtgctg ttggactggt | 2760 |
| gtgccagctg gcggtatagg ctgaaggcga actcagccag gttgggggtg atcttgttga | 2820 |
| aggttgggtg atcctgatca tggtgggatg tatctgtctt ctgggcagca tctccctggg | 2880 |
| gatcctcagc cagggagaca gggaccaggc agcacaggcc tgccagcagg aggatgcccc | 2940 |
| acgagacaga agacggcatt gtcgattcac tgtcccaggt cagtggtggt gcctgaagct | 3000 |
| gaggagacag ggccctgtcc tcgtccgtat ttaagcagtg gatccagagg ggcaacgggg | 3060 |
| gaggctgctg gtgaatatta accaaggtca ccccagttat cggaggagca aacagggct | 3120 |
| aagtccactg gctgggatct gagtcgcccg cctacgctgc ccggacgctt tgcctgggca | 3180 |

```
gtgtacagct tccactgcac ttaccgaaag gagtcattgt                        3220
```

<210> SEQ ID NO 16
<211> LENGTH: 3199
<212> TYPE: DNA
<213> ORGANISM: Homo sapiens

<400> SEQUENCE: 16

```
tgcaagaaat gtagttctat ttattctctg ttctaatggg tataaacatt ttgttatcta    60
acttgaacat cataccaact caaaggcagg tcttactagc aatgactggg gctcagagag   120
gtttggcgac ttcacgaagg tcacacagct gtcaggggga aaagtcagaa cttggatcca   180
ggtcttcaga ctctcaggtc tggtgtcatc ctaggggct tggtgatggc catatcttta    240
atgtatttgt ggagagtgaa aggctgtcag tgagtaagct taagagaaca ggagacttgt   300
gtgggaaaca gtcggtatcc attgattaga ctgaatcatg tagaattgct aatttcacca   360
ttttgaacta tcgaaatcac tatttggtat gactcaacct catcctttaa gtacacattc   420
atgacagtga gtggttagac agtgattcct agattagttt gggatggggc agtgccttcc   480
ataggacaag gccattcctg gtagagacgg agggagcagg ctgtccttca gctaggggcc   540
caggggactt cctggctgct gtgtccttta gcagggcctt ggaggatgga aggactctcc   600
tgcccttac cacaggggct attcaggaac agcctcctgc cgtggcactg agctgcggt    660
ggccctctga agactgcagg gacagcaaca ggcacaaaga agtcaggctg catgtggccc   720
cagtcgggac tcagaggagg aaagggaggg gttgcggggg tcaatgggtg atgtgcttcc   780
tctcccatag ctgaggagtc cttgcaatgg ccttcctgag ccatcagcag gcctatggcc   840
atgtgactag ggaggagaag ggatataggg taatggtctt ctggggcctg ctgggcctgg   900
tcaagtctga ggaggagata gagaaaacaa agcagagacc ctcctcttca tctggggaga   960
agggacctga ttctaaacgg agatatgtga ggctttctgg ggcagcgatg gaaggacaag  1020
gacagaatag gtgtccttgt tgccccatgg agaatgggct tcaggaagaa tctgcctcag  1080
tcattttcca gaagtgcctg agaggtgcag ggcccgagtc tggttaggtg acagcgggtc  1140
aagaggagga cattgtcctc tctcttgtgt tgctgcagat gccacaaaac tgggccacgg  1200
cacgatcagg cagttctggg gcccccagga gggcagcctt ggggtgggca cagccagccc  1260
tggcaggatg agcaactctg ggtgggggg agtgggggat gagcagggg acatgaagat   1320
gcttggtgga gcctggggtc atggctggta tctggttcct cccctgtgat tccttcttgg  1380
ggactccaag acaggacaag gaagactgga gccctccaga aacagatggg cccaggtccg  1440
taagctgagg attcagtccc ccctggattc aagcccagca tgtgcctacc cagccagatg  1500
ctccatgaac acagttcagg gggcccgaag acagcactgt tacctggagc ccacatacag  1560
cctcagcagg caaagggaga ctcagagaaa acatgggagg gatttacagt cacatgcagg  1620
cagggaccag ctcaacccct ctttaatgtc atccagggag ggggcaggg atggagggga    1680
ggggttgagg agcgagaggc agttattttt gggtgggatt caccactttt cccatgaaga  1740
ggggagactt ggtattttgt tcaatcatta agaagacaaa gggtttgttg aacttgacct  1800
cggggggat agacatgggt atggcctcta aaaacatggc cccagcagct tcagtccctt    1860
tctcgtcgat ggtcagcaca gccttatgca cggccttgga gagcttcagg ggtgcctcct  1920
ctgtgacccc ggagaggtca gccccattgc tgaagacctt agtgatgccc agttgaccca  1980
ggacgctctt cagatcatag gttccagtaa tggacagttt gggtaaatgt aagctggcag  2040
```

| | |
|---|---|
| accttctgtc ttcattttcc aggaacttgg tgatgatatc gtgggtgagt tcattttcca | 2100 |
| ggtgctgtag tttcccctca tcaggcagga agaagatggc ggtggcattg cccaggtatt | 2160 |
| tcatcagcag cacccagctg gacagcttct tacagtgctg gatgttaaac atgcctaaac | 2220 |
| gcttcatcat aggcaccttc acggtggtca cctggtccac gtggaagtcc tcttcctcgg | 2280 |
| tgtccttgac ttcaaagggt ctctcccatt tgcctttaaa gaagatgtaa ttcaccagag | 2340 |
| caaaaactgt gtctctgtca agctccttga ccaaatccac aatttccct tgagtaccct | 2400 |
| tctccacgta atcgttgatc tgtttcttgg cctcttcggt gtccccgaag ttgacagtga | 2460 |
| aggcttctga gtggtacaac ttttaacat cctccaaaaa cttatccact agcttcaggc | 2520 |
| cctcgctgag gaacaggcca ttgccggtgg tcagctggag ctggctgtct ggctggttga | 2580 |
| gggtacggag gagttcctgg aagccttcat ggatctgagc ctccggaatc tccgtgaggt | 2640 |
| tgaaattcag gccctccagg atttcatcgt gagtgtcagc cttggtcccc agggagagca | 2700 |
| ttgcaaaggc tgtagcgatg ctcactgggg agaagaagat attggtgctg ttggactggt | 2760 |
| gtgccagctg gcggtatagg ctgaaggcga actcagccag gttggggtg atcttgttga | 2820 |
| aggttgggtg atcctgatca tggtgggatg tatctgtctt ctgggcagca tctccctggg | 2880 |
| gatcctcagc cagggagaca gggaccaggc agcacaggcc tgccagcagg aggatgcccc | 2940 |
| acgagacaga agacggcatt gtcctttcct gctctcctca agctctcctc aagctctgtc | 3000 |
| tcttctggca ggcacaggag agtggcctga aggctggcag gaggttgccg cccctccaac | 3060 |
| ctggaattcc tggcagcagc agcggctagg ccttcctcgg aggcccgacc ccctcctcct | 3120 |
| tcttggttca gctcaggact ctgagggttg ctgcgtggag gcagtgcatg ccctgggcac | 3180 |
| agtgcccagt tcctgccca | 3199 |

<210> SEQ ID NO 17
<211> LENGTH: 3513
<212> TYPE: DNA
<213> ORGANISM: Homo sapiens

<400> SEQUENCE: 17

| | |
|---|---|
| tgcaagaaat gtagttctat ttattctctg ttctaatggg tataaacatt ttgttatcta | 60 |
| acttgaacat cataccaact caaaggcagg tcttactagc aatgactggg gctcagagag | 120 |
| gtttggcgac ttcacgaagg tcacacagct gtcaggggga aaagtcagaa cttggatcca | 180 |
| ggtcttcaga ctctcaggtc tggtgtcatc ctaggggggct tggtgatggc catatcttta | 240 |
| atgtatttgt ggagagtgaa aggctgtcag tgagtaagct taagaaaca ggagacttgt | 300 |
| gtgggaaaca gtcggtatcc attgattaga ctgaatcatg tagaattgct aatttcacca | 360 |
| ttttgaacta tcgaaatcac tatttggtat gactcaacct catcctttaa gtacacattc | 420 |
| atgacagtga gtggttagac agtgattcct agattagttt gggatgggc agtgccttcc | 480 |
| ataggacaag gccattcctg gtagagacgg agggagcagg ctgtccttca gctaggggcc | 540 |
| caggggactt cctggctgct gtgtccttta gcagggcctt ggaggatgga aggactctcc | 600 |
| tggcccttac cacaggggct attcaggaac agcctcctgc cgtggcactg gagctgcggt | 660 |
| ggccctctga agactgcagg gacagcaaca ggcacaaaga agtcaggctg catgtggccc | 720 |
| cagtcgggac tcagaggagg aaagggaggg gttgcggggg tcaatgggtg atgtgcttcc | 780 |
| tctcccatag ctgaggagtc cttgcaatgg ccttcctgag ccatcagcag gcctatggcc | 840 |
| atgtgactag ggaggagaag ggatataggg taatggtctt ctggggcctg ctgggcctgg | 900 |
| tcaagtctga ggaggagata gagaaaacaa agcagagacc ctcctcttca tctggggaga | 960 |

```
agggacctga ttctaaacgg agatatgtga ggctttctgg ggcagcgatg gaaggacaag    1020
gacagaatag gtgtccttgt tgccccatgg agaatgggct tcaggaagaa tctgcctcag    1080
tcattttcca gaagtgcctg agaggtgcag ggcccgagtc tggttaggtg acagcgggtc    1140
aagaggagga cattgtcctc tctcttgtgt tgctgcagat gccacaaaac tgggccacgg    1200
cacgatcagg cagttctggg gcccccagga gggcagcctt ggggtgggca cagccagccc    1260
tggcaggatg agcaactctg ggtgggggggg agtgggggat gagcagggggg acatgaagat    1320 gcttggtgga gcctggggtc atggctggta tctggttcct cccctgtgat tccttcttgg    1380
ggactccaag acaggacaag gaagactgga gccctccaga aacagatggg cccaggtccg    1440
taagctgagg attcagtccc ccctggattc aagcccagca tgtgcctacc agccagatg    1500 ctccatgaac acagttcagg gggcccgaag acagcactgt tacctggagc ccacatacag    1560
cctcagcagg caaagggaga ctcagagaaa acatgggagg gatttacagt cacatgcagg    1620
cagggaccag ctcaacccctt ctttaatgtc atccagggag ggggccaggg atggagggga    1680
ggggttgagg agcgagaggc agttattttt gggtgggatt caccacttt cccatgaaga    1740 ggggagactt ggtattttgt tcaatcatta agaagacaaa gggtttgttg aacttgacct    1800 cggggggggat agacatgggt atggcctcta aaaacatggc cccagcagct tcagtccctt    1860
tctcgtcgat ggtcagcaca gccttatgca cggccttgga gagcttcagg ggtgcctcct    1920
ctgtgacccc ggagaggtca gccccattgc tgaagacctt agtgatgccc agttgaccca    1980
ggacgctctt cagatcatag gttccagtaa tggacagttt gggtaaatgt aagctggcag    2040
accttctgtc ttcatttcc aggaacttgg tgatgatatc gtgggtgagt tcattttcca    2100
ggtgctgtag tttcccctca tcaggcagga agaagatggc ggtggcattg cccaggtatt    2160
tcatcagcag cacccagctg gacagcttct tacagtgctg gatgttaaac atgcctaaac    2220
gcttcatcat aggcaccttc acggtggtca cctggtccac gtggaagtcc tcttcctcgg    2280
tgtccttgac ttcaaagggt ctctcccatt tgcctttaaa gaagatgtaa ttcaccagag    2340
caaaaactgt gtctctgtca agctcccttga ccaaatccac aattttccct tgagtaccct    2400
tctccacgta atcgttgatc tgtttcttgg cctcttcggt gtccccgaag ttgacagtga    2460
aggcttctga gtggtacaac tttttaacat cctccaaaaa cttatccact agcttcaggc    2520
cctcgctgag aacaggcca ttgccggtgg tcagctggag ctggctgtct ggctggttga    2580
gggtacggag gagttcctgg aagccttcat ggatctgagc ctccggaatc tccgtgaggt    2640
tgaaattcag gccctccagg atttcatcgt gagtgtcagc cttggtcccc agggagagca    2700
ttgcaaaggc tgtagcgatg ctcactgggg agaagaagat attggtgctg ttggactggt    2760
gtgccagctg gcggtatagg ctgaaggcga actcagccag gttgggggtg atcttgttga    2820
aggttgggtg atcctgatca tggtgggatg tatctgtctt ctgggcagca tctccctggg    2880
gatcctcagc cagggagaca gggaccaggc agcacaggcc tgccagcagg aggatgcccc    2940
acgagacaga agacggcatt gtcgattcac tgtcccaggt cagtggtggt gcctgaagct    3000
gaggagacag ggccctgtcc tcgtccgtat ttaagcagtg gatccagagg ggcaacgggg    3060
gaggctgcga aaggagtcat tgtacctggc tcagaaacca cagcgtcctg tgtccaaggt    3120
ggagggggtg gcgtgagtca gacagtctct gggagagtac cacttagctg gccctctgct    3180
ctcactgcag aatccttagt ggctgttcca ctggtagcaa gatctaccat ttactgagtc    3240 acccccaaaat gcctgatgct gaagacttac tgccgccctt tcctgctctc ctcaagctct    3300
```

```
cctcaagctc tgtctcttct ggcaggcaca ggagagtggc ctgaaggctg gcaggaggtt    3360
gccgcccctc caacctggaa ttcctggcag cagcagcggc taggccttcc tcggaggccc    3420
gaccccctcc tccttcttgg ttcagctcag gactctgagg gttgctgcgt ggaggcagtg    3480
catgccctgg gcacagtgcc cagttcctgc cca                                 3513
```

<210> SEQ ID NO 18
<211> LENGTH: 3236
<212> TYPE: DNA
<213> ORGANISM: Homo sapiens

<400> SEQUENCE: 18

```
tgcaagaaat gtagttctat ttattctctg ttctaatggg tataaacatt ttgttatcta      60
acttgaacat cataccaact caaaggcagg tcttactagc aatgactggg gctcagagag     120
gtttggcgac ttcacgaagg tcacacagct gtcaggggga aaagtcagaa cttggatcca     180
ggtcttcaga ctctcaggtc tggtgtcatc ctagggggct tggtgatggc catatcttta     240
atgtatttgt ggagagtgaa aggctgtcag tgagtaagct taagagaaca ggagacttgt     300
gtgggaaaca gtcggtatcc attgattaga ctgaatcatg tagaattgct aatttcacca     360
ttttgaacta tcgaaatcac tatttggtat gactcaacct catcctttaa gtacacattc     420
atgacagtga gtggttagac agtgattcct agattagttt gggatggggc agtgccttcc     480
ataggacaag gccattcctg gtagagacgg agggagcagg ctgtccttca gctaggggcc     540
caggggactt cctggctgct gtgtccttta gcagggcctt ggaggatgga aggactctcc     600
tggcccttac cacaggggct attcaggaac agcctcctgc cgtggcactg gagctgcggt     660
ggccctctga agactgcagg gacagcaaca ggcacaaaga agtcaggctg catgtggccc     720
cagtcggac tcagaggagg aaagggaggg gttgcggggg tcaatgggtg atgtgcttcc     780
ctcccatag ctgaggagtc cttgcaatgg ccttcctgag ccatcagcag gcctatggcc     840
atgtgactag ggaggagaag ggatataggg taatggtctt ctggggcctg ctgggcctgg     900
tcaagtctga ggaggagata gagaaaacaa agcagagacc ctcctcttca tctggggaga     960
agggacctga ttctaaacgg agatatgtga ggctttctgg ggcagcgatg gaaggacaag    1020
gacagaatag gtgtccttgt tgccccatgg agaatgggct tcaggaagaa tctgcctcag    1080
tcattttcca gaagtgcctg agaggtgcag ggcccgagtc tggttaggtg acagcgggtc    1140
aagaggagga cattgtcctc tctcttgtgt tgctgcagat gccacaaaac tgggccacgg    1200
cacgatcagg cagttctggg gcccccagga gggcagcctt ggggtgggca cagccagccc    1260
tggcaggatg agcaactctg ggtgggggggg agtgggggat gagcaggggg acatgaagat    1320
gcttggtgga gcctggggtc atggctggta tctggttcct cccctgtgat tccttcttgg    1380
ggactccaag acaggacaag gaagactgga gccctccaga aacagatggg cccaggtccg    1440
taagctgagg attcagtccc ccctggattc aagcccagca tgtgcctacc cagccagatg    1500
ctccatgaac acagttcagg gggcccgaag acagcactgt tacctggagc ccacatacag    1560
cctcagcagg caaagggaga ctcagagaaa acatgggagg gatttacagt cacatgcagg    1620
cagggaccag ctcaacccctt ctttaatgtc atccagggag ggggcaggg atggagggga    1680
ggggttgagg agcgagaggc agttattttt gggtgggatt caccactttt cccatgaaga    1740
ggggagactt ggtattttgt tcaatcatta agaagacaaa gggtttgttg aacttgacct    1800
cggggggggat agacatgggt atggcctcta aaaacatggc cccagcagct tcagtccctt    1860
tctcgtcgat ggtcagcaca gccttatgca cggccttgga gagcttcagg ggtgcctcct    1920
```

| | |
|---|---|
| ctgtgacccc ggagaggtca gccccattgc tgaagacctt agtgatgccc agttgaccca | 1980 |
| ggacgctctt cagatcatag gttccagtaa tggacagttt gggtaaatgt aagctggcag | 2040 |
| accttctgtc ttcattttcc aggaacttgg tgatgatatc gtgggtgagt tcattttcca | 2100 |
| ggtgctgtag tttcccctca tcaggcagga agaaagatggc ggtggcattg cccaggtatt | 2160 |
| tcatcagcag cacccagctg gacagcttct tacagtgctg gatgttaaac atgcctaaac | 2220 |
| gcttcatcat aggcaccttc acggtggtca cctggtccac gtggaagtcc tcttcctcgg | 2280 |
| tgtccttgac ttcaaagggt ctctcccatt tgcctttaaa gaagatgtaa ttcaccagag | 2340 |
| caaaaactgt gtctctgtca agctccttga ccaaatccac aattttccct tgagtaccct | 2400 |
| tctccacgta atcgttgatc tgtttcttgg cctcttcggt gtccccgaag ttgacagtga | 2460 |
| aggcttctga gtggtacaac tttttaacat cctccaaaaa cttatccact agcttcaggc | 2520 |
| cctcgctgag gaacaggcca ttgccggtgg tcagctggag ctggctgtct ggctggttga | 2580 |
| gggtacggag gagttcctgg aagccttcat ggatctgagc ctccggaatc tccgtgaggt | 2640 |
| tgaaattcag gccctccagg atttcatcgt gagtgtcagc cttggtcccc agggagagca | 2700 |
| ttgcaaaggc tgtagcgatg ctcactgggg agaagaagat attggtgctg ttggactggt | 2760 |
| gtgccagctg gcggtatagg ctgaaggcga actcagccag gttggggggtg atcttgttga | 2820 |
| aggttgggtg atcctgatca tggtgggatg tatctgtctt ctgggcagca tctccctggg | 2880 |
| gatcctcagc cagggagaca gggaccaggc agcacaggcc tgccagcagg aggatgcccc | 2940 |
| acgagacaga agacggcatt gtcctgtgga actgagtgag cagcagcagc aatgtcccac | 3000 |
| cttttcctgct ctcctcaagc tctcctcaag ctctgtctct tctggcaggc acaggagagt | 3060 |
| ggcctgaagg ctggcaggag gttgccgccc ctccaacctg gaattcctgg cagcagcagc | 3120 |
| ggctaggcct tcctcggagg cccgaccccc tcctccttct tggttcagct caggactctg | 3180 |
| agggttgctg cgtggaggca gtgcatgccc tgggcacagt gcccagttcc tgccca | 3236 |

<210> SEQ ID NO 19
<211> LENGTH: 3532
<212> TYPE: DNA
<213> ORGANISM: Homo sapiens

<400> SEQUENCE: 19

| | |
|---|---|
| tgcaagaaat gtagttctat ttattctctg ttctaatggg tataaacatt ttgttatcta | 60 |
| acttgaacat cataccaact caaaggcagg tcttactagc aatgactggg gctcagagag | 120 |
| gtttggcgac ttcacgaagg tcacacagct gtcaggggga aaagtcagaa cttggatcca | 180 |
| ggtcttcaga ctctcaggtc tggtgtcatc ctaggggget tggtgatggc catatcttta | 240 |
| atgtatttgt ggagagtgaa aggctgtcag tgagtaagct taagagaaca ggagacttgt | 300 |
| gtgggaaaca gtcggtatcc attgattaga ctgaatcatg tagaattgct aatttcacca | 360 |
| ttttgaacta tcgaaatcac tatttggtat gactcaacct catcctttaa gtacacattc | 420 |
| atgacagtga gtggttagac agtgattcct agattagttt gggatggggc agtgccttcc | 480 |
| ataggacaag gccattcctg gtagagacgg agggagcagg ctgtccttca gctaggggcc | 540 |
| caggggactt cctggctgct gtgtccttta gcagggcctt ggaggatgga aggactctcc | 600 |
| tggcccttac cacaggggct attcaggaac agcctcctgc cgtggcactg agctgcggt | 660 |
| ggccctctga agactgcagg gacagcaaca ggcacaaaga agtcaggctg catgtggccc | 720 |
| cagtcgggac tcagaggagg aaagggaggg gttgcggggg tcaatgggtg atgtgcttcc | 780 |

```
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtggggggg agtgggggat gagcaggggg acatgaagat   1320
gcttggtgga gcctgggtc atggctggta tctggttcct ccctgtgat tccttcttgg    1380 ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaacccctt ctttaatgtc atccaggag ggggcaggg atggagggga    1680 ggggttgagg agcgagaggc agttattttt gggtgggatt caccacttt cccatgaaga    1740 ggggagactt ggtattttgt tcaatcatta agaagacaaa gggtttgttg aacttgacct   1800
cgggggggat agacatgggt atggcctcta aaaacatggc cccagcagct tcagtcccct   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcatttcc aggaacttgg tgatgatatc gtgggtgagt tcattttcca    2100
ggtgctgtag tttcccctca tcaggcagga agaaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgccttaaa gaagatgtaa ttcaccagag    2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac tttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctgctg gctcagaaac cacagcgtcc tgtgtccaag gtgagggggg tggcgtgagt   3120
cagacagtct ctgggagagt accacttagc tggccctctg ctctcactgc agaatcctta   3180
```

```
gtggctgttc cactggtagc aagatctacc atttactgag tcaccccaaa atgcctgatg    3240
ctgaagactt actgccgccc tgtggaactg agtgagcagc agcagcaatg tcccacctttt   3300 cctgctctcc tcaagctctc ctcaagctct gtctcttctg gcaggcacag gagagtggcc    3360
tgaaggctgg caggaggttg ccgcccctcc aacctggaat tcctggcagc agcagcggct    3420
aggccttcct cggaggcccg acccctcct ccttcttggt tcagctcagg actctgaggg     3480
ttgctgcgtg gaggcagtgc atgccctggg cacagtgccc agttcctgcc ca            3532

<210> SEQ ID NO 20
<211> LENGTH: 3340
<212> TYPE: DNA
<213> ORGANISM: Homo sapiens

<400> SEQUENCE: 20
tgcaagaaat gtagttctat ttattctctg ttctaatggg tataaacatt tgttatcta      60 acttgaacat cataccaact caaaggcagg tcttactagc aatgactggg gctcagagag    120
gtttggcgac ttcacgaagg tcacacagct gtcagggga aaagtcagaa cttggatcca     180
ggtcttcaga ctctcaggtc tggtgtcatc ctaggggct tggtgatggc catatcttta     240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtcccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggataatggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagc cagttctggg gcccccagga gggcagcctt gggtgggca cagccagccc    1260 tgcaggatg agcaactctg ggtggggggg agtgggggat gagcagggg acatgaagat    1320 gcttggtgga gcctggggtc atggctggta tctggttcct ccctgtgat tccttcttgg    1380 ggactccaag acaggacaag gaagactgga gccctccaga aacagatggg cccaggtccg   1440
taagctgagg attcagtccc ccctggattc aagcccagca tgtgcctacc cagccagatg   1500
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccagggag ggggcaggg atggagggga    1680 ggggttgagg agcgagaggc agttatttt gggtgggatt caccactttt cccatgaaga   1740
```

```
ggggagactt ggtattttgt tcaatcatta agaagacaaa gggtttgttg aacttgacct      1800
cgggggggat agacatgggt atggcctcta aaaacatggc cccagcagct tcagtccctt      1860
tctcgtcgat ggtcagcaca gccttatgca cggccttgga gagcttcagg ggtgcctcct      1920
ctgtgacccc ggagaggtca gccccattgc tgaagacctt agtgatgccc agttgaccca      1980
ggacgctctt cagatcatag gttccagtaa tggacagttt gggtaaatgt aagctggcag      2040
accttctgtc ttcatttttcc aggaacttgg tgatgatatc gtgggtgagt tcattttcca     2100
ggtgctgtag tttcccctca tcaggcagga agaagatggc ggtggcattg cccaggtatt      2160
tcatcagcag cacccagctg acagcttct tacagtgctg gatgttaaac atgcctaaac      2220
gcttcatcat aggcaccttc acggtggtca cctggtccac gtggaagtcc tcttcctcgg      2280
tgtccttgac ttcaaagggt ctctcccatt tgcctttaaa gaagatgtaa ttcaccagag      2340
caaaaactgt gtctctgtca agctccttga ccaaatccac aattttccct tgagtaccct      2400
tctccacgta atcgttgatc tgtttcttgg cctcttcggt gtccccgaag ttgacagtga      2460
aggcttctga gtggtacaac ttttttaacat cctccaaaaa cttatccact agcttcaggc      2520
cctcgctgag gaacaggcca ttgccggtgg tcagctggag ctggctgtct ggctggttga      2580
gggtacggag gagttcctgg aagccttcat ggatctgagc ctccggaatc tccgtgaggt      2640
tgaaattcag gccctccagg atttcatcgt gagtgtcagc cttggtcccc agggagagca      2700
ttgcaaaggc tgtagcgatg ctcactgggg agaagaagat attggtgctg ttggactggt      2760
gtgccagctg gcggtatagg ctgaaggcga actcagccag gttgggggtg atcttgttga      2820
aggttgggtg atcctgatca tggtgggatg tatctgtctt ctgggcagca tctccctggg      2880
gatcctcagc cagggagaca gggaccaggc agcacaggcc tgccagcagg aggatgcccc      2940
acgagacaga agacggcatt gtcgattcac tgtcccaggt cagtggtggt gcctgaagct      3000
gaggagacag ggccctgtcc tcgtccgtat ttaagcagtg gatccagagg ggcaacgggg      3060
gaggctgctg tggaactgag tgagcagcag cagcaatgtc ccacctttcc tgctctcctc      3120
aagctctcct caagctctgt ctcttctggc aggcacagga gagtggcctg aaggctggca      3180
ggaggttgcc gccctccaa cctggaattc ctggcagcag cagcggctag gccttcctcg      3240
gaggcccgac ccctcctcc ttcttggttc agctcaggac tctgagggtt gctgcgtgga      3300
ggcagtgcat gccctgggca cagtgcccag ttcctgccca                            3340
```

<210> SEQ ID NO 21
<211> LENGTH: 3495
<212> TYPE: DNA
<213> ORGANISM: Homo sapiens

<400> SEQUENCE: 21

```
tgcaagaaat gtagttctat ttattctctg ttcaatggg tataaacatt ttgttatcta       60
acttgaacat cataccaact caaaggcagg tcttactagc aatgactggg gctcagagag     120
gtttggcgac ttcacgaagg tcacacagct gtcaggggga aaagtcagaa cttggatcca     180
ggtcttcaga ctctcaggtc tggtgtcatc ctagggggct tggtgatggc catatcttta     240
atgtatttgt ggagagtgaa aggctgtcag tgagtaagct taagagaaca ggagacttgt     300
gtgggaaaca gtcggtatcc attgattaga ctgaatcatg tagaattgct aatttcacca     360
ttttgaacta tcgaaatcac tatttggtat gactcaacct catcctttaa gtacacattc     420
atgacagtga gtggttagac agtgattcct agattagttt gggatgggc agtgccttcc      480 ataggacaag gccattcctg gtagagacgg agggagcagg ctgtccttca gctaggggcc     540
```

```
caggggactt cctggctgct gtgtccttta gcagggcctt ggaggatgga aggactctcc    600
tggcccttac cacaggggct attcaggaac agcctcctgc cgtggcactg gagctgcggt    660
ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctggggcctg ctgggcctgg    900
tcaagtctga ggaggagata gagaaaacaa agcagagacc ctcctcttca tctggggaga    960
agggacctga ttctaaacgg agatatgtga ggctttctgg ggcagcgatg gaaggacaag   1020
gacagaatag gtgtccttgt tgccccatgg agaatgggct tcaggaagaa tctgcctcag   1080
tcattttcca gaagtgcctg agaggtgcag ggcccgagtc tggttaggtg acagcgggtc   1140
aagaggagga cattgtcctc tctcttgtgt tgctgcagat gccacaaaac tgggccacgg   1200
cacgatcagg cagttctggg gcccccagga gggcagcctt ggggtgggca cagccagccc   1260
tggcaggatg agcaactctg ggtgggggggg agtgggggat gagcaggggg acatgaagat   1320
gcttggtgga gcctggggtc atggctggta tctggttcct cccctgtgat tccttcttgg   1380
ggactccaag acaggacaag gaagactgga gccctccaga aacagatggg cccaggtccg   1440
taagctgagg attcagtccc ccctggattc aagcccagca tgtgcctacc agccagatg    1500 ctccatgaac acagttcagg gggcccgaag acagcactgt tacctggagc ccacatacag   1560
cctcagcagg caaagggaga ctcagagaaa acatggagg gatttacagt cacatgcagg   1620
cagggaccag ctcaacccctt ctttaatgtc atccaggag ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800
cgggggggat agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcatttttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg gacagcttct tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt tgcctttaaa gaagatgtaa ttcaccagag   2340
caaaaactgt gtctctgtca agtccttga ccaaatccac aatttttccct tgagtaccct   2400 tctccacgta atcgttgatc tgtttcttgg cctcttcggt gtccccgaag ttgacagtga   2460
aggcttctga gtggtacaac ttttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
```

```
gatcctcagc cagggagaca gggaccaggc agcacaggcc tgccagcagg aggatgcccc    2940
acgagacaga agacggcatt gtcgattcac tgtcccaggt cagtggtggt gcctgaagct    3000
gaggagacag ggccctgtcc tcgtccgtat ttaagcagtg gatccagagg ggcaacgggg    3060
gaggctgctg gctcagaaac acagcgtcc tgtgtccaag gtggagggg tggcgtgagt     3120 cagacagtct ctgggagagt accacttagc tggccctctg ctctcactgc agaatcctta    3180
gtggctgttc cactggtagc aagatctacc atttactgag tcaccccaaa atgcctgatg    3240
ctgaagactt actgccgccc tttcctgctc tcctcaagct ctcctcaagc tctgtctctt    3300
ctggcaggca caggagagtg gcctgaaggc tggcaggagg ttgccgcccc tccaacctgg    3360
aattcctggc agcagcagcg gctaggcctt cctcggaggc ccgacccct cctccttctt     3420 ggttcagctc aggactctga gggttgctgc gtggaggcag tgcatgccct gggcacagtg    3480
cccagttcct gccca                                                    3495
```

<210> SEQ ID NO 22
<211> LENGTH: 3492
<212> TYPE: DNA
<213> ORGANISM: Homo sapiens

<400> SEQUENCE: 22

```
tgcaagaaat gtagttctat ttattctctg ttctaatggg tataaacatt ttgttatcta      60
acttgaacat cataccaact caaaggcagg tcttactagc aatgactggg gctcagagag     120
gtttggcgac ttcacgaagg tcacacagct gtcaggggga aaagtcagaa cttggatcca     180
ggtcttcaga ctctcaggtc tggtgtcatc ctagggggct tggtgatggc catatcttta     240
atgtatttgt ggagagtgaa aggctgtcag tgagtaagct taagagaaca ggagacttgt     300
gtgggaaaca gtcggtatcc attgattaga ctgaatcatg tagaattgct aatttcacca     360
ttttgaacta tcgaaatcac tatttggtat gactcaacct catcctttaa gtacacattc     420
atgacagtga gtgttagac agtgattcct agattagttt gggatggggc agtgccttcc      480
ataggacaag gccattcctg gtagagacgg agggagcagg ctgtccttca gctaggggcc     540
caggggactt cctggctgct gtgtccttta gcagggcctt ggaggatgga aggactctcc     600
tggcccttac cacaggggct attcaggaac agcctcctgc cgtggcactg gagctgcggt     660
ggccctctga agactgcagg gacagcaaca ggcacaaaga agtcaggctg catgtggccc     720
cagtcgggac tcagaggagg aaagggaggg gttgcggggg tcaatgggtg atgtgcttcc     780
tctcccatag ctgaggagtc cttgcaatgg ccttcctgag ccatcagcag gcctatggcc     840
atgtgactag ggaggagaag ggatataggg taatggtctt ctggggcctg ctgggcctgg     900
tcaagtctga ggaggagata gagaaaacaa agcagagacc ctcctcttca tctggggaga     960
agggacctga ttctaaacgg agatatgtga ggctttctgg ggcagcgatg gaaggacaag    1020
gacagaatag gtgtccttgt tgccccatgg agaatgggct tcaggaagaa tctgcctcag    1080
tcattttcca gaagtgcctg agaggtgcag ggcccgagtc tggttaggtg acagcgggtc    1140
aagaggagga cattgtcctc tctcttgtgt tgctgcagat gccacaaaac tgggccacgg    1200
cacgatcagg cagttctggg gccccagga gggcagcctt gggtgggca agcagcccc      1260 tgcaggatg agcaactctg ggtgggggg agtgggggat gagcaggggg acatgaagat      1320
gcttggtgga gcctggggtc atggctggta tctggttcct ccctgtgat tccttcttgg     1380 ggactccaag acaggacaag gaagactgga gccctccaga aacagatggg cccaggtccg    1440
taagctgagg attcagtccc ccctggattc aagcccagca tgtgcctacc cagccagatg    1500
```

```
ctccatgaac acagttcagg gggcccgaag acagcactgt tacctggagc ccacatacag   1560
cctcagcagg caaagggaga ctcagagaaa acatgggagg gatttacagt cacatgcagg   1620
cagggaccag ctcaaccctt ctttaatgtc atccaggag  ggggccaggg atggagggga   1680
ggggttgagg agcgagaggc agttattttt gggtgggatt caccactttt cccatgaaga   1740
ggggagactt ggtattttgt tcaatcatta agaagacaaa gggtttgttg aacttgacct   1800 cggggggat  agacatgggt atggcctcta aaaacatggc cccagcagct tcagtccctt   1860
tctcgtcgat ggtcagcaca gccttatgca cggccttgga gagcttcagg ggtgcctcct   1920
ctgtgacccc ggagaggtca gccccattgc tgaagacctt agtgatgccc agttgaccca   1980
ggacgctctt cagatcatag gttccagtaa tggacagttt gggtaaatgt aagctggcag   2040
accttctgtc ttcattttcc aggaacttgg tgatgatatc gtgggtgagt tcattttcca   2100
ggtgctgtag tttcccctca tcaggcagga agaagatggc ggtggcattg cccaggtatt   2160
tcatcagcag cacccagctg acagcttct  tacagtgctg gatgttaaac atgcctaaac   2220
gcttcatcat aggcaccttc acggtggtca cctggtccac gtggaagtcc tcttcctcgg   2280
tgtccttgac ttcaaagggt ctctcccatt gcctttaaa  gaagatgtaa ttcaccagag   2340
caaaaactgt gtctctgtca agctccttga ccaaatccac aattttccct tgagtaccct   2400
tctccacgta atcgttgatc tgtttcttgg cctcttcggt gtccccgaag ttgacagtga   2460
aggcttctga gtggtacaac ttttttaacat cctccaaaaa cttatccact agcttcaggc   2520
cctcgctgag gaacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccagga agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggctggct cagaaaccac agcgtcctgt gtccaaggtg gaggggtgg  cgtgagtcag   3120 acagtctctg ggagagtacc acttagctgg ccctctgctc tcactgcaga atccttagtg   3180
gctgttccac tggtagcaag atctaccatt tactgagtca ccccaaaatg cctgatgctg   3240
aagacttact gccgcccttt cctgctctcc tcaagctctc ctcaagctct gtctcttctg   3300
gcaggcacag gagagtggcc tgaaggctgg caggaggttg ccgcccctcc aacctggaat   3360
tcctggcagc agcagcggct aggccttcct cggaggcccg accccctcct ccttcttggt   3420
tcagctcagg actctgaggg ttgctgcgtg gaggcagtgc atgccctggg cacagtgccc   3480
agttcctgcc ca                                                       3492
```

<210> SEQ ID NO 23
<211> LENGTH: 3510
<212> TYPE: DNA
<213> ORGANISM: Homo sapiens

<400> SEQUENCE: 23

```
tgcaagaaat gtagttctat ttattctctg ttctaatggg tataaacatt ttgttatcta      60
```

| | |
|---|---|
| acttgaacat cataccaact caaaggcagg tcttactagc aatgactggg gctcagagag | 120 |
| gtttggcgac ttcacgaagg tcacacagct gtcaggggga aaagtcagaa cttggatcca | 180 |
| ggtcttcaga ctctcaggtc tggtgtcatc ctaggggggct tggtgatggc catatcttta | 240 |
| atgtatttgt ggagagtgaa aggctgtcag tgagtaagct taagagaaca ggagacttgt | 300 |
| gtgggaaaca gtcggtatcc attgattaga ctgaatcatg tagaattgct aatttcacca | 360 |
| ttttgaacta tcgaaatcac tatttggtat gactcaacct catcctttaa gtacacattc | 420 |
| atgacagtga gtggttagac agtgattcct agattagttt gggatgggggc agtgccttcc | 480 |
| ataggacaag gccattcctg gtagagacgg agggagcagg ctgtccttca gctaggggcc | 540 |
| caggggactt cctggctgct gtgtccttta gcagggcctt ggaggatgga aggactctcc | 600 |
| tgcccttac cacaggggct attcaggaac agcctcctgc cgtggcactg gagctgcgt | 660 |
| ggccctctga agactgcagg gacagcaaca ggcacaaaga agtcaggctg catgtggccc | 720 |
| cagtcgggac tcagaggagg aaagggaggg gttgcggggg tcaatgggtg atgtgcttcc | 780 |
| tctcccatag ctgaggagtc cttgcaatgg ccttcctgag ccatcagcag gcctatggcc | 840 |
| atgtgactag ggaggagaag ggatataggg taatggtctt ctggggcctg ctgggcctgg | 900 |
| tcaagtctga ggaggagata gagaaaacaa agcagagacc ctcctcttca tctggggaga | 960 |
| agggacctga ttctaaacgg agatatgtga ggctttctgg ggcagcgatg gaaggacaag | 1020 |
| gacagaatag gtgtccttgt tgccccatgg agaatgggct tcaggaagaa tctgcctcag | 1080 |
| tcattttcca gaagtgcctg agaggtgcag ggcccgagtc tggttaggtg acagcgggtc | 1140 |
| aagaggagga cattgtcctc tctcttgtgt tgctgcagat gccacaaaac tgggccacgg | 1200 |
| cacgatcagg cagttctggg gcccccagga gggcagcctt ggggtgggca cagccagccc | 1260 |
| tggcaggatg agcaactctg ggtgggggggg agtgggggat gagcagggggg acatgaagat | 1320 |
| gcttggtgga gcctggggtc atggctggta tctggttcct cccctgtgat tccttcttgg | 1380 |
| ggactccaag acaggacaag gaagactgga gccctccaga aacagatggg cccaggtccg | 1440 |
| taagctgagg attcagtccc cctggattc aagcccagca tgtgcctacc agccagatg | 1500 |
| ctccatgaac acagttcagg gggcccgaag acagcactgt tacctggagc ccacatacag | 1560 |
| cctcagcagg caaagggaga ctcagagaaa acatgggagg gatttacagt cacatgcagg | 1620 |
| cagggaccag ctcaacccct ctttaatgtc atccagggag ggggccaggg atggagggga | 1680 |
| ggggttgagg agcgagaggc agttattttt gggtgggatt caccactttt cccatgaaga | 1740 |
| ggggagactt ggtattttgt tcaatcatta agaagacaaa gggtttgttg aacttgacct | 1800 |
| cgggggggat agacatgggt atggcctcta aaaacatggc cccagcagct tcagtccctt | 1860 |
| tctcgtcgat ggtcagcaca gccttatgca cggccttgga gagcttcagg ggtgcctcct | 1920 |
| ctgtgacccc ggagaggtca gccccattgc tgaagacctt agtgatgccc agttgaccca | 1980 |
| ggacgctctt cagatcatag gttccagtaa tggacagttt gggtaaatgt aagctggcag | 2040 |
| accttctgtc ttcatttttcc aggaacttgg tgatgatatc gtgggtgagt tcattttcca | 2100 |
| ggtgctgtag tttcccctca tcaggcagga agaagatggc ggtggcattg cccaggtatt | 2160 |
| tcatcagcag cacccagctg gacagcttct tacagtgctg gatgttaaac atgcctaaac | 2220 |
| gcttcatcat aggcaccttc acggtggtca cctggtccac gtggaagtcc tcttcctcgg | 2280 |
| tgtccttgac ttcaaagggt ctctcccatt tgcctttaaa gaagatgtaa ttcaccagag | 2340 |
| caaaaactgt gtctctgtca agctccttga ccaaatccac aattttccct tgagtaccct | 2400 |
| tctccacgta atcgttgatc tgtttcttgg cctcttcggt gtccccgaag ttgacagtga | 2460 |

```
aggcttctga gtggtacaac ttttttaacat cctccaaaaa cttatccact agcttcaggc   2520
cctcgctgag aacaggcca ttgccggtgg tcagctggag ctggctgtct ggctggttga   2580
gggtacggag gagttcctgg aagccttcat ggatctgagc ctccggaatc tccgtgaggt   2640
tgaaattcag gccctccagg atttcatcgt gagtgtcagc cttggtcccc agggagagca   2700
ttgcaaaggc tgtagcgatg ctcactgggg agaagaagat attggtgctg ttggactggt   2760
gtgccagctg gcggtatagg ctgaaggcga actcagccag gttgggggtg atcttgttga   2820
aggttgggtg atcctgatca tggtgggatg tatctgtctt ctgggcagca tctccctggg   2880
gatcctcagc cagggagaca gggaccaggc agcacaggcc tgccagcagg aggatgcccc   2940
acgagacaga agacggcatt gtcgattcac tgtcccaggt cagtggtggt gcctgaagct   3000
gaggagacag ggccctgtcc tcgtccgtat ttaagcagtg gatccagagg ggcaacgggg   3060
gaggcgaaag gagtcattgt acctggctca gaaaccacag cgtcctgtgt ccaaggtgga   3120
gggggtggcg tgagtcagac agtctctggg agagtaccac ttagctggcc ctctgctctc   3180
actgcagaat ccttagtggc tgttccactg gtagcaagat ctaccattta ctgagtcacc   3240
ccaaaatgcc tgatgctgaa gacttactgc cgcccttttcc tgctctcctc aagctctcct   3300
caagctctgt ctcttctggc aggcacagga gagtggcctg aaggctggca ggaggttgcc   3360 gccccctccaa cctggaattc ctggcagcag cagcggctag gccttcctcg gaggcccgac   3420
cccctcctcc ttcttggttc agctcaggac tctgagggtt gctgcgtgga ggcagtgcat   3480
gccctgggca cagtgcccag ttcctgccca                                   3510

<210> SEQ ID NO 24
<211> LENGTH: 3303
<212> TYPE: DNA
<213> ORGANISM: Homo sapiens

<400> SEQUENCE: 24
tgcaagaaat gtagttctat ttattctctg ttctaatggg tataaacatt ttgttatcta     60
acttgaacat cataccaact caaaggcagg tcttactagc aatgactggg gctcagagag    120
gtttggcgac ttcacgaagg tcacacagct gtcagggga aaagtcagaa cttggatcca    180
ggtcttcaga ctctcaggtc tggtgtcatc ctagggggct tggtgatggc catatcttta    240
atgtatttgt ggagagtgaa aggctgtcag tgagtaagct taagagaaca ggagacttgt    300
gtgggaaaca gtcggtatcc attgattaga ctgaatcatg tagaattgct aatttcacca    360
ttttgaacta tcgaaatcac tatttggtat gactcaacct catcctttaa gtacacattc    420
atgacagtga gtggttagac agtgattcct agattagttt gggatggggc agtgccttcc    480
ataggacaag gccattcctg gtagagacgg agggagcagg ctgtccttca gctaggggcc    540
caggggactt cctggctgct gtgtccttta gcagggcctt ggaggatgga aggactctcc    600
tggcccttac cacaggggct attcaggaac agcctcctgc cgtggcactg agctgcggt    660 ggccctctga agactgcagg gacagcaaca ggcacaaaga agtcaggctg catgtggccc    720
cagtcgggac tcagaggagg aaagggaggg gttgcggggg tcaatgggtg atgtgcttcc    780
tctcccatag ctgaggagtc cttgcaatgg ccttcctgag ccatcagcag gcctatggcc    840
atgtgactag ggaggagaag ggatataggg taatggtctt ctgggcctg ctgggcctgg    900 tcaagtctga ggaggagata gagaaaacaa agcagagacc ctcctcttca tctggggaga    960
agggacctga ttctaaacgg agatatgtga ggctttctgg ggcagcgatg gaaggacaag   1020
```

-continued

```
gacagaatag gtgtccttgt tgccccatgg agaatgggct tcaggaagaa tctgcctcag    1080
tcattttcca gaagtgcctg agaggtgcag ggcccgagtc tggttaggtg acagcgggtc    1140
aagaggagga cattgtcctc tctcttgtgt tgctgcagat gccacaaaac tgggccacgg    1200
cacgatcagg cagttctggg gcccccagga gggcagcctt ggggtgggca cagccagccc    1260
tggcaggatg agcaactctg ggtgggggggg agtgggggat gagcaggggg acatgaagat    1320
gcttggtgga gcctggggtc atggctggta tctggttcct ccctgtgat  tccttcttgg    1380 ggactccaag acaggacaag gaagactgga gccctccaga acagatgggg cccaggtccg    1440
taagctgagg attcagtccc ccctggattc aagcccagca tgtgcctacc cagccagatg    1500
ctccatgaac acagttcagg gggcccgaag acagcactgt tacctggagc ccacatacag    1560
cctcagcagg caaagggaga ctcagagaaa acatggaggg gatttacagt cacatgcagg    1620
cagggaccag ctcaacccctt ctttaatgtc atccaggag  ggggccaggg atggagggga   1680
ggggttgagg agcgagaggc agttattttt gggtgggatt caccacttt  cccatgaaga    1740 ggggagactt ggtattttgt tcaatcatta agaagacaaa gggtttgttg aacttgacct    1800
cgggggggat agacatgggt atggcctcta aaaacatggc cccagcagct tcagtcccctt   1860 tctcgtcgat ggtcagcaca gccttatgca cggccttgga gagcttcagg ggtgcctcct    1920
ctgtgacccc ggagaggtca gccccattgc tgaagacctt agtgatgccc agttgaccca    1980
ggacgctctt cagatcatag gttccagtaa tggacagttt gggtaaatgt aagctggcag    2040
accttctgtc ttcatttttcc aggaacttgg tgatgatatc gtgggtgagt tcattttcca   2100
ggtgctgtag tttcccctca tcaggcagga agaaagatggc ggtggcattg cccaggtatt   2160
tcatcagcag cacccagctg gacagcttct tacagtgctg gatgttaaac atgcctaaac    2220
gcttcatcat aggcaccttc acggtggtca cctggtccac gtggaagtcc tcttcctcgg    2280
tgtccttgac ttcaaagggt ctctcccatt tgccttttaaa gaagatgtaa ttcaccagag   2340
caaaaactgt gtctctgtca agctccttga ccaaatccac aattttccct tgagtaccct    2400
tctccacgta atcgttgatc tgtttcttgg cctcttcggt gtccccgaag ttgacagtga    2460
aggcttctga gtggtacaac ttttttaacat cctccaaaaa cttatccact agcttcaggc   2520
cctcgctgag gaacaggcca ttgccggtgg tcagctggag ctggctgtct ggctggttga    2580
gggtacggag gagttcctgg aagccttcat ggatctgagc ctccggaatc tccgtgaggt    2640
tgaaattcag gccctccagg atttcatcgt gagtgtcagc cttggtcccc agggagagca    2700
ttgcaaaggc tgtagcgatg ctcactgggg agaagaagat attggtgctg ttggactggt    2760
gtgccagctg gcggtatagg ctgaaggcga actcagccag gttggggggtg atcttgttga   2820 aggttgggta tcctgatca  tggtgggatg tatctgtctt ctgggcagca tctccctggg    2880
gatcctcagc cagggagaca gggaccaggc agcacaggcc tgccagcagg aggatgcccc    2940
acgagacaga agacggcatt gtcgattcac tgtcccaggt cagtggtggt gcctgaagct    3000
gaggagacag ggcctgtcc  tcgtccgtat ttaagcagtg gatccagagg ggcaacgggg    3060
gaggctgctt tcctgctctc ctcaagctct cctcaagctc tgtctcttct ggcaggcaca    3120
ggagagtggc ctgaaggctg gcaggaggtt gccgccctc  caacctggaa ttcctggcag    3180
cagcagcggc taggccttcc tcggaggccc gaccccctcc tccttcttgg ttcagctcag    3240
gactctgagg gttgctgcgt ggaggcagtg catgccctgg gcacagtgcc cagttcctgc    3300
cca                                                                 3303
```

```
<210> SEQ ID NO 25
<211> LENGTH: 3300
<212> TYPE: DNA
<213> ORGANISM: Homo sapiens

<400> SEQUENCE: 25
tgcaagaaat gtagttctat ttattctctg ttctaatggg tataaacatt ttgttatcta      60
acttgaacat cataccaact caaaggcagg tcttactagc aatgactggg gctcagagag     120
gtttggcgac ttcacgaagg tcacacagct gtcaggggga aaagtcagaa cttggatcca     180
ggtcttcaga ctctcaggtc tggtgtcatc ctaggggget tggtgatggc catatcttta     240
atgtatttgt ggagagtgaa aggctgtcag tgagtaagct taagagaaca ggagacttgt     300
gtgggaaaca gtcggtatcc attgattaga ctgaatcatg tagaattgct aatttcacca     360
ttttgaacta tcgaaatcac tatttggtat gactcaacct catcctttaa gtacacattc     420
atgacagtga gtggttagac agtgattcct agattagttt gggatggggc agtgccttcc     480
ataggacaag gccattcctg gtagagacgg agggagcagg ctgtccttca gctaggggcc     540
caggggactt cctggctgct gtgtccttta gcagggcctt ggaggatgga aggactctcc     600
tggcccttac cacaggggct attcaggaac agcctcctgc cgtggcactg agctgcggt     660 ggccctctga agactgcagg acagcaaca ggcacaaaga agtcaggctg catgtggccc     720
cagtcgggac tcagaggagg aaagggaggg gttgcggggg tcaatgggtg atgtgcttcc     780
tctcccatag ctgaggagtc cttgcaatgg ccttcctgag ccatcagcag gcctatggcc     840
atgtgactag ggaggagaag ggatataggg taatggtctt ctggggcctg ctgggcctgg     900
tcaagtctga ggaggagata gagaaaacaa agcagagacc ctcctcttca tctggggaga     960
agggacctga ttctaaacgg agatatgtga ggctttctgg ggcagcgatg gaaggacaag    1020
gacagaatag gtgtccttgt tgccccatgg agaatgggct tcaggaagaa tctgcctcag    1080
tcattttcca gaagtgcctg agaggtgcag ggcccgagtc tggttaggtg acagcgggtc    1140
aagaggagga cattgtcctc tctcttgtgt tgctgcagat gccacaaaac tgggccacgg    1200
cacgatcagg cagttctggg gcccccagga gggcagcctt ggggtgggca cagccagccc    1260
tggcaggatg agcaactctg ggtgggggg agtggggat gagcagggg acatgaagat    1320 gcttggtgga gcctggggtc atggctggta tctggttcct cccctgtgat tccttcttgg    1380
ggactccaag acaggacaag gaagactgga gccctccaga aacagatggg cccaggtccg    1440
taagctgagg attcagtccc ccctggattc aagcccagca tgtgcctacc cagccagatg    1500
ctccatgaac acagttcagg gggcccgaag acagcactgt tacctggagc ccacatacag    1560
cctcagcagg caaagggaga ctcagagaaa acatgggagg gatttacagt cacatgcagg    1620
cagggaccag ctcaaccctt ctttaatgtc atccagggag ggggcaggg atggagggga    1680 ggggttgagg agcgagaggc agttattttt gggtgggatt caccacttt cccatgaaga    1740 ggggagactt ggtatttgt tcaatcatta agaagacaaa gggtttgttg aacttgacct    1800 cggggggat agacatgggt atggcctcta aaaacatggc cccagcagct tcagtccctt    1860
tctcgtcgat ggtcagcaca gccttatgca cggccttgga gagcttcagg ggtgcctcct    1920
ctgtgacccc ggagaggtca gccccattgc tgaagacctt agtgatgccc agttgaccca    1980
ggacgctctt cagatcatag gttccagtaa tggacagttt gggtaaatgt aagctggcag    2040
accttctgtc ttcattttcc aggaacttgg tgatgatatc gtgggtgagt tcatttttcca    2100 ggtgctgtag tttcccctca tcaggcagga agaagatggc ggtggcattg cccaggtatt    2160
```

| | | | | |
|---|---|---|---|---|
| tcatcagcag | cacccagctg | acagcttct | tacagtgctg | atgttaaaac | atgcctaaac | 2220 |
| gcttcatcat | aggcaccttc | acggtggtca | cctggtccac | gtggaagtcc | tcttcctcgg | 2280 |
| tgtccttgac | ttcaaagggt | ctctcccatt | tgcctttaaa | gaagatgtaa | ttcaccagag | 2340 |
| caaaaactgt | gtctctgtca | agctccttga | ccaaatccac | aattttccct | tgagtaccct | 2400 |
| tctccacgta | atcgttgatc | tgtttcttgg | cctcttcggt | gtccccgaag | ttgacagtga | 2460 |
| aggcttctga | gtggtacaac | tttttaacat | cctccaaaaa | cttatccact | agcttcaggc | 2520 |
| cctcgctgag | gaacaggcca | ttgccggtgg | tcagctggag | ctggctgtct | ggctggttga | 2580 |
| gggtacggag | gagttcctgg | aagccttcat | ggatctgagc | ctccggaatc | tccgtgaggt | 2640 |
| tgaaattcag | gccctccagg | atttcatcgt | gagtgtcagc | cttggtcccc | agggagagca | 2700 |
| ttgcaaaggc | tgtagcgatg | ctcactgggg | agaagaagat | attggtgctg | ttggactggt | 2760 |
| gtgccagctg | gcggtatagg | ctgaaggcga | actcagccag | gttggggtg | atcttgttga | 2820 |
| aggttgggtg | atcctgatca | tggtgggatg | tatctgtctt | ctgggcagca | tctccctggg | 2880 |
| gatcctcagc | cagggagaca | gggaccaggc | agcacaggcc | tgccagcagg | aggatgcccc | 2940 |
| acgagacaga | agacggcatt | gtcgattcac | tgtcccaggt | cagtggtggt | gcctgaagct | 3000 |
| gaggagacag | ggccctgtcc | tcgtccgtat | ttaagcagtg | gatccagagg | ggcaacgggg | 3060 |
| gaggctttcc | tgctctcctc | aagctctcct | caagctctgt | ctcttctggc | aggcacagga | 3120 |
| gagtggcctaa | aaggctggca | ggaggttgcc | gcccctccaa | cctggaattc | ctggcagcag | 3180 |
| cagcggctag | gccttcctcg | gaggcccgac | cccctcctcc | ttcttggttc | agctcaggac | 3240 |
| tctgagggtt | gctgcgtgga | ggcagtgcat | gccctgggca | cagtgcccag | ttcctgccca | 3300 |

<210> SEQ ID NO 26
<211> LENGTH: 1321
<212> TYPE: DNA
<213> ORGANISM: Macaca mulatta

<400> SEQUENCE: 26

| | | | | | | |
|---|---|---|---|---|---|---|
| atgtcattca | gggagggggc | cagggatgga | ggggagggggc | tgaggagtga | caggcagtta | 60 |
| tttctgggtg | ggattcacca | cttttcccat | gaagaggggga | gacttggtat | tttgttcaat | 120 |
| cattaagaag | acaaagggtt | tgttgaactt | gacctcgggg | ggaatagaca | tgggtatggc | 180 |
| ctctaaaaac | atggccccag | cagcttcagt | ccctttctca | tcgatggtca | gcacagcctt | 240 |
| atgcacggcc | ttggagagct | tcaggggtgc | ctcctccgtg | atccccgaga | ggtcagcccc | 300 |
| attgctgaag | accttagtga | tacccaggtg | gcccaggact | gtcttcagat | cataggttcc | 360 |
| agtaatggcc | agtctgggta | atgtaagtt | ggcagacctg | ctgttttcat | tttccaggaa | 420 |
| cttggtgatg | atatcatggg | tgagttcatt | ttccaggtgc | tgcagtttcc | cctcatcagg | 480 |
| caggaagaag | atggcggtgg | cattgcccag | gtatttcatc | agcagcaccc | agctggacag | 540 |
| cttctcacag | tggtagatgt | taaacatgcc | taaacgcctc | atcatgggca | ccttcacggt | 600 |
| ggtcgcctgg | tccacgtgga | agtcctcttc | cttggtggcc | tcaacgtcaa | agggtctctc | 660 |
| ccatttgcct | ttaaagaaga | tgtaattcac | cagagcaaaa | actgtgtctc | tgtcaagctc | 720 |
| cttgaccaaa | tccacaattt | tcccttgagt | tccttctcc | acgtaattgt | tgatctgttt | 780 |
| cttggcctct | tcggtgtcct | caaagttgac | agagaaggct | tctgagtggt | acagtttttt | 840 |
| gacatcctcc | aaaaacttat | ccactacctt | caggctcttg | ttgaggaaca | ggccgttgcc | 900 |
| ggtggtcagc | tggagctggc | tgtctggctt | gttgagggta | tggaggagtt | cctgaagcc | 960 |
| ttcatggacc | tgagcctccg | gaatctccgt | gacgttgaaa | ttcaggccct | ccaggatttc | 1020 |

```
actgtgagtg tcagccttgg tccccaggga gagcattgca aaggctgtag cgatgctcac    1080
tggggagaag aagatattgg tgctgttgga ctggtgtgcc agctggcggt ataggctgaa    1140
gccgaactca gccaggctgg gggtgatctt gttgagggtt gggtggtcct gatcatggtg    1200
ggatgtatcc gtcttctggg cagcatctcc ctggggatcc tcagccagag agccggggag    1260
caggcagcac aggcctgcca gcaggaggac gccccatgag acagaagatg cattgtcct    1320 g                                                                   1321
```

<210> SEQ ID NO 27
<211> LENGTH: 2064
<212> TYPE: DNA
<213> ORGANISM: Macaca mulatta

<400> SEQUENCE: 27

```
gtttgcagtc acacacgcag gcagggacca gctcaaccct tctttaatgt cattcaggga     60
gggggccagg gatggagggg aggggctgag gagtgacagg cagttatttc tgggtgggat    120
tcaccacttt tcccatgaag aggggagact tggtattttg ttcaatcatt aagaagacaa    180
agggtttgtt gaacttgacc tcgggggaa tagacatggg tatggcctct aaaaacatgg     240
ccccagcagc ttcagtccct ttctcatcga tggtcagcac agccttatgc acggccttgg    300
agagcttcag gggtgcctcc tccgtgatcc ccgagaggtc agccccattg ctgaagacct    360
tagtgatacc caggtggccc aggactgtct tcagatcata ggttccagta atggccagtc    420
tgggtaaatg taagttggca gacctgctgt tttcattttc caggaacttg gtgatgatat    480
catgggtgag ttcatttttcc aggtgctgca gtttcccctc atcaggcagg aagaagatgg    540
cggtggcatt gcccaggtat ttcatcagca gcacccagct ggacagcttc tcacagtggt    600
agatgttaaa catgcctaaa cgcctcatca tgggcacctt cacggtggtc gcctggtcca    660
cgtggaagtc ctcttccttg gtggcctcaa cgtcaaaggg tctctcccat ttgcctttaa    720
agaagatgta attcaccaga gcaaaaactg tgtctctgtc aagctccttg accaaatcca    780
caattttccc ttgagtttcc ttctccacgt aattgttgat ctgtttcttg gcctcttcgg    840
tgtcctcaaa gttgacagag aaggcttctg agtggtacag ttttttgaca tcctccaaaa    900
acttatccac taccttcagg ctcttgttga ggaacaggcc gttgccggtg gtcagctgga    960
gctggctgtc tggcttgttg agggtatgga ggagttcctg gaagccttca tggacctgag   1020
cctccggaat ctccgtgacg ttgaaattca ggccctccag gatttcactg tgagtgtcag   1080
ccttggtccc cagggagagc attgcaaagg ctgtagcgat gctcactggg gagaagaaga   1140
tattggtgct gttggactgg tgtgccagct ggcggtatag gctgaagccg aactcagcca   1200 ggctggggt gatcttgttg agggttgggt ggtcctgatc atggtgggat gtatccgtct   1260
tctgggcagc atctccctgg gatcctcag ccagagagcc ggggagcagg cagcacaggc   1320
ctgccagcag gaggacgccc catgagacag aagatgcat tgtcgattca ccgtcccagg   1380
tcagtggtgg tgcctgaggc tgaggagaca gagccctgtc cttgtccgta tttaagcagt   1440
gggtgcagag gggcaacggg ggaggctgct ggtgaatatt aaccaagatc accccagtta   1500
ccggaggagc aaacagggac taagttcaca ggctgggcgc tgagtcgccc gcccacgctg   1560
tccggacgct ctgcctgagc agcatacagc ctccactgca cgtaccaaaa ggagtcattg   1620
tacctggctc agaaaccaca gtgtcctgcg tccaaggtgg aggggtggc gtgagtcagc   1680 cagtcgctgg gagagtacca ctttgctggc cctctgctct cactgcagaa tccttagcgg   1740
```

```
ctgttccact ggtagcaaga tctaccattt actaattcac cccgaaatgc ctgatgctga    1800
agactgatgc cgccctggaa ttcctggcag cagcagtggc taggccttcc tcagagtgct    1860
gatcccctcc tcctcctttg ctcagctcag tactctgagg gttgctgcgt ggaggcagtg    1920
cacgccctgg gcacagggcc cagttcctgc ccacccagga agttggcctc gggtggcggg    1980
tggcggaggc aataggttgg ggaggggcgg ggagcttggg caggaagggg ccttgcccat    2040
tgccaggcag acacaagact gggc                                           2064
```

<210> SEQ ID NO 28
<211> LENGTH: 1608
<212> TYPE: DNA
<213> ORGANISM: Macaca mulatta
<400> SEQUENCE: 28

```
gtttgcagtc acacacgcag gcagggacca gctcaaccct tctttaatgt cattcaggga      60
gggggccagg gatggagggg aggggctgag gagtgacagg cagttatttc tgggtgggat     120
tcaccacttt tcccatgaag aggggagact tggtattttg ttcaatcatt aagaagacaa     180
agggtttgtt gaacttgacc tcgggggaa tagacatggg tatggcctct aaaaacatgg      240
ccccagcagc ttcagtccct ttctcatcga tggtcagcac agccttatgc acggccttgg     300
agagcttcag gggtgcctcc tccgtgatcc ccgagaggtc agccccattg ctgaagacct     360
tagtgatacc caggtggccc aggactgtct tcagatcata ggttccagta atggccagtc     420
tgggtaaatg taagttggca gacctgctgt tttcattttc caggaacttg gtgatgatat     480
catgggtgag ttcattttcc aggtgctgca gtttcccctc atcaggcagg aagaagatgg     540
cggtggcatt gcccaggtat tcatcagca gcacccagct ggacagcttc tcacagtggt     600
agatgttaaa catgcctaaa cgcctcatca tgggcacctt cacggtggtc gcctggtcca    660
cgtggaagtc ctcttccttg gtggcctcaa cgtcaaaggg tctctcccat ttgcctttaa    720
agaagatgta attcaccaga gcaaaaactg tgtctctgtc aagctccttg accaaatcca    780
caattttccc ttgagtttcc ttctccacgt aattgttgat ctgtttcttg gcctcttcgg    840
tgtcctcaaa gttgacagag aaggcttctg agtggtacag tttttttgaca tcctccaaaa    900 acttatccac taccttcagg ctcttgttga ggaacaggcc gttgccggtg gtcagctgga    960
gctggctgtc tggcttgttg agggtatgga ggagttcctg gaagccttca tggacctgag   1020
cctccggaat ctccgtgacg ttgaaattca ggccctccag gatttcactg tgagtgtcag   1080
ccttggtccc cagggagagc attgcaaagg ctgtagcgat gctcactggg gagaagaaga   1140
tattggtgct gttggactgg tgtgccagct ggcggtatag gctgaagccg aactcagcca   1200
ggctgggggt gatcttgttg agggttgggt ggtcctgatc atggtgggat gtatccgtct   1260
tctgggcagc atctccctgg ggatcctcag ccagagagcc ggggagcagg cagcacaggc   1320
ctgccagcag gaggacgccc catgagacag aagatggcat tgtcctggaa ttcctggcag   1380
cagcagtggc taggccttcc tcagagtgct gatcccctcc tcctcctttg ctcagctcag   1440
tactctgagg gttgctgcgt ggaggcagtg cacgccctgg gcacagggcc cagttcctgc   1500
ccacccagga agttggcctc gggtggcggg tggcggaggc aataggttgg ggaggggcgg   1560
ggagcttggg caggaagggg ccttgcccat tgccaggcag acacaaga                1608
```

<210> SEQ ID NO 29
<211> LENGTH: 16
<212> TYPE: PRT
<213> ORGANISM: Unknown

```
<220> FEATURE:
<221> NAME/KEY: source
<223> OTHER INFORMATION: /note="Description of Unknown:
      RFGF peptide"

<400> SEQUENCE: 29

Ala Ala Val Ala Leu Leu Pro Ala Val Leu Leu Ala Leu Leu Ala Pro
1               5                   10                  15

<210> SEQ ID NO 30
<211> LENGTH: 11
<212> TYPE: PRT
<213> ORGANISM: Unknown
<220> FEATURE:
<221> NAME/KEY: source
<223> OTHER INFORMATION: /note="Description of Unknown:
      RFGF analogue peptide"

<400> SEQUENCE: 30

Ala Ala Leu Leu Pro Val Leu Leu Ala Ala Pro
1               5                   10

<210> SEQ ID NO 31
<211> LENGTH: 13
<212> TYPE: PRT
<213> ORGANISM: Human immunodeficiency virus

<400> SEQUENCE: 31

Gly Arg Lys Lys Arg Arg Gln Arg Arg Arg Pro Pro Gln
1               5                   10

<210> SEQ ID NO 32
<211> LENGTH: 16
<212> TYPE: PRT
<213> ORGANISM: Drosophila sp.

<400> SEQUENCE: 32

Arg Gln Ile Lys Ile Trp Phe Gln Asn Arg Arg Met Lys Trp Lys Lys
1               5                   10                  15

<210> SEQ ID NO 33
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 33
cuuacgcuga guacuucgat t                                             21

<210> SEQ ID NO 34
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
actaaggtct tcagcaatgg g                                             21
```

<210> SEQ ID NO 35
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 35
gcttcagtcc ctttctcatc g                                              21

<210> SEQ ID NO 36
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 36
tggtcagcac agccttatgc acg                                            23

<210> SEQ ID NO 37
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 37
gcatcctggg ctacactga                                                 19

<210> SEQ ID NO 38
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic primer"

<400> SEQUENCE: 38
tgggtgtcgc tgttgaagtc                                                20

<210> SEQ ID NO 39
<211> LENGTH: 16
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic probe"

<400> SEQUENCE: 39
ccaggtggtc tcctcc                                                    16

<210> SEQ ID NO 40
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"

```
<220> FEATURE:
<221> NAME/KEY: source
<223> OTHER INFORMATION: /note="Description of Combined DNA/RNA
      Molecule: Synthetic oligonucleotide"

<400> SEQUENCE: 40
ucgaaguacu cagcguaagt t                                              21

<210> SEQ ID NO 41
<211> LENGTH: 21
<212> TYPE: RNA
<213> ORGANISM: Homo sapiens

<400> SEQUENCE: 41
guccaacagc accaauaucu u                                              21

<210> SEQ ID NO 42
<211> LENGTH: 21
<212> TYPE: RNA
<213> ORGANISM: Homo sapiens

<400> SEQUENCE: 42
guccaacagc accaauaucu u                                              21

<210> SEQ ID NO 43
<211> LENGTH: 21
<212> TYPE: RNA
<213> ORGANISM: Homo sapiens

<400> SEQUENCE: 43
uaaugauuga acaaaauacc a                                              21

<210> SEQ ID NO 44
<211> LENGTH: 21
<212> TYPE: RNA
<213> ORGANISM: Homo sapiens

<400> SEQUENCE: 44
uaaugauuga acaaaauacc a                                              21

<210> SEQ ID NO 45
<211> LENGTH: 21
<212> TYPE: RNA
<213> ORGANISM: Homo sapiens

<400> SEQUENCE: 45
cuucuuaaug auugaacaaa a                                              21

<210> SEQ ID NO 46
<211> LENGTH: 21
<212> TYPE: RNA
<213> ORGANISM: Homo sapiens

<400> SEQUENCE: 46
cuucuuaaug auugaacaaa a                                              21

<210> SEQ ID NO 47
<211> LENGTH: 21
<212> TYPE: RNA
<213> ORGANISM: Homo sapiens

<400> SEQUENCE: 47
auugaacaaa auaccaaguc u                                              21
```

```
<210> SEQ ID NO 48
<211> LENGTH: 21
<212> TYPE: RNA
<213> ORGANISM: Homo sapiens

<400> SEQUENCE: 48
auugaacaaa auaccaaguc u                                              21

<210> SEQ ID NO 49
<211> LENGTH: 21
<212> TYPE: RNA
<213> ORGANISM: Homo sapiens

<400> SEQUENCE: 49
uucuuaauga uugaacaaaa u                                              21

<210> SEQ ID NO 50
<211> LENGTH: 21
<212> TYPE: RNA
<213> ORGANISM: Homo sapiens

<400> SEQUENCE: 50
uucuuaauga uugaacaaaa u                                              21

<210> SEQ ID NO 51
<211> LENGTH: 21
<212> TYPE: RNA
<213> ORGANISM: Homo sapiens

<400> SEQUENCE: 51
caaacccuuu gucuucuuaa u                                              21

<210> SEQ ID NO 52
<211> LENGTH: 21
<212> TYPE: RNA
<213> ORGANISM: Homo sapiens

<400> SEQUENCE: 52
caaacccuuu gucuucuuaa u                                              21

<210> SEQ ID NO 53
<211> LENGTH: 21
<212> TYPE: RNA
<213> ORGANISM: Homo sapiens

<400> SEQUENCE: 53
ugucuucuua augauugaac a                                              21

<210> SEQ ID NO 54
<211> LENGTH: 21
<212> TYPE: RNA
<213> ORGANISM: Homo sapiens

<400> SEQUENCE: 54
ugucuucuua augauugaac a                                              21

<210> SEQ ID NO 55
<211> LENGTH: 21
<212> TYPE: RNA
<213> ORGANISM: Homo sapiens

<400> SEQUENCE: 55
caccuggaaa augaacucac c                                              21
```

```
<210> SEQ ID NO 56
<211> LENGTH: 21
<212> TYPE: RNA
<213> ORGANISM: Homo sapiens

<400> SEQUENCE: 56
caccuggaaa augaacucac c                                              21

<210> SEQ ID NO 57
<211> LENGTH: 21
<212> TYPE: RNA
<213> ORGANISM: Homo sapiens

<400> SEQUENCE: 57
uuuugcucug gugaauuaca u                                              21

<210> SEQ ID NO 58
<211> LENGTH: 21
<212> TYPE: RNA
<213> ORGANISM: Homo sapiens

<400> SEQUENCE: 58
uuuugcucug gugaauuaca u                                              21

<210> SEQ ID NO 59
<211> LENGTH: 21
<212> TYPE: RNA
<213> ORGANISM: Homo sapiens

<400> SEQUENCE: 59
acccuuuguc uucuuaauga u                                              21

<210> SEQ ID NO 60
<211> LENGTH: 21
<212> TYPE: RNA
<213> ORGANISM: Homo sapiens

<400> SEQUENCE: 60
acccuuuguc uucuuaauga u                                              21

<210> SEQ ID NO 61
<211> LENGTH: 21
<212> TYPE: RNA
<213> ORGANISM: Homo sapiens

<400> SEQUENCE: 61
uugaacaaaa uaccaagucu c                                              21

<210> SEQ ID NO 62
<211> LENGTH: 21
<212> TYPE: RNA
<213> ORGANISM: Homo sapiens

<400> SEQUENCE: 62
uugaacaaaa uaccaagucu c                                              21

<210> SEQ ID NO 63
<211> LENGTH: 21
<212> TYPE: RNA
<213> ORGANISM: Homo sapiens

<400> SEQUENCE: 63
```
guucaacaaa cccuuugucu u                                              21

<210> SEQ ID NO 64
<211> LENGTH: 21
<212> TYPE: RNA
<213> ORGANISM: Homo sapiens

<400> SEQUENCE: 64
guucaacaaa cccuuugucu u                                              21

<210> SEQ ID NO 65
<211> LENGTH: 21
<212> TYPE: RNA
<213> ORGANISM: Homo sapiens

<400> SEQUENCE: 65
aaauaccaag ucuccccucu u                                              21

<210> SEQ ID NO 66
<211> LENGTH: 21
<212> TYPE: RNA
<213> ORGANISM: Homo sapiens

<400> SEQUENCE: 66
aaauaccaag ucuccccucu u                                              21

<210> SEQ ID NO 67
<211> LENGTH: 21
<212> TYPE: RNA
<213> ORGANISM: Homo sapiens

<400> SEQUENCE: 67
uuuuugcucu ggugaauuac a                                              21

<210> SEQ ID NO 68
<211> LENGTH: 21
<212> TYPE: RNA
<213> ORGANISM: Homo sapiens

<400> SEQUENCE: 68
uuuuugcucu ggugaauuac a                                              21

<210> SEQ ID NO 69
<211> LENGTH: 21
<212> TYPE: RNA
<213> ORGANISM: Homo sapiens

<400> SEQUENCE: 69
aguucaacaa acccuuuguc u                                              21

<210> SEQ ID NO 70
<211> LENGTH: 21
<212> TYPE: RNA
<213> ORGANISM: Homo sapiens

<400> SEQUENCE: 70
aguucaacaa acccuuuguc u                                              21

<210> SEQ ID NO 71
<211> LENGTH: 21
<212> TYPE: RNA
<213> ORGANISM: Homo sapiens

<400> SEQUENCE: 71

-continued aaugauugaa caaaauacca a         21

<210> SEQ ID NO 72
<211> LENGTH: 21
<212> TYPE: RNA
<213> ORGANISM: Homo sapiens

<400> SEQUENCE: 72
aaugauugaa caaaauacca a         21

<210> SEQ ID NO 73
<211> LENGTH: 21
<212> TYPE: RNA
<213> ORGANISM: Homo sapiens

<400> SEQUENCE: 73
uacuggaacc uaugaucuga a         21

<210> SEQ ID NO 74
<211> LENGTH: 21
<212> TYPE: RNA
<213> ORGANISM: Homo sapiens

<400> SEQUENCE: 74
uacuggaacc uaugaucuga a         21

<210> SEQ ID NO 75
<211> LENGTH: 21
<212> TYPE: RNA
<213> ORGANISM: Homo sapiens

<400> SEQUENCE: 75
acauuaaaga aggguugagc u         21

<210> SEQ ID NO 76
<211> LENGTH: 21
<212> TYPE: RNA
<213> ORGANISM: Homo sapiens

<400> SEQUENCE: 76
acauuaaaga aggguugagc u         21

<210> SEQ ID NO 77
<211> LENGTH: 21
<212> TYPE: RNA
<213> ORGANISM: Homo sapiens

<400> SEQUENCE: 77
aaaauugugg auuuggucaa g         21

<210> SEQ ID NO 78
<211> LENGTH: 21
<212> TYPE: RNA
<213> ORGANISM: Homo sapiens

<400> SEQUENCE: 78
aaaauugugg auuuggucaa g         21

<210> SEQ ID NO 79
<211> LENGTH: 21
<212> TYPE: RNA
<213> ORGANISM: Homo sapiens

```
<400> SEQUENCE: 79
auuacuggaa ccuaugaucu g                                              21

<210> SEQ ID NO 80
<211> LENGTH: 21
<212> TYPE: RNA
<213> ORGANISM: Homo sapiens

<400> SEQUENCE: 80
auuacuggaa ccuaugaucu g                                              21

<210> SEQ ID NO 81
<211> LENGTH: 21
<212> TYPE: RNA
<213> ORGANISM: Homo sapiens

<400> SEQUENCE: 81
cacaguuuuu gcucgguga a                                               21

<210> SEQ ID NO 82
<211> LENGTH: 21
<212> TYPE: RNA
<213> ORGANISM: Homo sapiens

<400> SEQUENCE: 82
cacaguuuuu gcucgguga a                                               21

<210> SEQ ID NO 83
<211> LENGTH: 21
<212> TYPE: RNA
<213> ORGANISM: Homo sapiens

<400> SEQUENCE: 83
uuaaagaagg guugagcugg u                                              21

<210> SEQ ID NO 84
<211> LENGTH: 21
<212> TYPE: RNA
<213> ORGANISM: Homo sapiens

<400> SEQUENCE: 84
uuaaagaagg guugagcugg u                                              21

<210> SEQ ID NO 85
<211> LENGTH: 21
<212> TYPE: RNA
<213> ORGANISM: Homo sapiens

<400> SEQUENCE: 85
agugagcauc gcuacagccu u                                              21

<210> SEQ ID NO 86
<211> LENGTH: 21
<212> TYPE: RNA
<213> ORGANISM: Homo sapiens

<400> SEQUENCE: 86
agugagcauc gcuacagccu u                                              21

<210> SEQ ID NO 87
<211> LENGTH: 21
<212> TYPE: RNA
<213> ORGANISM: Homo sapiens
```

-continued

```
<400> SEQUENCE: 87
aaggagcuug acagagacac a                                       21

<210> SEQ ID NO 88
<211> LENGTH: 21
<212> TYPE: RNA
<213> ORGANISM: Homo sapiens

<400> SEQUENCE: 88
aaggagcuug acagagacac a                                       21

<210> SEQ ID NO 89
<211> LENGTH: 21
<212> TYPE: RNA
<213> ORGANISM: Homo sapiens

<400> SEQUENCE: 89
guggauaagu uuuuggagga u                                       21

<210> SEQ ID NO 90
<211> LENGTH: 21
<212> TYPE: RNA
<213> ORGANISM: Homo sapiens

<400> SEQUENCE: 90
guggauaagu uuuuggagga u                                       21

<210> SEQ ID NO 91
<211> LENGTH: 21
<212> TYPE: RNA
<213> ORGANISM: Homo sapiens

<400> SEQUENCE: 91
gauugaacaa aauaccaagu c                                       21

<210> SEQ ID NO 92
<211> LENGTH: 21
<212> TYPE: RNA
<213> ORGANISM: Homo sapiens

<400> SEQUENCE: 92
gauugaacaa aauaccaagu c                                       21

<210> SEQ ID NO 93
<211> LENGTH: 21
<212> TYPE: RNA
<213> ORGANISM: Homo sapiens

<400> SEQUENCE: 93
gcucuccaag gccgugcaua a                                       21

<210> SEQ ID NO 94
<211> LENGTH: 21
<212> TYPE: RNA
<213> ORGANISM: Homo sapiens

<400> SEQUENCE: 94
gcucuccaag gccgugcaua a                                       21

<210> SEQ ID NO 95
<211> LENGTH: 21
<212> TYPE: RNA
```

<213> ORGANISM: Homo sapiens

<400> SEQUENCE: 95
accuggaaaa ugaacucacc c                                          21

<210> SEQ ID NO 96
<211> LENGTH: 21
<212> TYPE: RNA
<213> ORGANISM: Homo sapiens

<400> SEQUENCE: 96
accuggaaaa ugaacucacc c                                          21

<210> SEQ ID NO 97
<211> LENGTH: 21
<212> TYPE: RNA
<213> ORGANISM: Homo sapiens

<400> SEQUENCE: 97
gggaccaagg cugacacuca c                                          21

<210> SEQ ID NO 98
<211> LENGTH: 21
<212> TYPE: RNA
<213> ORGANISM: Homo sapiens

<400> SEQUENCE: 98
gggaccaagg cugacacuca c                                          21

<210> SEQ ID NO 99
<211> LENGTH: 21
<212> TYPE: RNA
<213> ORGANISM: Homo sapiens

<400> SEQUENCE: 99
gccauguuuu uagaggccau a                                          21

<210> SEQ ID NO 100
<211> LENGTH: 21
<212> TYPE: RNA
<213> ORGANISM: Homo sapiens

<400> SEQUENCE: 100
gccauguuuu uagaggccau a                                          21

<210> SEQ ID NO 101
<211> LENGTH: 21
<212> TYPE: RNA
<213> ORGANISM: Homo sapiens

<400> SEQUENCE: 101
ccuggaaaau gaacucaccc a                                          21

<210> SEQ ID NO 102
<211> LENGTH: 21
<212> TYPE: RNA
<213> ORGANISM: Homo sapiens

<400> SEQUENCE: 102
ccuggaaaau gaacucaccc a                                          21

<210> SEQ ID NO 103
<211> LENGTH: 21

```
<212> TYPE: RNA
<213> ORGANISM: Homo sapiens

<400> SEQUENCE: 103
aagaggccaa gaaacagauc a                                              21

<210> SEQ ID NO 104
<211> LENGTH: 21
<212> TYPE: RNA
<213> ORGANISM: Homo sapiens

<400> SEQUENCE: 104
aagaggccaa gaaacagauc a                                              21

<210> SEQ ID NO 105
<211> LENGTH: 21
<212> TYPE: RNA
<213> ORGANISM: Homo sapiens

<400> SEQUENCE: 105
ggcaaauggg agagacccuu u                                              21

<210> SEQ ID NO 106
<211> LENGTH: 21
<212> TYPE: RNA
<213> ORGANISM: Homo sapiens

<400> SEQUENCE: 106
ggcaaauggg agagacccuu u                                              21

<210> SEQ ID NO 107
<211> LENGTH: 21
<212> TYPE: RNA
<213> ORGANISM: Homo sapiens

<400> SEQUENCE: 107
ugggaaaagu ggugaauccc a                                              21

<210> SEQ ID NO 108
<211> LENGTH: 21
<212> TYPE: RNA
<213> ORGANISM: Homo sapiens

<400> SEQUENCE: 108
ugggaaaagu ggugaauccc a                                              21

<210> SEQ ID NO 109
<211> LENGTH: 21
<212> TYPE: RNA
<213> ORGANISM: Homo sapiens

<400> SEQUENCE: 109
ggggaccaag gcugacacuc a                                              21

<210> SEQ ID NO 110
<211> LENGTH: 21
<212> TYPE: RNA
<213> ORGANISM: Homo sapiens

<400> SEQUENCE: 110
ggggaccaag gcugacacuc a                                              21

<210> SEQ ID NO 111
```

```
<211> LENGTH: 21
<212> TYPE: RNA
<213> ORGANISM: Homo sapiens

<400> SEQUENCE: 111
gacauuaaag aaggguugag c                                              21

<210> SEQ ID NO 112
<211> LENGTH: 21
<212> TYPE: RNA
<213> ORGANISM: Homo sapiens

<400> SEQUENCE: 112
gacauuaaag aaggguugag c                                              21

<210> SEQ ID NO 113
<211> LENGTH: 21
<212> TYPE: RNA
<213> ORGANISM: Homo sapiens

<400> SEQUENCE: 113
ggccauguuu uuagaggcca u                                              21

<210> SEQ ID NO 114
<211> LENGTH: 21
<212> TYPE: RNA
<213> ORGANISM: Homo sapiens

<400> SEQUENCE: 114
ggccauguuu uuagaggcca u                                              21

<210> SEQ ID NO 115
<211> LENGTH: 21
<212> TYPE: RNA
<213> ORGANISM: Homo sapiens

<400> SEQUENCE: 115
uuccugccug augaggggaa a                                              21

<210> SEQ ID NO 116
<211> LENGTH: 21
<212> TYPE: RNA
<213> ORGANISM: Homo sapiens

<400> SEQUENCE: 116
uuccugccug augaggggaa a                                              21

<210> SEQ ID NO 117
<211> LENGTH: 21
<212> TYPE: RNA
<213> ORGANISM: Homo sapiens

<400> SEQUENCE: 117
cucuccaagg ccgugcauaa g                                              21

<210> SEQ ID NO 118
<211> LENGTH: 21
<212> TYPE: RNA
<213> ORGANISM: Homo sapiens

<400> SEQUENCE: 118
cucuccaagg ccgugcauaa g                                              21
```

```
<210> SEQ ID NO 119
<211> LENGTH: 21
<212> TYPE: RNA
<213> ORGANISM: Homo sapiens

<400> SEQUENCE: 119
agcucuccaa ggccgugcau a                                              21

<210> SEQ ID NO 120
<211> LENGTH: 21
<212> TYPE: RNA
<213> ORGANISM: Homo sapiens

<400> SEQUENCE: 120
agcucuccaa ggccgugcau a                                              21

<210> SEQ ID NO 121
<211> LENGTH: 21
<212> TYPE: RNA
<213> ORGANISM: Homo sapiens

<400> SEQUENCE: 121
uccuggaggg ccugaauuuc a                                              21

<210> SEQ ID NO 122
<211> LENGTH: 21
<212> TYPE: RNA
<213> ORGANISM: Homo sapiens

<400> SEQUENCE: 122
uccuggaggg ccugaauuuc a                                              21

<210> SEQ ID NO 123
<211> LENGTH: 21
<212> TYPE: RNA
<213> ORGANISM: Homo sapiens

<400> SEQUENCE: 123
uuggucaagg agcuugacag a                                              21

<210> SEQ ID NO 124
<211> LENGTH: 21
<212> TYPE: RNA
<213> ORGANISM: Homo sapiens

<400> SEQUENCE: 124
uuggucaagg agcuugacag a                                              21

<210> SEQ ID NO 125
<211> LENGTH: 21
<212> TYPE: RNA
<213> ORGANISM: Homo sapiens

<400> SEQUENCE: 125
uuuggucaag gagcuugaca g                                              21

<210> SEQ ID NO 126
<211> LENGTH: 21
<212> TYPE: RNA
<213> ORGANISM: Homo sapiens

<400> SEQUENCE: 126
uuuggucaag gagcuugaca g                                              21
```

-continued

```
<210> SEQ ID NO 127
<211> LENGTH: 21
<212> TYPE: RNA
<213> ORGANISM: Homo sapiens

<400> SEQUENCE: 127
uccccaguga gcaucgcuac a                                              21

<210> SEQ ID NO 128
<211> LENGTH: 21
<212> TYPE: RNA
<213> ORGANISM: Homo sapiens

<400> SEQUENCE: 128
uccccaguga gcaucgcuac a                                              21

<210> SEQ ID NO 129
<211> LENGTH: 23
<212> TYPE: RNA
<213> ORGANISM: Homo sapiens

<400> SEQUENCE: 129
aagauauugg ugcuguugga cug                                            23

<210> SEQ ID NO 130
<211> LENGTH: 23
<212> TYPE: RNA
<213> ORGANISM: Homo sapiens

<400> SEQUENCE: 130
aagauauugg ugcuguugga cug                                            23

<210> SEQ ID NO 131
<211> LENGTH: 23
<212> TYPE: RNA
<213> ORGANISM: Homo sapiens

<400> SEQUENCE: 131
ugguauuuug uucaaucauu aag                                            23

<210> SEQ ID NO 132
<211> LENGTH: 23
<212> TYPE: RNA
<213> ORGANISM: Homo sapiens

<400> SEQUENCE: 132
ugguauuuug uucaaucauu aag                                            23

<210> SEQ ID NO 133
<211> LENGTH: 23
<212> TYPE: RNA
<213> ORGANISM: Homo sapiens

<400> SEQUENCE: 133
uuuuguucaa ucauuaagaa gac                                            23

<210> SEQ ID NO 134
<211> LENGTH: 23
<212> TYPE: RNA
<213> ORGANISM: Homo sapiens

<400> SEQUENCE: 134
uuuuguucaa ucauuaagaa gac                                            23
```

-continued

```
<210> SEQ ID NO 135
<211> LENGTH: 23
<212> TYPE: RNA
<213> ORGANISM: Homo sapiens

<400> SEQUENCE: 135
agacuuggua uuuguucaa uca                                                23

<210> SEQ ID NO 136
<211> LENGTH: 23
<212> TYPE: RNA
<213> ORGANISM: Homo sapiens

<400> SEQUENCE: 136
agacuuggua uuuguucaa uca                                                23

<210> SEQ ID NO 137
<211> LENGTH: 23
<212> TYPE: RNA
<213> ORGANISM: Homo sapiens

<400> SEQUENCE: 137
auuuuguuca aucauuaaga aga                                               23

<210> SEQ ID NO 138
<211> LENGTH: 23
<212> TYPE: RNA
<213> ORGANISM: Homo sapiens

<400> SEQUENCE: 138
auuuuguuca aucauuaaga aga                                               23

<210> SEQ ID NO 139
<211> LENGTH: 23
<212> TYPE: RNA
<213> ORGANISM: Homo sapiens

<400> SEQUENCE: 139
auuaagaaga caaaggguuu guu                                               23

<210> SEQ ID NO 140
<211> LENGTH: 23
<212> TYPE: RNA
<213> ORGANISM: Homo sapiens

<400> SEQUENCE: 140
auuaagaaga caaaggguuu guu                                               23

<210> SEQ ID NO 141
<211> LENGTH: 23
<212> TYPE: RNA
<213> ORGANISM: Homo sapiens

<400> SEQUENCE: 141
uguucaauca uuaagaagac aaa                                               23

<210> SEQ ID NO 142
<211> LENGTH: 23
<212> TYPE: RNA
<213> ORGANISM: Homo sapiens

<400> SEQUENCE: 142
```

```
uguucaauca uuaagaagac aaa                                          23

<210> SEQ ID NO 143
<211> LENGTH: 23
<212> TYPE: RNA
<213> ORGANISM: Homo sapiens

<400> SEQUENCE: 143
ggugaguuca uuuuccaggu gcu                                          23

<210> SEQ ID NO 144
<211> LENGTH: 23
<212> TYPE: RNA
<213> ORGANISM: Homo sapiens

<400> SEQUENCE: 144
ggugaguuca uuuuccaggu gcu                                          23

<210> SEQ ID NO 145
<211> LENGTH: 23
<212> TYPE: RNA
<213> ORGANISM: Homo sapiens

<400> SEQUENCE: 145
auguaauuca ccagagcaaa aac                                          23

<210> SEQ ID NO 146
<211> LENGTH: 23
<212> TYPE: RNA
<213> ORGANISM: Homo sapiens

<400> SEQUENCE: 146
auguaauuca ccagagcaaa aac                                          23

<210> SEQ ID NO 147
<211> LENGTH: 23
<212> TYPE: RNA
<213> ORGANISM: Homo sapiens

<400> SEQUENCE: 147
aucauuaaga agacaaaggg uuu                                          23

<210> SEQ ID NO 148
<211> LENGTH: 23
<212> TYPE: RNA
<213> ORGANISM: Homo sapiens

<400> SEQUENCE: 148
aucauuaaga agacaaaggg uuu                                          23

<210> SEQ ID NO 149
<211> LENGTH: 23
<212> TYPE: RNA
<213> ORGANISM: Homo sapiens

<400> SEQUENCE: 149
gagacuuggu auuuuguuca auc                                          23

<210> SEQ ID NO 150
<211> LENGTH: 23
<212> TYPE: RNA
<213> ORGANISM: Homo sapiens

<400> SEQUENCE: 150
```

```
gagacuuggu auuuuguuca auc                                              23

<210> SEQ ID NO 151
<211> LENGTH: 23
<212> TYPE: RNA
<213> ORGANISM: Homo sapiens

<400> SEQUENCE: 151
aagacaaagg guuguugaa cuu                                               23

<210> SEQ ID NO 152
<211> LENGTH: 23
<212> TYPE: RNA
<213> ORGANISM: Homo sapiens

<400> SEQUENCE: 152
aagacaaagg guuguugaa cuu                                               23

<210> SEQ ID NO 153
<211> LENGTH: 23
<212> TYPE: RNA
<213> ORGANISM: Homo sapiens

<400> SEQUENCE: 153
aagaggggag acuugguauu uug                                              23

<210> SEQ ID NO 154
<211> LENGTH: 23
<212> TYPE: RNA
<213> ORGANISM: Homo sapiens

<400> SEQUENCE: 154
aagaggggag acuugguauu uug                                              23

<210> SEQ ID NO 155
<211> LENGTH: 23
<212> TYPE: RNA
<213> ORGANISM: Homo sapiens

<400> SEQUENCE: 155
uguaauucac cagagcaaaa acu                                              23

<210> SEQ ID NO 156
<211> LENGTH: 23
<212> TYPE: RNA
<213> ORGANISM: Homo sapiens

<400> SEQUENCE: 156
uguaauucac cagagcaaaa acu                                              23

<210> SEQ ID NO 157
<211> LENGTH: 23
<212> TYPE: RNA
<213> ORGANISM: Homo sapiens

<400> SEQUENCE: 157
agacaaaggg uuuguugaac uug                                              23

<210> SEQ ID NO 158
<211> LENGTH: 23
<212> TYPE: RNA
<213> ORGANISM: Homo sapiens
```

```
<400> SEQUENCE: 158
agacaaaggg uuuguugaac uug                                              23

<210> SEQ ID NO 159
<211> LENGTH: 23
<212> TYPE: RNA
<213> ORGANISM: Homo sapiens

<400> SEQUENCE: 159
uugguauuuu guucaaucau uaa                                              23

<210> SEQ ID NO 160
<211> LENGTH: 23
<212> TYPE: RNA
<213> ORGANISM: Homo sapiens

<400> SEQUENCE: 160
uugguauuuu guucaaucau uaa                                              23

<210> SEQ ID NO 161
<211> LENGTH: 23
<212> TYPE: RNA
<213> ORGANISM: Homo sapiens

<400> SEQUENCE: 161
uucagaucau agguuccagu aau                                              23

<210> SEQ ID NO 162
<211> LENGTH: 23
<212> TYPE: RNA
<213> ORGANISM: Homo sapiens

<400> SEQUENCE: 162
uucagaucau agguuccagu aau                                              23

<210> SEQ ID NO 163
<211> LENGTH: 23
<212> TYPE: RNA
<213> ORGANISM: Homo sapiens

<400> SEQUENCE: 163
agcucaaccc uucuuuaaug uca                                              23

<210> SEQ ID NO 164
<211> LENGTH: 23
<212> TYPE: RNA
<213> ORGANISM: Homo sapiens

<400> SEQUENCE: 164
agcucaaccc uucuuuaaug uca                                              23

<210> SEQ ID NO 165
<211> LENGTH: 23
<212> TYPE: RNA
<213> ORGANISM: Homo sapiens

<400> SEQUENCE: 165
cuugaccaaa uccacaauuu ucc                                              23

<210> SEQ ID NO 166
<211> LENGTH: 23
<212> TYPE: RNA
<213> ORGANISM: Homo sapiens
```

```
<400> SEQUENCE: 166
cuugaccaaa uccacaauuu ucc                                      23

<210> SEQ ID NO 167
<211> LENGTH: 23
<212> TYPE: RNA
<213> ORGANISM: Homo sapiens

<400> SEQUENCE: 167
cagaucauag guuccaguaa ugg                                      23

<210> SEQ ID NO 168
<211> LENGTH: 23
<212> TYPE: RNA
<213> ORGANISM: Homo sapiens

<400> SEQUENCE: 168
cagaucauag guuccaguaa ugg                                      23

<210> SEQ ID NO 169
<211> LENGTH: 23
<212> TYPE: RNA
<213> ORGANISM: Homo sapiens

<400> SEQUENCE: 169
uucaccagag caaaaacugu guc                                      23

<210> SEQ ID NO 170
<211> LENGTH: 23
<212> TYPE: RNA
<213> ORGANISM: Homo sapiens

<400> SEQUENCE: 170
uucaccagag caaaaacugu guc                                      23

<210> SEQ ID NO 171
<211> LENGTH: 23
<212> TYPE: RNA
<213> ORGANISM: Homo sapiens

<400> SEQUENCE: 171
accagcucaa cccuucuuua aug                                      23

<210> SEQ ID NO 172
<211> LENGTH: 23
<212> TYPE: RNA
<213> ORGANISM: Homo sapiens

<400> SEQUENCE: 172
accagcucaa cccuucuuua aug                                      23

<210> SEQ ID NO 173
<211> LENGTH: 23
<212> TYPE: RNA
<213> ORGANISM: Homo sapiens

<400> SEQUENCE: 173
aaggcuguag cgaugcucac ugg                                      23

<210> SEQ ID NO 174
<211> LENGTH: 23
<212> TYPE: RNA
```

<213> ORGANISM: Homo sapiens

<400> SEQUENCE: 174
aaggcuguag cgaugcucac ugg                                     23

<210> SEQ ID NO 175
<211> LENGTH: 23
<212> TYPE: RNA
<213> ORGANISM: Homo sapiens

<400> SEQUENCE: 175
ugugucucug ucaagcuccu uga                                     23

<210> SEQ ID NO 176
<211> LENGTH: 23
<212> TYPE: RNA
<213> ORGANISM: Homo sapiens

<400> SEQUENCE: 176
ugugucucug ucaagcuccu uga                                     23

<210> SEQ ID NO 177
<211> LENGTH: 23
<212> TYPE: RNA
<213> ORGANISM: Homo sapiens

<400> SEQUENCE: 177
auccuccaaa aacuuaucca cua                                     23

<210> SEQ ID NO 178
<211> LENGTH: 23
<212> TYPE: RNA
<213> ORGANISM: Homo sapiens

<400> SEQUENCE: 178
auccuccaaa aacuuaucca cua                                     23

<210> SEQ ID NO 179
<211> LENGTH: 23
<212> TYPE: RNA
<213> ORGANISM: Homo sapiens

<400> SEQUENCE: 179
gacuugguau uuuguucaau cau                                     23

<210> SEQ ID NO 180
<211> LENGTH: 23
<212> TYPE: RNA
<213> ORGANISM: Homo sapiens

<400> SEQUENCE: 180
gacuugguau uuuguucaau cau                                     23

<210> SEQ ID NO 181
<211> LENGTH: 23
<212> TYPE: RNA
<213> ORGANISM: Homo sapiens

<400> SEQUENCE: 181
uuaugcacgg ccuuggagag cuu                                     23

<210> SEQ ID NO 182
<211> LENGTH: 23

```
<212> TYPE: RNA
<213> ORGANISM: Homo sapiens

<400> SEQUENCE: 182
uuaugcacgg ccuuggagag cuu                                              23

<210> SEQ ID NO 183
<211> LENGTH: 23
<212> TYPE: RNA
<213> ORGANISM: Homo sapiens

<400> SEQUENCE: 183
gggugaguuc auuuuccagg ugc                                              23

<210> SEQ ID NO 184
<211> LENGTH: 23
<212> TYPE: RNA
<213> ORGANISM: Homo sapiens

<400> SEQUENCE: 184
gggugaguuc auuuuccagg ugc                                              23

<210> SEQ ID NO 185
<211> LENGTH: 23
<212> TYPE: RNA
<213> ORGANISM: Homo sapiens

<400> SEQUENCE: 185
gugaguguca gccuuggucc cca                                              23

<210> SEQ ID NO 186
<211> LENGTH: 23
<212> TYPE: RNA
<213> ORGANISM: Homo sapiens

<400> SEQUENCE: 186
gugaguguca gccuuggucc cca                                              23

<210> SEQ ID NO 187
<211> LENGTH: 23
<212> TYPE: RNA
<213> ORGANISM: Homo sapiens

<400> SEQUENCE: 187
uauggccucu aaaaacaugg ccc                                              23

<210> SEQ ID NO 188
<211> LENGTH: 23
<212> TYPE: RNA
<213> ORGANISM: Homo sapiens

<400> SEQUENCE: 188
uauggccucu aaaaacaugg ccc                                              23

<210> SEQ ID NO 189
<211> LENGTH: 23
<212> TYPE: RNA
<213> ORGANISM: Homo sapiens

<400> SEQUENCE: 189
ugggugaguu cauuuuccag gug                                              23

<210> SEQ ID NO 190
```

```
<211> LENGTH: 23
<212> TYPE: RNA
<213> ORGANISM: Homo sapiens

<400> SEQUENCE: 190
ugggugaguu cauuuccag gug                                              23

<210> SEQ ID NO 191
<211> LENGTH: 23
<212> TYPE: RNA
<213> ORGANISM: Homo sapiens

<400> SEQUENCE: 191
ugaucuguuu cuuggccucu ucg                                             23

<210> SEQ ID NO 192
<211> LENGTH: 23
<212> TYPE: RNA
<213> ORGANISM: Homo sapiens

<400> SEQUENCE: 192
ugaucuguuu cuuggccucu ucg                                             23

<210> SEQ ID NO 193
<211> LENGTH: 23
<212> TYPE: RNA
<213> ORGANISM: Homo sapiens

<400> SEQUENCE: 193
aaagggucuc ucccauuugc cuu                                             23

<210> SEQ ID NO 194
<211> LENGTH: 23
<212> TYPE: RNA
<213> ORGANISM: Homo sapiens

<400> SEQUENCE: 194
aaagggucuc ucccauuugc cuu                                             23

<210> SEQ ID NO 195
<211> LENGTH: 23
<212> TYPE: RNA
<213> ORGANISM: Homo sapiens

<400> SEQUENCE: 195
ugggauucac cacuuuccc aug                                              23

<210> SEQ ID NO 196
<211> LENGTH: 23
<212> TYPE: RNA
<213> ORGANISM: Homo sapiens

<400> SEQUENCE: 196
ugggauucac cacuuuccc aug                                              23

<210> SEQ ID NO 197
<211> LENGTH: 23
<212> TYPE: RNA
<213> ORGANISM: Homo sapiens

<400> SEQUENCE: 197
ugagugucag ccuuggucccc cag                                            23
```

```
<210> SEQ ID NO 198
<211> LENGTH: 23
<212> TYPE: RNA
<213> ORGANISM: Homo sapiens

<400> SEQUENCE: 198 ugagucag ccuugguccc cag                                            23

<210> SEQ ID NO 199
<211> LENGTH: 23
<212> TYPE: RNA
<213> ORGANISM: Homo sapiens

<400> SEQUENCE: 199
gcucaacccu ucuuuaaugu cau                                          23

<210> SEQ ID NO 200
<211> LENGTH: 23
<212> TYPE: RNA
<213> ORGANISM: Homo sapiens

<400> SEQUENCE: 200
gcucaacccu ucuuuaaugu cau                                          23

<210> SEQ ID NO 201
<211> LENGTH: 23
<212> TYPE: RNA
<213> ORGANISM: Homo sapiens

<400> SEQUENCE: 201
auggccucua aaaacauggc ccc                                          23

<210> SEQ ID NO 202
<211> LENGTH: 23
<212> TYPE: RNA
<213> ORGANISM: Homo sapiens

<400> SEQUENCE: 202
auggccucua aaaacauggc ccc                                          23

<210> SEQ ID NO 203
<211> LENGTH: 23
<212> TYPE: RNA
<213> ORGANISM: Homo sapiens

<400> SEQUENCE: 203 uuucccuca ucaggcagga aga                                           23

<210> SEQ ID NO 204
<211> LENGTH: 23
<212> TYPE: RNA
<213> ORGANISM: Homo sapiens

<400> SEQUENCE: 204 uuucccuca ucaggcagga aga                                           23

<210> SEQ ID NO 205
<211> LENGTH: 23
<212> TYPE: RNA
<213> ORGANISM: Homo sapiens

<400> SEQUENCE: 205
cuuaugcacg gccuuggaga gcu                                          23
```

```
<210> SEQ ID NO 206
<211> LENGTH: 23
<212> TYPE: RNA
<213> ORGANISM: Homo sapiens

<400> SEQUENCE: 206
cuuaugcacg gccuuggaga gcu                                              23

<210> SEQ ID NO 207
<211> LENGTH: 23
<212> TYPE: RNA
<213> ORGANISM: Homo sapiens

<400> SEQUENCE: 207
uaugcacggc cuuggagagc uuc                                              23

<210> SEQ ID NO 208
<211> LENGTH: 23
<212> TYPE: RNA
<213> ORGANISM: Homo sapiens

<400> SEQUENCE: 208
uaugcacggc cuuggagagc uuc                                              23

<210> SEQ ID NO 209
<211> LENGTH: 23
<212> TYPE: RNA
<213> ORGANISM: Homo sapiens

<400> SEQUENCE: 209
ugaaauucag gcccuccagg auu                                              23

<210> SEQ ID NO 210
<211> LENGTH: 23
<212> TYPE: RNA
<213> ORGANISM: Homo sapiens

<400> SEQUENCE: 210
ugaaauucag gcccuccagg auu                                              23

<210> SEQ ID NO 211
<211> LENGTH: 23
<212> TYPE: RNA
<213> ORGANISM: Homo sapiens

<400> SEQUENCE: 211
ucugucaagc uccuugacca aau                                              23

<210> SEQ ID NO 212
<211> LENGTH: 23
<212> TYPE: RNA
<213> ORGANISM: Homo sapiens

<400> SEQUENCE: 212
ucugucaagc uccuugacca aau                                              23

<210> SEQ ID NO 213
<211> LENGTH: 23
<212> TYPE: RNA
<213> ORGANISM: Homo sapiens

<400> SEQUENCE: 213
cugucaagcu ccuugaccaa auc                                              23
```

<210> SEQ ID NO 214
<211> LENGTH: 23
<212> TYPE: RNA
<213> ORGANISM: Homo sapiens

<400> SEQUENCE: 214
cugucaagcu ccuugaccaa auc                                        23

<210> SEQ ID NO 215
<211> LENGTH: 23
<212> TYPE: RNA
<213> ORGANISM: Homo sapiens

<400> SEQUENCE: 215
uguagcgaug cucacugggg aga                                        23

<210> SEQ ID NO 216
<211> LENGTH: 23
<212> TYPE: RNA
<213> ORGANISM: Homo sapiens

<400> SEQUENCE: 216
uguagcgaug cucacugggg aga                                        23

<210> SEQ ID NO 217
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
guccaacagc accaauaucu u                                          21

<210> SEQ ID NO 218
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
guccaacagc accaauaucu u                                          21

<210> SEQ ID NO 219
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
uaaugauuga acaaaauacc a                                          21

<210> SEQ ID NO 220
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 220
uaaugauuga acaaaauacc a                                              21

<210> SEQ ID NO 221
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
cuucuuaaug auugaacaaa a                                              21

<210> SEQ ID NO 222
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
cuucuuaaug auugaacaaa a                                              21

<210> SEQ ID NO 223
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
auugaacaaa auaccaaguc u                                              21

<210> SEQ ID NO 224
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
auugaacaaa auaccaaguc u                                              21

<210> SEQ ID NO 225
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
uucuuaauga uugaacaaaa u                                              21
```

```
<210> SEQ ID NO 226
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
uucuuaauga uugaacaaaa u                                              21

<210> SEQ ID NO 227
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
caaacccuuu gucuucuuaa u                                              21

<210> SEQ ID NO 228
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
caaacccuuu gucuucuuaa u                                              21

<210> SEQ ID NO 229
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
ugucuucuua augauugaac a                                              21

<210> SEQ ID NO 230
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
ugucuucuua augauugaac a                                              21

<210> SEQ ID NO 231
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 231
caccuggaaa augaacucac c                                              21

<210> SEQ ID NO 232
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
caccuggaaa augaacucac c                                              21

<210> SEQ ID NO 233
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
uuuugcucug gugaauuaca u                                              21

<210> SEQ ID NO 234
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
uuuugcucug gugaauuaca u                                              21

<210> SEQ ID NO 235
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
acccuuuguc uucuuaauga u                                              21

<210> SEQ ID NO 236
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
acccuuuguc uucuuaauga u                                              21

<210> SEQ ID NO 237
<211> LENGTH: 21
<212> TYPE: RNA
<213> ORGANISM: Artificial Sequence
```

-continued

```
<220> FEATURE:
<221> NAME/KEY: source
<223> OTHER INFORMATION: /note="Description of Artificial Sequence:
      Synthetic oligonucleotide"

<400> SEQUENCE: 237
uugaacaaaa uaccaagucu c                                               21

<210> SEQ ID NO 238
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
uugaacaaaa uaccaagucu c                                               21

<210> SEQ ID NO 239
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 239
guucaacaaa cccuuugucu u                                               21

<210> SEQ ID NO 240
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 240
guucaacaaa cccuuugucu u                                               21

<210> SEQ ID NO 241
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 241
aaauaccaag ucuccccucu u                                               21

<210> SEQ ID NO 242
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 242
aaauaccaag ucuccccucu u                                               21
```

```
<210> SEQ ID NO 243
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 243
uuuuugcucu ggugaauuac a                                              21

<210> SEQ ID NO 244
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 244
uuuuugcucu ggugaauuac a                                              21

<210> SEQ ID NO 245
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
aguucaacaa acccuuuguc u                                              21

<210> SEQ ID NO 246
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
aguucaacaa acccuuuguc u                                              21

<210> SEQ ID NO 247
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 247
aaugauugaa caaaauacca a                                              21

<210> SEQ ID NO 248
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 248
aaugauugaa caaaauacca a                                          21

<210> SEQ ID NO 249
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 249
uacuggaacc uaugaucuga a                                          21

<210> SEQ ID NO 250
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 250
uacuggaacc uaugaucuga a                                          21

<210> SEQ ID NO 251
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 251
acauuaaaga aggguugagc u                                          21

<210> SEQ ID NO 252
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 252
acauuaaaga aggguugagc u                                          21

<210> SEQ ID NO 253
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 253
aaaauugugg auuuggucaa g                                          21

<210> SEQ ID NO 254
<211> LENGTH: 21
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 254
aaaauugugg auuuggucaa g                                              21

<210> SEQ ID NO 255
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 255
auuacuggaa ccuaugaucu g                                              21

<210> SEQ ID NO 256
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 256
auuacuggaa ccuaugaucu g                                              21

<210> SEQ ID NO 257
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 257
cacaguuuuu gcucugguga a                                              21

<210> SEQ ID NO 258
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 258
cacaguuuuu gcucugguga a                                              21

<210> SEQ ID NO 259
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 259
uuaaagaagg guugagcugg u                                              21
```

```
<210> SEQ ID NO 260
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 260
uuaaagaagg guugagcugg u                                              21

<210> SEQ ID NO 261
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 261
agugagcauc gcuacagccu u                                              21

<210> SEQ ID NO 262
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 262
agugagcauc gcuacagccu u                                              21

<210> SEQ ID NO 263
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 263
aaggagcuug acagagacac a                                              21

<210> SEQ ID NO 264
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 264
aaggagcuug acagagacac a                                              21

<210> SEQ ID NO 265
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 265
guggauaagu uuuuggagga u                                              21

<210> SEQ ID NO 266
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 266
guggauaagu uuuuggagga u                                              21

<210> SEQ ID NO 267
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 267
gauugaacaa aauaccaagu c                                              21

<210> SEQ ID NO 268
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 268
gauugaacaa aauaccaagu c                                              21

<210> SEQ ID NO 269
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 269
gcucuccaag gccgugcaua a                                              21

<210> SEQ ID NO 270
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 270
gcucuccaag gccgugcaua a                                              21

<210> SEQ ID NO 271
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 271
accuggaaaa ugaacucacc c                                              21

<210> SEQ ID NO 272
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 272
accuggaaaa ugaacucacc c                                              21

<210> SEQ ID NO 273
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 273
gggaccaagg cugacacuca c                                              21

<210> SEQ ID NO 274
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 274
gggaccaagg cugacacuca c                                              21

<210> SEQ ID NO 275
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 275
gccauguuuu uagaggccau a                                              21

<210> SEQ ID NO 276
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 276
```

```
gccauguuuu uagaggccau a                                              21
```

<210> SEQ ID NO 277
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 277

```
ccuggaaaau gaacucaccc a                                              21
```

<210> SEQ ID NO 278
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 278

```
ccuggaaaau gaacucaccc a                                              21
```

<210> SEQ ID NO 279
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 279

```
aagaggccaa gaaacagauc a                                              21
```

<210> SEQ ID NO 280
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 280

```
aagaggccaa gaaacagauc a                                              21
```

<210> SEQ ID NO 281
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 281

```
ggcaaauggg agagacccuu u                                              21
```

<210> SEQ ID NO 282
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 282
ggcaaauggg agagacccuu u                                              21

<210> SEQ ID NO 283
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 283
ugggaaaagu ggugaauccc a                                              21

<210> SEQ ID NO 284
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 284
ugggaaaagu ggugaauccc a                                              21

<210> SEQ ID NO 285
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 285
ggggaccaag gcugacacuc a                                              21

<210> SEQ ID NO 286
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 286
ggggaccaag gcugacacuc a                                              21

<210> SEQ ID NO 287
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 287
gacauuaaag aaggguugag c                                              21

<210> SEQ ID NO 288
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 288
gacauuaaag aaggguugag c                                             21

<210> SEQ ID NO 289
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 289
ggccauguuu uuagaggcca u                                             21

<210> SEQ ID NO 290
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 290
ggccauguuu uuagaggcca u                                             21

<210> SEQ ID NO 291
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 291
uuccugccug augaggggaa a                                             21

<210> SEQ ID NO 292
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 292
uuccugccug augaggggaa a                                             21

<210> SEQ ID NO 293
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 293
```

```
cucuccaagg ccgugcauaa g                                              21

<210> SEQ ID NO 294
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 294
cucuccaagg ccgugcauaa g                                              21

<210> SEQ ID NO 295
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 295
agcucuccaa ggccgugcau a                                              21

<210> SEQ ID NO 296
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 296
agcucuccaa ggccgugcau a                                              21

<210> SEQ ID NO 297
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 297
uccuggaggg ccugaauuuc a                                              21

<210> SEQ ID NO 298
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 298
uccuggaggg ccugaauuuc a                                              21

<210> SEQ ID NO 299
<211> LENGTH: 21
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 299
uuggucaagg agcuugacag a                                              21

<210> SEQ ID NO 300
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 300
uuggucaagg agcuugacag a                                              21

<210> SEQ ID NO 301
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 301
uuuggucaag gagcuugaca g                                              21

<210> SEQ ID NO 302
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 302
uuuggucaag gagcuugaca g                                              21

<210> SEQ ID NO 303
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 303
uccccaguga gcaucgcuac a                                              21

<210> SEQ ID NO 304
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 304
uccccaguga gcaucgcuac a                                              21
```

```
<210> SEQ ID NO 305
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 305
aagauauugg ugcuguugga cug                                              23

<210> SEQ ID NO 306
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 306
aagauauugg ugcuguugga cug                                              23

<210> SEQ ID NO 307
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 307
ugguauuuug uucaaucauu aag                                              23

<210> SEQ ID NO 308
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 308
ugguauuuug uucaaucauu aag                                              23

<210> SEQ ID NO 309
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 309
uuuuguucaa ucauuaagaa gac                                              23

<210> SEQ ID NO 310
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 310
uuuuguucaa ucauuaagaa gac                                              23

<210> SEQ ID NO 311
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 311
agacuuggua uuuguucaa uca                                               23

<210> SEQ ID NO 312
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 312
agacuuggua uuuguucaa uca                                               23

<210> SEQ ID NO 313
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 313
auuuuguuca aucauuaaga aga                                              23

<210> SEQ ID NO 314
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 314
auuuuguuca aucauuaaga aga                                              23

<210> SEQ ID NO 315
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 315
auuaagaaga caaaggguuu guu                                              23

<210> SEQ ID NO 316
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 316
auuaagaaga caaaggguuu guu                                            23

<210> SEQ ID NO 317
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 317
uguucaauca uuaagaagac aaa                                            23

<210> SEQ ID NO 318
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 318
uguucaauca uuaagaagac aaa                                            23

<210> SEQ ID NO 319
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 319
ggugaguuca uuuuccaggu gcu                                            23

<210> SEQ ID NO 320
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 320
ggugaguuca uuuuccaggu gcu                                            23

<210> SEQ ID NO 321
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 321
auguaauuca ccagagcaaa aac                                            23
```

<210> SEQ ID NO 322
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 322
auguaauuca ccagagcaaa aac                                              23

<210> SEQ ID NO 323
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 323
aucauuaaga agacaaaggg uuu                                              23

<210> SEQ ID NO 324
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 324
aucauuaaga agacaaaggg uuu                                              23

<210> SEQ ID NO 325
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 325
gagacuuggu auuuguuca auc                                               23

<210> SEQ ID NO 326
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 326
gagacuuggu auuuguuca auc                                               23

<210> SEQ ID NO 327
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 327
aagacaaagg guuguugaa cuu                                          23

<210> SEQ ID NO 328
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 328
aagacaaagg guuguugaa cuu                                          23

<210> SEQ ID NO 329
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 329
aagaggggag acuugguauu uug                                         23

<210> SEQ ID NO 330
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 330
aagaggggag acuugguauu uug                                         23

<210> SEQ ID NO 331
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 331
uguaauucac cagagcaaaa acu                                         23

<210> SEQ ID NO 332
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 332
uguaauucac cagagcaaaa acu                                         23

<210> SEQ ID NO 333
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 333
agacaaaggg uuuguugaac uug                                       23

<210> SEQ ID NO 334
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 334
agacaaaggg uuuguugaac uug                                       23

<210> SEQ ID NO 335
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 335
uugguauuuu guucaaucau uaa                                       23

<210> SEQ ID NO 336
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 336
uugguauuuu guucaaucau uaa                                       23

<210> SEQ ID NO 337
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 337
uucagaucau agguccagu aau                                        23

<210> SEQ ID NO 338
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 338
uucagaucau agguccagu aau                                        23

<210> SEQ ID NO 339
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 339
agcucaaccc uucuuuaaug uca                                              23

<210> SEQ ID NO 340
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 340
agcucaaccc uucuuuaaug uca                                              23

<210> SEQ ID NO 341
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 341
cuugaccaaa uccacaauuu ucc                                              23

<210> SEQ ID NO 342
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 342
cuugaccaaa uccacaauuu ucc                                              23

<210> SEQ ID NO 343
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 343
cagaucauag guuccaguaa ugg                                              23

<210> SEQ ID NO 344
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 344
cagaucauag guuccaguaa ugg                                          23

<210> SEQ ID NO 345
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 345
uucaccagag caaaaacugu guc                                          23

<210> SEQ ID NO 346
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 346
uucaccagag caaaaacugu guc                                          23

<210> SEQ ID NO 347
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 347
accagcucaa cccuucuuua aug                                          23

<210> SEQ ID NO 348
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 348
accagcucaa cccuucuuua aug                                          23

<210> SEQ ID NO 349
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 349
aaggcuguag cgaugcucac ugg                                          23

<210> SEQ ID NO 350
<211> LENGTH: 23

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 350
aaggcuguag cgaugcucac ugg                                              23

<210> SEQ ID NO 351
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 351
ugugucucug ucaagcuccu uga                                              23

<210> SEQ ID NO 352
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 352
ugugucucug ucaagcuccu uga                                              23

<210> SEQ ID NO 353
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 353
auccuccaaa aacuuaucca cua                                              23

<210> SEQ ID NO 354
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 354
auccuccaaa aacuuaucca cua                                              23

<210> SEQ ID NO 355
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 355
```
gacuugguau uuuguucaau cau                                          23

<210> SEQ ID NO 356
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 356
gacuugguau uuuguucaau cau                                          23

<210> SEQ ID NO 357
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 357
uuaugcacgg ccuuggagag cuu                                          23

<210> SEQ ID NO 358
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 358
uuaugcacgg ccuuggagag cuu                                          23

<210> SEQ ID NO 359
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 359
gggugaguuc auuuuccagg ugc                                          23

<210> SEQ ID NO 360
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 360
gggugaguuc auuuuccagg ugc                                          23

<210> SEQ ID NO 361
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 361
gugaguguca gccuuggucc cca                                                23

<210> SEQ ID NO 362
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 362
gugaguguca gccuuggucc cca                                                23

<210> SEQ ID NO 363
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 363
uauggccucu aaaacaugg ccc                                                 23

<210> SEQ ID NO 364
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 364
uauggccucu aaaacaugg ccc                                                 23

<210> SEQ ID NO 365
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 365
ugggugaguu cauuuccag gug                                                 23

<210> SEQ ID NO 366
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
Synthetic oligonucleotide"

<400> SEQUENCE: 366
ugggugaguu cauuuccag gug                                                 23

<210> SEQ ID NO 367

```
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 367
ugaucuguuu cuuggccucu ucg                                           23

<210> SEQ ID NO 368
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 368
ugaucuguuu cuuggccucu ucg                                           23

<210> SEQ ID NO 369
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 369
aaagggucuc ucccauuugc cuu                                           23

<210> SEQ ID NO 370
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 370
aaagggucuc ucccauuugc cuu                                           23

<210> SEQ ID NO 371
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 371
ugggauucac cacuuuuccc aug                                           23

<210> SEQ ID NO 372
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 372
```
ugggauucac cacuuuuccc aug                                            23

<210> SEQ ID NO 373
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 373
ugagugucag ccuugguccc cag                                            23

<210> SEQ ID NO 374
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 374
ugagugucag ccuugguccc cag                                            23

<210> SEQ ID NO 375
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 375
gcucaacccu ucuuuaaugu cau                                            23

<210> SEQ ID NO 376
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 376
gcucaacccu ucuuuaaugu cau                                            23

<210> SEQ ID NO 377
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 377
auggccucua aaacauggc ccc                                             23

<210> SEQ ID NO 378
<211> LENGTH: 23
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 378
auggccucua aaacauggc ccc                                              23

<210> SEQ ID NO 379
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 379
uuuccccuca ucaggcagga aga                                             23

<210> SEQ ID NO 380
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 380
uuuccccuca ucaggcagga aga                                             23

<210> SEQ ID NO 381
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 381
cuuaugcacg gccuuggaga gcu                                             23

<210> SEQ ID NO 382
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 382
cuuaugcacg gccuuggaga gcu                                             23

<210> SEQ ID NO 383
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 383
uaugcacggc cuuggagagc uuc                                             23
```

```
<210> SEQ ID NO 384
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 384
uaugcacggc cuuggagagc uuc                                              23

<210> SEQ ID NO 385
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 385
ugaaauucag gcccuccagg auu                                              23

<210> SEQ ID NO 386
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 386
ugaaauucag gcccuccagg auu                                              23

<210> SEQ ID NO 387
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 387
ucugucaagc uccuugacca aau                                              23

<210> SEQ ID NO 388
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 388
ucugucaagc uccuugacca aau                                              23

<210> SEQ ID NO 389
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 389
cugucaagcu ccuugaccaa auc                                          23

<210> SEQ ID NO 390
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 390
cugucaagcu ccuugaccaa auc                                          23

<210> SEQ ID NO 391
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 391
uguagcgaug cucacugggg aga                                          23

<210> SEQ ID NO 392
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 392
uguagcgaug cucacugggg aga                                          23

<210> SEQ ID NO 393
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 393
guccaacagc accaauaucu u                                            21

<210> SEQ ID NO 394
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 394
aagauauugg ugcuguugga cug                                          23

<210> SEQ ID NO 395
<211> LENGTH: 21
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 395
guccaacagc accaauaucu u                                              21

<210> SEQ ID NO 396
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 396
aagauauugg ugcuguugga cug                                            23

<210> SEQ ID NO 397
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 397
guccaacagc accaauaucu u                                              21

<210> SEQ ID NO 398
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 398
aagauauugg ugcuguugga cug                                            23

<210> SEQ ID NO 399
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 399
guccaacagc accaauaucu u                                              21

<210> SEQ ID NO 400
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 400
aagauauugg ugcuguugga cug                                            23
```

<210> SEQ ID NO 401
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 401
cuucuuaaug auugaacaaa a                                              21

<210> SEQ ID NO 402
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 402
cuucuuaaug auugaccaaa a                                              21

<210> SEQ ID NO 403
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 403
cuucuuaaug auugaucaaa a                                              21

<210> SEQ ID NO 404
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 404
cuucuuaaug auugagcaaa a                                              21

<210> SEQ ID NO 405
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 405
cuucuuaaug auugaccaaa a                                              21

<210> SEQ ID NO 406
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 406
cuucuuaaug auugaccaaa a                             21

<210> SEQ ID NO 407
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 407
cuucuuaaug auugaacaaa a                             21

<210> SEQ ID NO 408
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 408
cuucuuaaug auugaacaaa a                             21

<210> SEQ ID NO 409
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 409
uuuuguucaa ucauuaagaa gac                           23

<210> SEQ ID NO 410
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 410
uuuuggucaa ucauuaagaa gac                           23

<210> SEQ ID NO 411
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 411
uuuugaucaa ucauuaagaa gac                           23

<210> SEQ ID NO 412
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 412
uuuugcucaa ucauuaagaa gac                                                 23

<210> SEQ ID NO 413
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: Inosine

<400> SEQUENCE: 413
uuuugnucaa ucauuaagaa gac                                                 23

<210> SEQ ID NO 414
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, u or g

<400> SEQUENCE: 414
uuuugnucaa ucauuaagaa gac                                                 23

<210> SEQ ID NO 415
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, u or g

<400> SEQUENCE: 415
uuuugnucaa ucauuaagaa gac                                                 23

<210> SEQ ID NO 416
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: a, c, u or g

<400> SEQUENCE: 416
```
uuuugnucaa ucauuaagaa gac 23

<210> SEQ ID NO 417
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 417
cuucuuaaug auugaacaaa a 21

<210> SEQ ID NO 418
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 418
cuucuuaaug auugaacaaa a 21

<210> SEQ ID NO 419
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 419
uuuuguucaa ucauuaagaa gac 23

<210> SEQ ID NO 420
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 420
uuuuguucaa ucauuaagaa gac 23

<210> SEQ ID NO 421
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 421
cuucuuaaug auugaacaaa a 21

<210> SEQ ID NO 422
<211> LENGTH: 21
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 422
cuucuuaaug auugaccaaa a                                              21

<210> SEQ ID NO 423
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 423
cuucuuaaug auugaucaaa a                                              21

<210> SEQ ID NO 424
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 424
cuucuuaaug auugagcaaa a                                              21

<210> SEQ ID NO 425
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 425
cuucuuaaug auugaccaaa a                                              21

<210> SEQ ID NO 426
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 426
cuucuuaaug auugaccaaa a                                              21

<210> SEQ ID NO 427
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 427
cuucuuaaug auugaacaaa a                                              21
```

```
<210> SEQ ID NO 428
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 428
cuucuuaaug auugaacaaa a                                              21

<210> SEQ ID NO 429
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 429
uuuuguucaa ucauuaagaa gac                                            23

<210> SEQ ID NO 430
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 430
uuuuggucaa ucauuaagaa gac                                            23

<210> SEQ ID NO 431
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 431
uuuugaucaa ucauuaagaa gac                                            23

<210> SEQ ID NO 432
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 432
uuuugcucaa ucauuaagaa gac                                            23

<210> SEQ ID NO 433
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: modified_base
<222> LOCATION: (6)..(6)
<223> OTHER INFORMATION: Inosine

<400> SEQUENCE: 433
uuuugnucaa ucauuaagaa gac                                             23

<210> SEQ ID NO 434
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Deoxyriboinosine

<400> SEQUENCE: 434
uuuugnucaa ucauuaagaa gac                                             23

<210> SEQ ID NO 435
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
<220> FEATURE:
<221> NAME/KEY: modified_base
<222> LOCATION: (6)..(6)
<223> OTHER INFORMATION: Deoxyriboinosine

<400> SEQUENCE: 435
uuuugnucaa ucauuaagaa gac                                             23

<210> SEQ ID NO 436
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: modified_base
<222> LOCATION: (6)..(6)
<223> OTHER INFORMATION: 2-hydroxymethyl-tetrahydrofurane-4-methoxy-3-
      phosphate

<400> SEQUENCE: 436
uuuugnucaa ucauuaagaa gac                                             23
```

We claim:

1. A double stranded ribonucleic acid (dsRNA) agent for inhibiting expression of a serine peptidase inhibitor, clade A member 1 (Serpina1) in a cell, wherein said dsRNA agent comprises a sense strand and an antisense strand forming a double-stranded region, wherein the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419), wherein the sense strand and the antisense strand are each independently 19-25 nucleotides in length, wherein substantially all of the nucleotides of said sense strand and substantially all of the nucleotides of said antisense strand are modified nucleotides, and
wherein at least one strand is conjugated to a ligand through a bivalent or trivalent branched linker.

2. The dsRNA agent of claim 1, wherein one of the 3 nucleotide differences in the nucleotide sequence of the antisense strand is a nucleotide mismatch in the seed region of the antisense strand.

3. The dsRNA agent of claim 1, wherein the ligand is one or more GalNAc derivatives.

4. The dsRNA agent of claim 1, wherein said agent further comprises at least one phosphorothioate or methylphosphonate internucleotide linkage.

5. A cell containing the dsRNA agent of claim 1.

6. A pharmaceutical composition comprising the dsRNA agent of claim 1.

7. A method of inhibiting Serpina1 expression in a cell, the method comprising
(a) contacting the cell with the dsRNA agent of claim 1, or the pharmaceutical composition of claim 6; and
(b) maintaining the cell produced in step (a) for a time sufficient to obtain degradation of the mRNA transcript of a Serpina1 gene, thereby inhibiting expression of the Serpina1 gene in the cell.

8. A method of treating a subject having a Serpina1 deficiency variant-associated associated liver disorder, the method comprising administering to the subject a therapeutically effective amount of the dsRNA agent of claim 1, or the pharmaceutical composition of claim 6, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby treating the subject.

9. A method of treating a subject having a Serpina1 deficiency variant-associated liver disorder to reduce the progression of the liver disorder to hepatocellular carcinoma, the method comprising administering to the subject a therapeutically effective amount of the dsRNA agent of claim 1, or the pharmaceutical composition of claim 6, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby treating the subject.

10. A method of reducing the accumulation of misfolded Serpina1 in the liver of a subject having a Serpina1 deficiency variant-associated liver disorder, the method comprising administering to the subject a therapeutically effective amount of the dsRNA agent of claim 1, or the pharmaceutical composition of claim 6, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby reducing the accumulation of misfolded Serpina1 in the liver of the subject.

11. The dsRNA agent of claim 1, wherein all of the nucleotides of said sense strand and all of the nucleotides of said antisense strand are modified nucleotides.

12. The dsRNA agent of claim 1, wherein at least one of said modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, and a terminal nucleotide linked to a cholesteryl derivative or a dodecanoic acid bisdecylamide group.

13. The dsRNA agent of claim 1, wherein at least one strand comprises a 3' overhang of at least 1 nucleotide; or a 3' overhang of at least 2 nucleotides.

14. The dsRNA agent of claim 1, wherein the sense strand is 21 nucleotides in length and the antisense strand is 23 nucleotides in length.

15. The dsRNA agent of claim 3, wherein the ligand is

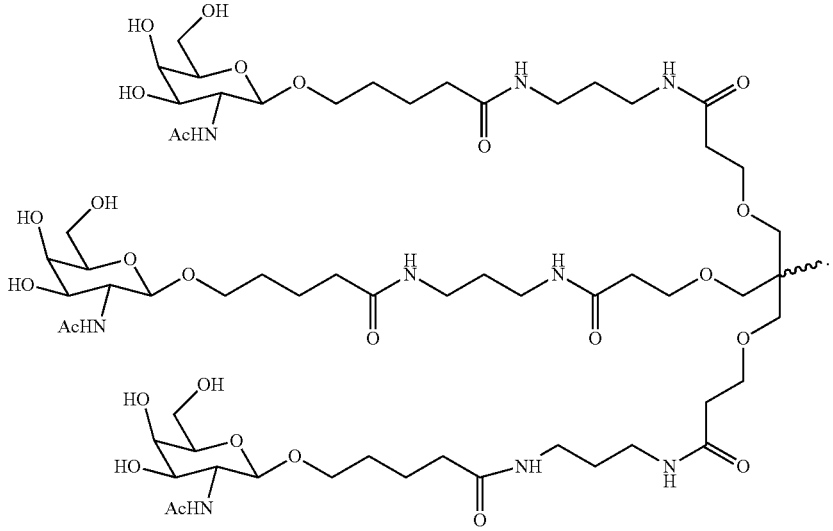 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

16. The dsRNA agent of claim 15, wherein the at least one ligand is conjugated to the 3'-end of the sense strand.

17. The dsRNA agent of claim 16, wherein the dsRNA agent is conjugated to the ligand as shown in the following schematic

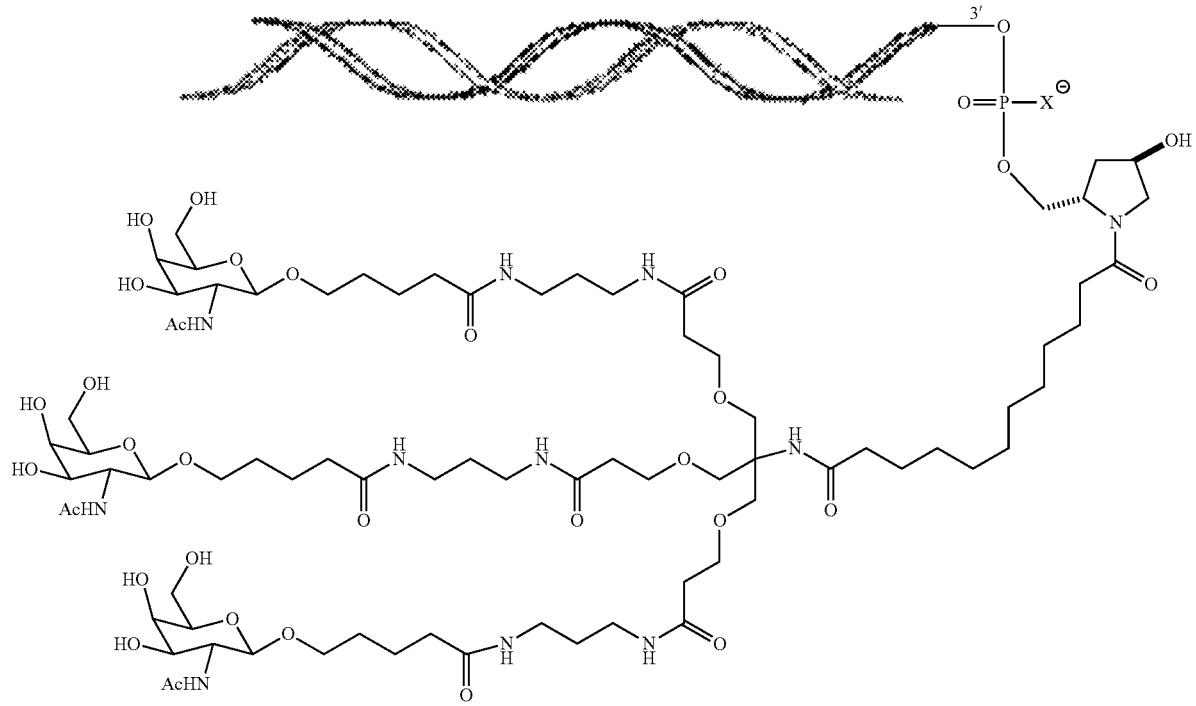

and, wherein X is O or S.

18. The dsRNA agent of claim 17, wherein the X is O.

19. The dsRNA agent of claim 1, wherein the antisense strand comprises the nucleotide sequence 5'-UUUUGUUCAAUCAUUAAGAAGAC-3' (SEQ ID NO: 419).

20. The dsRNA agent of claim 1, wherein the sense strand comprises the nucleotide sequence 5'-CUUCUUAAUGAUUGAACAAAA-3' (SEQ ID NO: 417) and the antisense strand comprises the nucleotide sequence 5'-UUUUGUUCAAUCAUUAAGAAGAC-3' (SEQ ID NO: 419).

21. The dsRNA agent of claim 1, wherein the sense strand comprises the nucleotide sequence 5'-csusucuuaauGfAfuugaacaaaa-3' (SEQ ID NO: 418) and the antisense strand comprises the nucleotide sequence 5'-usUfsuUfgU-fuCfaAfucaUfuAfaGfaAfgsasc-3' (SEQ ID NO: 420),
wherein a, g, c, and u are 2'-O-methyl (2'-OMe) A, G, C, and U, respectively; Af, Gf, Cf, and Uf, are 2'-fluoro A, G, C, and U, respectively; and s is a phosphorothioate linkage.

22. The dsRNA agent of claim 21, further comprising a ligand conjugated to the 3'-end of the sense strand.

23. The dsNA agent of claim 1, wherein the sense strand consists of the nucleotide sequence 5'-csusucuuaauGfAfuugaacaaaaL96-3' (SEQ ID NO: 418) and the antisense strand consists of the nucleotide sequence 5'-usUfsuUfgU-fuCfaAfucaUfuAfaGfaAfgsasc-3' (SEQ ID NO: 420),
wherein a, g, c, and u are 2'-O-methyl (2'-OMe) A, G, C, and U, respectively; Af, Gf, Cf, and Uf, are 2'-fluoro A, G, C, and U, respectively; s is a phosphorothioate linkage; and L96 is N-[tris(GalNAc-alkyl)-aminododecanoyl)]-4-hydroxyprolinol.

24. A double stranded ribonucleic acid (dsRNA) agent for inhibiting expression of a serine peptidase inhibitor, clade A, member 1 (Serpina1) in a cell, wherein said dsRNA agent comprises a sense strand and an antisense strand forming a double-stranded region, wherein the antisense strand comprises at least 19 contiguous nucleotides differing by no more than 3 nucleotides from the nucleotide sequence of 5'-UUUUGUUCAAUCAUUAAGAAGAC-3' (SEQ ID NO: 419),
wherein the sense strand and the antisense strand are each independently 19-25 nucleotides in length,
wherein substantially all of the nucleotides of said sense strand comprise a modification selected from the group consisting of a 2'-O-methyl modification and a 2'-fluoro modification,
wherein said sense strand comprises two phosphorothioate internucleotide linkages at the 5'-terminus,
wherein substantially all of the nucleotides of said antisense strand comprise a modification selected from the group consisting of a 2'-O-methyl modification and a 2'-fluoro modification,
wherein said antisense strand comprises two phosphorothioate internucleotide linkages at the 5'-terminus and two phosphorothioate internucleotide linkages at the 3'-terminus, and
wherein said sense strand is conjugated to one or more GalNAc derivatives attached through a branched bivalent or trivalent linker at the 3'-terminus.

25. The dsRNA agent of claim 24, wherein all of the nucleotides of said sense strand and all of the nucleotides of said antisense strand comprise a modification.

26. A cell containing the dsRNA agent of claim 24.

27. A pharmaceutical composition comprising the dsRNA agent of claim 24.

28. The method of claim 7, wherein the cell is within a subject.

29. The method of claim 8, wherein the subject is a human.

30. The method of claim 8, wherein the liver disorder is selected from the group consisting of chronic liver disease, liver inflammation, cirrhosis, liver fibrosis, and hepatocellular carcinoma.

31. A pharmaceutical composition comprising the dsRNA agent of claim 23.

32. A method of inhibiting Serpina1 expression in a cell, the method comprising:
(a) contacting the cell with the dsRNA agent of claim 24 or the pharmaceutical composition of claim 27; and
(b) maintaining the cell produced in step (a) for a time sufficient to obtain degradation of the mRNA transcript of a Serpina1 gene, thereby inhibiting expression of the Serpina1 gene in the cell.

33. The method of claim 32, wherein the cell is within a subject.

34. A method of inhibiting Serpina1 expression in a cell, the method comprising:
(a) contacting the cell with the dsRNA agent of claim 23 or the pharmaceutical composition of claim 31; and
(b) maintaining the cell produced in step (a) for a time sufficient to obtain degradation of the mRNA transcript of a Serpina1 gene, thereby inhibiting expression of the Serpina1 gene in the cell.

35. The method of claim 34, wherein the cell is within a subject.

36. A method of treating a subject having a Serpina1 deficiency variant-associated associated liver disorder, the method comprising administering to the subject a therapeutically effective amount of the dsRNA agent of claim 24 or the pharmaceutical composition of claim 27, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby treating the subject.

37. The method of claim 36, wherein the subject is a human.

38. The method of claim 36, wherein the liver disorder is selected from the group consisting of chronic liver disorder, liver inflammation, cirrhosis, liver fibrosis, and hepatocellular carcinoma.

39. A method of treating a subject having a Serpina1 deficiency variant-associated associated liver disorder, the method comprising administering to the subject a therapeutically effective amount of the dsRNA agent of claim 23 or the pharmaceutical composition of claim 31, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby treating the subject.

40. The method of claim 39, wherein the subject is a human.

41. The method of claim 39, wherein the liver disease is selected from the group consisting of chronic liver disease, liver inflammation, cirrhosis, liver fibrosis, and hepatocellular carcinoma.

42. A method of treating a subject having a Serpina1 deficiency variant-associated liver disorder to reduce the progression of the liver disorder to hepatocellular carcinoma, the method comprising administering to the subject a therapeutically effective amount of the dsRNA agent of claim 24 or the pharmaceutical composition of claim 27, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby treating the subject.

43. A method of treating a subject having a Serpina1 deficiency variant-associated liver disorder to reduce the progression of the liver disorder to hepatocellular carcinoma, the method comprising administering to the subject a therapeutically effective amount of the dsRNA agent of claim 23 or the pharmaceutical composition of claim 31, thereby treating the subject.

44. A method of reducing the accumulation of misfolded Serpina1 in the liver of a subject having a Serpina1 deficiency variant-associated liver disorder, the method comprising administering to the subject a therapeutically effective amount of the dsRNA agent of claim 24 or the pharmaceutical composition of claim 27, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby reducing the accumulation of misfolded Serpina1 in the liver of the subject.

45. A method of reducing the accumulation of misfolded Serpina1 in the liver of a subject having a Serpina1 deficiency variant-associated liver disorder, the method comprising administering to the subject a therapeutically effective amount of the dsRNA agent of claim 23 or the pharmaceutical composition of claim 31, wherein the subject has one or more of a Serpina1 Z deficiency allele or a Serpina1 PIM(Malton) deficiency allele and the Serpina1 deficiency variant-associated associated liver disorder is associated with the Serpina1 deficiency allele, thereby reducing the accumulation of misfolded Serpina1 in the liver of the subject.

* * * * *